US011879145B2

(12) United States Patent
Romesberg et al.

(10) Patent No.: US 11,879,145 B2
(45) Date of Patent: Jan. 23, 2024

(54) REAGENTS AND METHODS FOR REPLICATION, TRANSCRIPTION, AND TRANSLATION IN SEMI-SYNTHETIC ORGANISMS

(71) Applicant: The Scripps Research Institute, La Jolla, CA (US)

(72) Inventors: Floyd E. Romesberg, La Jolla, CA (US); Vivian T. Dien, San Diego, CA (US); Aaron W. Feldman, San Diego, CA (US); Rebekah J. Karadeema, San Diego, CA (US); Lingjun Li, Xin Xiang (CN); Michael P. Ledbetter, La Jolla, CA (US); Anne Xiaozhou Zhou, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 461 days.

(21) Appl. No.: 16/900,154

(22) Filed: Jun. 12, 2020

(65) Prior Publication Data

US 2020/0392550 A1 Dec. 17, 2020

Related U.S. Application Data

(60) Provisional application No. 62/861,901, filed on Jun. 14, 2019.

(51) Int. Cl.
*C07H 19/24* (2006.01)
*C07H 21/04* (2006.01)
*C12P 19/34* (2006.01)

(52) U.S. Cl.
CPC .............. *C12P 19/34* (2013.01); *C07H 19/24* (2013.01); *C07H 21/04* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan, Jr. et al. |
| 4,469,863 | A | 9/1984 | Ts et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,683,195 | A | 7/1987 | Mullis et al. |
| 4,683,202 | A | 7/1987 | Mullis |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh et al. |
| 4,849,513 | A | 7/1989 | Smith et al. |
| 4,876,335 | A | 10/1989 | Yamane et al. |
| 4,904,582 | A | 2/1990 | Tullis |
| 4,910,300 | A | 3/1990 | Urdea et al. |
| 4,948,882 | A | 8/1990 | Ruth |
| 4,958,013 | A | 9/1990 | Letsinger |
| 4,965,188 | A | 10/1990 | Mullis et al. |
| 4,981,957 | A | 1/1991 | Lebleu et al. |
| 5,015,733 | A | 5/1991 | Smith et al. |
| 5,023,243 | A | 6/1991 | Tullis |
| 5,034,506 | A | 7/1991 | Summerton et al. |
| 5,082,830 | A | 1/1992 | Brakel et al. |
| 5,093,232 | A | 3/1992 | Urdea et al. |
| 5,109,124 | A | 4/1992 | Ramachandran et al. |
| 5,112,963 | A | 5/1992 | Pieles et al. |
| 5,118,800 | A | 6/1992 | Smith et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,235,033 | A | 8/1993 | Summerton et al. |

(Continued)

FOREIGN PATENT DOCUMENTS

| | | | |
|---|---|---|---|
| EP | 0614907 | A1 | 9/1994 |
| EP | 0629633 | A2 | 12/1994 |

(Continued)

OTHER PUBLICATIONS

Montgomery et al., Journal of Organic Chemistry, 1969, vol. 34(9), pp. 2646-2649. (Year: 1969).*
Montero et al., Journal of Heterocyclic Chemistry, 1978, 15(6), pp. 929-935. (Year: 1978).*
PCT/US2020/037437 International Search Report and Written Opinion dated Sep. 28, 2020.
Acsadi et al. Human Dystrophin Expression in mdx Mice After Intramuscular Injection of DNA Constructs. Nature 352:815-818 (1991).
Adhikary et al. Adaptive Mutations Alter Antibody Structure and Dynamics During Affinity Maturation. Biochemistry 54(11):2085-93 (2015).

(Continued)

*Primary Examiner* — Traviss C McIntosh, III
(74) *Attorney, Agent, or Firm* — Thomas Fitting

(57) ABSTRACT

Disclosed herein are compositions, methods, cells, engineered microorganisms, and kits for increasing the production of proteins or polypeptides comprising one or more unnatural amino acids. Further provided are compositions, cells, engineered microorganisms, and kits for increasing the retention of unnatural nucleic acids encoding the unnatural amino acids in an engineered cell, or semi-synthetic organism.

7 Claims, 25 Drawing Sheets

Specification includes a Sequence Listing.

(56) References Cited

U.S. PATENT DOCUMENTS 5,245,022 A 9/1993 Weis et al.
5,254,469 A 10/1993 Warren, III et al.
5,258,506 A 11/1993 Urdea et al.
5,262,536 A 11/1993 Hobbs, Jr.
5,264,423 A 11/1993 Cohen et al.
5,264,562 A 11/1993 Matteucci
5,264,564 A 11/1993 Matteucci
5,272,250 A 12/1993 Spielvogel et al.
5,276,019 A 1/1994 Cohen et al.
5,278,302 A 1/1994 Caruthers et al.
5,286,717 A 2/1994 Cohen et al.
5,292,873 A 3/1994 Rokita et al.
5,317,098 A 5/1994 Shizuya et al.
5,319,080 A 6/1994 Leumann
5,321,131 A 6/1994 Agrawal et al.
5,359,044 A 10/1994 Cook et al.
5,367,066 A 11/1994 Urdea et al.
5,371,241 A 12/1994 Brush
5,391,723 A 2/1995 Priest
5,393,878 A 2/1995 Leumann
5,399,676 A 3/1995 Froehler
5,405,938 A 4/1995 Summerton et al.
5,405,939 A 4/1995 Suhadolnik et al.
5,414,077 A 5/1995 Lin et al.
5,416,203 A 5/1995 Letsinger
5,432,272 A 7/1995 Benner
5,434,257 A 7/1995 Matteucci et al.
5,446,137 A 8/1995 Maag et al.
5,451,463 A 9/1995 Nelson et al.
5,453,496 A 9/1995 Caruthers et al.
5,455,233 A 10/1995 Spielvogel et al.
5,457,187 A 10/1995 Gmeiner et al.
5,459,255 A 10/1995 Cook et al.
5,466,677 A 11/1995 Baxter et al.
5,466,786 A 11/1995 Buhr et al.
5,470,967 A 11/1995 Huie et al.
5,476,925 A 12/1995 Letsinger et al.
5,484,908 A 1/1996 Froehler et al.
5,486,603 A 1/1996 Buhr
5,489,677 A 2/1996 Sanghvi et al.
5,502,177 A 3/1996 Matteucci et al.
5,510,475 A 4/1996 Agrawal et al.
5,512,439 A 4/1996 Hornes et al.
5,512,667 A 4/1996 Reed et al.
5,514,785 A 5/1996 Van Ness et al.
5,519,126 A 5/1996 Hecht
5,519,134 A 5/1996 Acevedo et al.
5,525,465 A 6/1996 Haralambidis et al.
5,525,711 A 6/1996 Hawkins et al.
5,536,821 A 7/1996 Agrawal et al.
5,539,082 A 7/1996 Nielsen et al.
5,541,306 A 7/1996 Agrawal et al.
5,541,307 A 7/1996 Cook et al.
5,541,313 A 7/1996 Ruth
5,545,730 A 8/1996 Urdea et al.
5,550,111 A 8/1996 Suhadolnik et al.
5,552,538 A 9/1996 Urdea et al.
5,552,540 A 9/1996 Haralambidis
5,561,225 A 10/1996 Maddry et al.
5,563,253 A 10/1996 Agrawal et al.
5,565,552 A 10/1996 Magda et al.
5,567,810 A 10/1996 Weis et al.
5,567,811 A 10/1996 Misiura et al.
5,571,799 A 11/1996 Tkachuk et al.
5,574,142 A 11/1996 Meyer, Jr. et al.
5,576,427 A 11/1996 Cook et al.
5,578,717 A 11/1996 Urdea et al.
5,578,718 A 11/1996 Cook et al.
5,580,731 A 12/1996 Chang et al.
5,585,481 A 12/1996 Arnold, Jr. et al.
5,587,361 A 12/1996 Cook et al.
5,587,371 A 12/1996 Sessler et al.
5,587,469 A 12/1996 Cook et al.
5,591,584 A 1/1997 Chang et al.
5,591,722 A 1/1997 Montgomery et al.
5,594,121 A 1/1997 Froehler et al.
5,595,726 A 1/1997 Magda et al.
5,595,899 A 1/1997 Sato et al.
5,596,086 A 1/1997 Matteucci et al.
5,596,091 A 1/1997 Switzer
5,597,696 A 1/1997 Linn et al.
5,597,909 A 1/1997 Urdea et al.
5,599,923 A 2/1997 Sessler et al.
5,599,928 A 2/1997 Hemmi et al.
5,602,240 A 2/1997 Mesmaeker et al.
5,608,046 A 3/1997 Cook et al.
5,610,289 A 3/1997 Cook et al.
5,610,300 A 3/1997 Altmann et al.
5,614,617 A 3/1997 Cook et al.
5,618,704 A 4/1997 Sanghvi et al.
5,623,070 A 4/1997 Cook et al.
5,625,050 A 4/1997 Beaton et al.
5,627,053 A 5/1997 Usman et al.
5,633,360 A 5/1997 Bischofberger et al.
5,639,873 A 6/1997 Barascut et al.
5,645,985 A 7/1997 Froehler et al.
5,646,265 A 7/1997 McGee
5,656,493 A 8/1997 Mullis et al.
5,658,873 A 8/1997 Bertsch-Frank et al.
5,663,312 A 9/1997 Chaturvedula
5,670,633 A 9/1997 Cook et al.
5,677,437 A 10/1997 Teng et al.
5,677,439 A 10/1997 Weis et al.
5,681,941 A 10/1997 Cook et al.
5,688,941 A 11/1997 Cook et al.
5,700,920 A 12/1997 Altmann et al.
5,714,331 A 2/1998 Buchardt et al.
5,719,262 A 2/1998 Buchardt et al.
5,750,692 A 5/1998 Cook et al.
5,763,588 A 6/1998 Matteucci et al.
5,830,653 A 11/1998 Froehler et al.
5,888,732 A 3/1999 Hartley et al.
6,005,096 A 12/1999 Matteucci et al.
6,143,557 A 11/2000 Hartley et al.
6,171,861 B1 1/2001 Hartley et al.
6,268,490 B1 7/2001 Imanishi et al.
6,270,969 B1 8/2001 Hartley et al.
6,277,608 B1 8/2001 Hartley et al.
6,525,191 B1 2/2003 Ramasamy
6,670,461 B1 12/2003 Wengel et al.
6,720,140 B1 4/2004 Hartley et al.
6,770,748 B2 8/2004 Imanishi et al.
6,794,499 B2 9/2004 Wengel et al.
6,955,807 B1 10/2005 Shanafelt et al.
7,034,133 B2 4/2006 Wengel et al.
7,053,207 B2 5/2006 Wengel
7,399,845 B2 7/2008 Seth et al.
7,427,672 B2 9/2008 Imanishi et al.
9,682,934 B2 6/2017 Stafford et al.
9,840,493 B2 12/2017 Yang et al.
9,938,516 B2 4/2018 Zimmerman et al.
9,988,619 B2 6/2018 Zimmerman et al.
10,513,706 B2 12/2019 Romesberg et al.
10,626,138 B2 4/2020 Romesberg et al.
10,696,719 B2 6/2020 Romesberg et al.
10,696,720 B2 6/2020 Romesberg et al.
11,634,451 B2 4/2023 Romesberg et al.
2002/0007051 A1 1/2002 Cheo et al.
2004/0171570 A1 9/2004 Allerson et al.
2005/0130923 A1 6/2005 Bhat et al.
2006/0074035 A1 4/2006 Hong et al.
2007/0154952 A1 7/2007 Chin et al.
2007/0287831 A1 12/2007 Seth et al.
2008/0039618 A1 2/2008 Allerson et al.
2008/0300163 A1 12/2008 Cho et al.
2012/0244112 A1 9/2012 Ast et al.
2014/0328791 A1 11/2014 Bossard et al.
2017/0369871 A1 12/2017 Ptacin et al.
2018/0086734 A1 3/2018 Yang et al.
2019/0218257 A1 7/2019 Romesberg et al.
2019/0376054 A1 12/2019 Ptacin et al.
2020/0017540 A1 1/2020 Romesberg et al.
2020/0024597 A1 1/2020 Ptacin et al.
2020/0095591 A1 3/2020 Romesberg et al.

(56) References Cited

U.S. PATENT DOCUMENTS

| | | | |
|---|---|---|---|
| 2020/0131555 A1 | 4/2020 | Ptacin et al. | |
| 2020/0224234 A1 | 7/2020 | Romesberg et al. | |
| 2020/0277342 A1 | 9/2020 | Romesberg et al. | |
| 2020/0318122 A1 | 10/2020 | Romesberg et al. | |
| 2020/0377877 A1 | 12/2020 | Romesberg et al. | |
| 2021/0222147 A1 | 7/2021 | Ptacin et al. | |
| 2022/0228148 A1 | 7/2022 | Romesberg et al. | |
| 2022/0243244 A1 | 8/2022 | Romesberg et al. | |
| 2023/0235339 A1 | 7/2023 | Romesberg et al. | |

FOREIGN PATENT DOCUMENTS

| | | | |
|---|---|---|---|
| WO | WO-9213869 A1 | 8/1992 | |
| WO | WO-9422890 A1 | 10/1994 | |
| WO | WO-9735869 A1 | 10/1997 | |
| WO | WO-9914226 A2 | 3/1999 | |
| WO | WO-9962923 A2 | 12/1999 | |
| WO | WO-0105801 A1 | 1/2001 | |
| WO | WO-0132887 A1 | 5/2001 | |
| WO | WO-02070533 A2 | 9/2002 | |
| WO | WO-2004007713 A1 | 1/2004 | |
| WO | WO-2004106356 A1 | 12/2004 | |
| WO | WO-2005021570 A1 | 3/2005 | |
| WO | WO-2005026187 A1 | 3/2005 | |
| WO | WO-2005045015 A2 | 5/2005 | |
| WO | WO-2006049297 A1 | 5/2006 | |
| WO | WO-2007015557 A1 | 2/2007 | |
| WO | WO-2007066737 A1 | 6/2007 | |
| WO | WO-2007090071 A2 | 8/2007 | |
| WO | WO-2007134181 A2 | 11/2007 | |
| WO | WO-2008101157 A1 | 8/2008 | |
| WO | WO-2008150729 A2 | 12/2008 | |
| WO | WO-2008154401 A2 | 12/2008 | |
| WO | WO-2009006478 A2 | 1/2009 | |
| WO | WO-2009123216 A1 | 10/2009 | |
| WO | WO-2011043385 A1 | 4/2011 | |
| WO | WO-2011139699 A2 | 11/2011 | |
| WO | WO-2014160025 A2 | 10/2014 | |
| WO | WO-2015021432 A1 * | 2/2015 | ............. C07H 19/00 |
| WO | WO-2015086795 A1 | 6/2015 | |
| WO | WO-2015157555 A2 | 10/2015 | |
| WO | WO-2016073433 A1 | 5/2016 | |
| WO | WO-2016094867 A1 | 6/2016 | |
| WO | WO-2016115168 A1 | 7/2016 | |
| WO | WO-2017106767 A1 | 6/2017 | |
| WO | WO-2017223528 A1 | 12/2017 | |
| WO | WO-2019014262 A1 | 1/2019 | |
| WO | WO-2019014267 A1 | 1/2019 | |
| WO | WO-2019133883 A1 | 7/2019 | |
| WO | WO-2020252262 A1 | 12/2020 | |
| WO | WO-2021072167 A1 | 4/2021 | |

OTHER PUBLICATIONS

Akbergenov et al. ARC-1, a sequence element complementary to an internal 18S rRNA segment, enhances translation efficiency in plants when present in the leader or intercistronic region of mRNAs. Nucleic Acids Res 32(1):239-247 (2004).

Ambrogelly et al. Pyrrolysine is not hardwired for cotranslational insertion at UAG condons. PNAS 104(9):3141-3146 (2007).

Amiri et al. Deep origin of plastid/parasite ATP/ADP translocases. J. Mol. Evol. 56:137-150 (2003).

Arenas-Ramirez et al. Improved cancer immunotherapy by a CD25-mimobody conferring selectivity to human interleukin-2. Sci Transl Med 8:367ra166 (Nov. 30, 2016). 13 pages.

Arie et al. Phylogenetic identification of n-alkane assimilating Candida yeasts based on nucleotide divergence in the 59 end of LSU rDNA gene. J Gen Appl Microbiol. 46(5):257-262 (2000).

Asagarasu et al. Design and synthesis of piperazinylpyridine derivatives as novel 5-HT1A agonists/5-HT3 antagonists for the treatment of irritable bowel syndrome (IBS). Chem. Pharm. Bull. (Tokyo)57:34-42 (2009).

Ast et al. Diatom plastids depend on nucleotide import from the cytosol. PNAS USA 106:3621-3626 (2009).

Beigelman et al. Synthesis of 5'-C-Methyl-D-allo- & L-Talo-ribonucleoside 3'-O-Phosphoramidites & Their Incorporation into Hammerhead Ribozymes. Nucleosides and Nucleotides 14(3-5):901-905 (1995).

Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).

Berger et al. Stability and selectivity of unnatural DNA with five-membered-ring nucleobase analogues. J Am Chem Soc 124(7):1222-6 (2002).

Berger et al. Stable and selective hybridization of oligonucleotides with unnatural hydrophobic bases. Angew Chem Int Ed Engl 39:2940-2942 (2000).

Berger et al. Universal bases for hybridization, replication and chain termination. Nucleic Acids Res 28(15):2911-2914 (2000).

Betz et al. KlenTaq polymerase replicates unnatural base pairs by inducing a Watson-Crick geometry. Nat Chem Biol 8:612-614 (2012).

Betz et al. Structural insights into DNA replication without hydrogen bonds. J Am Chem Soc 135:18637-18643 (2013).

Bhatt et al. Peripheral Blood Lymphocyte Responses in Patients with Renal Cell Carcinoma treated with High-Dose Interleukin-2. Poster (SITC 2018).

Biocentury Innovations publication Oct. 27, 2016 (26 pgs).

Bohringer et al. Synthesis of 5'-deoxy-5'-methylphosphonate linked thymidine oligonucleotides. Tet Lett 34:2723-2726 (1993).

Bordo et al. Suggestions for "safe" residue substitutions in site-directed mutagenesis. J Mol Biol 217:721-729 (1991).

Boyman et al. Selective Stimulation of T Cell subsets with Antibody-Cytokine Immune Complexes. Science 311:1924-1927 (2006).

Boyman et al. Selectively Expanding Subsets of T Cells in Mice by Injection of Interleukin-2/Antibody Complexes: Implications for Transplantation Tolerance. Transplantation Proceedings 44:1032-1034 (2012).

Boyman et al. The role of interleukin-2 during homeostatis and activation of the immune system. Nature 12:180-190 (2012).

Braasch et al. Locked nucleic acid (LNA): fine-tuning the recognition of DNA and RNA. Chem Bio 8:1-7 (2001).

Branca. Rekindling cancer vaccines. Nat Biotechnol 34(10):1019-1025 (2016).

Cameron et al. Tunable protein degradation in bacteria. Nature Biotechnology 32:1276-1281 (2014).

Cann et al. A heterodimeric DNA polymerase: Evidence that members of Euryarchaeota possess a distinct DNA polymerase. PNAS USA 95:14250 (1998).

Cantrell. Vectors for the expression of recombinant proteins in *E. coli*. Methods Mol Biol. 235:257-75 (2003).

Cariello et al. Fidelity of Thermococcus litoralis DNA polymerase (VentTM) in PCR determined by denaturing gradient gel electrophoresis Nucl Acid Res 19:4193-4198 (1991).

Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).

Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016) (w/Supplemental Figures).

Chastgner et al. Lack of intermediate-affinity interleukin-2 receptor in mice leads to dependence on interkeukin-2 receptor α,β and γ chain expression for T cell growth. Eur J Immunol 26:201-206 (1996).

Chatterjee et al. A Versatile Platform for Single- and Multiple-Unnatural Amino Acid Mutagenesis in *Escherichia coli*. Biochemistry 52(10):1828-1837 (2013).

Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).

(56) References Cited

OTHER PUBLICATIONS

Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).
Chen et al. A novel human IL-2 mutein with minimal systemic toxicity exerts greater antitumor efficacy than wild-type IL-2. Cell Death& Disease 9:989 (2018).
Chen et al. Directed polymerase evolution. FEBS Lett. 588(2):219-229 (2014).
Chen et al. Phosphonate Analogues of Cytosine Arabinoside Monophosphate. Phosphorus, Sulfur and Silicon 177:1783-1786 (2002).
Chen et al. The expanding world of DNA and RNA. Curr Opin Chem Biol 34:80-87 (2016).
Chien et al. Deoxyribonucleic acid polymerase from the extreme thermophile Thermus aquaticus. J Bacteriol 127:1550-1557 (1976).
Collingwood et al. The Synthesis and Incorporation in Oligonucleotides of a Thymidine Dimer Containing an Internucleoside Phosphinate Linkage. Synlett 7:703-705 (1995).
Crooke et al. Pharmacokinetic properties of several novel oligonucleotide analogs in mice. J Pharmacol Exp Ther 277:923-937 (1996).
Database UniParc [Online] May 31, 2010 (May 31, 2010), Database accession No. UPI0001D42ADE (2 pgs).
Datsenko et al. One-step inactivation of chromosomal genes in *Escherichia coli* K-12 using PCR products. PNAS USA 97(12):6640-6645 (2000).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).
Deuschle et al. Promoters of *Escherichia coli*: a hierarchy of in vivo strength indicates alternate structures. EMBO J 5:2987-2994 (1986).
Dhami et al. Systematic exploration of a class of hydrophobic unnatural base pairs yields multiple new candidates for the expansion of the genetic alphabet. Nucleic Acids Res 42:10235-10244 (2014).
Diab et al. NKTR-214 (CD-122-biased agonist) plus nivolumab in patients with advanced solid tumors: Preliminary phase 1/2 results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al. Progress Toward a Semi-Synthetic Organism with an Unrestricted Expanded Genetic Alphabet. J Am Chem Soc. 140:16115-16123 (2018).
Doudna et al. Genome editing. The new frontier of genome engineering with CRISPR-Cas9. Science 346:1258096 (2014).
Dranoff. Cytokines in cancer pathogenesis and cancer therapy. Nature Reviews Cancer 4:11-22 (2004).
Dumas et al. Designing logical codon reassignment—Expanding the chemistry in biology. Chem Sci 6:50-69 (2015).
Dupradeau et al. Differential solvation and tautomer stability of a model base pair within the minor and major grooves of DNA. J Am Chem Soc 127(44):15612-7 (2005).
Egholm et al. PNA hybridizes to complementary oligonucleotides obeying the Watson-Crick hydrogen-bonding rules. Nature 365(6446):566-568 (1993).
Elayadi et al. Application of PNA and LNA oligomers to chemotherapy. Curr Opinion Invens Drugs 2:558-561 (2001).
Ellington et al. In vitro selection of RNA molecules that bind specific ligands. Nature 346:818-822 (1990).
Engler et al. A one pot, one step, precision cloning method with high throughput capability. PLoS One 3:e3647 (2008).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fa et al. Expanding the substrate repertoire of a DNA polymerase by directed evolution. J Am Chem Soc 126(6):1748-54 (2004).
Fairhurst et al. Synthesis and Hybridisation Properties of Phosphonamidate Ester Modified Nucleic Acid. Synlett 4:467-472 (2001).
Fan et al. Rationally evolving tRNAPyl for efficient incorporation of noncanonical amino acids. Nucleic Acids Res 43(22):e156 (2015).
Feldman et al. A Tool for the Import of Natural and Unnatural Nucleoside Triphosphates into Bacteria. J Am Chem Soc 140(4):1447-1454 (2018).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. In Vivo Structure-Activity Relationships and Optimization of an Unnatural Base Pair for Replication in a Semi-Synthetic Organism. J Am Chem Soc 139:11427-11433 (2017).
Feldman et al. Optimization of Replication, Transcription, and Translation in a Semi-Synthetic Organism. J Am Chem Soc 141:10644-10653 (2019).
Feldman. Expansion of the Genetic Alphabet: A Chemist's Approach to Synthetic Biology. Acc Chem Res 51(2):394-403 (2018).
Fersht. Enzyme Structure and Mechanism, 2nd ed., W. H. Freeman & Co., New York (pp. 350-351) (1985).
Floros et al. Anticancer Cytokines: Biology and Clinical Effects of Interferon-α2, Interleukin (IL)-2, IL-15, IL-21, and IL-12. Semin Oncol 42(4):539-548 (2015).
Fluman et al. mRNA-programmed translation pauses in the targeting of *E. coli* membrane proteins. eLife 2014; 3:e03440.
Fu et al. Improving CRISPR-Cas nuclease specificity using truncated guide RNAs. Nat Biotechnol 32:279-284 (2014).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of eIF4F. Nucleic Acids Res 30(15):3401-3411 (2002).
Gallier et al. Ex-Chiral-Pool Synthesis of B-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279(12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Gibson, et al. Enzymatic assembly of DNA molecules up to several hundred kilobases. Nat Methods. May 2009;6(5):343-5.
Gietz et al. Improved method for high efficiency transformation of intact yeast cells. Nucleic Acids Res 20:1425 (1992).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Goldberg et al. Re: Z. Ram et al. In situ retroviral-mediated gene transfer for the treatment of brain tumors in rats. Cancer Res. 53:83-88 (1993).
Goodman et al. Causes and effects of N-terminal codon bias in bacterial genes. Science 342:475-479 (2013).
Guo et al. Directed evolution of an enhanced and highly efficient Fokl cleavage domain for zinc finger nucleases. J Mot Biol 400:96-107 (2010).

(56) References Cited

OTHER PUBLICATIONS

Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbiol. 60:1534-1545 (2006).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).
Hancock et al. Expanding the Genetic Code of Yeast for Incorporation of Diverse Unnatural Amino Acids via a Pyrrolysyl-tRNA Synthetase/tRNA Pair. JACS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacteriol. 150:662-670 (1982).
Hayes et al. Combining computational and experimental screening for rapid optimization of protein properties. PNAS USA 99:15926-15931 (2002).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Henry et al. Efforts to expand the genetic alphabet: identification of a replicable unnatural DNA self-pair. J Am Chem Soc 126(22):6923-31 (2004).
Hinnisdaels et al. Direct cloning of PCR products amplified with Pwo DNA polymerase. Biotechniques 20:186-188 (1996).
Hirao et al., Unnatural base pair systems toward the expansion of the genetic alphabet in the central dogma.Proceedings of the Japan Academy, Series B, Phys Biol Sci. 88:345-367 (2012).
Horn et al. Bacterial endosymbionts of free-living amoebae. J. Eukaryot. Microbiol. 5:509-514 (2004).
Horvath et al. CRISPR/Cas, the Immune System of Bacteria and Archaea. Science 327:167-170 (2010).
Hsu et al. Development and applications of CRISPR-Cas9 for genome engineering. Cell 157(6):1262-78 (2014).
Hu et al. The Generation of Low Toxicity Interleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Hutter et al. From Phosphate to Bis(methylene) Sulfone: Non-Ionic Backbone Linkers in DNA. Helvetica Chimica Acta 85:2777-2806 (2002).
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and solvation. Nucleic Acids Res 37(14):4757-4763 (2009).
Hwang et al. Unnatural substrate repertoire of A, B, and X family DNA polymerases. J Am Chem Soc 130(44):14872-14882 (2008).
Insight-Esprit Study Group et al. Interleukin-2 Therapy in Patients with HIV Infection. N Engl J Med. 361(16):1548-59 (2009).
Jager et al. Oligonucleotide N-alkylphosphoramidates: synthesis and binding to polynucleotides. Biochemistry 27:7247-7246 (1988).
Jinek et al. A programmable dual-RNA-guided DNA endonuclease in adaptive bacterial immunity. Science 337:816-821 (2012).
Johansson et al. The solution structures of mutant calbindin D9k's, as determined by NMR, show that the calcium-binding site can adopt different folds. Biochemistry 35(25):8429-8438 (1996).
Jones et al. A Subset of Latency-Reversing Agents Expose HIV-Infected Resting CD4+ T- Cells to Recognition by Cytotoxic T-Lymphocytes. PLoS Pathogens 12(4):e1005545 (2016).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).
Juncosa-Ginesta et al. Improved efficiency in site-directed mutagenesis by PCR using a *Pyrococcus* sp. GB-D polymerase. Biotechniques 16:820-823 (1994).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Kaur et al. Thermodynamic, Counterion, and Hydration Effects for the Incorporation of Locked Nucleic Acid Nucleotides into DNA Duplexes. Biochemistry 45(23):7347-7344 (2006).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Khlebnikov et al. Effect of IacY expression on homogeneity of induction from the P(tac) and P(trc) promoters by natural and synthetic inducers. Biotechnol Prog 18:672-674 (2002).
Kim et al. Stability and polymerase recognition of pyridine nucleobase analogues: role of minor-groove H-bond acceptors. Angew Chem Int Ed Engl 45(46):7809-12 (2006).
Kimoto et al. Chemical Biology of Nucleic Acids: Fundamentals and Clinical Applications (eds A. Volker Erdmann, T. Wojciech Markiewicz, & Jan Barciszewski) pp. 131-148 (Springer Berlin Heidelberg, 2014).
Kivimae et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimäe et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination can-

(56) References Cited

OTHER PUBLICATIONS cer immunotherapy: Overcoming limitations of aldesleukin and conventional IL-2-based immunocytokines. Oncoimmunology 6(3):e1277306 (2017).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Krieg et al. Improved IL-2 immunotherapy by selective stimulation of IL-2 receptors on lymphocytes and endothelial cells. PNAS USA 107(26):11906-11911 (Jun. 29, 2010).
Kuhlman et al. Site-specific chromosomal integration of large synthetic constructs. Nucleic Acids Res 38:e92 (2010).
Kumar et al. The First Analogues of LNA (Locked Nucleic Acids): Phosphorothioate LNA and 2'-Thio-LNA. Bioorg Med Chem Lett 8:2219-2222 (1998).
Landy. Mechanistic and structural complexity in the site-specific recombination pathways of Int and FLP. Curr Opin Genet Dev. 3(5):699-707 (1993).
Langowski et al. The CD122-biased immunostimulatory cytokine NKTR-214 combined with checkpoint blockade leads to mobilization of anti-tumor immunity and synergistic activity. Poster Abstract 311. 2016 CR-CIMT-EATIR-AACR Cancer Immunotherapy Conference (2016).
Lavergne et al. Expanding the scope of replicable unnatural DNA: Stepwise optimization of a predominantly hydrophobic base pair. JACS 135:5408-5419 (2013).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-53 (2016).
Lavergne et al. Major groove substituents and polymerase recognition of a class of predominantly hydrophobic unnatural base pairs. Chem. Eur. J. 18:1231-1239 (2012).
Lazear et al. Targeting of IL-2 to cytotoxic lymphocytes as an improved method of cytokine-driven immunotherapy. Oncoimmunology 6(2):e1265721 (2017).
Lecomte et al. Selective Inactivation of the 3' to 5' exonuclease activity of *Escherichia coli* DNA polymerase I by heat. Nucl Acids Res 11:7505-7515 (1983).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127(36):12470-1 (2005).
Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Letourneau et al. IL-2/anti-IL-2 antibody complexes show strong biological activity by avoiding interaction with IL-2 receptor alpha subunit CD25. PNAS USA 107:2171-2176 (2010).
Letsinger et al. Cholesteryl-conjugated oligonucleotides: Synthesis, properties, and activity as inhibitors of replication of human immunodeficiency virus in cell culture. PNAS 86:6553-6556 (1989).
Levin. It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using an Expanded Genetic Alphabet. Chem Eur J 19:14205-14209 (2013).
Liu et al. Adding new chemistries to the genetic code. Annu Rev Biochem 79:413-444 (2010).
Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. SciBX 3(27):2 pgs (2010).
Lundberg et al. High-fidelity amplification using a thermostable DNA polymerase isolated from Pyrococcus furiosus. Gene 108:1-6 (1991).
Malyshev et al. A semi-synthetic organism with an expanded genetic alphabet. Nature 509(7500):385-388 (2014).
Malyshev et al. Efficient and sequence-independent replication of DNA containing a third base pair establishes a functional six-letter genetic alphabet. PNAS USA 109:12005-12010 (2012).
Malyshev et al. PCR with an Expanded Genetic Alphabet. JACS 131(41):14620-14621 (2009).
Malyshev et al. Solution structure, mechanism of replication, and optimization of an unnatural base pair. Chem Eur J 16:12650-12659 (2010).
Malyshev et al. The expanded genetic alphabet. Angew Chem Int Ed Engl 54:11930-11944 (2015).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).
Manoharan et al. Oligonucleotide Conjugates: Alteration of the Pharmacokinetic Properties of Antisense Agents. Nucleosides & Nucleotides 14:969-973 (1995).
Marraffini et al. CRISPR interference: RNA-directed adaptive immunity in bacteria and archaea. Nat Rev Genet. 11(3):181-90 (2010).

(56) References Cited

OTHER PUBLICATIONS

Marshall et al., A link between integral membrane protein expression and simulated integration efficiency. Cell Reports 16(8): 2169-2177 (2016).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
Matteucci. Oligonucleotide Analogs: an Overview in Oligonucleotides as Therapeutic Agents, (Chadwick and Cardew, ed.) John Wiley and Sons, New York, NY; Zon, 1993, Oligonucleoside Phosphorothioates in Protocols for Oligonucleotides and Analogs, Synthesis and Properties, Humana Press, pp. 165-190 (1997).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc. 122:10714-10715 (2000).
Meghnem et al. Cutting Edge: Differential Fine-Tuning of IL-2- and IL-15-Dependent Functions by Targeting Their Common IL-2/15Rβ/γc Receptor. J Immunol 198(12):4563-4568 (May 2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Merchant et al. Preclinical characterization of IL-2 Superkines engineered with biased CD8+ T cell stimulating properties. Poster (SITC 2018).
Micklefield. Backbone Modification of Nucleic Acids: Synthesis, Structure and Therapeutic Applications. Current Medicinal Chemistry 8:1157-1179 (2001).
Mignone et al. Untranslated regions of mRNAs. Genome Biol. 3(3):REVIEWS0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).
Milla et al. THOR-707: An engineered IL-2 for the treatment of solid tumors with superior pre-clinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Miroux et al. Over-production of proteins in *Escherichia coli*: mutant hosts that allow synthesis of some membrane proteins and globular proteins at high levels. J Mol Biol 260:289-298 (1996).
Mishra et al. Improved leishmanicidal effect of phosphorotioate antisense oligonucleotides by LDL-mediated delivery. Biochem Biophys Acta 1264:229-237 (1995).
Morris et al. Synthetic Biology Parts for the Storage of Increased Genetic Information in Cells. ACS Synth Biol 6(10):1834-1840 (2017).
Mulligan et al. Expression of a bacterial gene in mammalian cells. Science 209:1422-1427 (1980).
Mutalik, et al., Precise and reliable gene expression via standard transcription and translation initiation elements. Nature Methods 10:354-360 (2013).
Myers et al. Reverse transcription and DNA amplification by a Thermus thermophilus DNA polymerase. Biochemistry 30:7661-7666 (1991).
Nawrot et al. A novel class of DNA analogs bearing 5'-C-phosphonothymidine units: synthesis and physicochemical and biochemical properties. Oligonucleotides16(1):68-82 (2006).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nelson et al. N3'-->P5' Oligodeoxyribonucleotide Phosphoramidates: A New Method of Synthesis Based on a Phosphoramidite Amine-Exchange Reaction. J Org Chem 62:7278-7287 (1997).
New et al. The thieno[3,2-c]pyridine and furo[3,2-c]pyridine rings: new pharmacophores with potential antipsychotic activity. J. Med. Chem. 32:1147-1156 (1989).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JACS 131:8720-8721 (2009).
Nicolini et al. The FAP-IL2v Immunocytokine is a Versatile Combination Partner for Cancer Immunotherapy. Poster (SITC 2018).
Nielsen et al. Sequence-selective recognition of DNA by strand displacement with a thymine-substituted polyamide. Science 254:1497-1500 (1991).
Nordstrom et al. Characterization of bacteriophage T7 DNA polymerase purified to homogeneity by antithioredoxin immunoadsorbent chromatography. J Biol Chem 256:3112-3117 (1981).
Oberhauser et al. Effective incorporation of 2'-O-methyl-oligoribonucleotides into liposomes and enhanced cell association through modification with thiocholesterol. Nucl. Acids Res. 20:533-538 (1992).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Okamoto. ECHO probes: a concept of fluorescence control for practical nucleic acid sensing. Chem. Soc. Rev. 40:5815-5828 (2011).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al. Locked nucleic acids: a promising molecular family for gene-function analysis and antisense drug development. Curr Opinion Mol Ther 3:239-243 (2001).
Owczarzy et al. Stability and mismatch discrimination of locked nucleic acid-DNA duplexes. Biochem. 50(43):9352-9367 (2011).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N(7)-2-aminopurine deoxynucleosides. Nucleic Acids Res. 29(11):2260-2267 (2001).
Parisi et al. Enhanced expansion and tumor targeting of adoptively transferred T cells with NKTR-214. Poster Abstract #3566. (AACR Apr. 17, 2018).
Paulous et al. Comparison of the capacity of different viral internal ribosome entry segments to direct translation initiation in poly(A)-dependent reticulocyte lysates. Nucleic Acids Res. 31(2):722-733 (2003).
PCT/US2017/039133 International Search Report and Written Opinion dated Sep. 20, 2017.

(56) References Cited

OTHER PUBLICATIONS

PCT/US2018/041503 International Search Report and Written Opinion dated Nov. 7, 2018.
PCT/US2018/045257 International Search Report and Written Opinion dated Nov. 21, 2018.
Peyrottes et al. Oligodeoxynucleoside phosphoramidates (P-NH2): synthesis and thermal stability of duplexes with DNA and RNA targets. Nucleic Acids Res 24:1841-1848 (1996).
Pfannenstiel et al. A Novel, Individualized Xenograft Model of Cancer Immunotherapy and Tumor Growth Inhibition by ALKS 4230. Poster #P351 (SITC 2017).
Pieper et al. NKTR-214 in combination with radiation produces a potent in situ vaccine in the syngeneic B78 melanoma model. Poster (STIC 2018).
Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Quan et al. Circular polymerase extension cloning for high-throughput cloning of complex and combinatorial DNA libraries. Nat Protoc 6(2):242-251 (2011).
Rath et al. The CRISPR-Cas immune system: biology, mechanisms and applications. Biochimie 117:119-128 (2015).
Roessler et al. Cooperative interactions between the interleukin 2 receptor α and β chains later the interleukin 2-binding affinity of the receptor subunits. PNAS USA 91:3344-3347 (1994).
Romesberg et al. Development of a universal nucleobase and modified nucleobases for expanding the genetic code. Curr Prot Nucleic Acid Chem Chapter 1:Unit 1.5 (2002).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Sabri et al. Knock-in/Knock-out (KIKO) vectors for rapid integration of large DNA sequences, including whole metabolic pathways, onto the *Escherichia coli* chromosome at well-characterised loci. Microb Cell Fact 12:60 (2013).
Saha et al. 5'-Methyl-DNA-A New Oligonucleotide Analog: Synthesis and Biochemical Properties J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi. Chapter 15: Heterocyclic Base Modifications in Nucleic Acids and Their Applications in Antisense Oligonucleotides. Antisense Research and Applications, Crookeand Lebleu Eds., CRC Press (pp. 273-288) (1993).
Sauer. Site-specific recombination: developments and applications. Curr Opin Biotechnol 5(5):521-527 (1994).
Schlegel et al. De-convoluting the genetic adaptations of *E. coli* C41(DE3) in real time reveals how alleviating protein production stress improves yields. Cell Rep 10:1758-1766 (2015).
Schmied et al. Efficient Multisite Unnatural Amino Acid Incorporation in Mammalian Cells via Optimized Pyrrolysyl tRNA Synthetase/tRNA Expression and Engineered eRF1. JACS 136:15577-15583 (2014).
Schneider et al. NIH Image to ImageJ: 25 years of image analysis. Nat Methods 9:671-675 (2012).
Schultz et al. Oligo-2'-fluoro-2'-deoxynucleotide N3'-->P5' phosphoramidates: synthesis and properties. Nucleic Acids Res 24:2966-2973 (1996).
Seo et al. Major groove derivatization of an unnatural base pair. Chembiochem 10(14):2394-2400 (2009).
Seo et al. Optimization of an unnatural base pair toward natural-like replication. J Am Chem Soc 131:3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JACS 131(14):5046-5047 (2009).
Shaloiko et al. Effective non-viral leader for cap-independent translation in a eukaryotic cell-free system. Biotechnology and Bioengineering 88(6):730-739 (2004).
Sharma et al. NKTR-214 enhances anti-tumor T cell immune responses induced by checkpoint blockade or vaccination. Poster (SITC 2017).
Shea et al. Synthesis, hybridization properties and antiviral activity of lipid-oligodeoxynucleotide conjugates. Nucl. Acids Res 18:3777-3783 (1990).
Siegel et al. Interleukin-2 Toxicity. J Clin Oncol 9(4):694-704 (1991).
Sikorski et al. A system of shuttle vectors and yeast host strains designed for efficient manipulation of DNA in *Saccharomyces cerevisiae*. Genetics 122:19-27 (1989).
Sim et al. IL2 Variant Circumvents ICOS+ Regulatory T-cell Expansion and Promotes NK Cell Activation. Cancer Immunol Res. 4(11):983-995 (Nov. 2016).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Sivakumar et al. Comparison of Vascular Leak Syndrome in Mice treated with IL21 or IL2. Comparative Medicine 63(1):13-21 (2013).
Southern et al. Transformation of mammalian cells to antibiotic resistance with a bacterial gene under control of the SV40 early region promoter. J Mol Appl Genet 1:327-341 (1982).
Spangler et al. Antibodies to Interleukin-2 Elicit Selective T Cell Subset Potentiation through Distinct Conformational Mechanism. Immunity 42:815-825 (2015).
Srivastava et al. Five- and six-membered conformationally locked 2',4'-carbocyclic ribo-thymidines: synthesis, structure, and biochemical studies. J Am Chem Soc 129(26):8362-8379 (2007).
Stauber et al. Crystal Structure of the IL-2 signaling complex: Paradigm for a heterotrimeric cytokine receptor. PNAS 103(8):2788-2793 (2006).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Sugden et al. A vector that replicates as a plasmid and can be efficiently selected in B-lymphoblasts transformed by Epstein-Barr virus. Mol. Cell. Biol. 5:410-413 (1985).
Sun et al. First-In-Human dose Selection of ALKS 4230, an Investigational Immunotherapeutic Agent. Poster 4088 (AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
Svinarchuk et al. Inhibition of HIV proliferation in MT-4 cells by antisense oligonucleotide conjugated to lipophilic groups. Biochimie 75:49-54 (1993).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under the Securities Act of 1933 filed Nov. 27, 2018 (355 pgs.).
Tae et al. Efforts toward expansion of the genetic alphabet: replication of DNA with three base pairs. J. Am. Chem. Soc. 123:7439-7440 (2001).

(56) References Cited

OTHER PUBLICATIONS

Takagi et al. Characterization of DNA polymerase from *Pyrococcus* sp. strain KOD1 and its application to PCR. Appl Environ Microbiol 63(11):4504-4510 (1997).
Takeshita et al. High-copy-number and low-copy-number plasmid vectors for IacZ alpha-complementation and chloramphenicol- or kanamycin-resistance selection. Gene 61, 63-74 (1987).
Tapp et al. Homogeneous scoring of single-nucleotide polymorphisms: comparison of the 5'-nuclease TaqMan assay and Molecular Beacon probes. Biotechniques 28(4):732-738 (2000).
The Concise Encyclopedia of Polymer Science and Engineering, Kroschwitz, J.I., Ed., John Wiley & Sons pp. 858-859 (1990).
Tuerk. Systematic evolution of ligands by exponential enrichment: RNA ligands to bacteriophage T4 DNA polymerase. Science 249:505-510 (1990).
Tyagi et al. Molecular Beacons: Probes that Fluoresce Upon Hybridization. Nature Biotechnology 14(3):303-308 (Mar. 1996).
U.S. Appl. No. 15/543,217 Office Action dated Apr. 3, 2020.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,209, filed May 15, 2019.
U.S. Appl. No. 16/413,219, filed May 15, 2019.
U.S. Appl. No. 16/434,999, filed Jun. 7, 2019.
U.S. Appl. No. 16/518,715, filed Jul. 22, 2019.
U.S. Appl. No. 16/530,742, filed Aug. 2, 2019.
U.S. Appl. No. 16/535,992, filed Aug. 8, 2019.
U.S. Appl. No. 16/546,097, filed Aug. 20, 2019.
U.S. Appl. No. 16/546,097 Office Action dated Feb. 7, 2020.
U.S. Appl. No. 16/546,097 Office Action dated Nov. 21, 2019.
U.S. Appl. No. 16/546,100, filed Aug. 20, 2019.
U.S. Appl. No. 16/546,100 Office Action dated Feb. 7, 2020.
U.S. Appl. No. 16/546,100 Office Action dated Nov. 27, 2019.
U.S. Appl. No. 16/577,347, filed Sep. 9, 2020.
U.S. Appl. No. 16/591,422, filed Oct. 2, 2019.
U.S. Appl. No. 16/839,741, filed Apr. 3, 2020.
Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Van Gool et al. Interleukin-5-producing group 2 innate lymphoid cells control eosinophilia induced by interleukin-2 therapy. Blood 124(24):3572-3576 (2014).
Van Haelst Pinsani et al. Administration of Interleukin-2 (IL-2) Results in Increased Plasma Concentrations of IL-5 and Eosinophilia in Patients with Cancer. Blood 78:1538-1544 (1991).
Vanbrunt et al. Genetically Encoded Azide Containing Amino Acid in Mammalian Cells Enables Site-Specific Antibody-Drug Conjugates Using Click Cycloaddition Chemistry. Bioconjug Chem. 26(11):2249-60 (2015).
Vazquez-Lombardi et al. Potent antitumour activity of the interleukin-2-Fc fusion proteins requires Fc-mediated depletion of regulatory T-cells. Nat Comm 8:15373 (2017).
Verma. Retroviral vectors for gene transfer. In: Microbiology (Leive L et al., eds., Ann. Soc. Microbiol) American Society of Microbiology, Washington, DC, p. 229-232 (1985).
Verma. The reverse transcriptase. Biochim Biophys Acta. 473:1-38 (1977).
Vrudhula et al. Isozyme-specific enzyme inhibitors. 13. S-[5'(R)-[(N-triphosphoamino) methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Waldmann et al. The Shared and Contrasting Roles of IL2 and IL15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).
Wan et al. Pyrrolysyl- tRNAPyrrolysyl-tRNA synthetase: an ordinary enzyme but an outstanding genetic code expansion tool. Biocheim Biophys Aceta 1844(6):1059-1070 (2014).
Wandry et al. Probing unnatural amino acid integration into enhanced green fluorescent protein by genetic code expansion with a high-throughput screening platform. J Biol Eng. 10:11 (2016).
Wang et al. An engineered rare codon device for optimization of metabolic pathways. Scientific Reports 6:20608 (2016).
Wang et al. Biophysical and biochemical properties of oligodeoxy-nucleotides containing 4'-C- and 5'-C-substituted thymidines. Bioorg Med Chem Lett 9:885-890 (1999).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its α, ß, and γc Receptors. Science 310:1159-63 (2005).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids 23(1 & 2):317-337 (2004).
Webster et al. In vivo expansion of T reg cells with IL-2-mAb complexes: induction of resistance to EAE and long-term acceptance of islet allografts without immunosuppression. J Med Chem 206(4):751-760 (2009).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Functionalization of the sugar moiety of oligoribonucleotides on solid support. Bioconjugate Chem 10:921-924 (1999).
Wu et al. Reverse transcriptase. CRC Crit Rev Biochem 3:289-347 (1975).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).
Wu et al. Synthesis of Site-Specific Radiolabeled Antibodies for Radioimmunotherapy via Genetic Code Expansion. Bioconjugate Chem. 27:2460-2468 (2016).
Xia et al. Directed evolution of novel polymerase activities: mutation of a DNA polymerase into an efficient RNA polymerase. PNAS USA 99(10):6597-602 (2002).
Yamaguchi et al. Role of IL-5 in IL-2-induced eosinophilia. In vivo and in vitro expression of IL-5 mRNA by IL-2. J Immunol 145:873-877 (1990).
Yu et al. Polymerase recognition of unnatural base pairs. Angew Chem Int Ed Engl 41(20):3841-4 (2002).
Zalevsky. Jefferies 2016 Global Healthcare Conference. PowerPoint presentation (Nov. 16, 2016).
Zhang et al. A semisynthetic organism engineered for the stable expansion of the genetic alphabet. PNAS USA 114(6):1317-1322 (2017).
Zhang et al. A Semi-Synthetic Organism that Stores and Retrieves Increased Genetic Information. Nature 551(7682):644-647 (2017).
Zhang et al. Evolution of functional six-nucleotide DNA. J Am Chem Soc 137:6734-6737 (2015).
Zhang et al. Semisynthetic Organisms with Expanded Genetic Codes. Biochemistry 57:2177-2178 (20180.
Zhou et al. Fine tuning of electrostatics around the internucleotidic phosphate through incorporation of modified 2',4'-carbocyclic-

(56) References Cited

OTHER PUBLICATIONS

LNAs and -ENAs leads to significant modulation of antisense properties. J Org Chem 74:118-134 (2009).
Zon. Chapter 8: Oligonucleotide Phosphorothioates in Protocols for Oligonucleotides and Analogs, Synthesis and Properties. Humana Press (pp. 165-190) (1993).
Hou et al. DNA Interstrand Cross-Linking upon Irradiation of Aryl Halide C-Nucleotides. J Org Chem 79(5):1877-1884 (2014)(2014).
Moreau et al. CD38 Structure-Based Inhibitor Design Using the N1-Cyclic Inosine 5'-Diphosphate Ribose Template. PLoS One 8(6):e66247 (2013).

* cited by examiner dNaM~d5SICS dCNMO~dTPT3 dNaM~dTPT3 dPTMO~dTPT3 dCNMO d5FM dClMO dMMO2 dPTMO dMTMO dNaM

NaM CNMO MMO2 5FM 2OMe

5F2OMe ClMO BrMO PTMO MTMO

TPT3 SICS FSICS 5SICS TAT1

3

4

5

6

7

8

9

10

11

12

X = S, 13
X = O, 14

15

16

17

18

19

20

21

22

23

6, 7, 24, 15, 16

17, 25, 26, 27, 28

14, 29, 30, 31

32, 33, 34, 35

36, 23, 37, 38, 39

18, 40, 41, 42, 43

44, 45, 46, 47, 20

21, 22, 48, 49, 50

51

52 53 54 55 56 57 58-60 61

62 63 64 65 66 67 68 69 70 71

72 73 74 75 76 77 78-81 82-86 87

88 89 90 91 92 93 94 95 96 97

43 44 45 46 47 48 49 50

51 52 53 54 55 56 57 58 59

60 61 62 63 64 65 66 67 68 69

70 71 72 73 74 75 76 77 78 79

80 81 82 83 84 85 86 87 88 89

90 91 92 93 94 95 96 97 98

99 100 101 102 103 104 105 106 107

108 109 110 111 112 113 114 115 116 117 118

119 120 121 122 123 124 125 126 127 128

129 130 131 132 133 134 135 136 137 138

139 140 141 142 143 144 145 146 147

148 149 150 151 152 153 154 155 156 157 158

159 160 161 162 163 164 165 166 167

Organism

- E. Coli
- other prokaryotes
- Yeast
- eukaryotic (cell culture)
- eukaryotic (organism)

aatransferase / tRNA pair

- Mj Tyr
- Ec Leuc
- Ec Tyr
- Mm/Mb pyl
- other

Function

- Bioconjugation
- Reporter
- Natural occuring PTM (or precursor)
- Photo-reactive (crosslinking / caging)
- Novel activity (chelating, redox)

SEQUENCE LISTING

<160> NUMBER OF SEQ ID NOS: 20

<210> SEQ ID NO 1
<211> LENGTH: 5923
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1
gtaaatcact gcataattcg tgtcgctcaa ggcgcactcc cgttctggat aatgtttttt 60
gcgccgacat cataacggtt ctggcaaata ttctgaaatg agctgttgac aattaatcat 120
cggctcgtat aatgtgtgga attgtgagcg gataacaatt tcacacagga aacagtattc 180
atggataaaa aaccgctgga cgttctgatc tccgctacgg gtctgtggat gagccgcacg 240
ggtacgctgc ataaaattaa acaccacgaa gtgtcacgtt cgaaaatcta tatcgaaatg 300
gcgtgcggtg atcatctggt ggttaacaat agccgttctt gtcgcaccgc gcgtgccttt 360
cgccatcaca aataccgcaa aacgtgcaaa cgttgtcgcg tgtcagatga agacattaac 420
aatttcctga cccgtagtac ggaatccaaa aactcagtga aagttcgcgt cgtgagtgct 480
ccgaaagtta aaaaagcgat gccgaaaagt gtctcccgtg ccccgaaacc gctggaaaac 540
tcagtgtcgg caaaagcttc caccaatacg agccgctctg ttccgtcgcc ggcaaaaagc 600
accccgaaca gctctgtccc ggcaagcgca ccggcaccgt ctctgacgcg tagtcagctg 660
gatcgcgtgg aagccctgct gtccccggaa gacaaaatct cactgaatat ggcaaaaccg 720
tttcgtgaac tggaaccgga actggttacc cgtcgcaaaa acgatttcca acgtctgtat 780
acgaatgatc gcgaagacta cctgggtaaa ctggaacgtg atatcaccaa atttttcgtg 840
gaccgcggct ttctggaaat caaatctccg attctgatcc cggctgaata tgttgaacgc 900
atgggtatta acaatgatac cgaactgagt aaacagattt ttcgtgtgga taaaaacctg 960
tgcctgcggc cgatgctggc accgacgctg tataattacc tgcgtaaact ggatcgcatt 1020
ctgccgggtc cgattaaaat ctttgaagtg ggcccgtgtt atcgtaaaga atcggatggc 1080
aaagaacacc tggaagaatt taccatggtt aacttctgcc aaatgggcag cggttgtacg 1140
cgcgaaaatc tggaagcgct gatcaaagaa ttcctggatt acctggaaat cgacttcgaa 1200
atcgtcggtg attcttgcat ggtgtatggc gataccctgg acatcatgca tggtgacctg 1260
gaactgagtt ccgctgttgt cggtccggtc agcctggatc gtgaatgggg cattgacaaa 1320
ccgtggatcg gcgcgggttt tggcctggaa cgcctgctga aagttatgca cggcttcaaa 1380
aacatcaaac gtgcgtctcg ctcggaatcg tattacaacg gcatctcaac caatctgtaa 1440
taatgactga cgatctgcct cgcgcgtttc ggtgatgacg gtgaaaacct ctgacacatg 1500
cagctcccgg agacggtcac agcttgtctg taagcggatg ccgggagcag acaagcccgt 1560
cagggcgcgt cagcgggtgt tggcgggtgt cggggcgcag ccatgaccca gtcacgtagc 1620
gatagcggag tgtataattc ttgaagacga aagggcctcg tgatacgcct atttttatag 1680
gttaatgtca tgataataat ggtttcttag acgtcaggtg gcacttttcg gggaaatgtg 1740
cgcggaaccc ctatttgttt atttttctaa atacattcaa atatgtatcc gctcatgaga 1800
caataaccct gataaatgct tcaataatat tgaaaaagga agagtatgag tattcaacat 1860
ttccgtgtcg cccttattcc cttttttgcg gcattttgcc ttcctgtttt tgctcaccca 1920
gaaacgctgg tgaaagtaaa agatgctgaa gatcagttgg gtgcacgagt gggttacatc 1980

-continued

```
gaactggatc tcaacagcgg taagatcctt gagagttttc gccccgaaga acgttttcca   2040
atgatgagca cttttaaagt tctgctatgt ggcgcggtat tatcccgtgt tgacgccggg   2100
caagagcaac tcggtcgccg catacactat tctcagaatg acttggttga gtactcacca   2160
gtcacagaaa agcatcttac ggatggcatg acagtaagag aattatgcag tgctgccata   2220
accatgagtg ataacactgc ggccaactta cttctgacaa cgatcggagg accgaaggag   2280
ctaaccgctt ttttgcacaa catgggggat catgtaactc gccttgatcg ttgggaaccg   2340
gagctgaatg aagccatacc aaacgacgag cgtgacacca cgatgcctgc agcaatggca   2400
acaacgttgc gcaaactatt aactggcgaa ctacttactc tagcttcccg gcaacaatta   2460
atagactgga tggaggcgga taaagttgca ggaccacttc tgcgctcggc ccttccggct   2520
ggctggttta ttgctgataa atctggagcc ggtgagcgtg ggtctcgcgg tatcattgca   2580
gcactggggc cagatggtaa gccctcccgt atcgtagtta tctacacgac ggggagtcag   2640
gcaactatgg atgaacgaaa tagacagatc gctgagatag gtgcctcact gattaagcat   2700
tggtaactgt cagaccaagt ttactcatat atactttaga ttgatttaaa acttcatttt   2760
taatttaaaa ggatctaggt gaagatcctt tttgataatc tcatgaccaa aatcccttaa   2820
cgtgagtttt cgttccactg agcgtcagac cccgtagaaa agatcaaagg atcttcttga   2880
gatccttttt ttctgcgcgt aatctgctgc ttgcaaacaa aaaaaccacc gctaccagcg   2940
gtggtttgtt tgccggatca agagctacca actctttttc cgaaggtaac tggcttcagc   3000
agagcgcaga taccaaatac tgtccttcta gtgtagccgt agttaggcca ccacttcaag   3060
aactctgtag caccgcctac atacctcgct ctgctaatcc tgttaccagt ggctgctgcc   3120
agtggcgata agtcgtgtct taccgggttg gactcaagac gatagttacc ggataaggcg   3180
cagcggtcgg gctgaacggg gggttcgtgc acacagccca gcttggagcg aacgacctac   3240
accgaactga gatacctaca gcgtgagcta tgagaaagcg ccacgcttcc cgaagggaga   3300
aaggcggaca ggtatccggt aagcggcagg gtcggaacag gagagcgcac gagggagctt   3360
ccagggggaa acgcctggta tctttatagt cctgtcgggt ttcgccacct ctgacttgag   3420
cgtcgatttt tgtgatgctc gtcagggggg cggagcctat ggaaaaacgc cagcaacgcg   3480
gcctttttac ggttcctggc cttttgctgg ccttttgctc acatgttctt tcctgcgtta   3540
tccccgagct cttagcgcga attgtcgagg gaaatttttt ctaaatacat tcaaatatgt   3600
atccgctcat gagacaataa ccctgataaa tgcttcaata atattaaata tggctggttc   3660
tcgcagaaag aaacatatcc atgaaatccc gccccgaatt gatatgtcca gattagataa   3720
aagtaaagtg attaacagcg cattagagct gcttaatgag gtcggaatcg aaggtttaac   3780
aacccgtaaa ctcgcccaga agctaggtgt agagcagcct acattgtatt ggcatgtaaa   3840
aaataagcgg gctttgctcg acgccttagc cattgagatg ttagataggc accatactca   3900
cttttgccct ttagaagggg aaagctggca agatttttta cgtaataacg ctaaaagttt   3960
tagatgtgct ttactaagtc atcgcgatgg agcaaaagta catttaggta cacggcctac   4020
agaaaaacag tatgaaactc tcgaaaatca attagccttt ttatgccaac aaggtttttc   4080
actagagaat gcattatatg cactcagcgc tgtggggcat tttactttag gttgcgtatt   4140
ggaagatcaa gagcatcaag tcgctaaaga agaaagggaa acacctacta ctgatagtat   4200
gccgccatta ttacgacaag ctatcgaatt atttgatcac caaggtgcag agccagcctt   4260
cttattcggc cttgaattga tcatttgcgg attagaaaaa caacttaaat gtgaaagtgg   4320
gtcttaagca ctaggtctag ggcggcggat ttgtcctact caggagagcg ttcaccgaca   4380
```

aacaacagat aaaacgaaag gcccagtctt tcgactgagc ctttcgtttt atttgatgcc 4440
tctagcacgc gtagagctag agccttcaac ccagtcagct ccttccggtg ggcgcggggc 4500
atgactaaca tgagaattac aacttatatc gtatggggct gacttcaggt gctacatttg 4560
aagagataaa ttgcactgaa atctagatga ttctgtggat aaccgtatta ccgcctttga 4620
gtgagctgat accgctcgcc gcagccgaac gaccgagcgc agcgagtcag tgagcgagga 4680
agcggaagag cgcctgatgc ggtattttct ccttacgcat ctgtgcggta tttcacaccg 4740
cataaattcc gacaccatcg aatggtgcaa aacctttcgc ggtatggcat gatagcgccc 4800
ggaagagagt caattcaggg tggtgaatgt gaaaccagta acgttatacg atgtcgcaga 4860
gtatgccggt gtctcttatc agaccgtttc ccgcgtggtg aaccaggcca gccacgtttc 4920
tgcgaaaacg cgggaaaaag tggaagcggc gatggcggag ctgaattaca ttcccaaccg 4980
cgtggcacaa caactggcgg gcaaacagtc gttgctgatt ggcgttgcca cctccagtct 5040
ggccctgcac gcgccgtcgc aaattgtcgc ggcgattaaa tctcgcgccg atcaactggg 5100
tgccagcgtg gtggtgtcga tggtagaacg aagcggcgtc gaagcctgta aagcggcggt 5160
gcacaatctt ctcgcgcaac gcgtcagtgg gctgatcatt aactatccgc tggatgacca 5220
ggatgccatt gctgtggaag ctgcctgcac taatgttccg gcgttatttc ttgatgtctc 5280
tgaccagaca cccatcaaca gtattatttt ctcccatgaa gacggtacgc gactgggcgt 5340
ggagcatctg gtcgcattgg gtcaccagca aatcgcgctg ttagcgggcc cattaagttc 5400
tgtctcggcg cgtctgcgtc tggctggctg gcataaatat ctcactcgca atcaaattca 5460
gccgatagcg gaacgggaag gcgactggag tgccatgtcc ggttttcaac aaaccatgca 5520
aatgctgaat gagggcatcg ttcccactgc gatgctggtt gccaacgatc agatggcgct 5580
gggcgcaatg cgcgccatta ccgagtccgg gctgcgcgtt ggtgcggata tctcggtagt 5640
gggatacgac gataccgaag acagctcatg ttatatcccg ccgttaacca ccatcaaaca 5700
ggattttcgc ctgctggggc aaaccagcgt ggaccgcttg ctgcaactct ctcagggcca 5760
ggcggtgaag ggcaatcagc tgttgcccgt ctcactggtg aaaagaaaaa ccaccctggc 5820
gcccaatacg caaaccgcct ctccccgcgc gttggccgat tcattaatgc agctggcacg 5880
acaggtttcc cgactggaaa gcgggcagtg agcgcaacgc aat 5923

<210> SEQ ID NO 2
<211> LENGTH: 3101
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2
taactagcat aaccccttgg ggcctctaaa cgggtcttga ggggtttttt gctgaaagga 60
ggaactatat ccggattggt taatacgact cactataggg gaattgtgag cggataacaa 120
ttcccctcta gaaaagcatt ggaaaccgag accggtaccg gtctcttaga ttcccggggt 180
ttccgccaaa ttcgaaaagc ctgctcaacg agcaggcttt tttgcatcta gcataacccc 240
ttggggcctc taaacgggtc ttgaggggtt ttttgcctga acgagcaggc ttttttgcat 300
aagcttccta gtggcagcgg ctaactaagc ggcctgctga ctttctcgcc gatcaaaagg 360
cattttgcta ttaagggatt gacgagggcg tatctgcgca gtaagatgcg ccccgcattg 420
gagacgccat ggcgtctcgg ttttagagct agaaatagca agttaaaata aggctagtcc 480

```
gttatcaact tgaaaaagtg gcaccgagtc ggtgcttttt ttaattcgaa aagcctgctc    540
aacgagcagg ctttttttggt cgacagtagt ggcagcggct aactaagcgg cctgctgact    600
ttctcgccga tcaaaaggca ttttgctatt aagggattga cgagggcgta tctgcgcagt    660
aagatgcgcc ccgcatgaga cggcatgccg tctctagagc tagaaatagc aagttaaaat    720
aaggctagtc cgttatcaac ttgaaaaagt ggcaccgagt cggtgctttt tttaattcga    780
aaagcctgct caacgagcag gctttttttgg tcgacagttc ataggtgatt gcggatcccg    840
tcgttgacaa ttaatcatcg gcatagtata tcggcatagt ataatacgac aaggtgagga    900
actaaaccat ggccaagttg accagtgccg ttccggtgct caccgcgcgc gacgtcgccg    960
gagcggtcga gttctggacc gaccggctcg ggttctcccg cgacttcgtg gaggacgact   1020
tcgccggtgt ggtccgggac gacgtgaccc tgttcatcag cgcggtccag gaccaggtgg   1080
tgccggacaa caccctggcc tgggtgtggg tgcgcggcct ggacgagctg tacgccgagt   1140
ggtcggaggt cgtgtccacg aacttccggg acgcctccgg gccggccatg accgagatcg   1200
gcgagcagcc gtgggggcgg gagttcgccc tgcgcgaccc ggccggcaac tgcgtgcact   1260
tcgtggccga ggagcaggac tgagagctcg cttggactcc tgttgataga tccagtaatg   1320
acctcagaac tccatctgga tttgttcaga acgctcggtt gccgccgggc gtttttttatt   1380
ggtgagaatc caagcactag ctagtaacaa cttatatcgt atggggctga cttcaggtgc   1440
tacatttgaa gagataaatt gcactgaaat ctagtaatat tttatctgat taataagatg   1500
atcttcttga gatcgttttg gtctgcgcgt aatctcttgc tctgaaaacg aaaaaaccgc   1560
cttgcagggc ggtttttcga aggttctctg agctaccaac tctttgaacc gaggtaactg   1620
gcttggagga gcgcagtcac caaaacttgt cctttcagtt tagccttaac cggcgcatga   1680
cttcaagact aactcctcta aatcaattac cagtggctgc tgccagtggt gcttttgcat   1740
gtctttccgg gttggactca agacgatagt taccggataa ggcgcagcgg tcggactgaa   1800
cggggggttc gtgcatacag tccagcttgg agcgaactgc ctacccggaa ctgagtgtca   1860
ggcgtggaat gagacaaacg cggccataac agcggaatga caccggtaaa ccgaaaggca   1920
ggaacaggag agcgcacgag ggagccgcca gggggaaacg cctggtatct ttatagtcct   1980
gtcgggtttc gccaccactg atttgagcgt cagatttcgt gatgcttgtc aggggggcgg   2040
agcctatgga aaaacggctt tgccgcggcc ctctcacttc cctgttaagt atcttcctgg   2100
catcttccag gaaatctccg ccccgttcgt aagccatttc cgctcgccgc agtcgaacga   2160
ccgagcgtag cgagtcagtg agcgaggaag cggaatatat cccttaatac gactcactat   2220
agggtcccta tcagtgatag agaggtctag aaataatttt gtttaacttt aagaaggaga   2280
tatacatatg tcgaaaggcg aagaactgtt tacgggagtg gtgcctatcc tggtagagct   2340
cgacggagat gtaaacggtc acaaattttc agtccgcggg gaaggcgaag gcgatgcgac   2400
caacggtaaa ttaactttga agtttatttg caccaccggc aaattaccgg tgccttggcc   2460
gacgcttgtg acgaccctga cttacggggt gcagtgtttc agtcgctacc cagatcacat   2520
gaaacgccat gacttcttca aatctgcgat gccggaaggc tatgtgcagg aacgtacaat   2580
tagctttaaa gacgacggca cgtataaaac gcgggcagag gttaaatttg agggagatac   2640
cctggtaaac cgtattgaac tgaaaggcat cgattttaaa gaagatggga acatcttggg   2700
ccacaagaga ccggtaccgg tctcggaatc aaagcaaatt tcaagatccg tcataacgtg   2760
gaggacggtt ccgtgcagct tgcagatcac tatcagcaga atacgccgat tggcgatggc   2820
```

ccggtgctgc tgcccgataa tcactacctc tctactcaga gtgttttatc gaaagacccg 2880
aacgagaagc gtgatcacat ggtgctgctt gaatttgtta ccgcggcagg tattacacac 2940
ggcatggatg agttgtataa gggatccgct tggagccacc cgcagttcga gaaaggtgga 3000
ggttccggag gtggatcggg aggttcggcg tggagccacc cgcagttcga aaaataaaag 3060
cttaattagc tgagcttgga ctccctgcca ccgctgagca a 3101

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
ctcgagtaca actttaactc acacaatgta tagatcacgg cagacaaaca aaagaatgga 60
atc 63

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
ctcgagtaca actttaactc acacaatgta tacatcacgg cagacaaaca aaagaatgga 60
atc 63

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (32)..(32)
<223> OTHER INFORMATION: An unnatural nucleotide

<400> SEQUENCE: 5
ctcgagtaca actttaactc acacaatgta ancatcacgg cagacaaaca aaagaatgga 60
atc 63

<210> SEQ ID NO 6
<211> LENGTH: 52
<212> TYPE: DNA
<213> ORGANISM: Methanosarcina mazei

<400> SEQUENCE: 6
gaatctaacc cggctgaacg gatttagagt ccgttcgatc tacatgatca gg 52

<210> SEQ ID NO 7
<211> LENGTH: 52
<212> TYPE: DNA
<213> ORGANISM: Methanosarcina mazei

<400> SEQUENCE: 7
gaatctaacc cggctgaacg gatttacagt ccgttcgatc tacatgatca gg 52

```
<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: An unnatural nucleotide

<400> SEQUENCE: 8

gaatctaacc cggctgaacg gattancagt ccgttcgatc tacatgatca gg             52


<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: An unnatural nucleotide

<400> SEQUENCE: 9

ctcgagtaca actttaactc acacancgta tacatcacgg cagacaaaca aaagaatgga     60

atc                                                                   63


<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(38)
<223> OTHER INFORMATION: An unnatural nucleotide

<400> SEQUENCE: 10

ctcgagtaca actttaactc acacaatgta tacatcancg cagacaaaca aaagaatgga     60

atc                                                                   63


<210> SEQ ID NO 11
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: An unnatural nucleotide
<220> FEATURE:
<221> NAME/KEY: modified_base
<222> LOCATION: (32)..(32)
<223> OTHER INFORMATION: An unnatural nucleotide

<400> SEQUENCE: 11

ctcgagtaca actttaactc acacancgta ancatcacgg cagacaaaca aaagaatgga     60

atc                                                                   63
```

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (32)..(32)
<223> OTHER INFORMATION: An unnatural nucleotide
<220> FEATURE:
<221> NAME/KEY: modified_base
<222> LOCATION: (38)..(38)
<223> OTHER INFORMATION: An unnatural nucleotide

<400> SEQUENCE: 12
ctcgagtaca actttaactc acacaatgta ancatcancg cagacaaaca aaagaatgga 60
atc 63

<210> SEQ ID NO 13
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (26)..(26)
<223> OTHER INFORMATION: An unnatural nucleotide
<220> FEATURE:
<221> NAME/KEY: modified_base
<222> LOCATION: (38)..(38)
<223> OTHER INFORMATION: An unnatural nucleotide

<400> SEQUENCE: 13
ctcgagtaca actttaactc acacancgta tacatcancg cagacaaaca aaagaatgga 60
atc 63

<210> SEQ ID NO 14
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (26)..(26)
<223> OTHER INFORMATION: An unnatural nucleotide
<220> FEATURE:
<221> NAME/KEY: modified_base
<222> LOCATION: (32)..(32)
<223> OTHER INFORMATION: An unnatural nucleotide
<220> FEATURE:
<221> NAME/KEY: modified_base
<222> LOCATION: (38)..(38)
<223> OTHER INFORMATION: An unnatural nucleotide

<400> SEQUENCE: 14
ctcgagtaca actttaactc acacancgta ancatcancg cagacaaaca aaagaatgga 60
atc 63

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 15

atgggtctca cacaaactcg agtacaactt taactcacac                          40


<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

atgggtctcg attccattct tttgtttgtc tgc                                 33


<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

atgggtctcg aaacctgatc atgtagatcg aacgg                               35


<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

atgggtctca tctaacccgg ctgaacgg                                       28


<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

ctcgagtaca actttaactc acac                                           24


<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

gattccattc ttttgtttgt ctgc                                           24
```

REAGENTS AND METHODS FOR REPLICATION, TRANSCRIPTION, AND TRANSLATION IN SEMI-SYNTHETIC ORGANISMS

CROSS-REFERENCE TO RELATED APPLICATIONS

This application claims priority to U.S. Provisional Application No. 62/861,901, filed on Jun. 14, 2019, the disclosure of which is hereby incorporated by reference in its entirety.

STATEMENT OF GOVERNMENT LICENSE RIGHTS

This invention was made with government support under grant numbers GM118178 and GM128376 awarded by The National Institutes of Health, and grant number DGE1346837 awarded by The National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jun. 10, 2020, is named 36271808201_SL.txt and is 18,171 bytes in size.

BACKGROUND OF THE INVENTION

Biological diversity allows life to adapt to different environments, and over time, evolve new forms and functions. The source of this diversity is the variation within protein sequences provided by the twenty natural amino acids, variation that is encoded in an organism's genome by the four natural DNA nucleotides. While the functional diversity provided by the natural amino acids may be high, the vastness of sequence space dramatically limits what might actually be explored, and moreover, some functionality is simply not available. Nature's use of cofactors for hydride transfer, redox activity, and electrophilic bond formation, etc. attests to these limitations. Furthermore, with the increasing focus on developing proteins as therapeutics, these limitations are problematic, as the physiochemical diversity of the natural amino acids is dramatically restricted compared to that of the small molecule drugs designed by chemists. In principle, it should be possible to circumvent these limitations by expanding the genetic code to include additional, non-canonical amino acids (ncAAs, or "unnatural" amino acids) with desired physiochemical properties.

Almost 20 years ago, a method was created to increase the diversity available to living organisms by expanding the genetic code using the amber stop codon (UAG) to encode ncAAs in *Escherichia coli*. This was achieved using a tRNA-amino acid tRNA synthetase (aaRS) pair from *Methanococcus jannaschii*, in which the tRNA was recoded to suppress the stop codon and the aaRS was evolved to charge the tRNA with an ncAA. This method of codon suppression has since been expanded to the other stop codons and even quadruplet codons, as well as to the use of several other orthogonal tRNA-aaRS pairs (most notably the Pyl tRNA-synthetase pair from *Methanosarcina barkeri/mazei*), broadening the scope of ncAAs that may be incorporated into proteins. These methods have already begun to revolutionize both chemical biology and protein therapeutics.

Though these methods enable incorporation of up to two different ncAAs in both prokaryotic and eukaryotic cells, the heterologous recoded tRNAs must compete with endogenous release factors (RFs), or in the case of quadruplet codons, normal decoding, which limits the efficiency and fidelity of ncAA incorporation. To eliminate competition with RF1, which recognizes the amber stop codon and terminates translation, efforts have been directed toward removal of many or all instances of the amber stop codon in the host genome or modification of RF2 to allow for the deletion of RF1. However, eukaryotes have only one release factor, and while it may be modified, it cannot be deleted, and with prokaryotes, deletion of RF1 results in greater mis-suppression of the amber stop codon by other tRNAs, which reduces the fidelity of ncAA incorporation. Efforts to further exploit codon redundancy to liberate natural codons for reassignment to ncAAs may be complicated by pleiotropic effects, as codons are not truly redundant, for example due to their effects on the rate of translation and protein folding. In addition, codon reappropriation is limited by the challenges of large-scale genome engineering, especially for eukaryotes.

An alternative approach to natural codon reassignment is the creation of entirely new codons that are free of any natural function or constraint, and whose recognition at the ribosome is inherently more orthogonal. This may be accomplished through the creation of organisms that harbor a fifth and sixth nucleotide that form an unnatural base pair (UBP). Such semi-synthetic organisms (SSOs) would need to faithfully replicate DNA containing the UBP, efficiently transcribe it into mRNAs and tRNAs containing the unnatural nucleotides, and then efficiently decode unnatural codons with cognate unnatural anticodons. Such SSOs would have a virtually unlimited number of new codons to encode ncAAs.

SUMMARY OF THE INVENTION

Described herein, in certain embodiments, are methods, cells, engineered microorganisms, plasmids, and kits for increased production of a nucleic acid molecule that comprises an unnatural nucleotide.

The following embodiments are encompassed.

Embodiment A1 is a nucleobase of the structure:

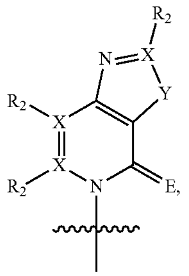

wherein:

each X is independently carbon or nitrogen;

$R_2$ is present when X is carbon and is independently hydrogen, alkyl, alkenyl, alkynyl, methoxy, methanethiol, methaneseleno, halogen, cyano, or azide group;

Y is sulfur, oxygen, selenium, or secondary amine; and

E is oxygen, sulfur, or selenium;

wherein the wavy line indicates a point of bonding to a ribosyl, deoxyribosyl, or dideoxyribosyl moiety or an analog thereof, wherein the ribosyl, deoxyribosyl, or dideoxyribosyl moiety or analog thereof is in free form, is connected to a mono-phosphate, diphosphate, triphosphate, α-thiotriphosphate, β-thiotriphosphate, or γ-thiotriphosphate group, or is included in an RNA or a DNA or in an RNA analog or a DNA analog.

Embodiment A2 is the nucleobase of embodiment A1, wherein X is carbon.

Embodiment A3 is the nucleobase of embodiment A1 or A2, wherein E is sulfur.

Embodiment A4 is the nucleobase of any one of embodiments A1 to A3, wherein Y is sulfur.

Embodiment A5 is the nucleobase of embodiment A1, which has the structure

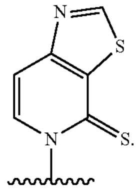 [SMILES: *n1ccc2ncsc2c1=S]

Embodiment A6 is the nucleobase of any one of embodiments A1 to A5, which is bound to a complementary base-pairing nucleobase to form an unnatural base pair (UBP).

Embodiment A7 is the nucleobase of embodiment A6, wherein the complementary base-pairing nucleobase is selected from:

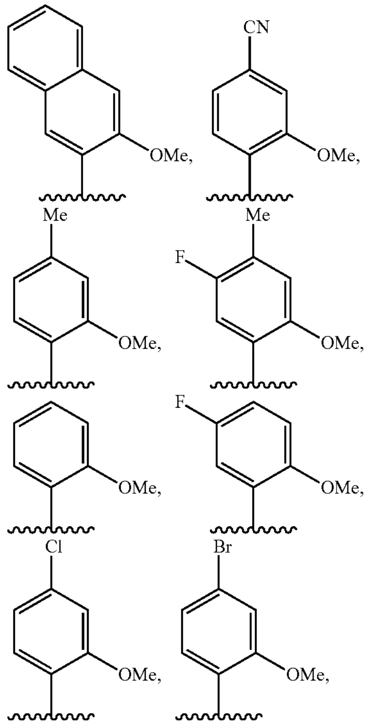

-continued

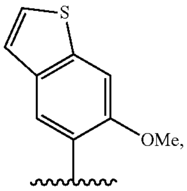

and

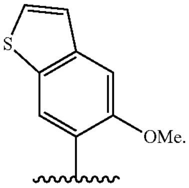

Embodiment A8 is a double stranded oligonucleotide duplex wherein a first oligonucleotide strand comprises the nucleobase of any one of embodiments A1 to A5, and a second complementary oligonucleotide strand comprises a complementary base-pairing nucleobase in a complementary base-pairing site thereof.

Embodiment A9 is the double stranded oligonucleotide duplex of embodiment A8, wherein the first oligonucleotide strand comprises

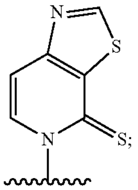

and the second strand comprises a complementary base pairing nucleobase selected from:

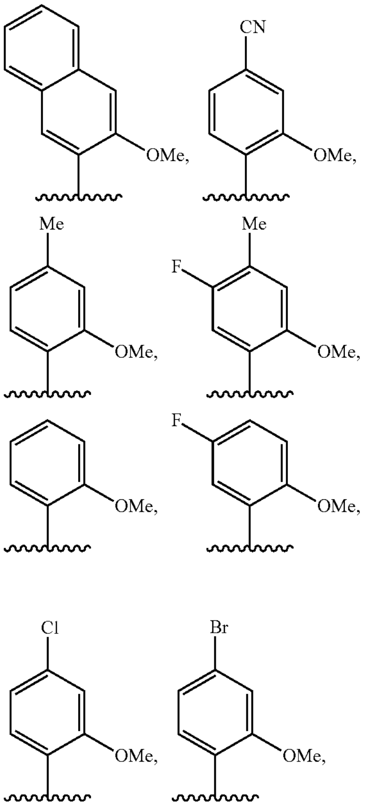

-continued

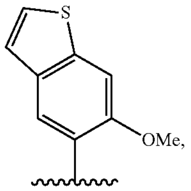

and

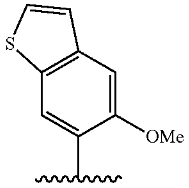

in a complementary base-pairing site thereof.

Embodiment A10 is the double stranded oligonucleotide duplex of Embodiment A9, wherein the second strand comprises the complementary base pairing nucleobase

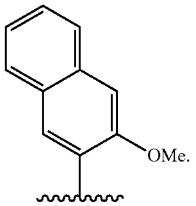 [SMILES: *c1cc2ccccc2cc1OC]

Embodiment A11 is the double stranded oligonucleotide duplex of embodiment A9, wherein the second strand comprises the complementary base pairing nucleobase

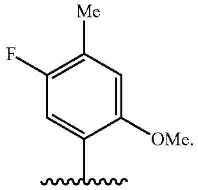 [SMILES: *c1cc(F)c(C)cc1OC]

Embodiment A12 is a plasmid comprising a gene encoding a transfer RNA (tRNA) and/or a gene encoding a protein of interest, wherein the gene comprises at least one nucleobase of any one of embodiments A1 to A5 or TPT3

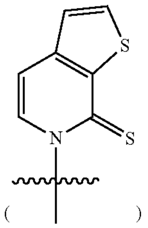

and at least one complementary base-pairing nucleobase of embodiment A7 or NaM

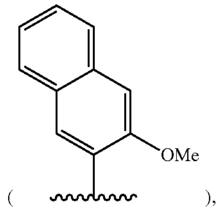 [SMILES: *c1cc2ccccc2cc1OC]

wherein the complementary base-pairing nucleobase is in a complementary base-pairing site.

Embodiment A13 is an mRNA encoded by the plasmid of embodiment A10 encoding the tRNA.

Embodiment A14 is an mRNA encoded by the plasmid of embodiment A10 encoding the protein.

Embodiment A15 is a transfer RNA (tRNA) comprising the nucleobase of any one of embodiments A1 to A5, comprising:

an anticodon, wherein the anticodon comprises the nucleobase, optionally wherein the nucleobase is at the first, second, or third position of the anticodon; and a recognition element, wherein the recognition element promotes selective charging of the tRNA with an unnatural amino acid by an aminoacyl tRNA synthetase.

Embodiment A16 is the tRNA of embodiment A15, wherein the aminoacyl tRNA synthetase is derived from *Methanosarcina*, or a variant thereof, or *Methanococcus* (*Methanocaldococcus*) or a variant thereof.

Embodiment A17 is the tRNA of embodiment A15, wherein the unnatural amino acid comprises an aromatic moiety.

Embodiment A18 is the tRNA of embodiment A15, wherein the unnatural amino acid is a lysine or phenylalanine derivative.

Embodiment A19 is a structure comprising the formula:

N1-Zx-N2 wherein:

each Z is independently a nucleobase of any one of embodiment A1 to A7, which is bonded to a ribosyl or deoxyribosyl or analog thereof;

N1 is one or more nucleotides or analogs thereof, or a terminal phosphate group attached at the 5' end of the ribosyl or deoxyribosyl or analog thereof of Z;

N2 is one or more nucleotides or analogs thereof, or a terminal hydroxyl group attached to the 3' end of the ribosyl or deoxyribosyl or analog thereof of Z; and x is an integer from 1 to 20.

Embodiment A20 is the structure of embodiment A19, wherein the structure encodes a gene, optionally wherein Zx is located in a translated region of the gene or wherein Zx is located in an untranslated region of the gene.

Embodiment A21 is a polynucleotide library, wherein the library comprises at least 5000 unique polynucleotides, and wherein each polynucleotide comprises at least one nucleobase of any one of embodiment A1 to A5.

Embodiment A22 is a nucleoside triphosphate comprising a nucleobase, wherein the nucleobase is selected from:

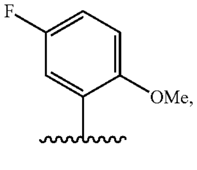

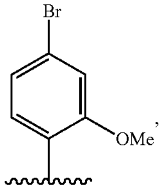

-continued

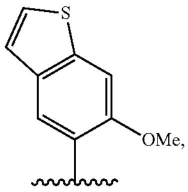

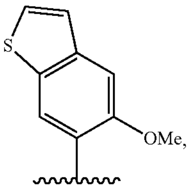

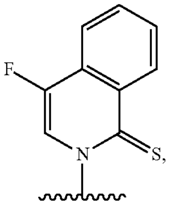

and

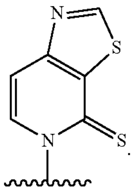 [SMILES: *n1ccc2ncsc2c1=S]

Embodiment A23 is the nucleoside triphosphate of embodiment A22, wherein the nucleobase is

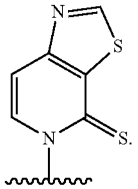 [SMILES: *n1ccc2ncsc2c1=S]

Embodiment A24 is the nucleoside triphosphate of embodiment A22 or A23, wherein the nucleoside comprises ribose or deoxyribose.

Embodiment A25 is a DNA comprising a nucleobase having the structure

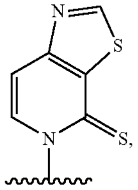

and a complementary base-pairing nucleobase having the structure

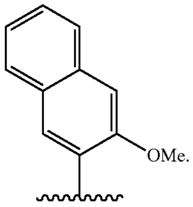 [SMILES: *c1cc2ccccc2cc1OC]

Embodiment A26 is a DNA comprising a nucleobase having the structure

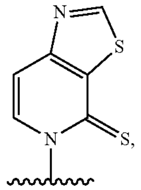 [SMILES: *n1ccc2ncsc2c1=S]

and a complementary base-pairing nucleobase having the structure

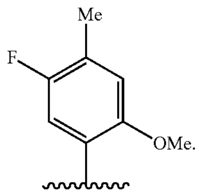 [SMILES: *c1cc(F)c(C)cc1OC]

Embodiment A27 is a method of transcribing a DNA to a tRNA or an mRNA encoding a protein comprising:

contacting a DNA comprising a gene encoding the tRNA or protein with ribonucleoside triphosphates and an RNA polymerase, wherein the gene encoding the tRNA or protein comprises a first unnatural base paired to and forming a first unnatural base pair with a second unnatural base, and wherein the ribonucleoside triphosphates comprise a third unnatural base capable of forming a second unnatural base pair with the first unnatural base, wherein the first unnatural base pair and the second unnatural base pair are not the same.

Embodiment A28 is the method of embodiment A27, wherein the ribonucleoside triphosphates further comprise a fourth unnatural base, wherein the fourth unnatural base is capable of forming a second unnatural base pair with the third unnatural base.

Embodiment A29 is the method of embodiment A28, wherein the first unnatural base pair and the second unnatural base pair are not the same.

Embodiment A30 is the method of anyone of embodiments A27-29, further comprising, before contacting the DNA with the ribonucleoside triphosphates and RNA polymerase, replicating the DNA by contacting the DNA with deoxyribonucleoside triphosphates and a DNA polymerase, wherein the ribonucleoside triphosphates comprise a fifth unnatural base capable of forming a fifth unnatural base pair with the first unnatural base, wherein the first unnatural base pair and the fifth unnatural base pair are not the same.

Embodiment A30 is the method of anyone of embodiments A27-A30, wherein the first unnatural base comprises TPT3, the second unnatural base comprises CNMO or NaM, the third unnatural base comprises TAT1, and the fourth unnatural bases comprises NaM or 5FM.

Embodiment A32 is the method of anyone of embodiments A27-A31, wherein the method comprises use of a semi-synthetic organism, optionally wherein the organism is a bacterium, optionally wherein the bacterium is *Escherichia coli.*

Embodiment A33 is the method of embodiment A32, wherein the organism comprises a microorganism.

Embodiment A34 is the method of embodiment A32, wherein the organism comprises a bacterium.

Embodiment A35 is the method of embodiment A34, wherein the organism comprises a Gram-positive bacterium.

Embodiment A36 is the method of embodiment A34, wherein the organism comprises a Gram-negative bacterium.

Embodiment A37 is the method of any one of embodiments A27-A34, wherein the organism comprises an *Escherichia coli.*

Embodiment A38 is the method of anyone of embodiments A27-A37, wherein at least one unnatural base is selected from the group consisting of (i) 2-thiouracil, 2-thio-thymine, 2'-deoxyuridine, 4-thio-uracil, 4-thio-thymine, uracil-5-yl, hypoxanthin-9-yl (I), 5-halouracil; 5-propynyl-uracil, 6-azo-thymine, 6-azo-uracil, 5-methylaminomethyluracil, 5-methoxyaminomethyl-2-thiouracil, pseudouracil, uracil-5-oxacetic acid methylester, uracil-5-oxacetic acid, 5-methyl-2-thiouracil, 3-(3-amino-3-N-2-carboxypropyl) uracil, 5-methyl-2-thiouracil, 4-thiouracil, 5-methyluracil, 5'-methoxycarboxymethyluracil, 5-methoxyuracil, uracil-5-oxyacetic acid, 5-(carboxyhydroxylmethyl)uracil, 5-carboxymethylaminomethyl-2-thiouridine, 5-carboxymethylaminomethyluracil, or dihydrouracil;

(ii) 5-hydroxymethyl cytosine, 5-trifluoromethyl cytosine, 5-halocytosine, 5-propynyl cytosine, 5-hydroxycytosine, cyclocytosine, cytosine arabinoside, 5,6-dihydrocytosine, 5-nitrocytosine, 6-azo cytosine, azacytosine, N4-ethylcytosine, 3-methylcytosine, 5-methylcytosine, 4-acetylcytosine, 2-thiocytosine, phenoxazine cytidine([5,4-b][1,4]benzoxazin-2(3H)-one), phenothiazine cytidine (1H-pyrimido[5,4-b][1,4]benzothiazin-2(3H)-one), phenoxazine cytidine (9-(2-aminoethoxy)-H-pyrimido[5,4-b][1,4]benzoxazin-2(3H)-one), carbazole cytidine (2H-pyrimido[4,5-b]indol-2-one), or pyridoindole cytidine (H-pyrido [3',2':4,5]pyrrolo [2,3-d]pyrimidin-2-one);

(iii) 2-aminoadenine, 2-propyl adenine, 2-amino-adenine, 2-F-adenine, 2-amino-propyl-adenine, 2-amino-2'-deoxyadenosine, 3-deazaadenine, 7-methyladenine, 7-deaza-adenine, 8-azaadenine, 8-halo, 8-amino, 8-thiol, 8-thioalkyl, and 8-hydroxyl substituted adenines, N6-isopentenyladenine, 2-methyladenine, 2,6-diaminopurine, 2-methythio-N6-isopentenyladenine, or 6-aza-adenine;

(iv) 2-methylguanine, 2-propyl and alkyl derivatives of guanine, 3-deazaguanine, 6-thio-guanine, 7-methylguanine, 7-deazaguanine, 7-deazaguanosine, 7-deaza-8-azaguanine, 8-azaguanine, 8-halo, 8-amino, 8-thiol, 8-thioalkyl, and 8-hydroxyl substituted guanines, 1-methylguanine, 2,2-dimethylguanine, 7-methylguanine, or 6-aza-guanine; and (v) hypoxanthine, xanthine, 1-methylinosine, queosine, beta-D-galactosylqueosine, inosine, beta-D-mannosylqueosine, wybutoxosine, hydroxyurea, (acp3)w, 2-aminopyridine, or 2-pyridone.

Embodiment A39 is the method of any one of embodiments A27-A37, wherein at least one of the first unnatural base, the second unnatural base, the third unnatural base, or the fourth unnatural base comprises:

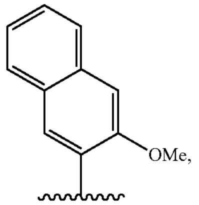 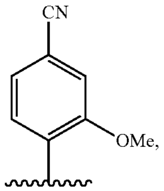

-continued

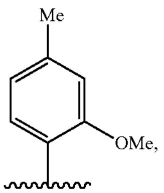 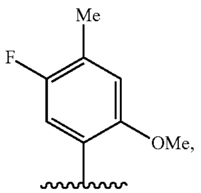

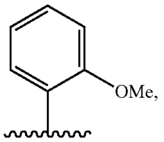 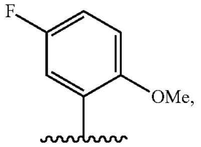

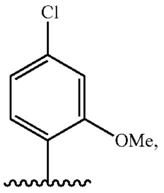 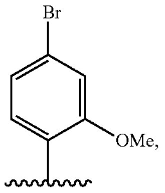

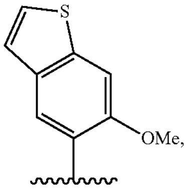 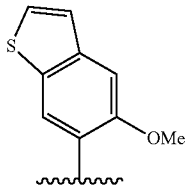

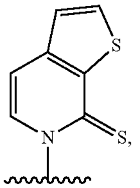 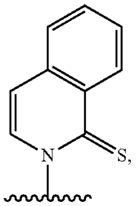 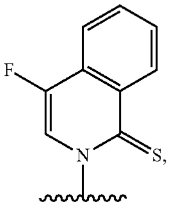

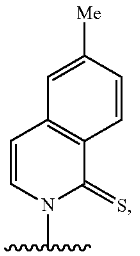 or 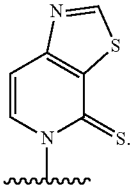

Embodiment A40 is the method of any one of embodiments A27-A39, wherein at least one of the first unnatural base, the second unnatural base, the third unnatural base, or the fourth unnatural base is selected from the group consisting of:

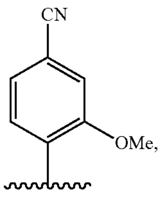 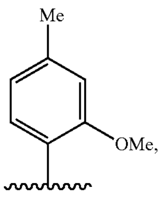

-continued

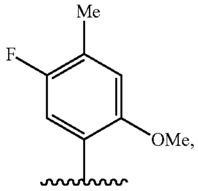, 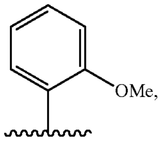,

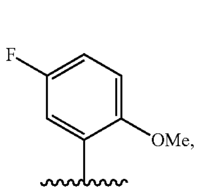, 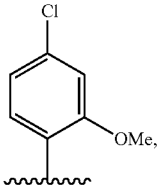, 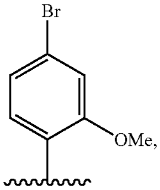,

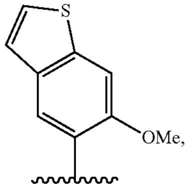, 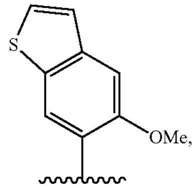,

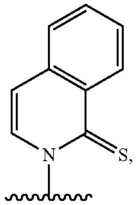, 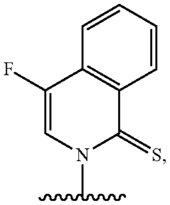,

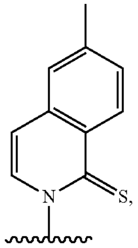, and 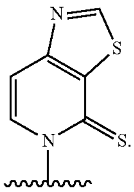 [SMILES: *n1ccc2ncsc2c1=S].

Embodiment A41 is the method of embodiment A40, wherein at least one of the first unnatural base, the second unnatural base, the third unnatural base, or the fourth unnatural base is selected from the group consisting of:

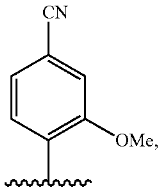, 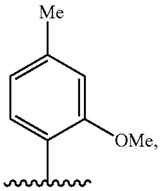,

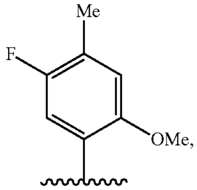, 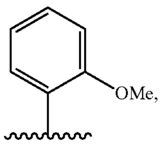,

-continued

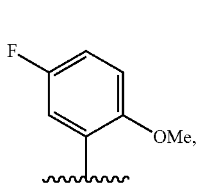, 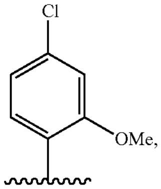,

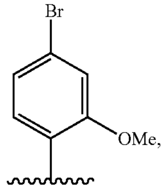, 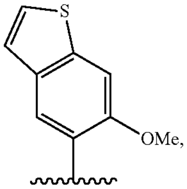, and

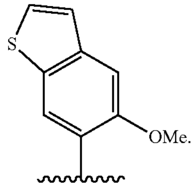.

Embodiment A42 is the method of embodiment A40, wherein at least one of the first unnatural base, the second unnatural base, the third unnatural base, or the fourth unnatural base is selected from the group consisting of:

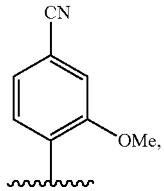, 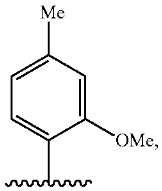,

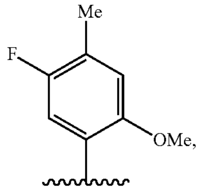, 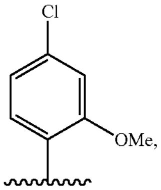,

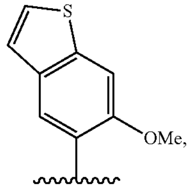, and 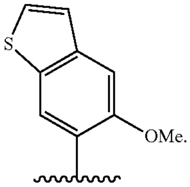.

Embodiment A43 is the method of embodiment A40, wherein at least one of the first unnatural base, the second unnatural base, the third unnatural base, or the fourth unnatural base is selected from the group consisting of:

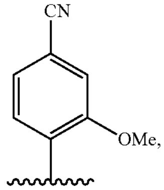, 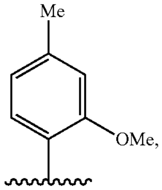,

-continued

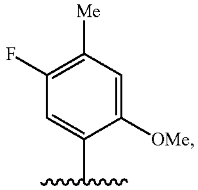

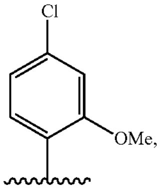

and

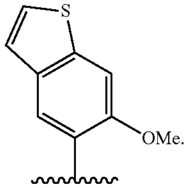

Embodiment A44 is the method of embodiment A40, wherein at least one of the first unnatural base, the second unnatural base, the third unnatural base, or the fourth unnatural base comprises:

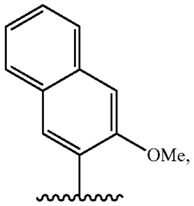

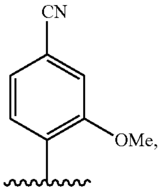 [SMILES: *c1ccc(C#N)cc1OC]

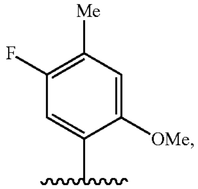

or

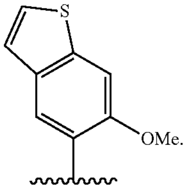

Embodiment A45 is the method of embodiment A40, wherein at least one of the first unnatural base, the second unnatural base, the third unnatural base, or the fourth unnatural base comprises:

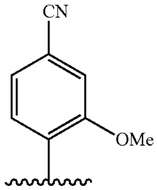

or

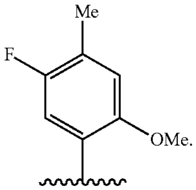

Embodiment A46 is the method of embodiment A40, wherein at least one of the first unnatural base, the second unnatural base, the third unnatural base, or the fourth unnatural base comprises:

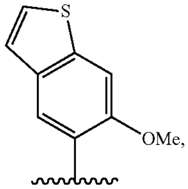

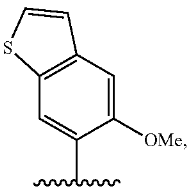

-continued

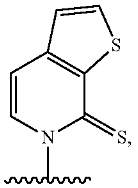

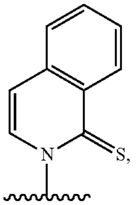

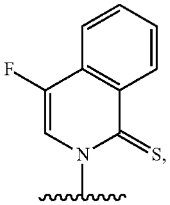

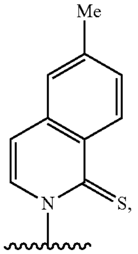

or

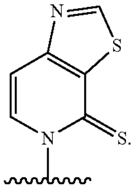

Embodiment A47 is the method of Embodiment A40, wherein at least one of the first unnatural base, the second unnatural base, the third unnatural base, or the fourth unnatural base is selected from the group consisting of:

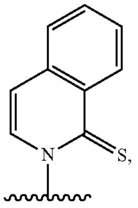

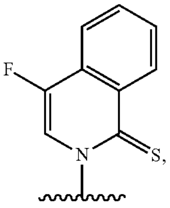

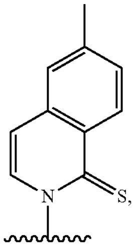

and

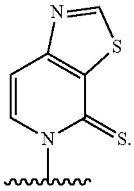

Embodiment A48 is the method of Embodiment A40, wherein at least one of the first unnatural base, the second unnatural base, the third unnatural base, or the fourth unnatural base is

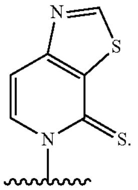

Embodiment A49 is the method of embodiment A40, wherein at least one of the first unnatural base, the second unnatural base, the third unnatural base, or the fourth unnatural base comprises:

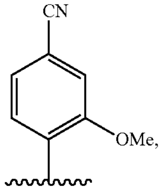
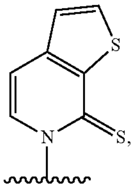
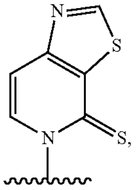
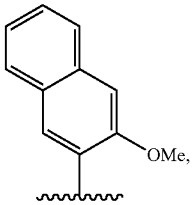
or
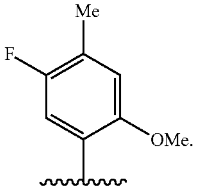

Embodiment A50 is the method of embodiment A40, wherein the first or second unnatural base is

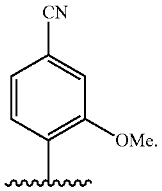

Embodiment A51 is the method of embodiment A40, wherein the first or second unnatural base is

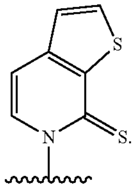 [SMILES: *n1ccc2ccsc2c1=S]

Embodiment A52 is the method of any one of embodiments A27-A40, wherein the first unnatural base is

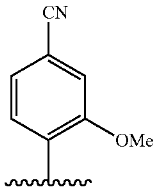 [SMILES: *c1ccc(C#N)cc1OC]

and the second unnatural base is

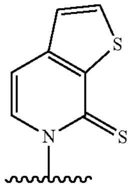 [SMILES: *n1ccc2ccsc2c1=S]

or the first unnatural base is

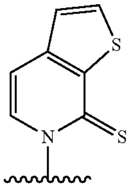

and the second unnatural base is

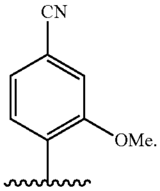 [SMILES: *c1ccc(C#N)cc1OC]

Embodiment A53 is the method of any one of embodiments A27-A40 and A52, wherein the third or fourth unnatural base is

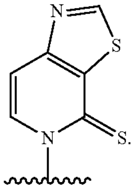 [SMILES: *n1ccc2ncsc2c1=S]

Embodiment A54 is the method of embodiment A53, wherein the third unnatural base is

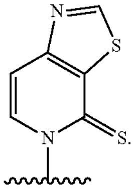 [SMILES: *n1ccc2ncsc2c1=S]

Embodiment A55 is the method of embodiment A54, wherein the fourth unnatural base is

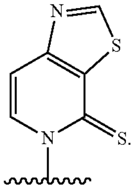 [SMILES: *n1ccc2ncsc2c1=S]

Embodiment A56 is the method of any one of embodiments A27-A52, wherein the third or fourth unnatural base is

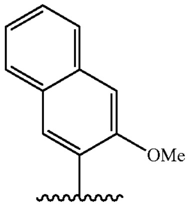
or
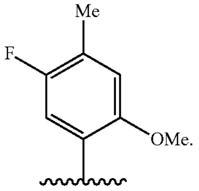

Embodiment A57 is the method of embodiment A56, wherein the third unnatural base is

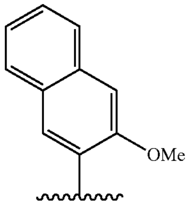
or
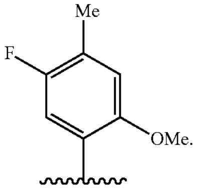

Embodiment A58 is the method of embodiment A56, wherein the fourth unnatural base is

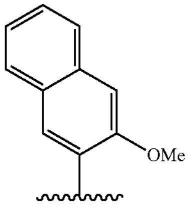
or
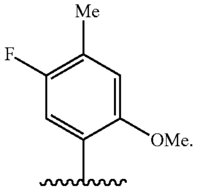

Embodiment A59 is the method of any one of Embodiment A27-A40, wherein the first unnatural base is

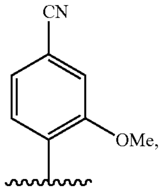 [SMILES: *c1ccc(C#N)cc1OC]

the second unnatural base is

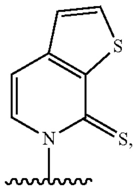

the third unnatural base is

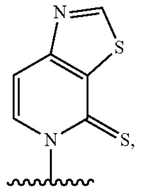 [SMILES: *n1ccc2ncsc2c1=S]

and the fourth unnatural base is

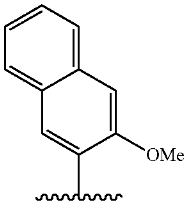
or
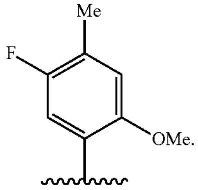

Embodiment A60 is the method of any one of embodiments A27-A40, wherein the first unnatural base is

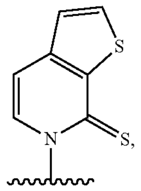

the second unnatural base is

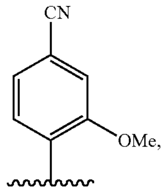 [SMILES: *c1ccc(C#N)cc1OC]

the third unnatural base is

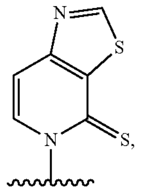 [SMILES: *n1ccc2ncsc2c1=S]

and the fourth unnatural base is

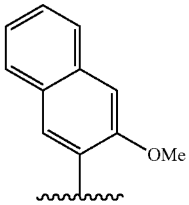

or

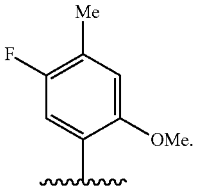

Embodiment A61 is the method of any one of embodiments A27-A40, wherein the first unnatural base is

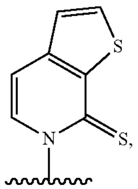 [SMILES: *n1ccc2ccsc2c1=S]

the second unnatural base is

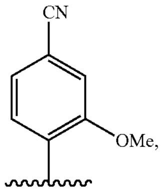 [SMILES: *c1ccc(C#N)cc1OC]

the third unnatural base is

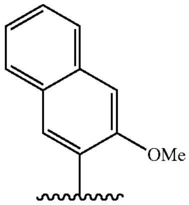

or

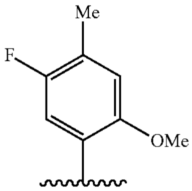

and the fourth unnatural base is

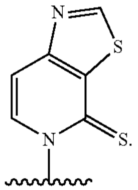 [SMILES: *n1ccc2ncsc2c1=S]

Embodiment A62 is the method of any one of embodiments A27-A40, wherein the third unnatural base is

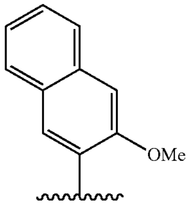

or

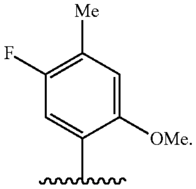

Embodiment A63 is the method of anyone of embodiments A27-A51, wherein the fourth unnatural base is

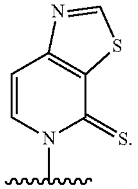 [SMILES: *n1ccc2ncsc2c1=S]

Embodiment A64 is the method of any one of embodiments A27-A40, wherein the first unnatural base is

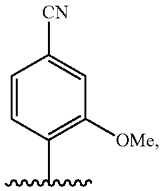 [SMILES: *c1ccc(C#N)cc1OC]

the second unnatural base is

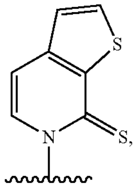 [SMILES: *n1ccc2ccsc2c1=S]

the third unnatural base is

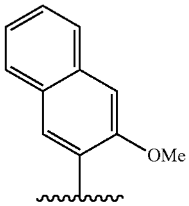

or

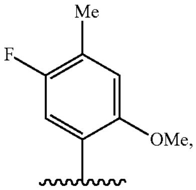

and the fourth unnatural base is

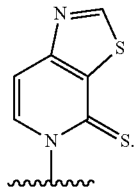 [SMILES: *n1ccc2ncsc2c1=S]

Embodiment A65 is the method of any one of embodiments A27-A64, wherein the third unnatural base and the fourth unnatural base comprise ribose.

Embodiment A66 is the method of any one of embodiments A27-A64, wherein the third unnatural base and the fourth unnatural base comprise deoxyribose.

Embodiment A65 is the method of any one of embodiments A27-A66, wherein the first and second unnatural bases comprise deoxyribose.

Embodiment A68 is the method of any one of embodiments A27-A64, wherein the first and second unnatural bases comprise deoxyribose and the third unnatural base and the fourth unnatural base comprise ribose.

Embodiment A69 is the method of any one of embodiments A27-A40, wherein the DNA comprises at least one unnatural base pair (UBP) selected from:

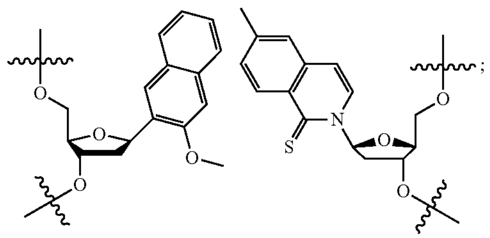

dNaM-d5SICS

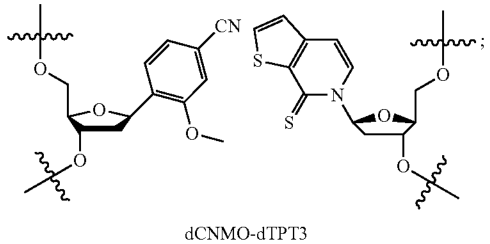

dCNMO-dTPT3

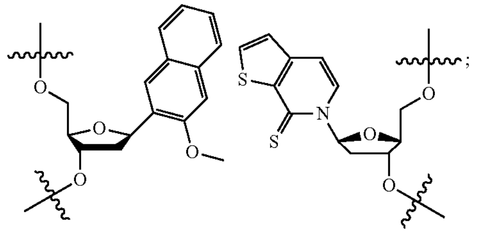

dNaM-dTPT3

-continued

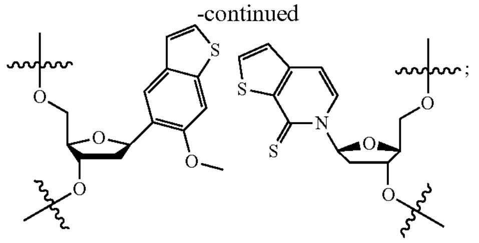

dPTMO-dTPT3

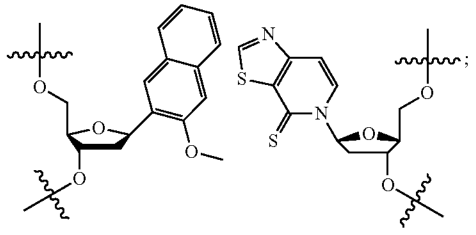

and dNaM-dTAT1

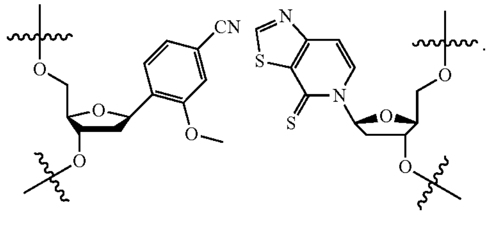

dCNMO-dTAT1

Embodiment A70 is the method of embodiment A69, wherein the DNA template comprises at least one unnatural base pair (UBP) which is dNaM-d5SICS.

Embodiment A71 is the method of embodiment A69, wherein the DNA template comprises at least one unnatural base pair (UBP) which is dCNMO-dTPT3.

Embodiment A72 is the method of embodiment A69, wherein the DNA template comprises at least one unnatural base pair (UBP) which is dNaM-dTPT3.

Embodiment A73 is the method of embodiment A69, wherein the DNA template comprises at least one unnatural base pair (UBP) which is dPTMO-dTPT3.

Embodiment A74 is the method of embodiment A69, wherein the DNA template comprises at least one unnatural base pair (UBP) which is dNaM-dTAT1.

Embodiment A75 is the method of embodiment A69, wherein the DNA template comprises at least one unnatural base pair (UBP) which is dCNMO-dTAT1.

Embodiment A76 is the method of any one of embodiments A27-A40, wherein the DNA comprises at least one unnatural base pair (UBP) selected from

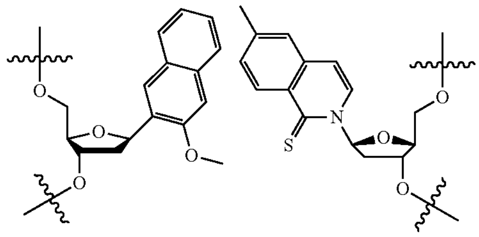

dNaM-d5SICS

-continued

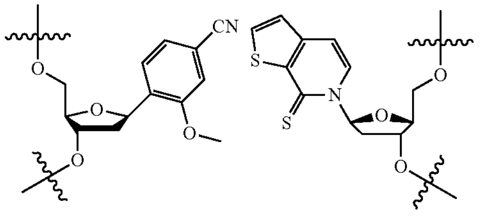

dCNMO-dTPT3

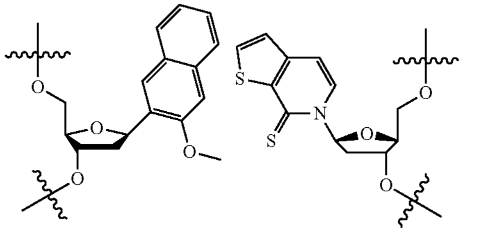

dNaM-dTPT3

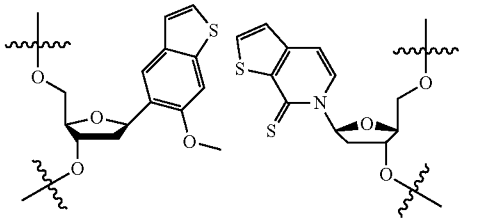

dPTMO-dTPT3

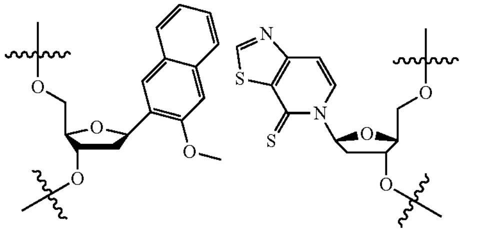

dNaM-dTAT1

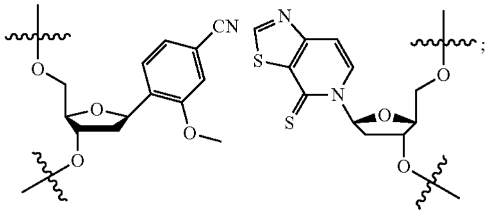

dCNMO-dTAT1 and wherein the mRNA and/or the tRNA comprise at least one unnatural base selected from:

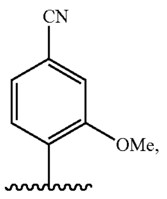

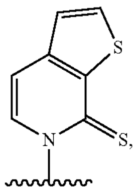

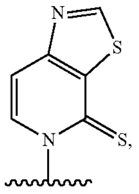

-continued

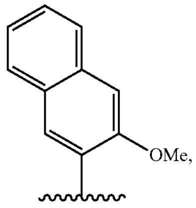

and

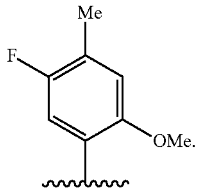

Embodiment A77 is the method according to embodiment A76, wherein the DNA template comprises at least one unnatural base pair (UBP) which is dNaM-d5SICS.

Embodiment A78 is the method of embodiment A76, wherein the DNA template comprises at least one unnatural base pair (UBP) which is dCNMO-dTPT3.

Embodiment A79 is the method of embodiment A76, wherein the DNA template comprises at least one unnatural base pair (UBP) which is dNaM-dTPT3.

Embodiment A80 is the method of embodiment A76, wherein the DNA template comprises at least one unnatural base pair (UBP) which is dPTMO-dTPT3.

Embodiment A81 is the method of embodiment A76, wherein the DNA template comprises at least one unnatural base pair (UBP) which is dNaM-dTAT1.

Embodiment A82 is the method of embodiment A76, wherein the DNA template comprises at least one unnatural base pair (UBP) which is dCNMO-dTAT1.

Embodiment A83 is the method of any one of embodiments A76-A82 wherein the mRNA and the tRNA comprise an unnatural base selected from

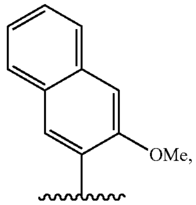

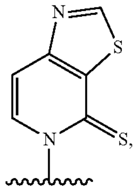

and

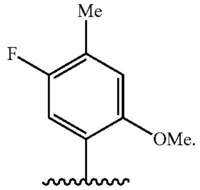

Embodiment A84 is the method of embodiment A83, wherein the mRNA and the tRNA comprise an unnatural base selected from

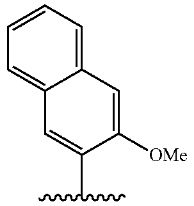 [SMILES: *c1cc2ccccc2cc1OC]

and

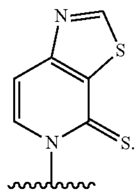 [SMILES: *n1ccc2ncsc2c1=S]

Embodiment A85 is the method of embodiment A83, wherein the mRNA comprises an unnatural base which is

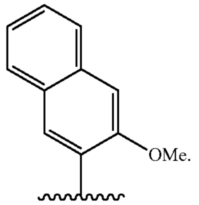

Embodiment A86 is the method of embodiment A83, wherein the mRNA comprises an unnatural base which is

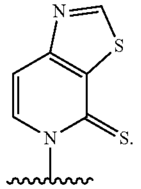

Embodiment A87 is the method of embodiment A83, wherein the mRNA comprises an unnatural base which is

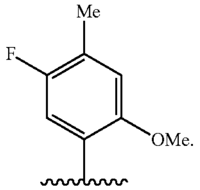 [SMILES: *c1cc(F)c(C)cc1OC]

Embodiment A88 is the method of any one of embodiments A76-A87, wherein the tRNA comprises an unnatural base selected from

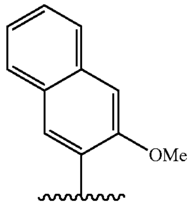

and

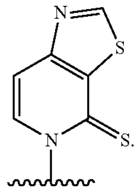

Embodiment A89 is the method of embodiment A88, wherein the tRNA comprises an unnatural base which is

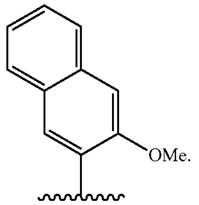 [SMILES: *c1cc2ccccc2cc1OC]

Embodiment A90 is the method of A88, wherein the tRNA comprises an unnatural base which is

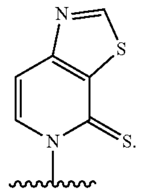 [SMILES: *n1ccc2ncsc2c1=S]

Embodiment A91 is the method of any one of embodiments A76-A87, wherein the tRNA comprises an unnatural base which is

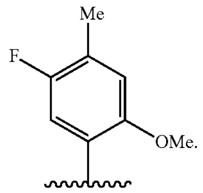 [SMILES: *c1cc(F)c(C)cc1OC]

Embodiment A92 is the method of any one of embodiments A27-A40, wherein the first unnatural base comprises dCNMO, and the second unnatural base comprises dTPT3.

Embodiment A93 is the method of any one of embodiments A27-40 and A92, wherein the third unnatural base comprises NaM, and the second unnatural base comprises TAT1.

Embodiment A94 is the method of any one of embodiments A27-A93, wherein the first unnatural base or the second unnatural base is recognized by a DNA polymerase.

Embodiment A95 is the method of any one of the embodiments A27-A94, wherein the third unnatural base or the fourth unnatural base is recognized by an RNA polymerase.

Embodiment A96 is the method of any one of embodiments A27-A95, wherein the mRNA is transcribed, and the method further comprises translating the mRNA into a protein, wherein the protein comprises an unnatural amino acid at a position corresponding to a codon of the mRNA that comprises the third unnatural base.

Embodiment A97 is the method of any one of embodiments A27-A96, wherein the protein comprises at least two unnatural amino acids.

Embodiment A98 is the method of any one of embodiments A27-A96, wherein the protein comprises at least three unnatural amino acids.

Embodiment A99 is the method of any one of embodiments A27-A98, wherein the protein comprises at least two different unnatural amino acids.

Embodiment A100 is the method of any one of embodiments A27-A98, wherein the protein comprises at least three different unnatural amino acids.

Embodiment A101 is the method of any one of embodiments A27-A100, wherein the at least one unnatural amino acid:

is a lysine analogue;
comprises an aromatic side chain;
comprises an azido group;
comprises an alkyne group; or
comprises an aldehyde or ketone group.

Embodiment A102 is the method of anyone of embodiments A27-A101, wherein the at least one unnatural amino acid does not comprise an aromatic side chain.

Embodiment A103 is the method of anyone of embodiments A27-A102, wherein the at least one unnatural amino acid comprises N6-azidoethoxy-carbonyl-L-lysine (AzK), N6-propargylethoxy-carbonyl-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine.

Embodiment A104 is the method of embodiment A102 or A103, wherein the at least one unnatural amino acid comprises N6-azidoethoxy-carbonyl-L-lysine (AzK) or N6-propargylethoxy-carbonyl-L-lysine (PraK).

Embodiment A105 is the method of embodiment A104, wherein the at least one unnatural amino acid comprises N6-azidoethoxy-carbonyl-L-lysine (AzK).

Embodiment A106 is the method of embodiment A104, wherein the at least one unnatural amino acid comprises N6-propargylethoxy-carbonyl-L-lysine (PraK).

Embodiment A107 is an mRNA produced from the method of anyone of embodiments A27-A106.

Embodiment A108 is a tRNA produced from the method of anyone of embodiments A27-A106.

Embodiment A109 is a protein encoded by the mRNA of embodiment A107 comprising an unnatural amino acid at a position corresponding to a codon of the mRNA that comprises the third unnatural base.

Embodiment A110 is a semi-synthetic organism comprising an expanded genetic alphabet, wherein the genetic alphabet comprises at least three distinct unnatural bases.

Embodiment A111 is the semi-synthetic organism of embodiment A110, wherein the organism comprises a microorganism, optionally wherein the microorganism is an *Escherichia coli.*

Embodiment A112 is the semi-synthetic organism of embodiment A110 or A111, wherein the organism comprises DNA comprising at least one unnatural nucleobase selected from:

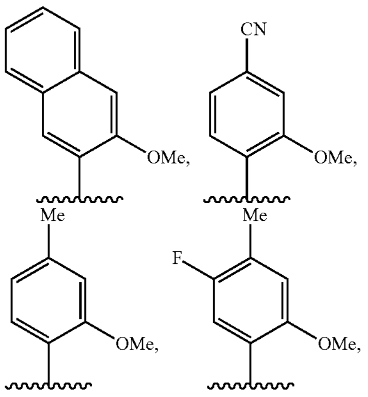

-continued

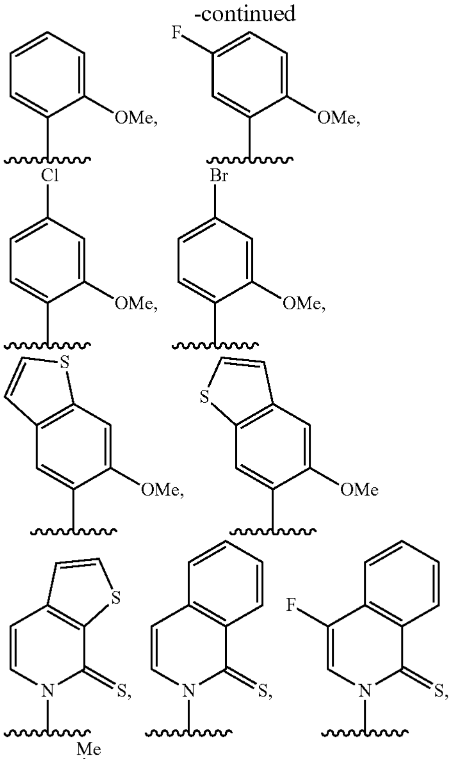

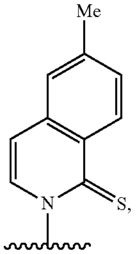

and

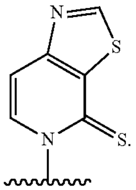 [SMILES: *n1ccc2ncsc2c1=S]

Embodiment A113 is the semi-synthetic organism of any one of embodiments A110-A113, wherein the DNA comprises at least one unnatural base pair (UBP), wherein the unnatural base pair (UBP) is dCNMO-dTPT3, dNaM-dTPT3, dCNMO-dTAT1, d5FM-dTAT1, or dNaM-dTAT1.

Embodiment A114 is the semi-synthetic organism of embodiment A112, wherein the DNA comprises at least one unnatural nucleobase which is

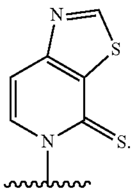 [SMILES: *n1ccc2ncsc2c1=S]

Embodiment A115 is the semi-synthetic organism of anyone of embodiments A110-A115, wherein the organism expresses a heterologous nucleoside triphosphate transporter.

Embodiment A116 is the semi-synthetic organism of embodiment A115, wherein the heterologous nucleoside triphosphate transporter is PtNTT2.

Embodiment A117 is the semi-synthetic organism of anyone of embodiments A110-A116, wherein the organism further expresses a heterologous tRNA synthetase.

Embodiment A118 is the semi-synthetic organism of embodiment A117, wherein the heterologous tRNA synthetase is *M. barkeri* pyrrolysyl-tRNA synthetase (Mb PylRS).

Embodiment A119 is the semi-synthetic organism of anyone of embodiments A110-A118, wherein the organism further expresses a heterologous RNA polymerase.

Embodiment A120 is the semi-synthetic organism of embodiment A119, wherein the heterologous RNA polymerase is T7 RNAP.

Embodiment A121 is the semi-synthetic organism of any one of embodiments A110-A120, wherein the organism does not express a protein having the function of DNA recombinational repair.

Embodiment A122 is the semi-synthetic organism of embodiment A121, wherein the organism does not express RecA.

Embodiment A123 is the semi-synthetic organism of anyone of embodiments A110-A122, further comprising a heterologous mRNA.

Embodiment A124 is the semi-synthetic organism of embodiment A123, wherein the heterologous mRNA comprises at least one unnatural base selected from:

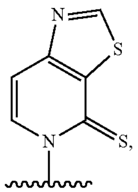, 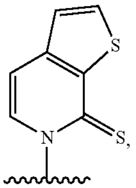, 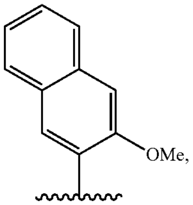, 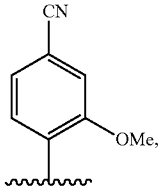, and 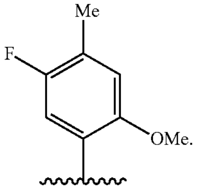.

Embodiment A125 is the semi-synthetic organism of any one of embodiments A110-A125, further comprising a heterologous tRNA.

Embodiment A126 is the semi-synthetic organism of Embodiment A125, wherein the heterologous tRNA comprises at least one unnatural base selected from:

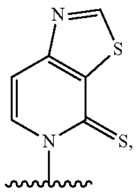, 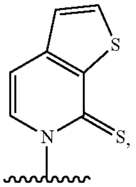, 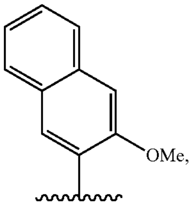,

-continued

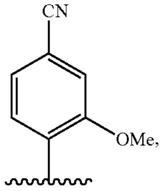, and 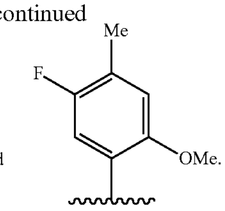.

Embodiment A127 is a method of transcribing DNA, the method comprising:

providing one or more DNAs comprising (1) a gene encoding a protein, wherein a template strand of the gene encoding the protein comprises a first unnatural base and (2) a gene encoding a tRNA, wherein a template strand of the gene encoding the tRNA comprises a second unnatural base capable of forming a base pair with the first unnatural base;

transcribing the gene encoding the protein to incorporate a third unnatural base into an mRNA, the third unnatural base capable of forming a first unnatural base pair with the first unnatural base;

transcribing the gene encoding a tRNA to incorporate a fourth unnatural base into a tRNA, wherein the fourth unnatural base is capable of forming a second unnatural base pair with the second unnatural base, wherein the first unnatural base pair and the second unnatural base pair are not the same.

Embodiment A128 is the method of embodiment A127, further comprising translating a protein from the mRNA utilizing the tRNA, wherein said protein comprises an unnatural amino acid at a position corresponding to a codon comprising the third unnatural base in the mRNA.

Embodiment A129 is a method of replicating a DNA, the method comprising:

providing a DNA comprising (1) a gene encoding a protein, wherein a template strand of the gene encoding the protein comprises a first unnatural base and (2) a gene encoding a tRNA, wherein a template strand of the gene encoding the tRNA comprises a second unnatural base capable of forming a base pair with the first unnatural base; and replicating the DNA to incorporate a first substitute unnatural base in place of the first unnatural base, and/or to incorporate a second substitute unnatural base in place of the second unnatural base;

wherein the method optionally further comprises:

transcribing the gene encoding a protein to incorporate a third unnatural base into an mRNA, the third unnatural base being capable of forming a first unnatural base pair with the first unnatural base and/or the first substitute unnatural base; and/or transcribing the gene encoding a tRNA to incorporate a fourth unnatural base into a tRNA, wherein the fourth unnatural base is capable of forming a second unnatural base pair with the second unnatural base and/or the second substitute unnatural base, wherein the first unnatural base pair and the second unnatural base pair are not the same.

Embodiment A130 is the method of embodiment A129, further comprising transcribing the gene encoding a protein to incorporate a third unnatural base into an mRNA, the third unnatural base being capable of forming a first unnatural base pair with the first unnatural base and/or the first substitute unnatural base.

Embodiment A131 is the method of embodiment A129 or A130, further comprising transcribing the gene encoding a tRNA to incorporate a fourth unnatural base into a tRNA, wherein the fourth unnatural base is capable of forming a second unnatural base pair with the second unnatural base and/or the second substitute unnatural base, wherein the first unnatural base pair and the second unnatural base pair are not the same.

Embodiment A132 is the method of anyone of embodiments A127-A131, wherein the method comprises use of a semi-synthetic organism.

Embodiment A133 is the method of embodiment A132, wherein the organism comprises a microorganism.

Embodiment A134 is the method of embodiment A132 or A133, wherein the method is an in vivo method comprising use of a semi-synthetic organism which is a bacterium.

Embodiment A135 is the method of embodiment A134, wherein the organism comprises a Gram-positive bacterium.

Embodiment A136 is the method of embodiment A134, wherein the organism comprises a gram-negative bacterium.

Embodiment A137 is the method of embodiments A132-A134, wherein the organism comprises an *Escherichia coli*.

Embodiment A138 is the method of any one of embodiments A127-A137, wherein at least one of the first unnatural base, the second unnatural base, the third unnatural base, or the fourth unnatural base comprises:

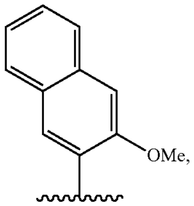,
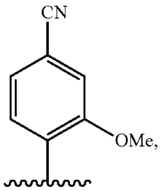,
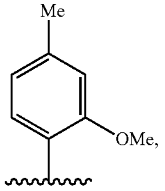,
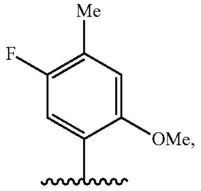,
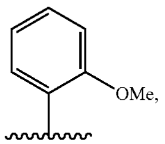,
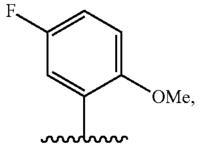,
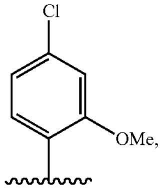,
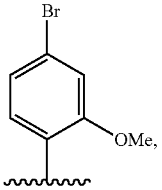,
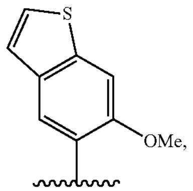,
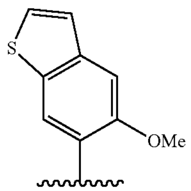

-continued

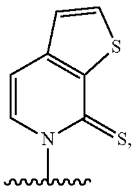,
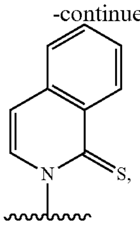,
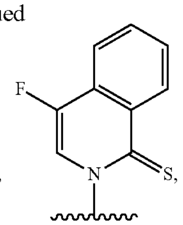,
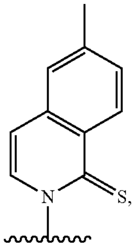, and
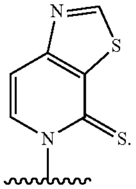.

Embodiment A139 is the method of embodiment A138, wherein at least one of the first unnatural base, the second unnatural base, the third unnatural base, or the fourth unnatural base comprises:

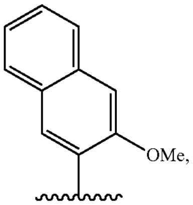,
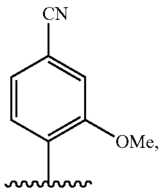 [SMILES: *c1ccc(C#N)cc1OC],
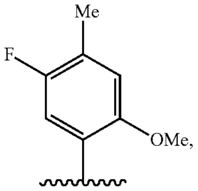, and
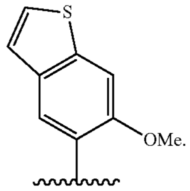.

Embodiment A140 is the method of embodiment A138, wherein at least one of the first unnatural base, the second unnatural base, the third unnatural base, or the fourth unnatural base comprises:

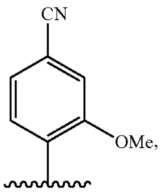, and
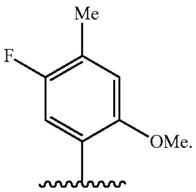.

Embodiment A141 is the method of embodiment A138, wherein at least one of the first unnatural base, the second unnatural base, the third unnatural base, or the fourth unnatural base comprises

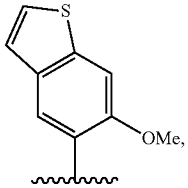, 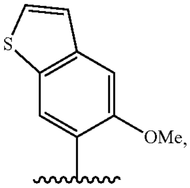, 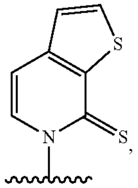, 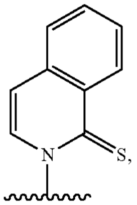, 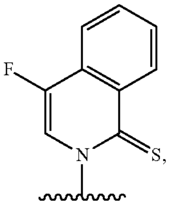, 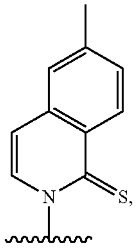, and 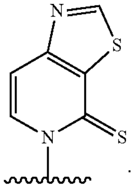.

Embodiment A142 is the method of embodiment A138, wherein at least one of the first unnatural base, the second unnatural base, the third unnatural base, or the fourth unnatural base is

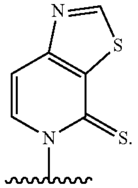

Embodiment A143 is the method of embodiment A138, wherein at least one of the first unnatural base, the second unnatural base, the third unnatural base, or the fourth unnatural base comprises:

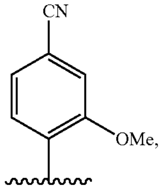, 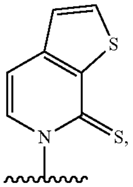, 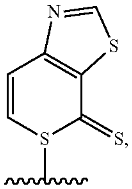, 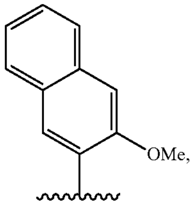, and 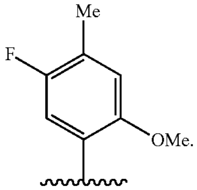.

Embodiment A144 is the method of embodiment A138, wherein the first or second unnatural base is

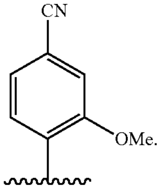

Embodiment A145 is the method of Embodiment A138, wherein the first or second unnatural base is

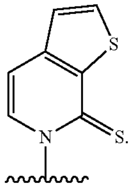 [SMILES: *n1ccc2ccsc2c1=S]

Embodiment A146 is the method of embodiment A138, wherein the first unnatural base is

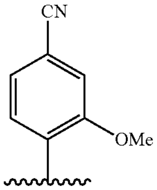 [SMILES: *c1ccc(C#N)cc1OC]

and the second unnatural base is

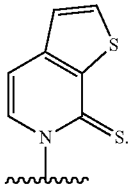 [SMILES: *n1ccc2ccsc2c1=S]

Embodiment A147 is the method of embodiment A138, wherein the first unnatural base is

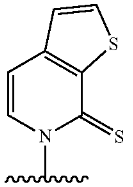 [SMILES: *n1ccc2ccsc2c1=S]

and the second unnatural base is

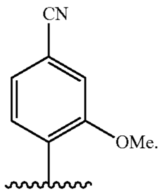 [SMILES: *c1ccc(C#N)cc1OC]

Embodiment A148 is the method of any one of embodiments A138, A146, and A147, wherein the third or fourth unnatural base is

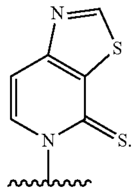 [SMILES: *n1ccc2ncsc2c1=S]

Embodiment A149 is the method of embodiment A148, wherein the third unnatural base is

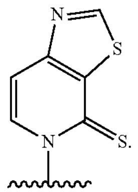 [SMILES: *n1ccc2ncsc2c1=S]

Embodiment A150 is the method of Embodiment A148, wherein the fourth unnatural base is

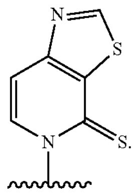 [SMILES: *n1ccc2ncsc2c1=S]

Embodiment A151 is the method of any one of embodiments A138, A146, and A147, wherein the third or fourth unnatural base is

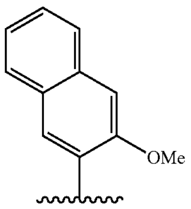

or

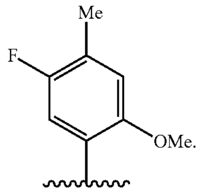

Embodiment A152 is the method of embodiment A151, wherein the third unnatural base is

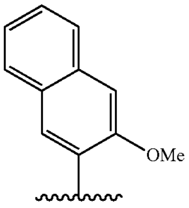

or

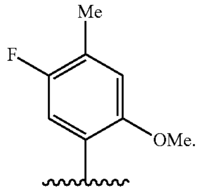

Embodiment A153 is the method of embodiment A151, wherein the fourth unnatural base is

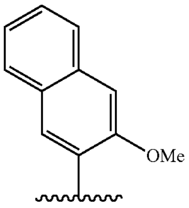

or

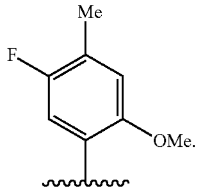

Embodiment A154 is the method of anyone of embodiment A138, wherein the first unnatural base is

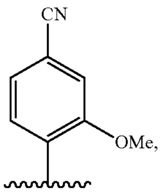 [SMILES: *c1ccc(C#N)cc1OC]

the second unnatural base is

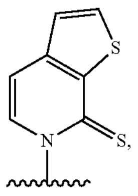

the third unnatural base is

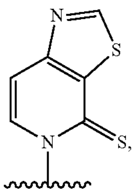 [SMILES: *n1ccc2ncsc2c1=S]

and the fourth unnatural base is

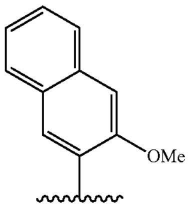
or
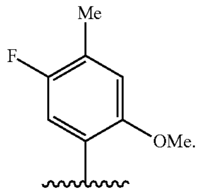

Embodiment A155 is the method of embodiment A138, wherein the first unnatural base is

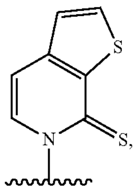

the second unnatural base is

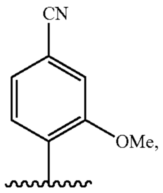 [SMILES: *c1ccc(C#N)cc1OC]

the third unnatural base is

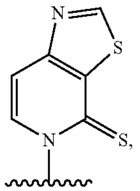 [SMILES: *n1ccc2ncsc2c1=S]

and the fourth unnatural base is

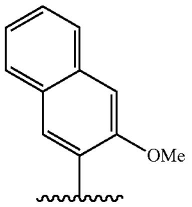
or
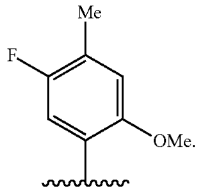

Embodiment A is the method of embodiment A138, wherein the first unnatural base is

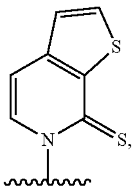

the second unnatural base is

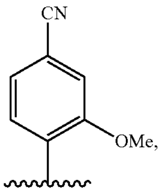 [SMILES: *c1ccc(C#N)cc1OC]

the third unnatural base is

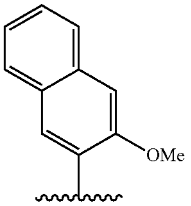
or
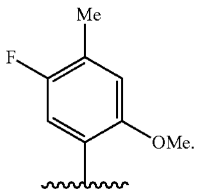

and the fourth unnatural base is

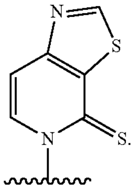 [SMILES: *n1ccc2ncsc2c1=S]

Embodiment A157 is the method of embodiment A138, wherein the third unnatural base is

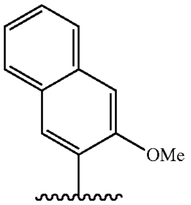
or
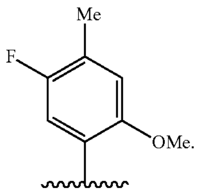

Embodiment A158 is the method of embodiment A138, wherein the fourth unnatural base is

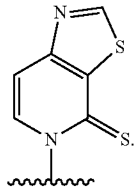 [SMILES: *n1ccc2ncsc2c1=S]

Embodiment A159 is the method of embodiment A138, wherein the first unnatural base is

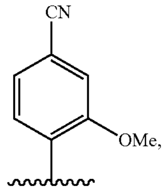 [SMILES: *c1ccc(C#N)cc1OC]

the second unnatural base is

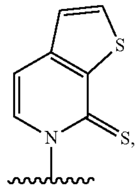 [SMILES: *n1ccc2ccsc2c1=S]

the third unnatural base is

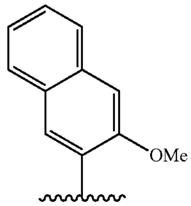

or

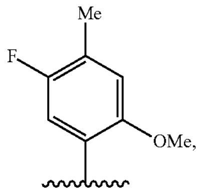

and the fourth unnatural base is

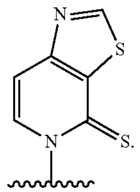 [SMILES: *n1ccc2ncsc2c1=S]

Embodiment A160 is the method of any one of embodiments A127-A159, wherein the third unnatural base and the fourth unnatural base comprise ribose.

Embodiment A161 is the method of any one of embodiments A127-A159, wherein the third unnatural base and the fourth unnatural base comprise deoxyribose.

Embodiment A162 is the method of any one of embodiments A127-A161, wherein the first and second unnatural bases comprise deoxyribose.

Embodiment A163 is the method of any one of embodiments A127-A159, wherein the first and second unnatural bases comprise deoxyribose and the third unnatural base and the fourth unnatural base comprise ribose.

Embodiment A164 is the method of any one of embodiments A127-A137, wherein the DNA template comprises at least one unnatural base pair (UBP) selected from the group consisting of

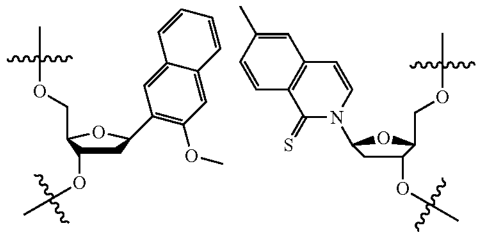

dNaM-d5SICS

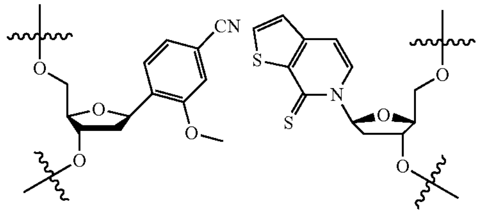

dCNMO-dTPT3

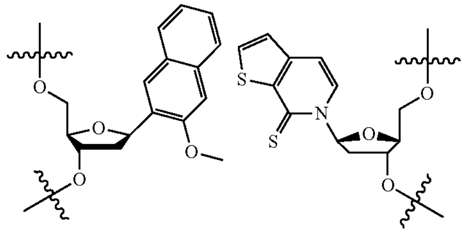

dNaM-dTPT3

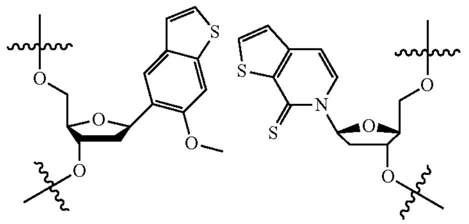

dPTMO-dTPT3

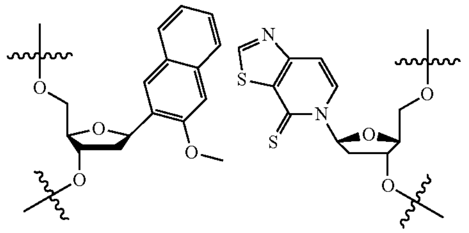

dNaM-dTAT1

-continued

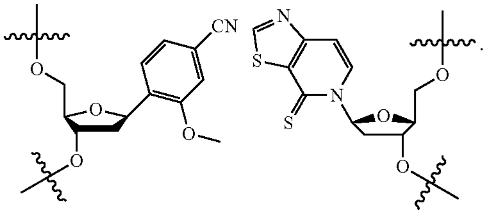

dCNMO-dTAT1

Embodiment A165 is the method of embodiment A164, wherein the DNA template comprises at least one unnatural base pair (UBP) which is dNaM-d5SICS.

Embodiment A166 is the method of embodiment A164, wherein the DNA template comprises at least one unnatural base pair (UBP) which is dCNMO-dTPT3.

Embodiment A167 is the method of embodiment A164, wherein the DNA template comprises at least one unnatural base pair (UBP) which is dNaM-dTPT3.

Embodiment A168 is the method of embodiment A164, wherein the DNA template comprises at least one unnatural base pair (UBP) which is dNaM-dTAT1.

Embodiment A169 is the method of embodiment A164, wherein the DNA template comprises at least one unnatural base pair (UBP) which is dCNMO-dTAT1.

Embodiment A170 is the method of any one of embodiments A127-A137, wherein the DNA template comprises at least one unnatural base pair (UBP) selected from the group consisting of

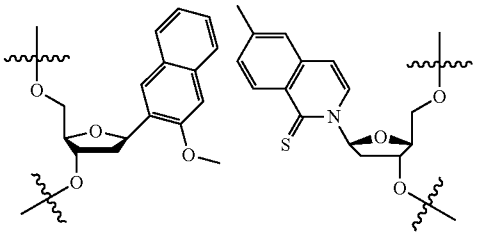

dNaM-d5SICS

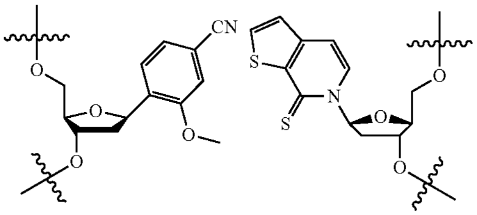

dCNMO-dTPT3

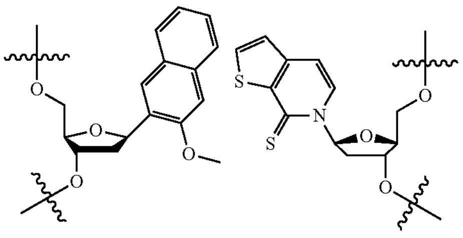

dNaM-dTPT3

-continued

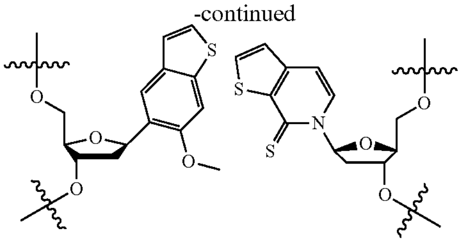

dPTMO-dTPT3

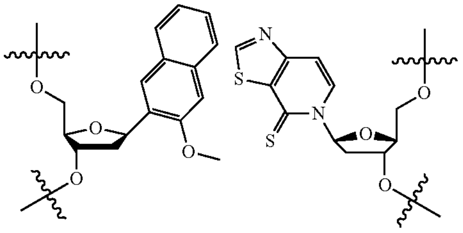

dNaM-dTAT1

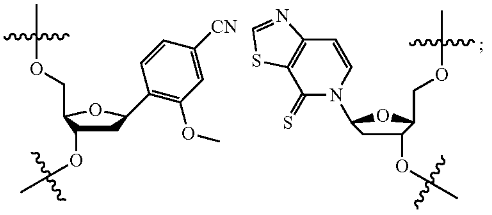

dCNMO-dTAT1 and wherein the mRNA and the tRNA comprise at least one unnatural base selected from.

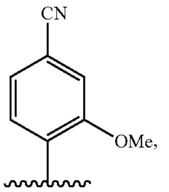 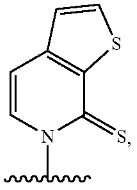 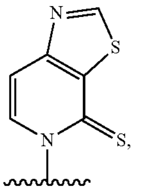

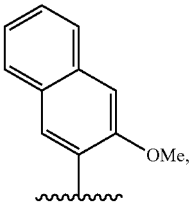 and 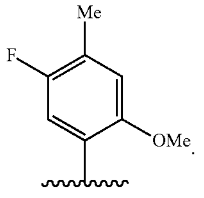

Embodiment A171 is the method according to embodiment A170, wherein the DNA template comprises at least one unnatural base pair (UBP) which is dNaM-d5 SICS.

Embodiment A172 is the method of embodiment A170, wherein the DNA template comprises at least one unnatural base pair (UBP) which is dCNMO-dTPT3.

Embodiment A173 is the method of embodiment A170, wherein the DNA template comprises at least one unnatural base pair (UBP) which is dNaM-dTPT3.

Embodiment A174 is the method of embodiment A170, wherein the DNA template comprises at least one unnatural base pair (UBP) which is dNaM-dTAT1.

Embodiment A175 is the method of embodiment A170, wherein the DNA template comprises at least one unnatural base pair (UBP) which is dCNMO-dTAT1.

Embodiment A176 is the method of any one of embodiments A127-A175, wherein the mRNA and the tRNA comprise an unnatural base selected from

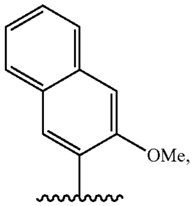
,
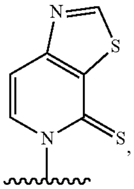
, and
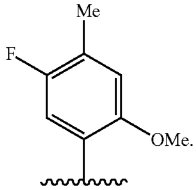

Embodiment A177 is the method of embodiment A176, wherein the mRNA and the tRNA comprise an unnatural base selected from

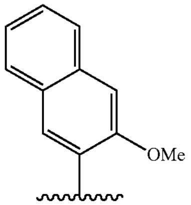 [SMILES: *c1cc2ccccc2cc1OC]
and
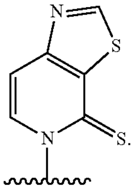

Embodiment A178 is the method of embodiment A176, wherein the mRNA comprises an unnatural base which is

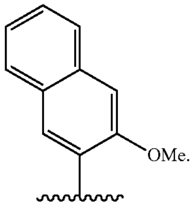

Embodiment A179 is the method of embodiment A176, wherein the mRNA comprises an unnatural base which is

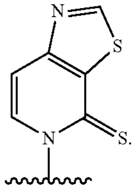

Embodiment A180 is the method of embodiment A176, wherein the mRNA comprises an unnatural base which is

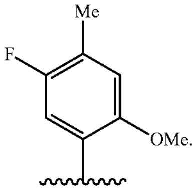 [SMILES: *c1cc(F)c(C)cc1OC]

Embodiment A181 is the method of embodiment A176, wherein the tRNA comprises an unnatural base selected from

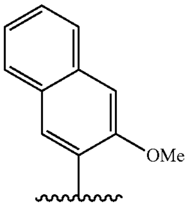 [SMILES: *c1cc2ccccc2cc1OC]
and
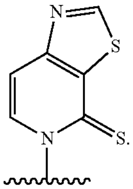 [SMILES: *n1ccc2ncsc2c1=S]

Embodiment A182 is the method of embodiment A176, wherein the tRNA comprises an unnatural base which is

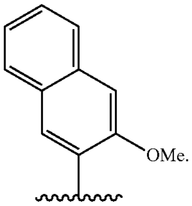

Embodiment A183 is the method of embodiment A176, wherein the tRNA comprises an unnatural base which is

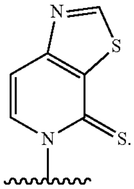

Embodiment A184 is the method of embodiment A176, wherein the tRNA comprises an unnatural base which is

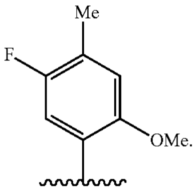 [SMILES: *c1cc(F)c(C)cc1OC]

Embodiment A185 is the method of any one of embodiments A127-A137, wherein the first unnatural base comprises dCNMO, and the second unnatural base comprises dTPT3.

Embodiment A186 is the method of anyone of embodiments A127-A137, wherein the third unnatural base comprises NaM, and the second unnatural base comprises TAT1.

Embodiment A187 is the method of anyone of embodiments A127-A186, wherein the protein comprises at least two unnatural amino acids.

Embodiment A188 is the method of anyone of embodiments A127-A186, wherein the protein comprises at least three unnatural amino acids.

Embodiment A189 is the method of anyone of embodiments A127-A186, wherein the protein comprises at least two different unnatural amino acids.

Embodiment A190 is the method of anyone of embodiments A127-A186, wherein the protein comprises at least three different unnatural amino acids.

Embodiment A191 is the method of any one of embodiments A127-A190, wherein the at least one unnatural amino acid:

is a lysine analogue;

comprises an aromatic side chain;

comprises an azido group;

comprises an alkyne group; or comprises an aldehyde or ketone group.

Embodiment A192 is the method of any one of embodiments A127-A191, wherein the at least one unnatural amino acid does not comprise an aromatic side chain.

Embodiment A193 is the method of embodiments A191 or A192, wherein the at least one unnatural amino acid comprises N6-azidoethoxy-carbonyl-L-lysine (AzK) or N6-propargylethoxy-carbonyl-L-lysine (PraK).

Embodiment A194 is the method of embodiment A193, wherein the at least one unnatural amino acid comprises N6-azidoethoxy-carbonyl-L-lysine (AzK).

Embodiment A195 is the method of embodiment A193, wherein the at least one unnatural amino acid comprises N6-propargylethoxy-carbonyl-L-lysine (PraK).

BRIEF DESCRIPTION OF THE DRAWINGS

Various aspects of the invention are set forthwith particularity in the appended claims. A better understanding of the features and advantages of the present invention will be obtained by reference to the following detailed description that sets forth illustrative embodiments, in which the principles of the invention are utilized, and the accompanying drawings of which:

FIG. 8E—UAA #43-89; FIG. 8F—UAA #90-128; FIG. 8G—UAA #129-167). FIGS. 8D-8G are adopted from Table 1 of Dumas et al., *Chemical Science* 2015, 6, 50-69.

DETAILED DESCRIPTION OF THE INVENTION

Certain Terminology

Figure 1A:
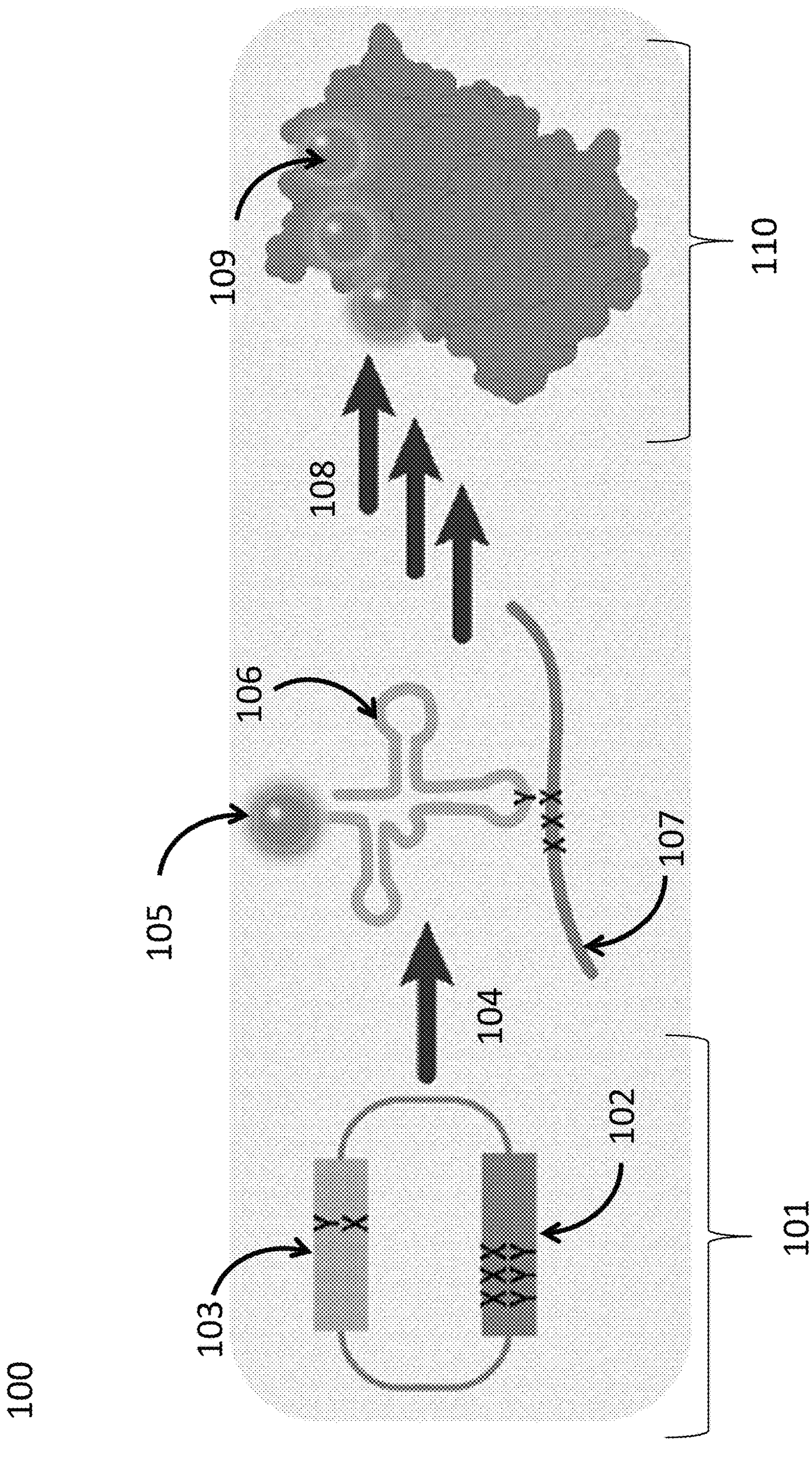
FIG. 1A illustrates a workflow using unnatural base pairs (UBPs) to site-specifically incorporate non-canonical amino acids (ncAAs) into a protein using an unnatural X-Y base pair. Incorporation of three ncAAs into a protein is shown as an example only; any number of ncAAs may be incorporated.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. To the extent any material incorporated herein by reference is inconsistent with the express content of this disclosure, the express content controls. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 μL" means "about 5 μL" and also constitutes description of "5 μL." Generally, the term "about" includes an amount that would be expected to be within experimental error.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. In some embodiments, a nucleotide analog is an unnatural nucleotide. In some embodiments, a nucleoside analog is an unnatural nucleoside. A related chemical structure that is readily derived synthetically from a parent chemical structure is referred to as a "derivative."

As used herein, "base" or "nucleobase" refers to at least the nucleobase portion of a nucleoside or nucleotide (nucleoside and nucleotide encompass the ribo or deoxyribo variants), which may in some cases contain further modifications to the sugar portion of the nucleoside or nucleotide. In some cases, "base" is also used to represent the entire nucleoside or nucleotide (for example, a "base" may be incorporated by a DNA polymerase into DNA, or by an RNA polymerase into RNA). However, the term "base" should not be interpreted as necessarily representing the entire nucleoside or nucleotide unless required by the context. In the chemical structures provided herein of a base or nucleobase, only the base of the nucleoside or nucleotide is shown, with the sugar moiety and, optionally, any phosphate residues omitted for clarity. As used in the chemical structures provided herein of a base or nucleobase, the wavy line represents connection to a nucleoside or nucleotide, in which the sugar portion of the nucleoside or nucleotide may be further modified. In some embodiments, the wavy line represents attachment of the base or nucleobase to the sugar portion, such as a pentose, of the nucleoside or nucleotide. In some embodiments, the pentose is a ribose or a deoxyribose.

In some embodiments, a nucleobase is generally the heterocyclic base portion of a nucleoside. Nucleobases may be naturally occurring, may be modified, may bear no similarity to natural bases, and/or may be synthesized, e.g., by organic synthesis. In certain embodiments, a nucleobase comprises any atom or group of atoms in a nucleoside or nucleotide, where the atom or group of atoms is capable of interacting with a base of another nucleic acid with or without the use of hydrogen bonds. In certain embodiments, an unnatural nucleobase is not derived from a natural nucleobase. It should be noted that unnatural nucleobases do not necessarily possess basic properties, however, they are referred to as nucleobases for simplicity. In some embodiments, when referring to a nucleobase, a "(d)" indicates that the nucleobase can be attached to a deoxyribose or a ribose, while "d" without parentheses indicates that the nucleobase is attached to deoxyribose.

In some embodiments, a nucleoside is a compound comprising a nucleobase moiety and a sugar moiety. Nucleosides include, but are not limited to, naturally occurring nucleosides (as found in DNA and RNA), abasic nucleosides, modified nucleosides, and nucleosides having mimetic bases and/or sugar groups. Nucleosides include nucleosides comprising any variety of substituents. A nucleoside can be a glycoside compound formed through glycosidic linking between a nucleic acid base and a reducing group of a sugar.

As used herein, "nucleotide" refers to a compound comprising a nucleoside moiety and a phosphate moiety. Exemplary natural nucleotides include, without limitation, adenosine triphosphate (ATP), uridine triphosphate (UTP), cytidine triphosphate (CTP), guanosine triphosphate (GTP), adenosine diphosphate (ADP), uridine diphosphate (UDP), cytidine diphosphate (CDP), guanosine diphosphate (GDP), adenosine monophosphate (AMP), uridine monophosphate (UMP), cytidine monophosphate (CMP), and guanosine monophosphate (GMP), deoxyadenosine triphosphate (dATP), deoxythymidine triphosphate (dTTP), deoxycytidine triphosphate (dCTP), deoxyguanosine triphosphate (dGTP), deoxyadenosine diphosphate (dADP), thymidine diphosphate (dTDP), deoxycytidine diphosphate (dCDP), deoxyguanosine diphosphate (dGDP), deoxyadenosine monophosphate (dAMP), deoxythymidine monophosphate (dTMP), deoxycytidine monophosphate (dCMP), and deoxyguanosine monophosphate (dGMP). Exemplary natural deoxyribonucleotides, which comprise a deoxyribose as the sugar moiety, include dATP, dTTP, dCTP, dGTP, dADP, dTDP, dCDP, dGDP, dAMP, dTMP, dCMP, and dGMP. Exemplary natural ribonucleotides, which comprise a ribose as the sugar moiety, include ATP, UTP, CTP, GTP, ADP, UDP, CDP, GDP, AMP, UMP, CMP, and GMP.

A polynucleotide, as used herein, refers to DNA, RNA, DNA- or RNA-like polymers such as peptide nucleic acids (PNA), locked nucleic acids (LNA), phosphorothioates, and the like, which examples of which are well-known in the art, and may contain unnatural bases. Polynucleotides can be synthesized in automated synthesizers, e.g., using phosphoroamidite chemistry or other chemical approaches adapted for synthesizer use.

DNA includes, but is not limited to, complementary DNA (cDNA) and genomic DNA (gDNA). DNA may be attached, by covalent or non-covalent means, to another molecule, including, but not limited to, RNA and peptide. RNA includes coding RNA, e.g. messenger RNA (mRNA). RNA also includes non-coding RNA, e.g. ribosomal RNA (rRNA). RNA also includes transfer RNA (tRNA), RNA interference (RNAi), small nucleolar RNA (snoRNA), microRNA (miRNA), small interfering RNA (siRNA) (also referred to as short interfering RNA), small nuclear RNA (snRNA), extracellular RNA (exRNA), PIWI-interacting RNA (piRNA), and long non-coding RNA (long ncRNA). In some embodiments, RNA is rRNA, tRNA, RNAi, snoRNA, microRNA, siRNA, snRNA, exRNA, piRNA, long ncRNA, or any combination or hybrid thereof. In some instances, RNA is a component of a ribozyme. DNA and RNA can be in any form, including, but not limited to, linear, circular, supercoiled, single-stranded, and double-stranded.

A peptide nucleic acid (PNA) is a synthetic DNA/RNA analog wherein a peptide-like backbone replaces the sugar-phosphate backbone of DNA or RNA. PNA oligomers show higher binding strength and greater specificity in binding to complementary DNAs, with a PNA/DNA base mismatch being more destabilizing than a similar mismatch in a DNA/DNA duplex. This binding strength and specificity also applies to PNA/RNA duplexes. PNAs are not easily recognized by either nucleases or proteases, making them resistant to enzyme degradation. PNAs are also stable over a wide pH range. See also Nielsen P E, Egholm M, Berg R H, Buchardt O (December 1991). "Sequence-selective recognition of DNA by strand displacement with a thymine-substituted polyamide", Science 254 (5037): 1497-500. doi:10.1126/science.1962210. PMID 1962210; and, Egholm M, Buchardt O, Christensen L, Behrens C, Freier S M, Driver D A, Berg R H, Kim S K, Nordén B, and Nielsen P E (1993), "PNA Hybridizes to Complementary Oligonucleotides Obeying the Watson-Crick Hydrogen Bonding Rules". *Nature* 365 (6446): 566-8. doi:10.1038/365566a0. PMID 7692304; the disclosures of each of which are hereby incorporated by reference in their entirety.

A locked nucleic acid (LNA) is a modified RNA nucleotide, wherein the ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers can be synthesized chemically and are commercially available. The locked ribose conformation enhances base stacking and backbone pre-organization. See, for example, Kaur, H; Arora, A; Wengel, J; Maiti, S (2006), "Thermodynamic, Counterion, and Hydration Effects for the Incorporation of Locked Nucleic Acid Nucleotides into DNA Duplexes", *Biochemistry* 45 (23): 7347-55. doi:10.1021/bi060307w. PMID 16752924; Owczarzy R.; You Y., Groth C. L., Tataurov A. V. (2011), "Stability and mismatch discrimination of locked nucleic acid-DNA duplexes.", *Biochem.* 50 (43): 9352-9367. doi:10.1021/bi200904e. PMC 3201676. PMID 21928795; Alexei A. Koshkin; Sanjay K. Singh, Poul Nielsen, Vivek K. Rajwanshi, Ravindra Kumar, Michael Meldgaard, Carl Erik Olsen, Jesper Wengel (1998), "LNA (Locked Nucleic Acids): Synthesis of the adenine, cytosine, guanine, 5-methylcytosine, thymine and uracil bicyclonucleoside monomers, oligomerisation, and unprecedented nucleic acid recognition", *Tetrahedron* 54 (14): 3607-30. doi:10.1016/50040-4020(98)00094-5; and, Satoshi Obika; Daishu Nanbu, Yoshiyuki Hari, Ken-ichiro Morio, Yasuko In, Toshimasa Ishida, Takeshi Imanishi (1997), "Synthesis of 2'-O,4'-C-methyleneuridine and -cytidine. Novel bicyclic nucleosides having a fixed C3'-endo sugar puckering", *Tetrahedron Lett.* 38 (50): 8735-8. doi:10.1016/0040-4039(97)10322-7; the disclosures of each of which are hereby incorporated by reference in their entirety.

As used herein, the term "gene" refers to a polynucleotide that encodes the synthesis of a gene product, such as an RNA or protein.

A molecular beacon or molecular beacon probe is an oligonucleotide hybridization probe that can detect the presence of a specific nucleic acid sequence in a homogenous solution. Molecular beacons are hairpin shaped molecules with an internally quenched fluorophore whose fluorescence is restored when they bind to a target nucleic acid sequence. See, for example, Tyagi S, Kramer F R (1996), "Molecular beacons: probes that fluoresce upon hybridization", *Nat Biotechnol.* 14 (3): 303-8. PMID 9630890; Tapp I, Malmberg L, Rennel E, Wik M, Syvänen A C (2000 April), "Homogeneous scoring of single-nucleotide polymorphisms: comparison of the 5'-nuclease TaqMan assay and Molecular Beacon probes", *Biotechniques* 28 (4): 732-8. PMID 10769752; and, Akimitsu Okamoto (2011), "ECHO probes: a concept of fluorescence control for practical nucleic acid sensing", *Chem. Soc. Rev.* 40: 5815-5828; the disclosures of each of which are hereby incorporated by reference in their entirety.

As used herein, the term "unnatural base" refers to a base other than A, C, G, T, U, and other naturally occurring bases (e.g., 5-methylcytosine, pseudouridine, and inosine).

As used herein, the term "unnatural base pair" refers to two bases that bond with each other and lie on opposing strands of a double-stranded polynucleotide (which may be, e.g., an at least partially self-hybridized molecule or a partially or completely hybridized pair of molecules), wherein at least one of the two bases is an unnatural base.

As used herein, a "semi-synthetic organism" is an organism comprising an unnatural component, e.g., an expanded genetic alphabet including one or more unnatural bases.

The section headings used herein are for organizational purposes only and are not to be construed as limiting the subject matter described.

Methods and Compositions Comprising Unnatural Base Pairs

Figure 1B:
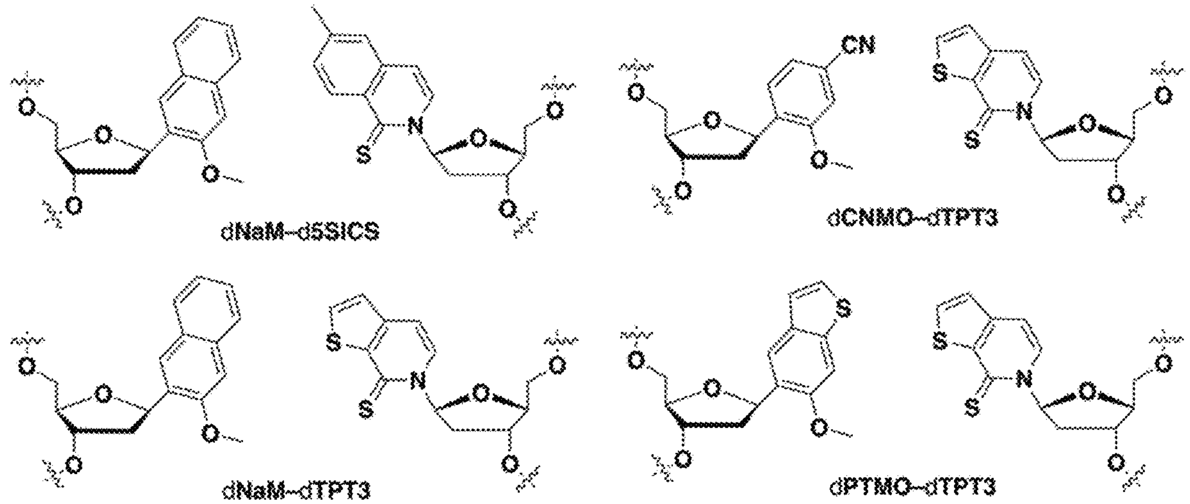
FIG. 1B depicts unnatural base pairs (UBP).

Disclosed herein in certain embodiments are in vitro and in vivo methods and compositions for producing a nucleic acid with an expanded genetic alphabet (FIG. 1). In some instances, the nucleic acid encodes an unnatural protein, wherein the unnatural protein comprises an unnatural amino acid. In some cases, an in vivo method or composition described herein utilizes or comprises a semi-synthetic organism. In some instances, the method comprises incorporating at least one unnatural base pair (UBP) into one or more nucleic acids. Such base pairs are formed by pairing between the nucleobases of two nucleosides. In an exemplary workflow, DNA 101 coding for a protein 102 and a tRNA 103, the template strand coding regions for the protein and tRNA comprising unnatural nucleobases (X, Y) that are complementary, capable of forming a base pair, and/or configured to form a base pair is transcribed 104 to generate a tRNA 106 and mRNA 107. After charging the tRNA with an unnatural amino acid 105, the mRNA 107 is translated 108 to generate a protein 110 comprising one or more unnatural amino acids 109. Methods and compositions described herein in some instances allow for site-specific incorporation of unnatural amino acids with high fidelity and yield. Also described herein are semi-synthetic organisms comprising an expanded genetic alphabet, and methods for using the semi-synthetic organisms to produce protein products, including those comprising at least one unnatural amino acid residue.

Selection of unnatural nucleobases allows for optimization of one or more steps in the methods described herein. For example, nucleobases are selected for high efficiency replication, transcription, and/or translation. In some instances, more than one unnatural nucleobase pair is utilized for the methods described herein. For example, a first set of nucleobases comprising a deoxyribo moiety are used for DNA replication (such as a first nucleobase and a second nucleobase, configured to form a first base pair), and a second set of nucleobases (such as a third nucleobase and a fourth nucleobase, wherein the third and fourth nucleobases are attached to ribose, configured to form a second base pair) are used for transcription/translation. In some embodiments, a first set of nucleobases is used to construct a plasmid (such as a first nucleobase and a second nucleobase, configured to form a first base pair), a second set of nucleobases is used for replication (such as a third nucleobase and a fourth nucleobase, configured to form a second base pair), and a third set of bases is used for transcription/translation (such as a fifth and sixth nucleobase, configured to form a third base pair). Complementary pairing between a nucleobase of the first set and a nucleobase of the second set in some instances allows for transcription of genes to generate tRNA or proteins from a DNA template comprising nucleobases from the first set. Complementary pairing between nucleobases of the second set (second base pair) in some instances allows for translation by matching tRNAs comprising unnatural nucleic acids and mRNA. In some cases, nucleobases in the first set are attached to a deoxyribose moiety. In some cases, nucleobases in the first set are attached to ribose moiety. In some instances, nucleobases of both sets are unique. In some instances, at least one nucleobase is the same in both sets. In some instances, a first nucleobase and a third nucleobase are the same. In some embodiments, the first base pair and the second base pair are not the same. In some cases, the first base pair, the second base pair, and the third base pair are not the same.

In one aspect, provided herein is an in vivo method of producing a protein comprising an unnatural amino acid, the method comprising:

- transcribing a DNA template comprising a first unnatural base and a second unnatural base that is complementary to, capable of forming a base pair with, and/or configured to form a base pair with the first unnatural base to incorporate a third unnatural base into a mRNA, the third unnatural base being complementary to, capable of forming a base pair with, and/or configured to form a first unnatural base pair with the first unnatural base;
- transcribing the DNA template to incorporate a fourth unnatural base into a tRNA, wherein the fourth unnatural base is complementary to, capable of forming a base pair with, and/or configured to form a second unnatural base pair with the second unnatural base, wherein the first unnatural base pair and the second unnatural base pair are not the same; and
- translating a protein from the mRNA and tRNA, wherein said protein comprises an unnatural amino acid.

Nucleic Acid Molecules

In some embodiments, a nucleic acid (e.g., also referred to herein as nucleic acid molecule of interest) is from any source or composition, such as DNA, cDNA, gDNA (genomic DNA), RNA, siRNA (short inhibitory RNA), RNAi, tRNA, mRNA or rRNA (ribosomal RNA), for example, and is in any form (e.g., linear, circular, supercoiled, single-stranded, double-stranded, and the like). In some embodiments, nucleic acids comprise nucleotides, nucleosides, or polynucleotides. In some cases, nucleic acids comprise natural and unnatural nucleic acids. In some cases, a nucleic acid also comprises unnatural nucleic acids, such as DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Exemplary natural deoxyribonucleotides include dATP, dTTP, dCTP, dGTP, dADP, dTDP, dCDP, dGDP, dAMP, dTMP, dCMP, and dGMP. Exemplary natural ribonucleotides include ATP, UTP, CTP, GTP, ADP, UDP, CDP, GDP, AMP, UMP, CMP, and GMP. For natural RNA, the uracil-containing nucleoside is uridine. A nucleic acid sometimes is a vector, plasmid, phagemid, autonomously replicating sequence (ARS), centromere, artificial chromosome, yeast artificial chromosome (e.g., YAC) or other nucleic acid able to replicate or be replicated in a host cell. In some cases, an unnatural nucleic acid is a nucleic acid analogue. In additional cases, an unnatural nucleic acid is from an extracellular source. In other cases, an unnatural nucleic acid is available to the intracellular space of an organism provided herein, e.g., a genetically modified organism. In some embodiments, an unnatural nucleotide is not a natural nucleotide. In some embodiments, a nucleotide that does not comprise a natural base comprises an unnatural nucleobase.

Unnatural Nucleic Acids

A nucleotide analog, or unnatural nucleotide, comprises a nucleotide which contains some type of modification to either the base, sugar, or phosphate moieties. The term "modification" (and related grammatical forms such as "modified") does not necessarily imply that the nucleotide analog or unnatural nucleotide is prepared by directly altering a natural nucleotide, but rather that the nucleotide analog or unnatural nucleotide differs from the natural nucleotide. In some embodiments, a modification comprises a chemical modification. In some cases, modifications occur at the 3'OH or 5'OH group, at the backbone, at the sugar component, or at the nucleotide base. Modifications, in some instances, optionally include non-naturally occurring linker molecules and/or interstrand or intrastrand cross links. In one aspect, the modified nucleic acid comprises modification of one or more of the 3'OH or 5'OH group, the backbone, the sugar component, or the nucleotide base, and/or addition of non-naturally occurring linker molecules. In one aspect, a modified backbone comprises a backbone other than a phosphodiester backbone. In one aspect, a modified sugar comprises a sugar other than deoxyribose (in modified DNA) or other than ribose (modified RNA). In one aspect, a modified base comprises a base other than adenine, guanine, cytosine or thymine (in modified DNA), or a base other than adenine, guanine, cytosine or uracil (in modified RNA). In some embodiments, an unnatural nucleotide comprises an unnatural base. In some embodiments, an unnatural base is a base with a ring or ring system other than a purine or pyrimidine (where a purine and a pyrimidine encompass purines and pyrimidines with exocyclic substituents), or comprises a ring or ring system containing one or more non-nitrogen heteroatoms and/or no nitrogens.

In some embodiments, the nucleic acid comprises at least one modified base. In some instances, the nucleic acid comprises 2, 3, 4, 5, 6, 7, 8, 9, 10, 15, 20, or more modified bases. In some cases, modifications to the base moiety include natural and synthetic modifications of adenine (A), cytosine (C), guanine (G), and thymine (T)/uracil (U), as well as different purine or pyrimidine bases. In some embodiments, a modification is to a modified form of adenine, guanine cytosine or thymine (in modified DNA) or a modified form of adenine, guanine cytosine or uracil (modified RNA).

Figure 2:
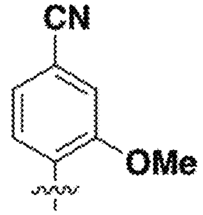
FIG. 2 depicts dXTP analogs. Ribose and phosphates have been omitted for clarity.
Figure 2:
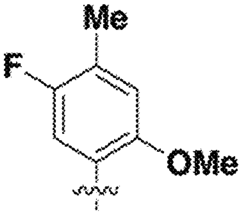
Figure 2:
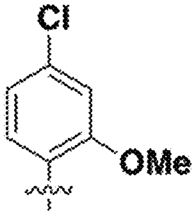
Figure 2:
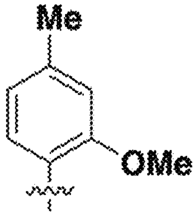
Figure 2:
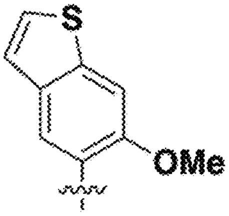
Figure 2:
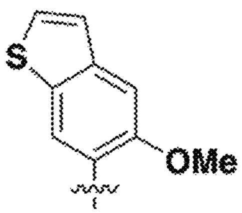
Figure 2:
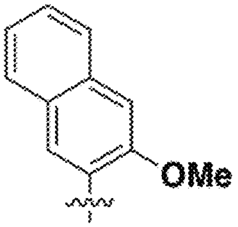
Figure 4A:
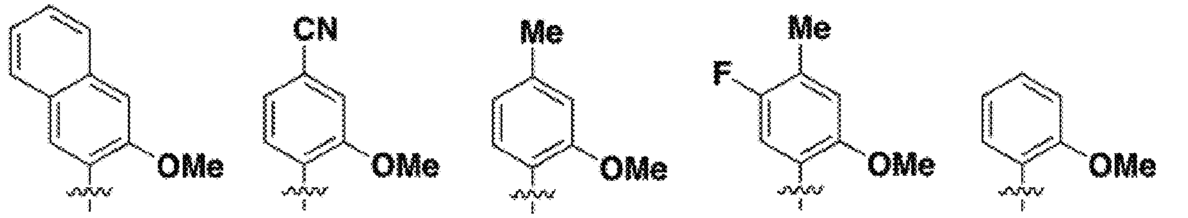
FIG. 4A depicts ribonucleotide XTP analogs. Ribose and phosphates have been omitted for clarity.
Figure 4A:
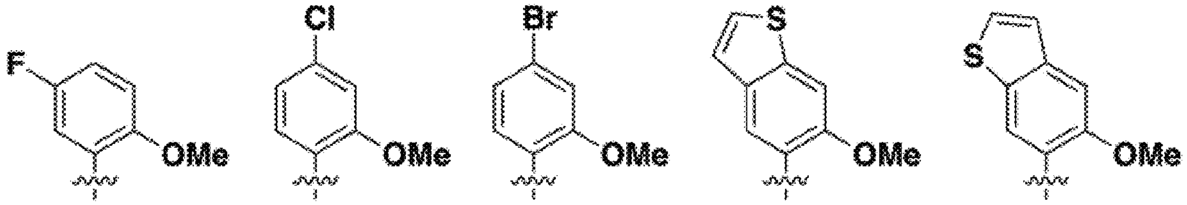
Figure 4B:
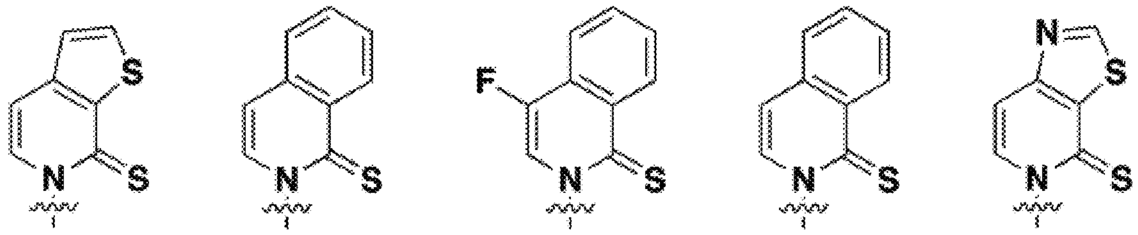
FIG. 4B depicts ribonucleotide YTP analogs. Ribose and phosphates have been omitted for clarity.

A modified base of a unnatural nucleic acid includes, but is not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, O-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl ($-C{\equiv}C-CH_3$) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thio-guanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke and Lebleu Eds., CRC Press, 1993, 273-288. Additional base modifications can be found, for example, in U.S. Pat. No. 3,687,808; Englisch et al., Angewandte Chemie, International Edition, 1991, 30, 613. In some instances, an unnatural nucleic acid comprises a nucleobase of FIG. 2. In some instances, an unnatural nucleic acid comprises a nucleobase of FIG. 4A. In some instances, an unnatural nucleic acid comprises a nucleobase of FIG. 4B.

Unnatural nucleic acids comprising various heterocyclic bases and various sugar moieties (and sugar analogs) are available in the art, and the nucleic acid, in some cases, includes one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo [2,3-d] pyrimidin-5-yl, 2-amino-4-oxopyrolo [2,3-d] pyrimidin-5-yl, 2-amino-4-oxopyrrolo [2,3-d] pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, a modified base of an unnatural nucleic acid is depicted below, wherein the wavy line identifies a point of attachment to the sugar of a nucleoside or nucleotide (e.g., deoxyribose or ribose).

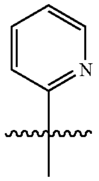
d2Py

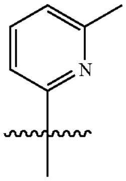
d3MPy

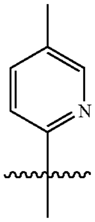
d4MPy

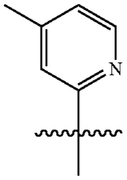
d5MPy

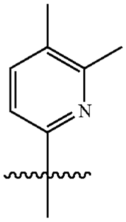
d34DMPy

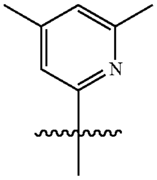
d35DMPy

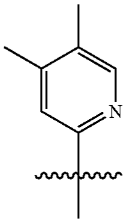
d45DMPy

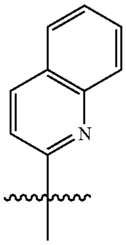
dQL

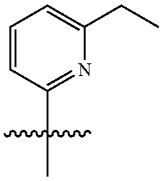
dEPy

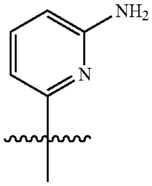
dAPy

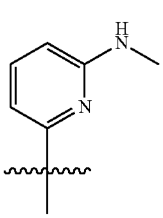
dMAPy

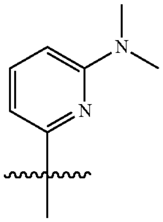
dDMAPy

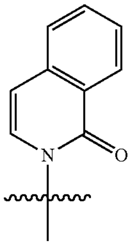
ICS

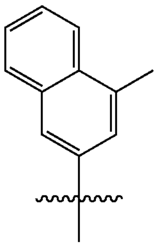
3MN

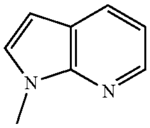
7AI

-continued

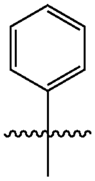
BEN

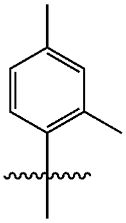
DM5

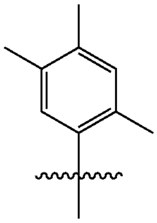
TM

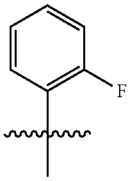
2FB

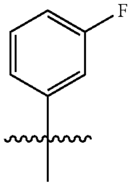
3FB

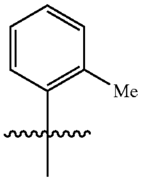
MM1

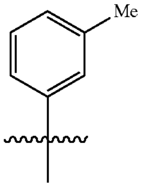
MM2

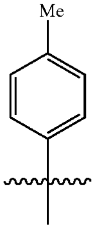
MM3

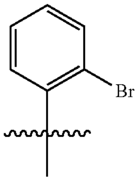
2Br

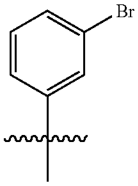
3Br

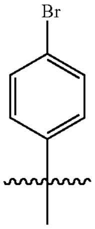
4Br

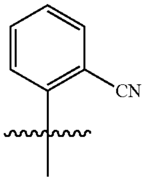
2CN

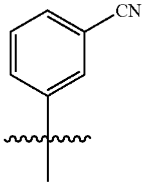
3CN

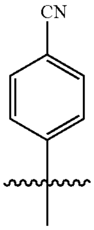
4CN

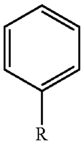
BEN

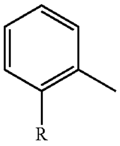
MM

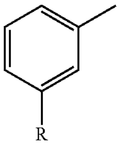
MM2

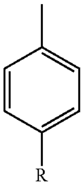
MM3

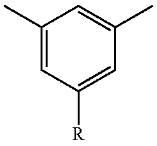
DM

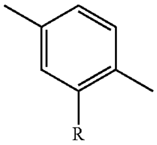
DM2

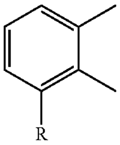
DM3

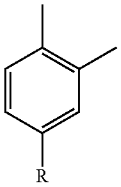
DM4

-continued
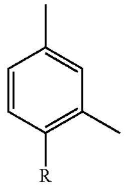
DM5
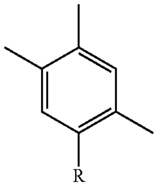
TM
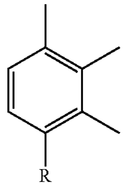
TM2
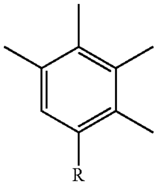
TM3
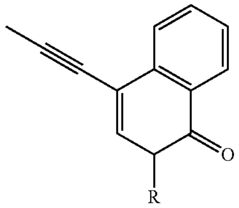
dPICS
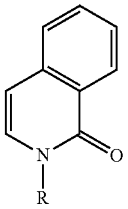
ICS
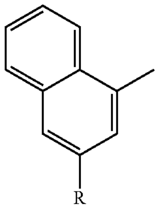
3MN
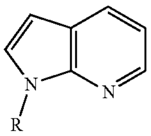
7AI
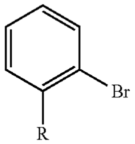
2Br
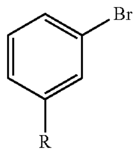
3Br
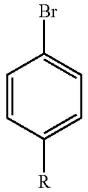
4Br
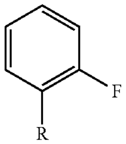
2FB
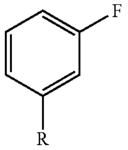
3FB
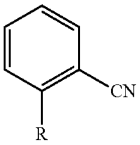
2CN
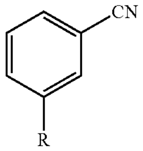
3CN
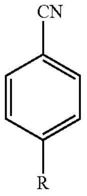
4CN
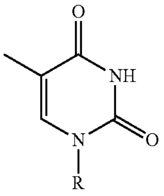
dT
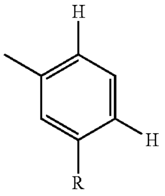
dH
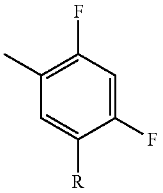
dF
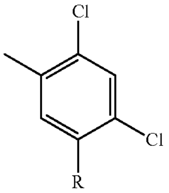
dL
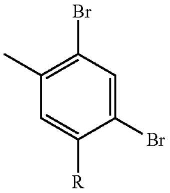
dB
-continued
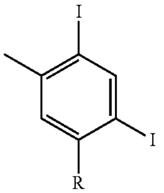
dI
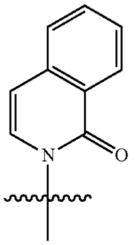
ICS
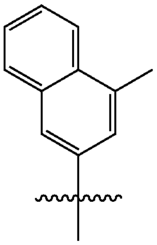
3MN
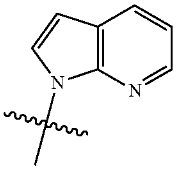
7AI
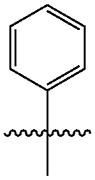
BEN
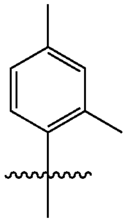
DM5
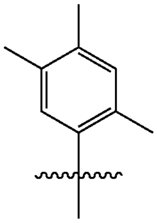
TM
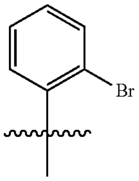
2Br
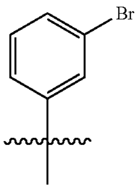
3Br
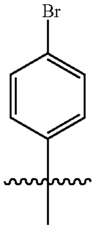
4Br
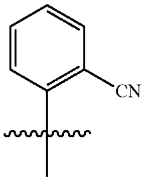
2CN
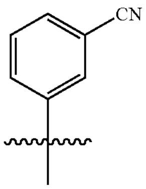
3CN
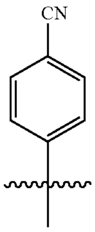
4CN
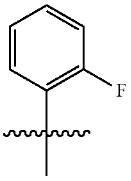
2FB
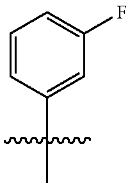
3FB
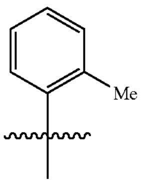
MM1
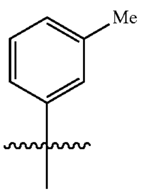
MM2
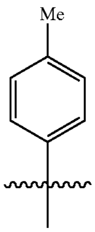
MM3

-continued
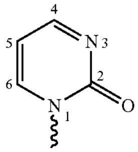
2-pyrimidinone
dZeb
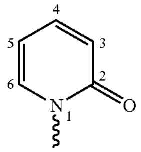
2-pyridone
2OPy
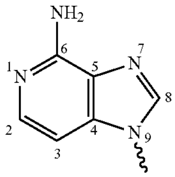
3-deazaadenine
3DA
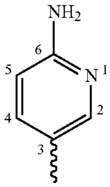
6-aminopyridin-3-yl
6AmPy
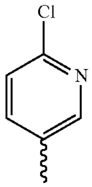
6-chloropyridin-3yl
6ClPy
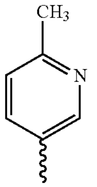
6-methylpyridin-3-yl
6MePy
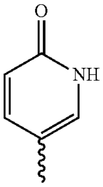
6-oxopyridin-3-yl
6OPy
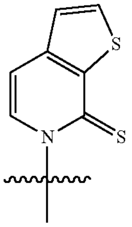
dTPT3
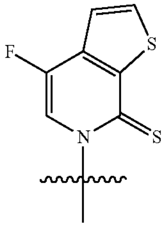
dFTPT3
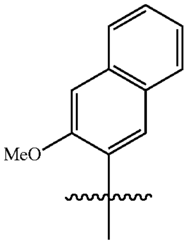
dNaM
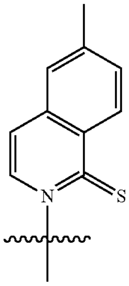
d5SICS
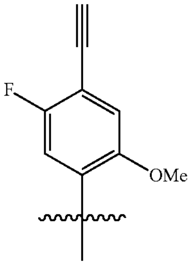
dFEMO
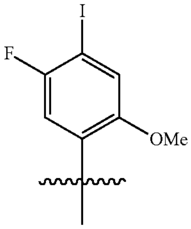
dFIMO
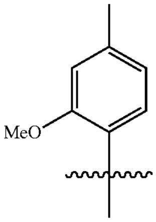
dMMO2
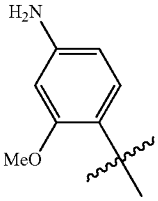
dAMO1
-continued
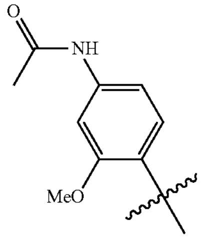
dAMO2
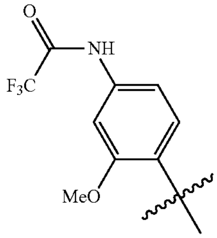
dAMO3
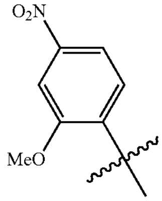
dNMO1
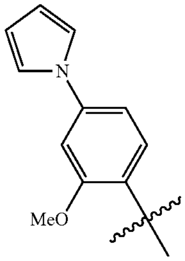
dPMO1
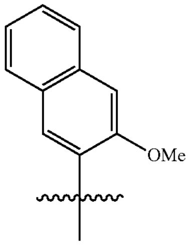
dNaM
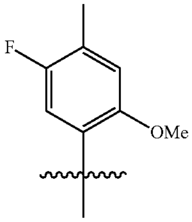
d5FM
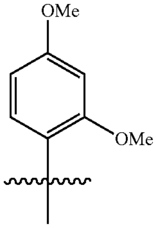
dDMO
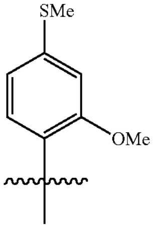
dTMO
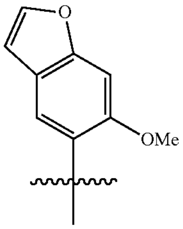
dFMO
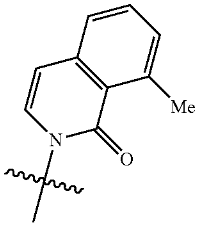
MICS
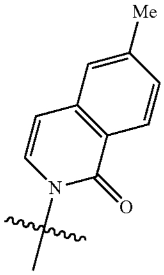
5MICS
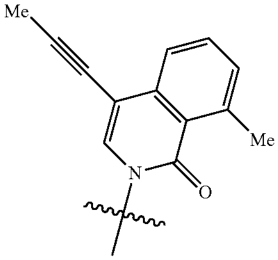
PIM -continued
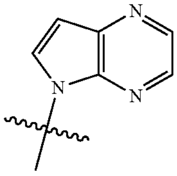
PP
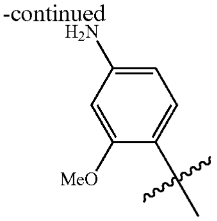
dAMO1
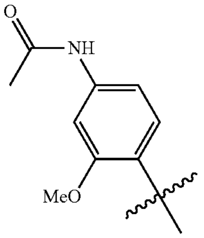
dAMO2
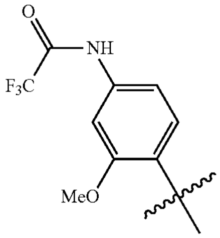
dAMO3
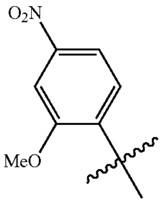
dNMO1
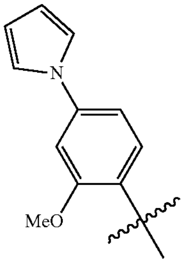
dPMO1
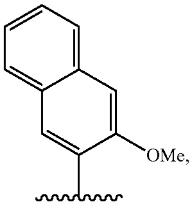
(NaM)
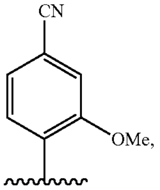
(CNMO)
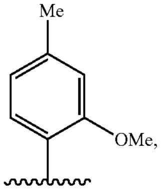
(MMO2)
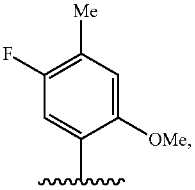
(5FM)
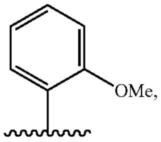
(2OMe)
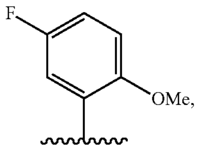
(5F2OMe)
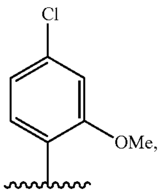
(ClMO)
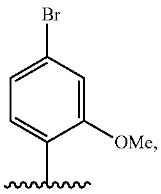
(BrMO)
-continued
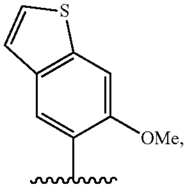
(PTMO)
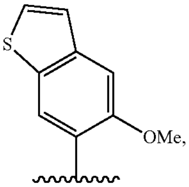
(MTMO)
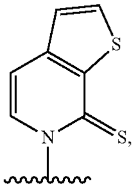
(TPT3)
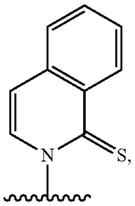
(SICS)
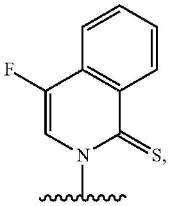
(FSICS)
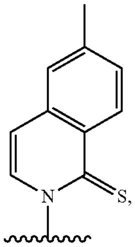
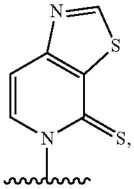
(TAT1)
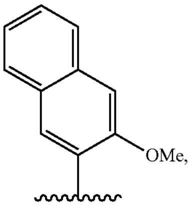
(dNaM)
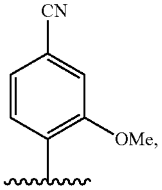
(dCNMO)
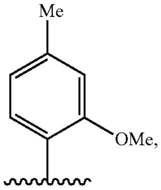
(dMMO2)
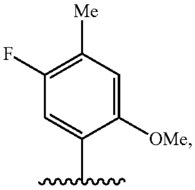
(d5FM)
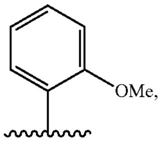
(d2OMe)
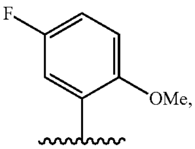
(d5F2OMe)
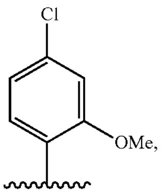
(dClMO)
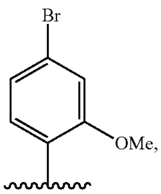
(dBrMO)
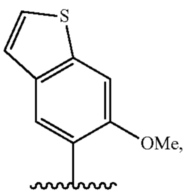
(dPTMO)

-continued

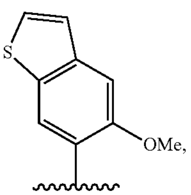
(dMTMO)

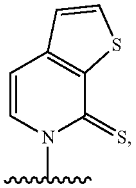
(dTPT3)

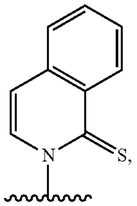
(dSICS)

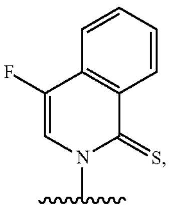
(dFSICS)

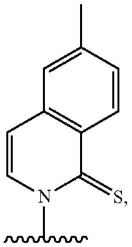
and

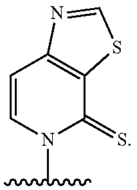 [SMILES: *n1ccc2ncsc2c1=S]
(dTAT1)

In some embodiments, the unnatural base (such as the at least one of the first unnatural base, the second unnatural base, the third unnatural base, or the fourth unnatural base of the method of producing a protein comprising an unnatural amino acid described herein) is selected from the group consisting of:

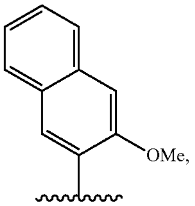
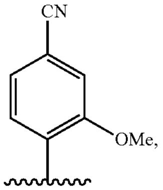
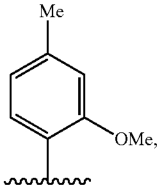
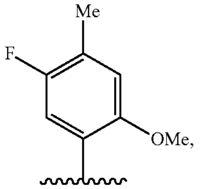
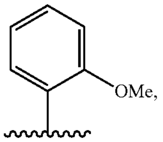
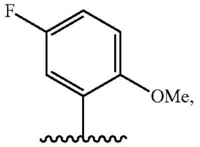
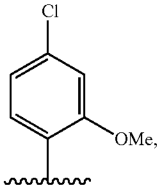
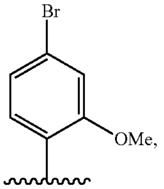

-continued

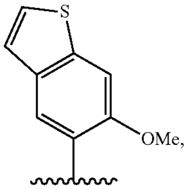
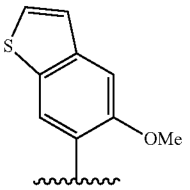
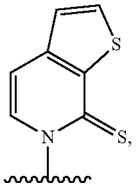
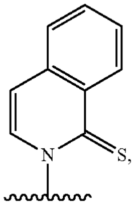
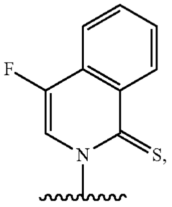
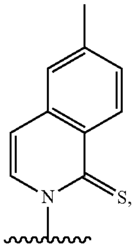
and
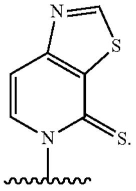

In some embodiments, the unnatural base is selected from the group consisting of:

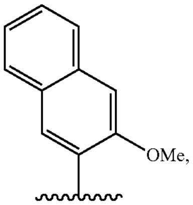
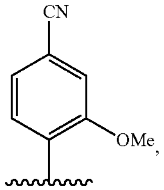 [SMILES: *c1ccc(C#N)cc1OC]
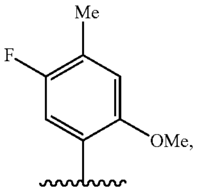
and
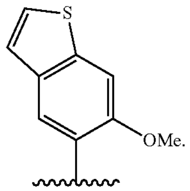

In some embodiments, the unnatural base is selected from the group consisting of:

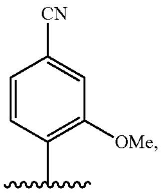
and
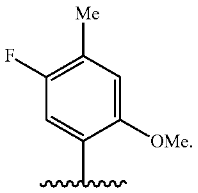

In some embodiments, the unnatural base is selected from the group consisting of

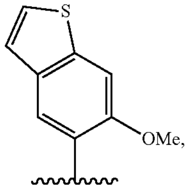,
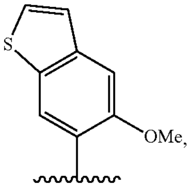,
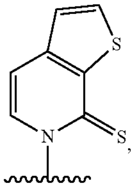,
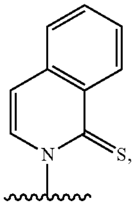,
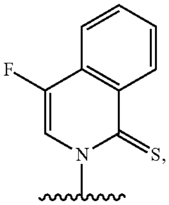,
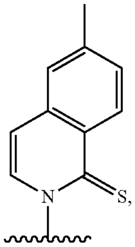, and
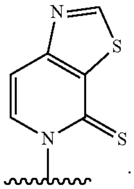.

In some embodiments, the unnatural base is

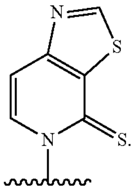.

In some embodiments, the unnatural base is selected from:

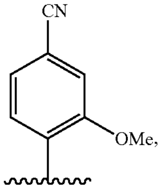,
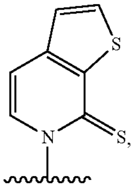,
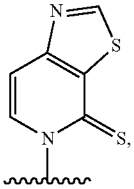,
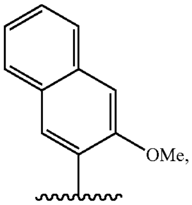, and
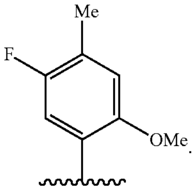.

In some embodiments, the unnatural base (such as the first or second unnatural base of the method of producing a protein comprising an unnatural amino acid described herein) is

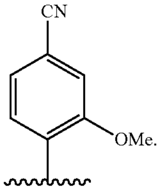.

In some embodiments, the unnatural base (such as the first or second unnatural base of the method of producing a protein comprising an unnatural amino acid described herein) is

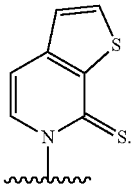.

In some embodiments, the first unnatural base is

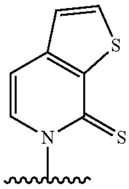 [SMILES: *n1ccc2ccsc2c1=S]

and the second unnatural base is

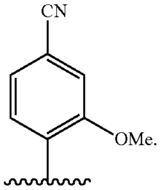 [SMILES: *c1ccc(C#N)cc1OC].

In some embodiments, the unnatural base (such as the third or fourth unnatural base of the method of producing a protein comprising an unnatural amino acid described herein) is

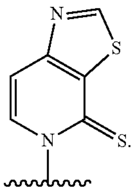 [SMILES: *n1ccc2ncsc2c1=S].

In some embodiments, the third unnatural base is

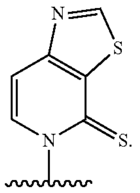 [SMILES: *n1ccc2ncsc2c1=S]

In some embodiments, the fourth unnatural base is

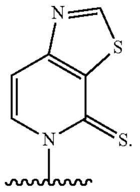 [SMILES: *n1ccc2ncsc2c1=S]

In some embodiments, the unnatural base (such as the third or fourth unnatural base of the method of producing a protein comprising an unnatural amino acid described herein) is

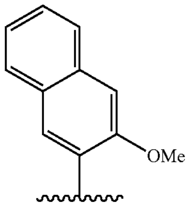
or
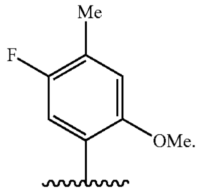

In some embodiments, the third unnatural base is

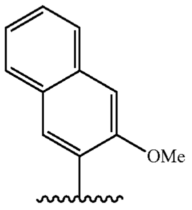
or
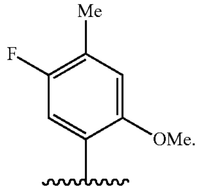

In some embodiments, the fourth unnatural base is

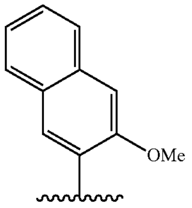
or
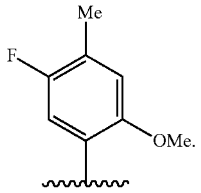

In some embodiments, the first unnatural base is

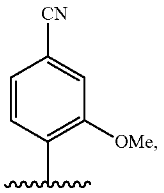 [SMILES: *c1ccc(C#N)cc1OC]

the second unnatural base is

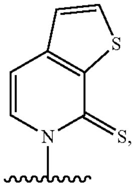 [SMILES: *n1ccc2ccsc2c1=S]

the third unnatural base is

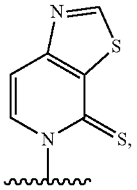 [SMILES: *n1ccc2ncsc2c1=S]

and the fourth unnatural base is

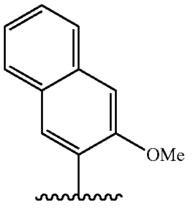
or
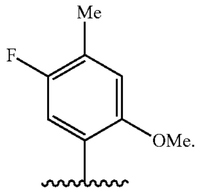

In some embodiments, the first unnatural base is

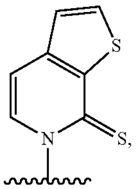 [SMILES: *n1ccc2ccsc2c1=S]

the second unnatural base is

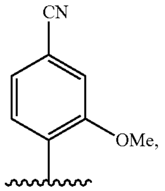 [SMILES: *c1ccc(C#N)cc1OC]

the third unnatural base is

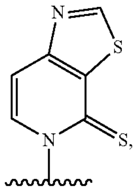 [SMILES: *n1ccc2ncsc2c1=S]

and the fourth unnatural base is

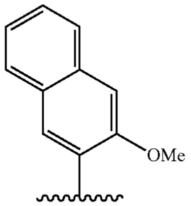

or

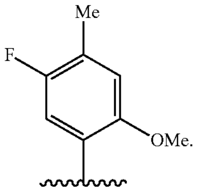

In some embodiments, the first unnatural base is

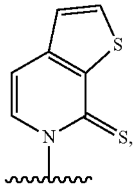 [SMILES: *n1ccc2ccsc2c1=S]

the second unnatural base is

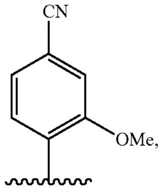 [SMILES: *c1ccc(C#N)cc1OC]

the third unnatural base is

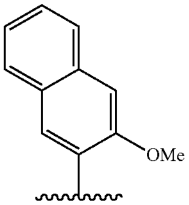

or

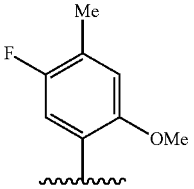

and the fourth unnatural base is

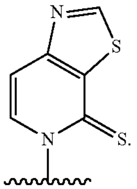 [SMILES: *n1ccc2ncsc2c1=S]

In some embodiments, the third unnatural base is

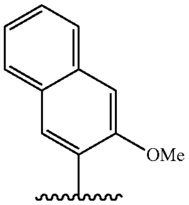

or

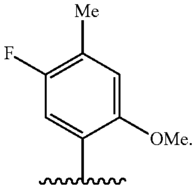

In some embodiments the fourth unnatural base is

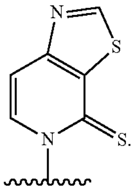 [SMILES: *n1ccc2ncsc2c1=S]

In some embodiments, the first unnatural base is

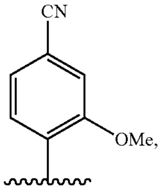 [SMILES: *c1ccc(C#N)cc1OC]

the second unnatural base is

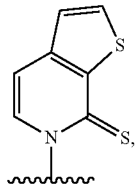 [SMILES: *n1ccc2ccsc2c1=S]

the third unnatural base is

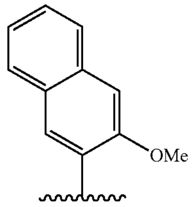

or

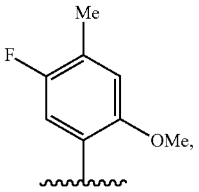

and the fourth unnatural base is

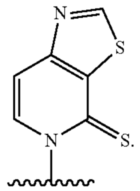 [SMILES: *n1ccc2ncsc2c1=S]

In some embodiments, the third unnatural base and the fourth unnatural base comprise ribose. In some embodiments, the third unnatural base and the fourth unnatural base comprise deoxyribose. In some embodiments, the first and second unnatural bases comprise deoxyribose. In some embodiments, the first and second unnatural bases comprise deoxyribose and the third unnatural base and the fourth unnatural base comprise ribose.

In some embodiments of the method of producing a protein comprising an unnatural amino acid described herein, the DNA comprises at least one unnatural base pair (UBP) selected from:

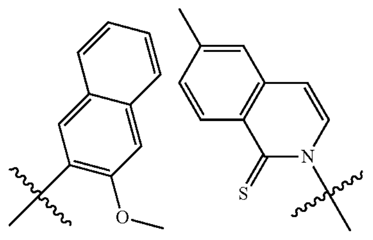

NaM-5SICS

-continued

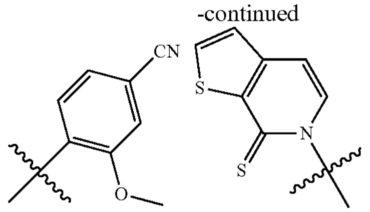

CNMO-TPT3

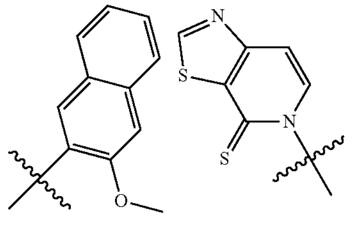

NaM-TAT1

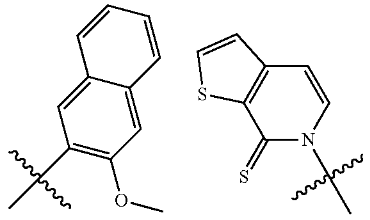

NAM-TPT3

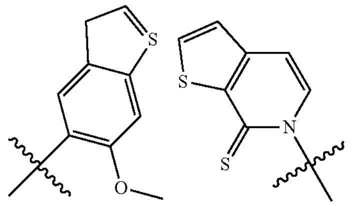

PTMO-TPT3

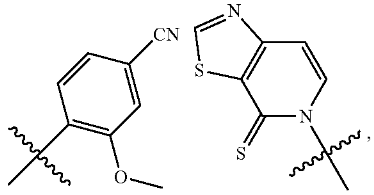

CNMO-TAT1 wherein each sugar moiety is independently any embodiment or variation described herein. In some embodiments, the sugar moiety of both bases in the base pair comprises ribose. In some embodiments, the sugar moiety of both bases in the base pair comprises deoxyribose. In some embodiments, the sugar moiety of one base in the base pair comprises ribose and the sugar moiety of the other base in the base pair comprises deoxyribose. In some embodiments, the DNA template comprises at least one unnatural base pair (UBP) which is NaM-5SICS. In some embodiments, the DNA comprises at least one unnatural base pair (UBP) which is CNMO-TPT3. In some embodiments, the DNA comprises at least one unnatural base pair (UBP) which is NaM-TPT3. In some embodiments, the DNA comprises at least one unnatural base pair (UBP) which is NaM-TAT1. In some embodiments, the DNA comprises at least one unnatural base pair (UBP) which is CNMO-TAT1.

In some embodiments of the method of producing a protein comprising an unnatural amino acid described herein, the DNA comprises at least one unnatural base pair (UBP) selected from the group consisting of

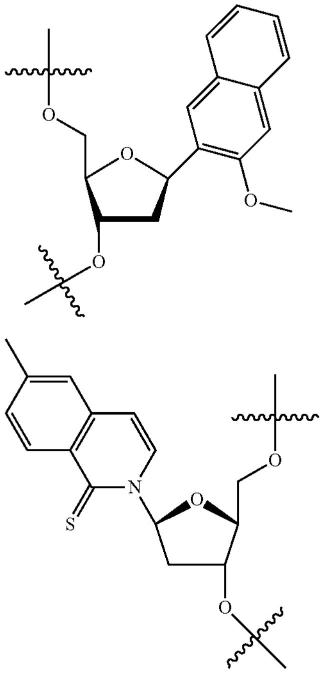
dNaM-d5SICS
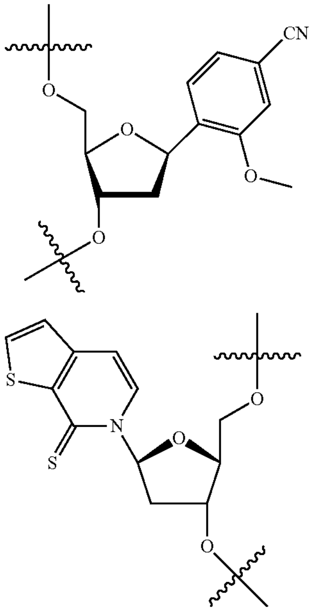
dCNMO-dTPT3
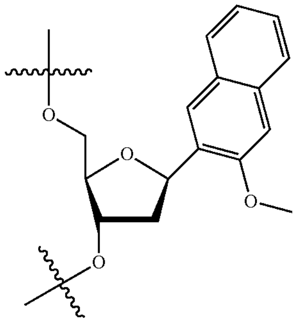
-continued
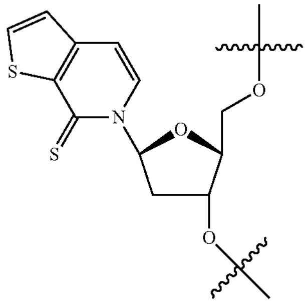
dNaM-dTPT3
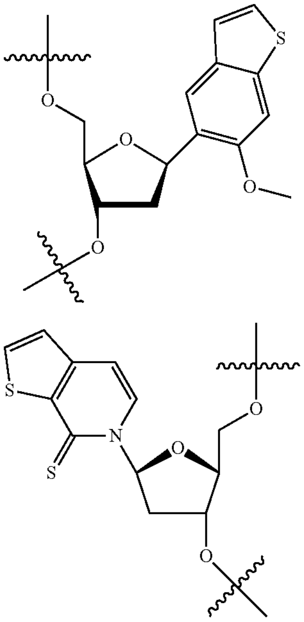
dPTMO-dTPT3
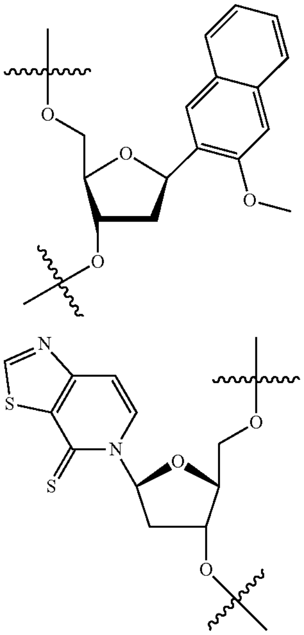
dNaM-dTAT1

-continued

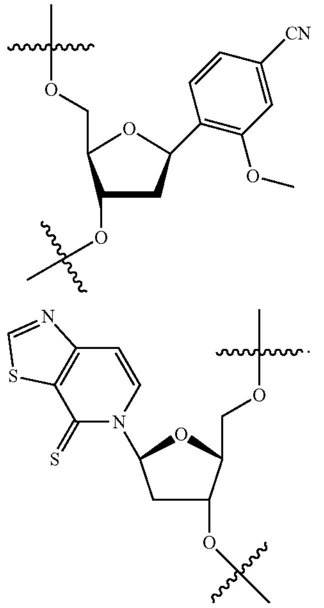

dCNMO-dTAT1

In some embodiments, the DNA comprises at least one unnatural base pair (UBP) which is dNaM-d5SICS. In some embodiments, the DNA comprises at least one unnatural base pair (UBP) which is dCNMO-dTPT3. In some embodiments, the DNA comprises at least one unnatural base pair (UBP) which is dNaM-dTPT3. In some embodiments, the DNA comprises at least one unnatural base pair (UBP) which is dNaM-dTAT1. In some embodiments, the DNA comprises at least one unnatural base pair (UBP) which is dCNMO-dTAT1.

In some embodiments of the method of producing a protein comprising an unnatural amino acid described herein, the DNA comprises at least one unnatural base pair (UBP) selected from:

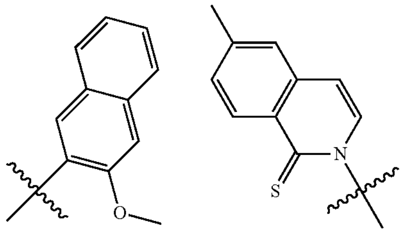

Nam-5SICS

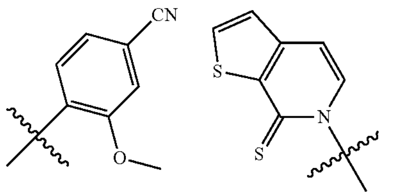

CNMO-TPT3

-continued

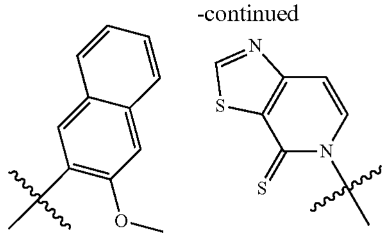

NaM-TAT1

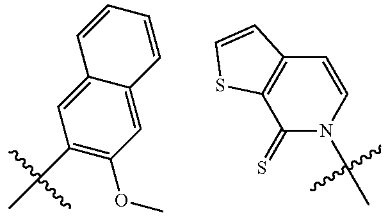

NAM-TPT3

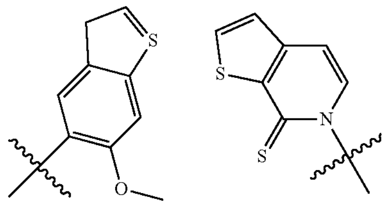

PTMO-TPT3

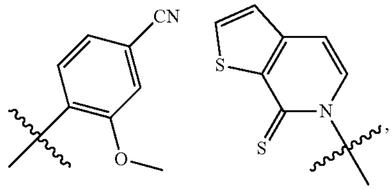

,

CNMO-TAT1 wherein each sugar moiety is independently any embodiment or variation described herein; and wherein the mRNA and the tRNA comprise at least one unnatural base selected from:

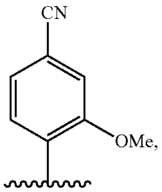

,

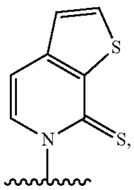

,

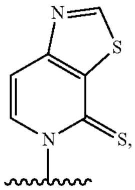

,

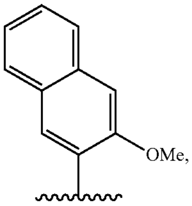

, and

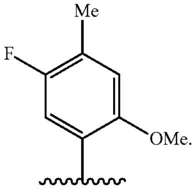

.

In some embodiments, the sugar moiety of both bases in the base pair comprises ribose. In some embodiments, the sugar moiety of both bases in the base pair comprises deoxyribose. In some embodiments, the sugar moiety of one base in the base pair comprises ribose and the sugar moiety of the other base in the base pair comprises deoxyribose. In some embodiments, the DNA comprises at least one unnatural base pair (UBP) which is dNaM-d5SICS. In some embodiments, the DNA comprises at least one unnatural base pair (UBP) which is dCNMO-dTPT3. In some embodiments, the DNA comprises at least one unnatural base pair (UBP) which is dNaM-dTPT3. In some embodiments, the DNA comprises at least one unnatural base pair (UBP) which is dNaM-dTAT1. In some embodiments, the DNA comprises at least one unnatural base pair (UBP) which is dCNMO-dTAT1.

In some embodiments of the method of producing a protein comprising an unnatural amino acid described herein, the DNA comprises at least one unnatural base pair (UBP) selected from the group consisting of

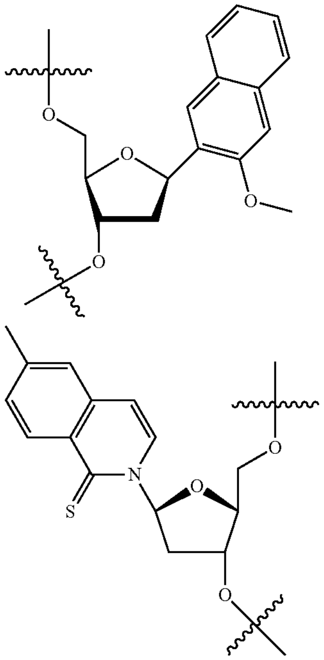

dNaM-d5SICS

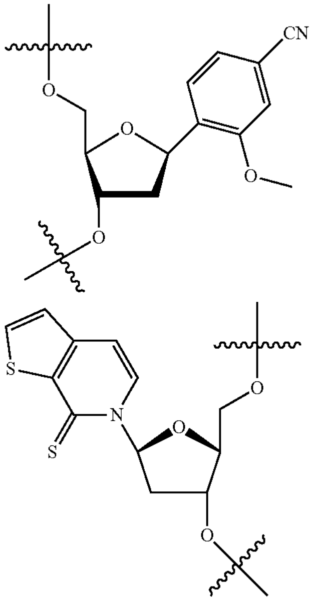

dCNMO-dTPT3

-continued

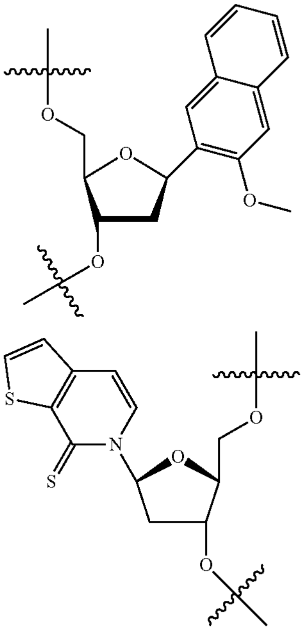

dNaM-dTPT3

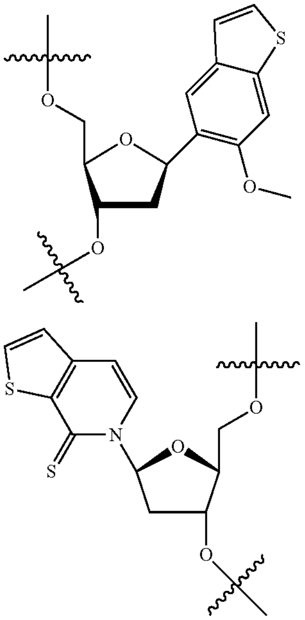

dPTMO-dTPT3

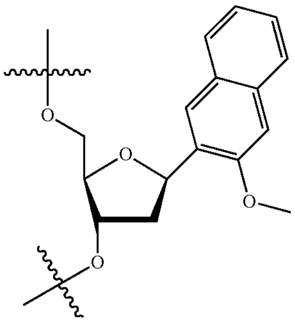

-continued

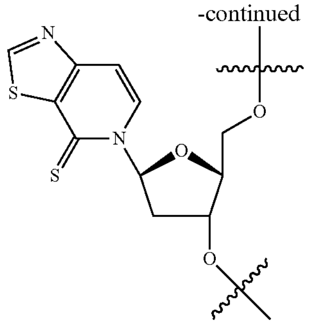

dNaM-dTAT1

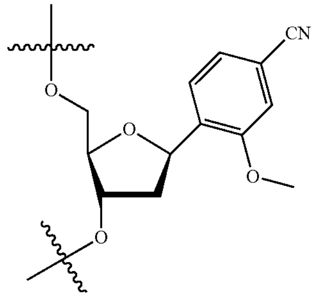

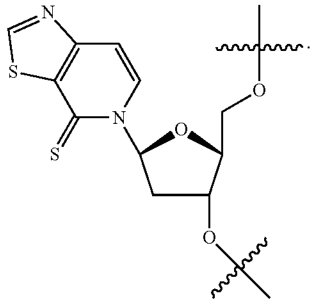

dCNMO-dTAT1 and wherein the mRNA and the tRNA comprise at least one unnatural base selected from:

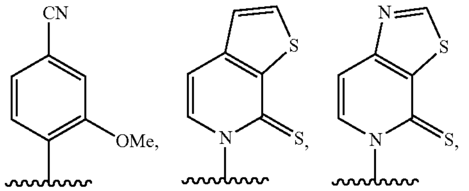

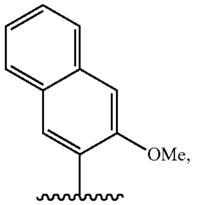

and

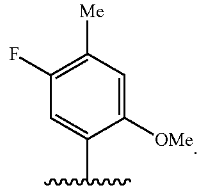

In some embodiments the DNA comprises at least one unnatural base pair (UBP) which is dNaM-d5SICS. In some embodiments, the DNA comprises at least one unnatural base pair (UBP) which is dCNMO-dTPT3. In some embodiments, the DNA comprises at least one unnatural base pair (UBP) which is dNaM-dTPT3. In some embodiments, the DNA comprises at least one unnatural base pair (UBP) which is dNaM-dTAT1. In some embodiments, the DNA comprises at least one unnatural base pair (UBP) which is dCNMO-dTAT1.

In some embodiments, the mRNA and the tRNA comprise an unnatural base selected from

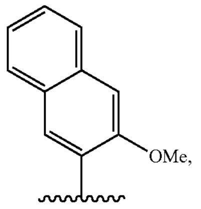

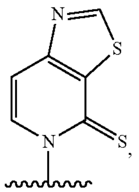

and

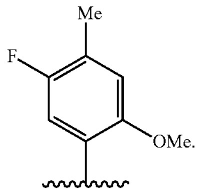

In some embodiments, the mRNA and the tRNA comprise an unnatural base selected from

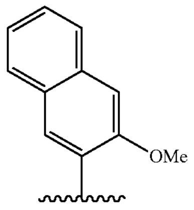 [SMILES: *c1cc2ccccc2cc1OC]

and

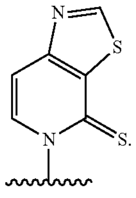 [SMILES: *n1ccc2ncsc2c1=S]

In some embodiments, the mRNA comprises an unnatural base which is

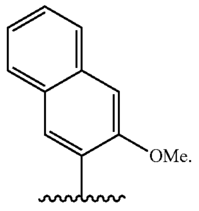

In some embodiments, the mRNA comprises an unnatural base which is

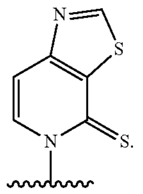

In some embodiments, the mRNA comprises an unnatural base which is

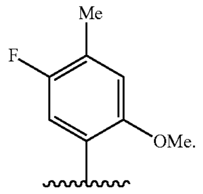 [SMILES: *c1cc(F)c(C)cc1OC]

In some embodiments, the tRNA comprises an unnatural base selected from

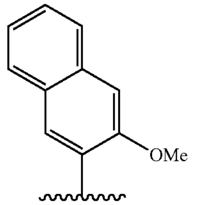

and

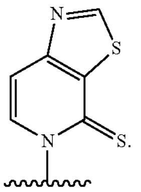

In some embodiments, the tRNA comprises an unnatural base which is

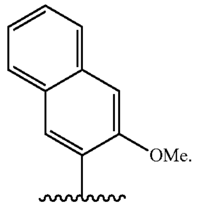 [SMILES: *c1cc2ccccc2cc1OC]

In some embodiments, the tRNA comprises an unnatural base which is

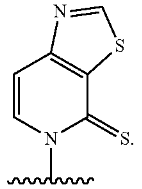 [SMILES: *n1ccc2ncsc2c1=S]

In some embodiments, the tRNA comprises an unnatural base which is

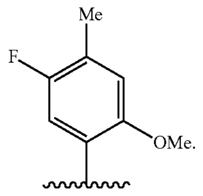 [SMILES: *c1cc(F)c(C)cc1OC]

In some embodiments of the method of producing a protein comprising an unnatural amino acid described herein, the first unnatural base comprises dCNMO, and the second unnatural base comprises dTPT3. In some embodiments, the third unnatural base comprises NaM, and the second unnatural base comprises TAT1.

Also provided herein is a protein comprising at least one unnatural amino acid, wherein the protein is produced according to any of the methods disclosed herein. In some embodiments, the protein comprises at least one unnatural amino acid. In some embodiments, the protein comprises one unnatural amino acid. In some embodiments, the protein comprises two or more unnatural amino acids. In some embodiments, the protein comprises two unnatural amino acids. In some embodiments, the protein comprises three or more unnatural amino acids.

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050; the disclosures of each of which are hereby incorporated by reference in their entirety.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337); the disclosures of each of which are hereby incorporated by reference in their entirety.

In some embodiments, unnatural nucleic acids include modifications at the 5'-position and the 2'-position of the sugar ring (PCT/US94/02993), such as 5'-$CH_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers that have been prepared for incorporation into oligonucleotides wherein the 3' linked nucleoside in the dimer (5' to 3') comprises a 2'-$OCH_3$ and a 5'-(S)—$CH_3$ (Mesmaeker et al., Synlett, 1997, 1287-1290). Unnatural nucleic acids can include 2'-substituted 5'-$CH_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414). The disclosures of each of the references listed in this paragraph are hereby incorporated by reference in their entirety.

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substituent groups (including 5' and/or 2' substituent groups; bridging of two ring atoms to form bicyclic nucleic acids (BNA); replacement of the ribosyl ring oxygen atom with S, N(R), or $C(R_1)(R_2)$ (R=H, $C_1$-$C_{12}$ alkyl or a protecting group); and combinations thereof. Examples of chemically modified sugars can be found in WO2008/101157, US2005/0130923, and WO2007/134181; the disclosures of each of which are hereby incorporated by reference in their entirety.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl, or $C_2$ to $C_{10}$ alkenyl and alkynyl. 2' sugar modifications also include, but are not limited to, $—O[(CH_2)_nO]_m CH_3$, $—O(CH_2)_nOCH_3$, $—O(CH_2)_nNH_2$, $—O(CH_2)_nCH_3$, $—O(CH_2)_nONH_2$, and $—O(CH_2)_nON[(CH_2)_n CH_3)]_2$, where n and m are from 1 to about 10.

Other modifications at the 2' position include, but are not limited to: $C_1$ to $C_{10}$ lower alkyl, substituted lower alkyl, alkaryl, aralkyl, O-alkaryl, O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,700,920, the disclosures of each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-$OCH_3$, and 2'-$O(CH_2)_2OCH_3$ substituent groups. The substituent at the 2' position can also be selected from allyl, amino, azido, thio, O-allyl, O—($C_1$-$C_{10}$ alkyl), $OCF_3$, $O(CH_2)_2SCH_3$, $O(CH_2)_2—O—N(R_m)(R_n)$, and $O—CH_2—C(=O)—N(R_m)(R_n)$, where each $R_m$ and $R_n$ is independently H or substituted or unsubstituted $C_1$-$C_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' and 4'-$CH(CH_2OCH_3)$—O-2', and analogs thereof (see, U.S. Pat. No. 7,399,845); 4'-$C(CH_3)(CH_3)$—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393; the disclosures of each of which are hereby incorporated by reference in their entirety.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino ($—CH_2—N(CH_3)—O—CH_2—$), thiodiester ($—O—C(O)—S—$), thionocarbamate ($—O—C(O)(NH)—S—$); siloxane ($—O—Si(H)_2—O—$); and N,N*-dimethylhydrazine ($—CH_2—N(CH_3)—N(CH_3)$). In certain embodiments, inter nucleic acids linkages having a chiral atom can be prepared as a racemic mixture, or as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to a nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, NY; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179; the disclosures of each of which are hereby incorporated by reference in their entirety.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179), the disclosure of which is hereby incorporated by reference in its entirety. A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439; the disclosures of each of which are hereby incorporated by reference in their entirety. It is also understood in a nucleotide substitute that both the sugar and the phosphate moieties of the nucleotide can be replaced, for example by an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance, for example, cellular uptake. Conjugates can be chemically linked to the nucleotide or nucleotide analogs. Such conjugates include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937); the disclosures of each of which are hereby incorporated by reference in their entirety. Numerous United States patents teach the preparation of such conjugates and include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941; the disclosures of each of which are hereby incorporated by reference in their entirety.

Described herein are nucleobases used in the compositions and methods for replication, transcription, translation, and incorporation of unnatural amino acids into proteins. In some embodiments, a nucleobase described herein comprises the structure:

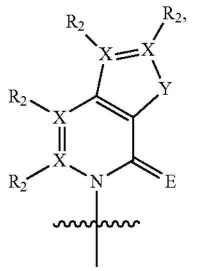

wherein each X is independently carbon or nitrogen;

$R_2$ is present when X is carbon and is independently hydrogen, alkyl, alkenyl, alkynyl, methoxy, methanethiol, methaneseleno, halogen, cyano, or azide group;

wherein each Y is independently sulfur, oxygen, selenium, or secondary amine;

wherein each E is independently oxygen, sulfur or selenium; and wherein the wavy line indicates a point of bonding to a ribosyl, deoxyribosyl, or dideoxyribosyl moiety or an analog thereof, wherein the ribosyl, deoxyribosyl, or dideoxyribosyl moiety or analog thereof is in free form, is connected to a mono-phosphate, diphosphate, or triphosphate group, optionally comprising an α-thiotriphosphate, β-thiotriphosphate, or γ-thiotriphosphate group, or is included in an RNA or a DNA or in an RNA analog or a DNA analog.

In some embodiments, $R_2$ is lower alkyl (e.g., $C_1$-$C_6$), hydrogen, or halogen. In some embodiments of a nucleobase described herein, $R_2$ is fluoro. In some embodiments of a nucleobase described herein, X is carbon. In some embodiments of a nucleobase described herein, E is sulfur. In some embodiments of a nucleobase described herein, Y is sulfur.

In some embodiments of a nucleobase described herein, a nucleobase has the structure:

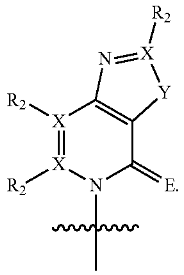

In some embodiments, the nucleobase described herein has the structure:

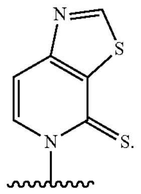 [SMILES: *n1ccc2ncsc2c1=S]

In some embodiments of a nucleobase described herein, E is sulfur and Y is sulfur. In some embodiments, the wavy line indicates a point of bonding to a ribosyl, deoxyribosyl, or dideoxyribosyl moiety or an analog thereof, wherein the ribosyl, deoxyribosyl, or dideoxyribosyl moiety or analog thereof is in free form, or is connected to a mono-phosphate, diphosphate, triphosphate, α-thiotriphosphate, β-thiotriphosphate, or γ-thiotriphosphate group, or is included in an RNA or a DNA or in an RNA analog or a DNA analog. In some embodiments of a nucleobase described herein, the wavy line indicates a point of bonding to a ribosyl or deoxyribosyl moiety. In some embodiments of a nucleobase described herein, the wavy line indicates a point of bonding to a ribosyl or deoxyribosyl moiety, connected to a triphosphate group. In some embodiments of a nucleobase described herein is a component of a nucleic acid polymer. In some embodiments of a nucleobase described herein, the nucleobase is a component of a tRNA. In some embodiments of a nucleobase described herein, the nucleobase is a component of an anticodon in a tRNA. In some embodiments of a nucleobase described herein, the nucleobase is a component of an mRNA. In some embodiments of a nucleobase described herein, the nucleobase is a component of a codon of an mRNA. In some embodiments of a nucleobase described herein, the nucleobase is a component of RNA or DNA. In some embodiments of a nucleobase described herein, the nucleobase is a component of a codon in DNA. In some embodiments of a nucleobase described herein, the nucleobase forms, is capable of forming, or is configured to form a nucleobase pair with another (e.g., complementary) nucleobase.

In some embodiments, the nucleobase described herein has the structure:

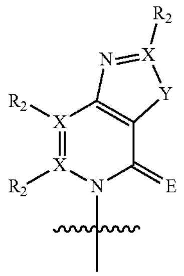

wherein:

each X is independently carbon or nitrogen;

$R_2$ is absent when X is nitrogen, and is present when X is carbon and is independently hydrogen, alkyl, alkenyl, alkynyl, methoxy, methanethiol, methaneseleno, halogen, cyano, or azide;

Y is sulfur, oxygen, selenium, or secondary amine;

E is oxygen, sulfur, or selenium; and the wavy line indicates a point of bonding to a ribosyl, deoxyribosyl, or dideoxyribosyl moiety or an analog thereof, wherein the ribosyl, deoxyribosyl, or dideoxyribosyl moiety or analog thereof is in free form, is connected to a mono-phosphate, diphosphate, triphosphate, α-thiotriphosphate, β-thiotriphosphate, or γ-thiotriphosphate group, or is included in an RNA or a DNA or in an RNA analog or a DNA analog.

In some embodiments, each X is carbon. In some embodiments, at least one X is carbon. In some embodiments, one X is carbon. In some embodiments, at least two X are carbon. In some embodiments, two X are carbon. In some embodiments, at least one X is nitrogen. In some embodiments, one X is nitrogen. In some embodiments, at least two X are nitrogen. In some embodiments, two X are nitrogen.

In some embodiments, Y is sulfur. In some embodiments, Y is oxygen. In some embodiments, Y is selenium. In some embodiments, Y is a secondary amine.

In some embodiments, E is sulfur. In some embodiments, E is oxygen. In some embodiments, E is selenium.

In some embodiments, $R_2$ is present when X is carbon. In some embodiments, $R^2$ is absent when X is nitrogen. In some embodiments, each $R_2$, where present, is hydrogen. In some embodiments, $R_2$ is alkyl, such as methyl, ethyl, or propyl. In some embodiments, $R_2$ is alkenyl, such as $—CH_2═CH_2$. In some embodiments, $R_2$ is alkynyl, such as ethynyl. In some embodiments, $R_2$ is methoxy. In some embodiments, $R_2$ is methanethiol. In some embodiments, $R_2$ is methaneseleno. In some embodiments, $R_2$ is halogen, such as chloro, bromo, or fluoro. In some embodiments, $R_2$ is cyano. In some embodiments, $R_2$ is azide.

In some embodiments, E is sulfur, Y is sulfur, and each X is independently carbon or nitrogen. In some embodiments, E is sulfur, Y is sulfur, and each X is carbon.

In some embodiments, the nucleobase has the structure

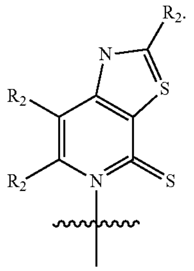

In some embodiments, the nucleobase has the structure

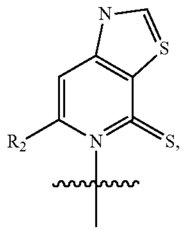

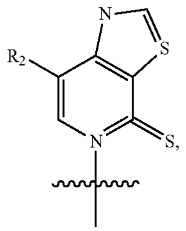

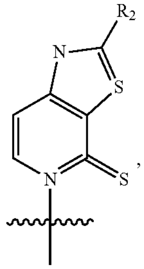

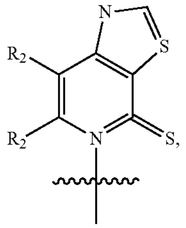

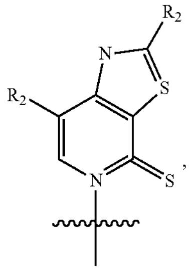

or

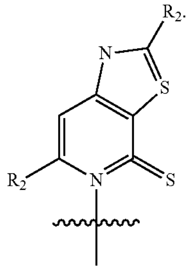

In some embodiments, the nucleobase has the structure

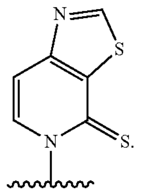 [SMILES: *n1ccc2ncsc2c1=S]

In some embodiments, the nucleobase disclosed herein is bound (e.g., noncovalently) to a complementary base-pairing nucleobase to form an unnatural base pair (UBP), or is capable of base pairing or configured to base pair with the nucleobase. In some embodiments, the complementary base-pairing nucleobase is selected from:

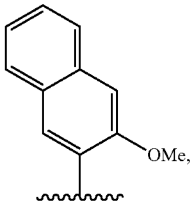
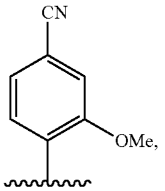
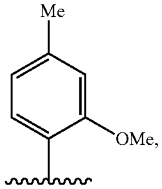
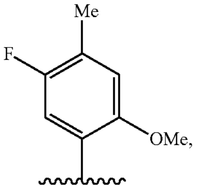
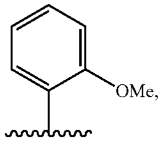
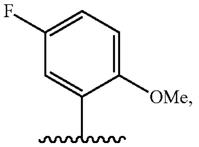
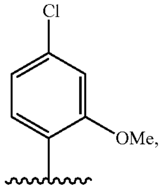
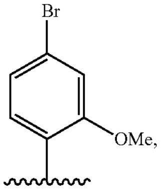
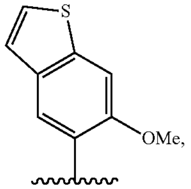
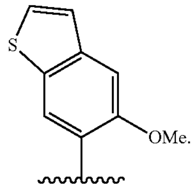

In one aspect, provided herein is a double stranded oligonucleotide duplex wherein a first oligonucleotide strand comprises a nucleobase disclosed herein, and a second complementary oligonucleotide strand comprises a complementary base-pairing nucleobase in a complementary base-pairing site thereof. In some embodiments, the first oligonucleotide strand comprises

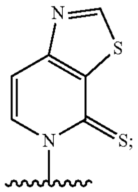 [SMILES: *n1ccc2ncsc2c1=S]

and the second strand comprises a complementary base pairing nucleobase selected from the group consisting of

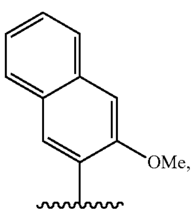
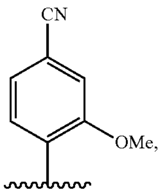

-continued

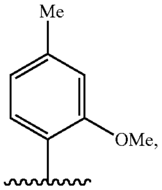
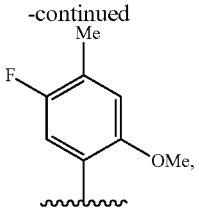
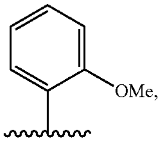
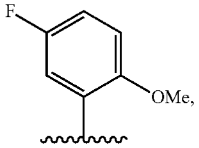
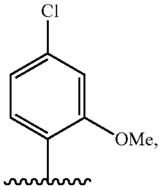
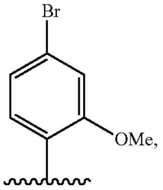
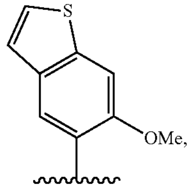
and
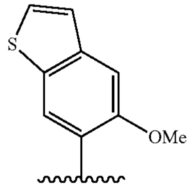

in a complementary base-pairing site thereof.

In a further aspect, provided herein is a transfer RNA (tRNA) comprising a nucleobase described herein, comprising: an anticodon, wherein the anticodon comprises the nucleobase; and a recognition element, wherein the recognition element promotes selective charging of the tRNA with an unnatural amino acid by an aminoacyl tRNA synthetase. In some embodiments, the nucleobase is located in an anticodon region of the tRNA. In some embodiments, the nucleobase is located in the first position of the anticodon. In some embodiments, the nucleobase is located in the second position of the anticodon. In some embodiments, the nucleobase is located in the third position of the anticodon. In some embodiments, the aminoacyl tRNA synthetase is derived from *Methanosarcina*, or a variant thereof. In some embodiments, the aminoacyl tRNA synthetase is derived from *Methanococcus* (*Methanocaldococcus*) or a variant thereof. In some embodiments, the unnatural amino acid comprises an aromatic moiety. In some embodiments, the unnatural amino acid is a lysine derivative. In some embodiments, the unnatural amino acid is a phenylalanine derivative.

Also provided herein is a structure comprising the formula:

N1-Zx-N2 wherein:

Z is a nucleobase as described herein, which is bonded to a ribosyl or deoxyribosyl or analog thereof;

N1 is one or more nucleotides or analogs thereof, or a terminal phosphate group attached at the 5' end of the ribosyl or deoxyribosyl or analog thereof of Z;

N2 is one or more nucleotides or analogs thereof, or a terminal hydroxyl group attached to the 3' end of the ribosyl or deoxyribosyl or analog thereof of Z; and x is an integer from 1 to 20.

In some embodiments, N1 is one or more nucleotides or analogs thereof attached at the 5' end of the ribosyl or deoxyribosyl moiety or analog thereof of Z. The attachment to the 5' end of the ribosyl or deoxyribosyl moiety may be through a phosphodiester. In some embodiments, N1 is a terminal phosphate group attached at the 5' end of the ribosyl or deoxyribosyl moiety or analog thereof of Z. In some embodiments, N2 is one or more nucleotides or analogs thereof attached to the 3' end of the ribosyl or deoxyribosyl moiety or analog thereof of Z. The attachment to the 3' end of the ribosyl or deoxyribosyl moiety may be through a phosphodiester. In some embodiments, N2 is a terminal hydroxyl group attached to the 3' end of the ribosyl or deoxyribosyl moiety or analog thereof of Z.

In some embodiments, x is an integer from 1 to 20. In some embodiments, x is an integer from 1 to 15. In some embodiments, x is an integer from 1 to 10. In some embodiments, x is an integer from 1 to 5. In some embodiments, x is 1. In some embodiments, x is 2. In some embodiments, x is 3. In some embodiments, x is 4. In some embodiments, x is 5. In some embodiments, x is 6. In some embodiments, x is 7. In some embodiments, x is 8. In some embodiments, x is 9. In some embodiments, x is 10. In some embodiments, x is 11. In some embodiments, x is 12. In some embodiments, x is 13. In some embodiments, x is 14. In some embodiments, x is 15. In some embodiments, x is 16. In some embodiments, x is 17. In some embodiments, x is 18. In some embodiments, x is 19. In some embodiments, x is 20.

In some embodiments, Z has the structure

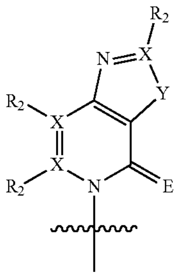

as detailed herein. In some embodiments, Z has the structure

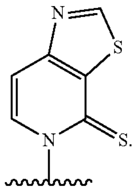 [SMILES: *n1ccc2ncsc2c1=S]

In some embodiments, the structure of formula N1-Zx-N2 encodes for a gene. In some embodiments, Zx is located in a translated region of the gene. In some embodiments, Zx is located in an untranslated region of the gene. In some embodiments, the structure further comprises a 5' or 3' untranslated region (UTR). In some embodiments, the structure further comprises a terminator region. In some embodiments, the structure further comprises a promoter region.

In a further aspect, provided herein is a polynucleotide library, wherein the library comprises at least 5000 unique polynucleotides, and wherein each polynucleotide comprises at least one nucleobase disclosed herein. In some embodiments, the polynucleotide library encodes for at least one gene.

In yet another aspect, provided herein is a nucleoside triphosphate, wherein the nucleobase is selected from

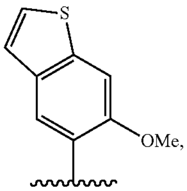

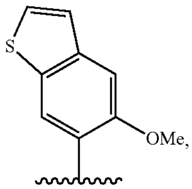

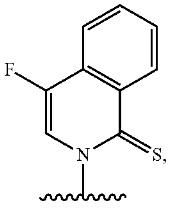

and

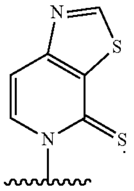

In some embodiments, the nucleobase is

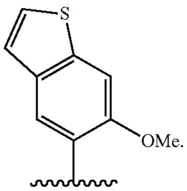 [SMILES: *c1cc2ccsc2cc1OC]

In some embodiments, the nucleobase is

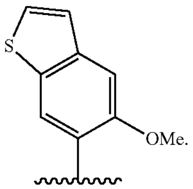 [SMILES: *c1cc2sccc2cc1OC]

In some embodiments, the nucleobase is

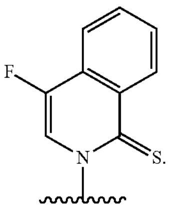

In some embodiments, the nucleobase is

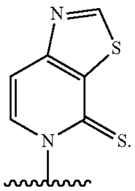 [SMILES: *n1ccc2ncsc2c1=S]

In some embodiments, the nucleoside comprises ribose. In some embodiments, the nucleoside comprises deoxyribose.

Nucleic Acid Base Pairing Properties; Exemplary Base Pairs

In some embodiments, an unnatural nucleotide forms a base pair (an unnatural base pair; UBP) with another unnatural nucleotide during or after incorporation into DNA or RNA. In some embodiments, a stably integrated unnatural nucleic acid is an unnatural nucleic acid that can form a base pair with another nucleic acid, e.g., a natural or unnatural nucleic acid. In some embodiments, a stably integrated unnatural nucleic acid is an unnatural nucleic acid that can form a base pair with another unnatural nucleic acid (unnatural nucleic acid base pair (UBP)). For example, a first unnatural nucleic acid can form a base pair with a second unnatural nucleic acid. For example, one pair of unnatural nucleoside triphosphates that can base pair during and after incorporation into nucleic acids includes a triphosphate of (d)5SICS ((d)5SICSTP) and a triphosphate of (d)NaM ((d) NaMTP). Other examples include, but are not limited to: a triphosphate of (d)CNMO ((d)CNMOTP) and a triphosphate of (d)TPT3 ((d)TPT3TP). Such unnatural nucleotides can have a ribose or deoxyribose sugar moiety (indicated by the "(d)"). For example, one pair of unnatural nucleoside triphosphates that can base pair when incorporated into nucleic acids includes a triphosphate of TAT1 ((d)TAT1TP) and a triphosphate of NaM ((d)NaMTP). In some embodiments, one pair of unnatural nucleoside triphosphates that can base pair when incorporated into nucleic acids includes a triphosphate of dCNMO (dCNMOTP) and a triphosphate of TAT1 (TAT1TP). In some embodiments, one pair of unnatural nucleoside triphosphates that can base pair when incorporated into nucleic acids includes a triphosphate of dTPT3 (dTPT3TP) and a triphosphate of NaM (NaMTP). In some embodiments, an unnatural nucleic acid does not substantially form a base pair with a natural nucleic acid (A, T, G, C). In some embodiments, a stably integrated unnatural nucleic acid can form a base pair with a natural nucleic acid.

In some embodiments, a stably integrated unnatural (deoxy)ribonucleotide is an unnatural (deoxy)ribonucleotide that can form a UBP, but does not substantially form a base pair with each any of the natural (deoxy)ribonucleotides. In some embodiments, a stably integrated unnatural (deoxy) ribonucleotide is an unnatural (deoxy)ribonucleotide that can form a UBP, but does not substantially form a base pair with one or more natural nucleic acids. For example, a stably integrated unnatural nucleic acid may not substantially form a base pair with A, T, and, C, but can form a base pair with G. For example, a stably integrated unnatural nucleic acid may not substantially form a base pair with A, T, and, G, but can form a base pair with C. For example, a stably integrated unnatural nucleic acid may not substantially form a base pair with C, G, and, A, but can form a base pair with T. For example, a stably integrated unnatural nucleic acid may not substantially form a base pair with C, G, and, T, but can form a base pair with A. For example, a stably integrated unnatural nucleic acid may not substantially form a base pair with A and T, but can form a base pair with C and G. For example, a stably integrated unnatural nucleic acid may not substantially form a base pair with A and C, but can form a base pair with T and G. For example, a stably integrated unnatural nucleic acid may not substantially form a base pair with A and G, but can form a base pair with C and T. For example, a stably integrated unnatural nucleic acid may not substantially form a base pair with C and T, but can form a base pair with A and G. For example, a stably integrated unnatural nucleic acid may not substantially form a base pair with C and G, but can form a base pair with T and G. For example, a stably integrated unnatural nucleic acid may not substantially form a base pair with T and G, but can form a base pair with A and G. For example, a stably integrated unnatural nucleic acid may not substantially form a base pair with, G, but can form a base pair with A, T, and, C. For example, a stably integrated unnatural nucleic acid may not substantially form a base pair with, A, but can form a base pair with G, T, and, C. For example, a stably integrated unnatural nucleic acid may not substantially form a base pair with, T, but can form a base pair with G, A, and, C. For example, a stably integrated unnatural nucleic acid may not substantially form a base pair with, C, but can form a base pair with G, T, and, A.

Exemplary, unnatural nucleotides capable of forming an unnatural DNA or RNA base pair (UBP) under conditions in vivo include, but are not limited to, 5SICS, d5SICS, NaM, dNaM, dTPT3, dMTMO, dCNMO, TAT1, and combinations thereof. In some embodiments, the unnatural nucleotides capable of forming an unnatural DNA or RNA base pair (UBP) under conditions in vivo include, but are not limited to, 5SICS, NaM, TPT3, MTMO, CNMO, TAT1, and combinations thereof, wherein the sugar moiety of the nucleotide is a deoxyribose sugar. In some embodiments, the unnatural nucleotides capable of forming an unnatural DNA or RNA base pair (UBP) under conditions in vivo include, but are not limited to, 5SICS, NaM, TPT3, MTMO, CNMO, TAT1, and combinations thereof, wherein the sugar moiety of the nucleotide is a ribose sugar. In some embodiments, the unnatural nucleotides capable of forming an unnatural DNA or RNA base pair (UBP) under conditions in vivo include, but are not limited to, (d)5SICS, (d)NaM, (d)TPT3, (d)MTMO, (d)CNMO, (d)TAT1, and combinations thereof. In some embodiments, unnatural nucleotide base pairs include, but are not limited to.

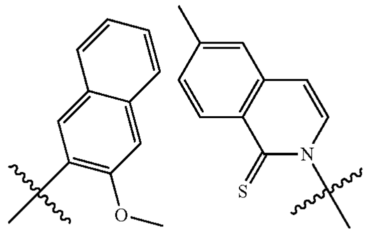

NaM-5SICS

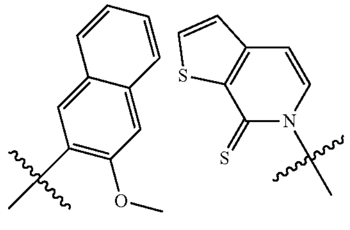

NaM-TPT3

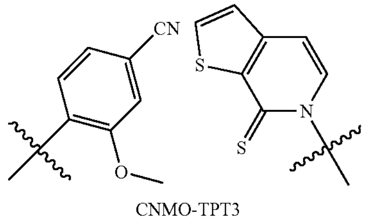

CNMO-TPT3

-continued

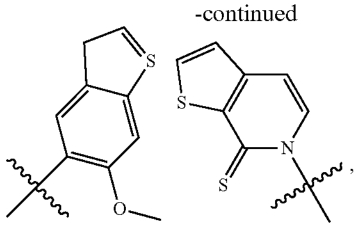

PTMO-TPT3 wherein the sugar moiety is any embodiment or variation described herein. In some embodiments, unnatural nucleotide base pairs include, but are not limited to:

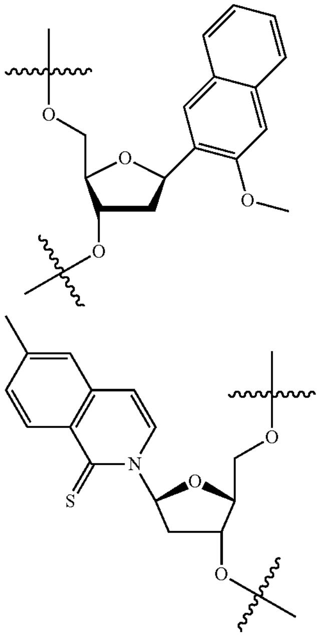

dNaM-d5SICS

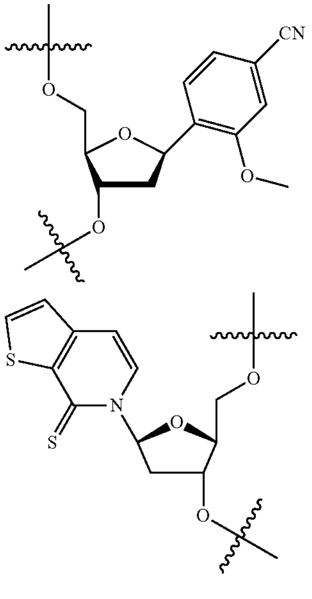

dCNMO-dTPT3

-continued dNaM-dTPT3

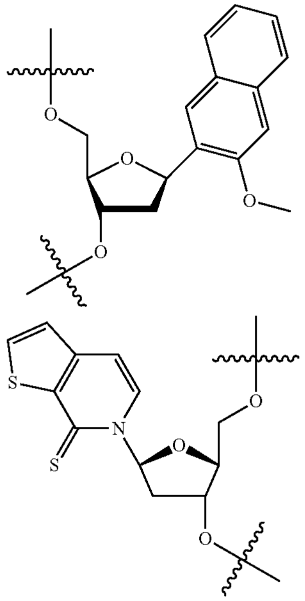

dPTMO-dTPT3

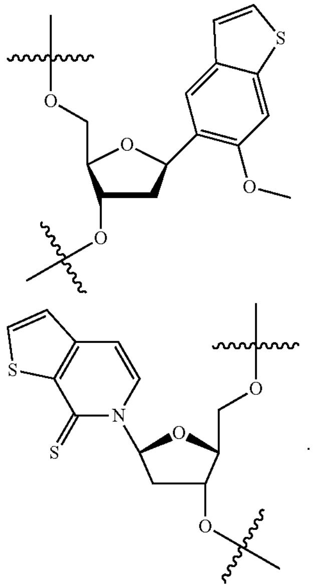

In any such embodiment, one or both of the deoxyriboses attached to the unnatural bases may be substituted with a ribose.

Engineered Organisms

In some embodiments, methods and plasmids disclosed herein are further used to generate an engineered organism, e.g. an organism that incorporates and replicates an unnatural nucleotide or an unnatural nucleic acid base pair (UBP) and may also use the nucleic acid containing the unnatural nucleotide to transcribe mRNA and tRNA, which are used to translate proteins containing an unnatural amino acid residue. In some instances, the organism is a non-human semi-synthetic organism (SSO). In some instances, the organism is a semi-synthetic organism (SSO). In some instances, the SSO is a cell. In some instances, the in vivo method comprises a semi-synthetic organism (SSO). In some instances, the semi-synthetic organism comprises a microorganism. In some instances, the organism comprises a bacterium. In some instances, the organism comprises a Gram-negative bacterium. In some instances, the organism comprises a Gram-positive bacterium. In some instances, the organism comprises an *Escherichia coli* (*E. coli*). Such modified organisms variously comprise additional components, such as DNA repair machinery, modified polymerases, nucleotide transporters, or other components. In some instances, the SSO comprises *E. coli* strain YZ3. In some instances, the SSO comprises *E. coli* strain ML1 or ML2, such as those strains described in FIG. 1 (B-D) of Ledbetter, et al. *J. Am Chem. Soc.* 2018, 140(2), 758, the disclosure of which is hereby incorporated by reference in its entirety.

In some instances, the cell employed is genetically transformed with an expression cassette encoding a heterologous protein, e.g., a nucleoside triphosphate transporter capable of transporting unnatural nucleoside triphosphates into the cell, and optionally a CRISPR/Cas9 system to eliminate DNA that has lost the unnatural nucleotide (e.g. *E. coli* strain YZ3, ML1, or ML2). In some instances, cells further comprise enhanced activity for unnatural nucleic acid uptake. In some cases, cells further comprise enhanced activity for unnatural nucleic acid import.

In some embodiments, Cas9 and an appropriate guide RNA (sgRNA) are encoded on separate plasmids. In some instances, Cas9 and sgRNA are encoded on the same plasmid. In some cases, the nucleic acid molecule encoding Cas9, sgRNA, or a nucleic acid molecule comprising an unnatural nucleotide are located on one or more plasmids. In some instances, Cas9 is encoded on a first plasmid and the sgRNA and the nucleic acid molecule comprising an unnatural nucleotide are encoded on a second plasmid. In some instances, Cas9, sgRNA, and the nucleic acid molecule comprising an unnatural nucleotide are encoded on the same plasmid. In some instances, the nucleic acid molecule comprises two or more unnatural nucleotides. In some instances, Cas9 is incorporated into the genome of the host organism and sgRNAs are encoded on a plasmid or in the genome of the organism.

In some instances, a first plasmid encoding Cas9 and sgRNA and a second plasmid encoding a nucleic acid molecule comprising an unnatural nucleotide are introduced into an engineered microorganism. In some instances, a first plasmid encoding Cas9 and a second plasmid encoding sgRNA and a nucleic acid molecule comprising an unnatural nucleotide are introduced into an engineered microorganism. In some instances, a plasmid encoding Cas9, sgRNA and a nucleic acid molecule comprising an unnatural nucleotide is introduced into an engineered microorganism. In some instances, the nucleic acid molecule comprises two or more unnatural nucleotides.

In some embodiments, a living cell is generated that incorporates within its DNA (plasmid or genome) at least one unnatural nucleotide and/or at least one unnatural base pair (UBP). In some instances, the unnatural base pair includes a pair of unnatural mutually base-pairing nucleotides capable of forming the unnatural base pair under in vivo conditions, when the unnatural mutually base-pairing nucleotides, as their respective triphosphates, are taken up into the cell by action of a nucleotide triphosphate transporter. In some instances, the unnatural base pair includes a pair of unnatural mutually base-pairing nucleotides configured to form the unnatural base pair under in vivo conditions, when the unnatural mutually base-pairing nucleotides, as their respective triphosphates, are taken up into the cell by action of a nucleotide triphosphate transporter. The cell can be genetically transformed by an expression cassette encoding a nucleotide triphosphate transporter so that the nucleotide triphosphate transporter is expressed and is available to transport the unnatural nucleotides into the cell. The cell can be a prokaryotic or eukaryotic cell, and the pair of unnatural mutually base-pairing nucleotides, as their respective triphosphates, can be a triphosphate of dTPT3 (dTP3TP) and a triphosphate of dNaM (dNaMTP) or dCNMO (dCNMOTP).

In some embodiments, cells are genetically transformed cells with a nucleic acid, e.g., an expression cassette encoding a nucleotide triphosphate transporter capable of transporting such unnatural nucleotides into the cell. A cell can comprise a heterologous nucleoside triphosphate transporter, where the heterologous nucleoside triphosphate transporter can transport natural and unnatural nucleoside triphosphates into the cell.

In some cases, a method described herein also includes contacting a genetically transformed cell with the respective triphosphates, in the presence of potassium phosphate and/or an inhibitor of phosphatases or nucleotidases. During or after such contact, the cell can be placed within a life-supporting medium suitable for growth and replication of the cell. The cell can be maintained in the life-supporting medium so that the respective triphosphate forms of unnatural nucleotides are incorporated into nucleic acids within the cells, and through at least one replication cycle of the cell. The pair of unnatural mutually base-pairing nucleotides as a respective triphosphate, can comprise a triphosphate of dTPT3 or (dTPT3TP) and a triphosphate of dCNMO or dNaM (dCNOM or dNaMTP), the cell can be *E. coli*, and the dTPT3TP and dNaMTP can be imported into *E. coli* by the transporter PtNTT2, wherein an *E. coli* polymerase, such as Pol III or Pol II, can use the unnatural triphosphates to replicate DNA containing a UBP, thereby incorporating unnatural nucleotides and/or unnatural base pairs into cellular nucleic acids within the cellular environment. Additionally, ribonucleotides such as NaMTP and TAT1TP, 5FMTP, and TPT3TP are in some instances imported into *E. coli* by the transporter PtNTT2.

Described herein are compositions and methods comprising the use of three or more unnatural base-pairing nucleotides. Such base pairing nucleotides in some cases enter a cell through use of nucleotide transporters, or through standard nucleic acid transformation methods known in the art (e.g., electroporation, chemical transformation, or other method). In some cases, a base pairing unnatural nucleotide enters a cell as part of a polynucleotide, such as a plasmid. One or more base pairing unnatural nucleotide which enter a cell as part of a polynucleotide (RNA or DNA) need not themselves be replicated in vivo. For example, a double-stranded DNA plasmid or other nucleic acid comprising a first unnatural deoxyribonucleotide and a second unnatural deoxyribonucleotide with bases configured to form a first unnatural base pair are electroporated into a cell. The cell media is treated with a third unnatural deoxyribonucleotide, a fourth unnatural deoxyribonucleotide with bases configured to form a second unnatural base pair with each other, wherein the first unnatural deoxyribonucleotide's base and the third unnatural deoxyribonucleotide's base form a second unnatural base pair, and wherein the second unnatural deoxyribonucleotide's base and the fourth unnatural deoxyribonucleotide's base form a third unnatural base pair. In some instances, in vivo replication of the originally transformed double-stranded DNA plasmid results in subsequent replicated plasmids comprising the third unnatural deoxyribonucleotide and the fourth unnatural deoxyribonucleotide. Alternatively or in combination, ribonucleotides variants of the third unnatural deoxyribonucleotide and fourth unnatural deoxyribonucleotide are added to the cell media. These ribonucleotides are in some instances incorporated into RNA, such as mRNA or tRNA. In some instances, the first, second, third, and fourth deoxynucleotides comprise different bases. In some instances, the first, third, and fourth deoxynucleotides comprise different bases. In some instances, the first and third deoxynucleotides comprise the same base.

By practice of a method of the invention, the person of ordinary skill can obtain a population of a living and propagating cells that has at least one unnatural nucleotide and/or at least one unnatural base pair (UBP) within at least one nucleic acid maintained within at least some of the individual cells, wherein the at least one nucleic acid is stably propagated within the cell, and wherein the cell expresses a nucleotide triphosphate transporter suitable for providing cellular uptake of triphosphate forms of one or more unnatural nucleotides when contacted with (e.g., grown in the presence of) the unnatural nucleotide(s) in a life-supporting medium suitable for growth and replication of the organism.

After transport into the cell by the nucleotide triphosphate transporter, the unnatural base-pairing nucleotides are incorporated into nucleic acids within the cell by cellular machinery, e.g., the cell's own DNA and/or RNA polymerases, a heterologous polymerase, or a polymerase that has been evolved using directed evolution (Chen T, Romesberg F E, FEBS Lett. 2014 Jan. 21; 588(2):219-29; Betz K et al., J Am Chem Soc. 2013 Dec. 11; 135(49):18637-43; the disclosures of each of which are hereby incorporated by reference in their entirety). The unnatural nucleotides can be incorporated into cellular nucleic acids such as genomic DNA, genomic RNA, mRNA, tRNA, structural RNA, microRNA, and autonomously replicating nucleic acids (e.g., plasmids, viruses, or vectors).

In some cases, genetically engineered cells are generated by introduction of nucleic acids, e.g., heterologous nucleic acids, into cells. Any cell described herein can be a host cell and can comprise an expression vector. In one embodiment, the host cell is a prokaryotic cell. In another embodiment, the host cell is *E. coli*. In some embodiments, a cell comprises one or more heterologous polynucleotides. Nucleic acid reagents can be introduced into microorganisms using various techniques. Non-limiting examples of methods used to introduce heterologous nucleic acids into various organisms include: transformation, transfection, transduction, electroporation, ultrasound-mediated transformation, conjugation, particle bombardment and the like. In some instances, the addition of carrier molecules (e.g., bis-benzoimidazolyl compounds, for example, see U.S. Pat. No. 5,595,899) can increase the uptake of DNA in cells typically thought to be difficult to transform by conventional methods. Conventional methods of transformation are readily available to the artisan and can be found in Maniatis, T., E. F. Fritsch and J. Sambrook (1982) Molecular Cloning: a Laboratory Manual; Cold Spring Harbor Laboratory, Cold Spring Harbor, N.Y., the disclosure of which is hereby incorporated by reference in its entirety.

In some instances, genetic transformation is obtained using direct transfer of an expression cassette in, but not limited to, plasmids, viral vectors, viral nucleic acids, phage nucleic acids, phages, cosmids, and artificial chromosomes, or via transfer of genetic material in cells or carriers such as cationic liposomes. Such methods are available in the art and readily adaptable for use in the methods described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991), the disclosures of each of which are hereby incorporated by reference in their entirety.

For example, DNA encoding a nucleoside triphosphate transporter or polymerase expression cassette and/or vector can be introduced to a cell by any method including, but not limited to, calcium-mediated transformation, electroporation, microinjection, lipofection, particle bombardment and the like.

In some cases, a cell comprises unnatural nucleoside triphosphates incorporated into one or more nucleic acids within the cell. For example, the cell can be a living cell capable of incorporating at least one unnatural nucleotide within DNA or RNA maintained within the cell. The cell can also incorporate at least one unnatural base pair (UBP) comprising a pair of unnatural mutually base-pairing nucleotides into nucleic acids within the cell under in vivo conditions, wherein the unnatural mutually base-pairing nucleotides, e.g., their respective triphosphates, are taken up into the cell by action of a nucleoside triphosphate transporter, the gene for which is present (e.g., was introduced) into the cell by genetic transformation. For example, upon incorporation into the nucleic acid maintained within the cell, dTPT3 and dCNMO can form a stable unnatural base pair that can be stably propagated by the DNA replication machinery of an organism, e.g., when grown in a life-supporting medium comprising dTPT3TP and dCNMOTP.

In some cases, cells are capable of replicating a nucleic acid containing an unnatural nucleotide. Such methods can include genetically transforming the cell with an expression cassette encoding a nucleoside triphosphate transporter capable of transporting into the cell, as a respective triphosphate, one or more unnatural nucleotides under in vivo conditions. Alternatively, a cell can be employed that has previously been genetically transformed with an expression cassette that can express an encoded nucleoside triphosphate transporter. The method can also include contacting or exposing the genetically transformed cell to potassium phosphate and the respective triphosphate forms of at least one unnatural nucleotide (for example, two mutually base-pairing nucleotides capable of forming the unnatural base pair (UBP)) in a life-supporting medium suitable for growth and replication of the cell, and maintaining the transformed cell in the life-supporting medium in the presence of the respective triphosphate forms of at least one unnatural nucleotide (for example, two mutually base-pairing nucleotides capable of forming the unnatural base pair (UBP)) under in vivo conditions, through at least one replication cycle of the cell. The method can also include contacting or exposing the genetically transformed cell to potassium phosphate and the respective triphosphate forms of at least one unnatural nucleotide (for example, two mutually base-pairing nucleotides configured to form the unnatural base pair (UBP)) in a life-supporting medium suitable for growth and replication of the cell, and maintaining the transformed cell in the life-supporting medium in the presence of the respective triphosphate forms of at least one unnatural nucleotide (for example, two mutually base-pairing nucleotides configured to form the unnatural base pair (UBP)) under in vivo conditions, through at least one replication cycle of the cell.

In some embodiments, a cell comprises a stably incorporated unnatural nucleic acid. Some embodiments comprise a cell (e.g., an *E. coli*) that stably incorporates nucleotides other than A, G, T, and C within nucleic acids maintained within the cell. For example, the nucleotides other than A, G, T, and C can be d5SICS, dCNMO, dNaM, and/or dTPT3, which upon incorporation into nucleic acids of the cell, can form a stable unnatural base pair within the nucleic acids. In one aspect, unnatural nucleotides and unnatural base pairs can be stably propagated by the replication apparatus of the organism, when an organism transformed with the gene for the triphosphate transporter is grown in a life-supporting medium that includes potassium phosphate and the triphosphate forms of d5SICS, dNaM, dCNMO, and/or dTPT3.

In some cases, a cell comprises an expanded genetic alphabet. A cell can comprise a stably incorporated unnatural nucleic acid. In some embodiments, a cell with an expanded genetic alphabet comprises an unnatural nucleic acid that contains an unnatural nucleotide that can pair with another unnatural nucleotide. In some embodiments, a cell with an expanded genetic alphabet comprises an unnatural nucleic acid that is hydrogen bonded to another nucleic acid. In some embodiments, a cell with an expanded genetic alphabet comprises an unnatural nucleic acid that is not hydrogen bonded to another nucleic acid to which it is base paired. In some embodiments, a cell with an expanded genetic alphabet comprises an unnatural nucleic acid that contains an unnatural nucleotide with a nucleobase that base pairs to the nucleobase or another unnatural nucleotide via hydrophobic and/or packing interactions. In some embodiments, a cell with an expanded genetic alphabet comprises an unnatural nucleic acid that base pairs to another nucleic acid via non-hydrogen bonding interactions. A cell with an expanded genetic alphabet can be a cell that can copy a homologous nucleic acid to form a nucleic acid comprising an unnatural nucleic acid. A cell with an expanded genetic alphabet can be a cell comprising an unnatural nucleic acid base paired with another unnatural nucleic acid (unnatural nucleic acid base pair (UBP)).

In some embodiments, cells form unnatural DNA base pairs (UBPs) from the imported unnatural nucleotides under in vivo conditions. In some embodiments, potassium phosphate and/or inhibitors of phosphatase and/or nucleotidase activities can facilitate transport of unnatural nucleotides. The methods include use of a cell that expresses a heterologous nucleoside triphosphate transporter. When such a cell is contacted with one or more nucleoside triphosphates, the nucleoside triphosphates are transported into the cell. The cell can be in the presence of potassium phosphate and/or inhibitors of phosphatases and nucleotidases. Unnatural nucleoside triphosphates can be incorporated into nucleic acids within the cell by the cell's natural machinery (i.e. polymerases) and, for example, mutually base-pair to form unnatural base pairs within the nucleic acids of the cell. In some embodiments, UBPs are formed between DNA and RNA nucleotides bearing unnatural bases.

In some embodiments, a UBP can be incorporated into a cell or population of cells when exposed to unnatural triphosphates. In some embodiments, a UBP can be incorporated into a cell or population of cells when substantially consistently exposed to unnatural triphosphates.

In some embodiments, induction of expression of a heterologous gene, e.g., a nucleoside triphosphate transporter (NTT), in a cell can result in slower cell growth and increased unnatural triphosphate uptake compared to the growth and uptake of one or more unnatural triphosphates in a cell without induction of expression of the heterologous gene. Uptake variously comprises transport of nucleotides into a cell, such as through diffusion, osmosis, or via the action of transporters. In some embodiments, induction of expression of a heterologous gene, e.g., an NTT, in a cell can result in increased cell growth and increased unnatural nucleic acid uptake compared to the growth and uptake of a cell without induction of expression of the heterologous gene.

In some embodiments, a UBP is incorporated during a log growth phase. In some embodiments, a UBP is incorporated during a non-log growth phase. In some embodiments, a UBP is incorporated during a substantially linear growth phase. In some embodiments, a UBP is stably incorporated into a cell or population of cells after growth for a time period. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, or 24 hours of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of growth. For example, a UBP can be stably incorporated into a cell or population of cells after growth for at least about 1, 2, 3, 4, 5, 6, 7, 8, 9, 10, 11, or 12 months of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 years of growth.

In some embodiments, the semi-synthetic organism disclosed herein comprises DNA comprising at least one unnatural nucleobase selected from the group consisting of:

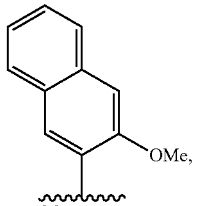 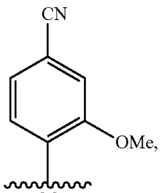

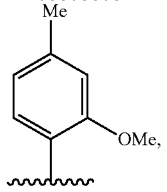 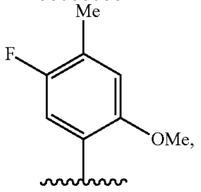

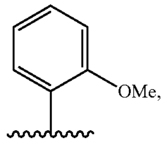 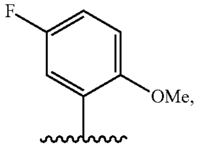

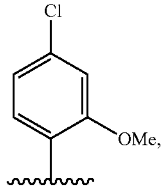 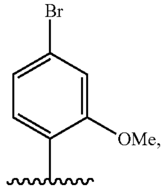

-continued

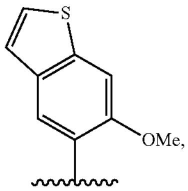, 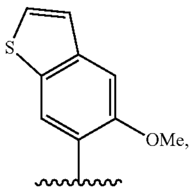,

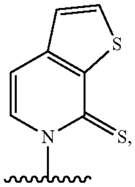 [SMILES: *n1ccc2ccsc2c1=S], 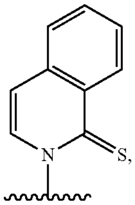, 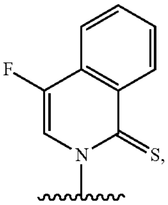,

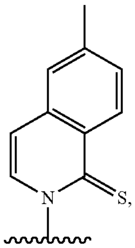, and 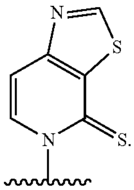.

In some embodiments, the DNA of the semi-synthetic organism comprising at least one of the unnatural bases forms an unnatural base pair (UBP). In some embodiments, the unnatural base pair (UBP) is dCNMO-dTPT3, dNaM-dTPT3, dCNMO-dTAT1, or dNaM-dTAT1. In some embodiments, the DNA comprises at least one unnatural nucleobase selected from the group consisting of:

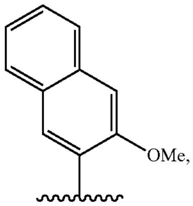, 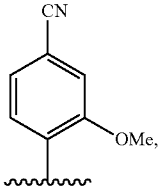 [SMILES: *c1ccc(C#N)cc1OC],

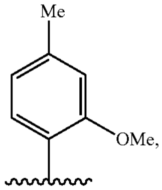, 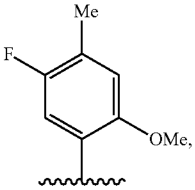,

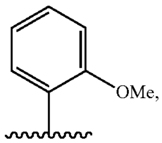, 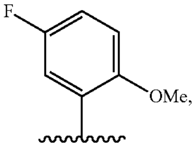,

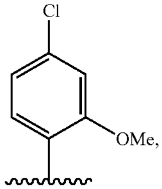, 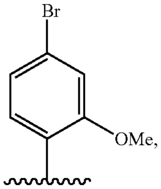,

-continued

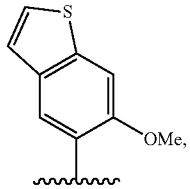, 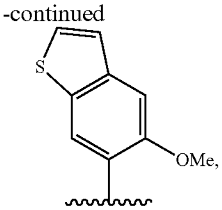,

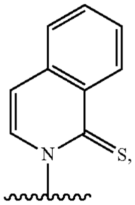, 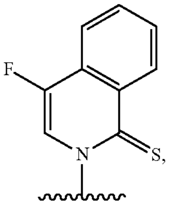,

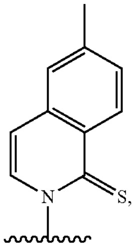, and 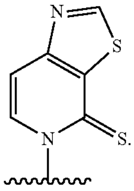.

In some embodiments, the DNA comprises at least one unnatural nucleobase selected from the group consisting of:

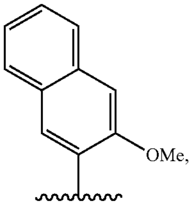, 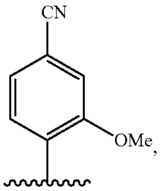,

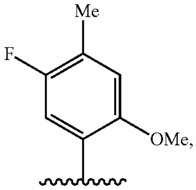, and 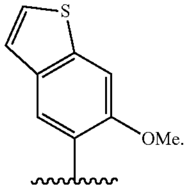.

In some embodiments, the DNA comprises at least one unnatural nucleobase selected from the group consisting of:

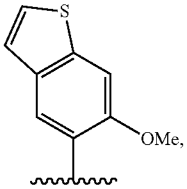, 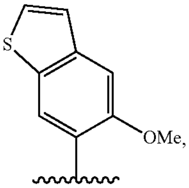,

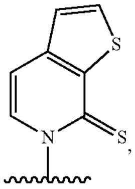, 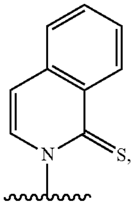, 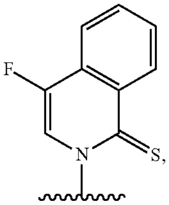,

-continued

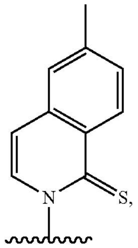

and

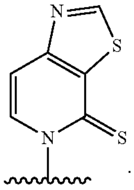

In some embodiments, the DNA comprises at least one unnatural nucleobase selected from the group consisting of:

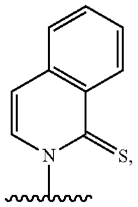

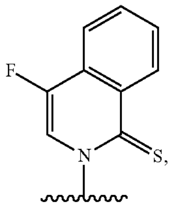

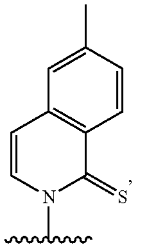

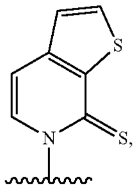

and

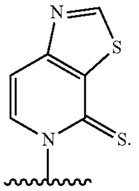

In some embodiments, the DNA comprises at least one unnatural nucleobase selected from and

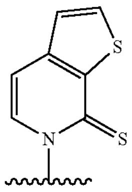

and

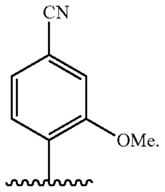 [SMILES: *c1ccc(C#N)cc1OC]

In some embodiments, the DNA comprises at least two unnatural nucleobases selected from

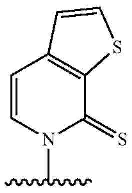

and

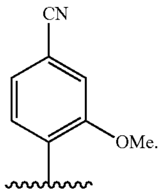

In some embodiments, the DNA comprises two strands, the first strand comprising at least one nucleobase which is

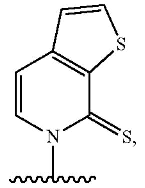

and the second strand comprising at least one nucleobase which is

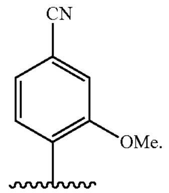

In some embodiments, the DNA comprises at least one unnatural nucleobase which is

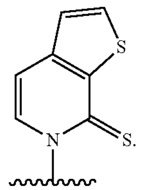

In some embodiments, a cell further utilizes an RNA polymerase to generate an mRNA which contains one or more unnatural nucleotides. In some embodiments, the RNA polymerase is a heterologous RNA polymerase. In some instances, a cell further utilizes a polymerase to generate a tRNA which contains an anticodon that comprises one or more unnatural nucleotides. In some embodiments, the tRNA is a heterologous tRNA. In some instances, the tRNA is charged with an unnatural amino acid. In some instances, the unnatural anticodon of the tRNA pairs with the unnatural codon of an mRNA during translation to synthesis a protein that contains an unnatural amino acid.

In some embodiments, the semi-synthetic organism disclosed herein expresses a heterologous nucleoside triphosphate transporter. In some embodiments, the heterologous nucleoside triphosphate transporter is PtNTT2. In some embodiments, the semi-synthetic organism further expresses a heterologous tRNA synthetase. In some embodiments, the heterologous tRNA synthetase is *M. barkeri* pyrrolysyl-tRNA synthetase (Mb PylRS). In some embodiments, the semi-synthetic organism expresses the nucleoside triphosphate transporter PtNTT2 and further expresses the tRNA synthetase *M. barkeri* pyrrolysyl-tRNA synthetase (Mb PylRS). In some embodiments, the semi-synthetic organism further expresses a heterologous RNA polymerase. In some embodiments, the heterologous RNA polymerase is T7 RNAP. In some embodiments, the semi-synthetic organism does not express a protein having the function of DNA recombinational repair. In some embodiments, the semi-synthetic organism is *E. coli* and the organism does not express RecA.

In some embodiments, the semi-synthetic organism further comprises a heterologous mRNA. In some embodiments, the heterologous mRNA comprises at least one unnatural base selected from

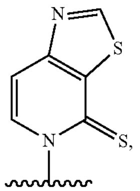
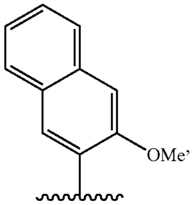
and
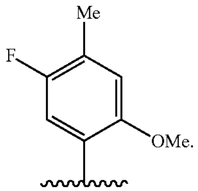 [SMILES: *c1cc(F)c(C)cc1OC]

In some embodiments, the heterologous mRNA comprises at least one unnatural base which is

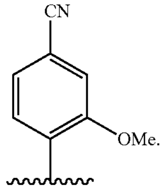 [SMILES: *c1ccc(C#N)cc1OC]

In some embodiments, the heterologous mRNA comprises at least one unnatural base which is

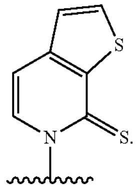 [SMILES: *n1ccc2ccsc2c1=S]

In some embodiments, the heterologous mRNA comprises at least one unnatural base which is

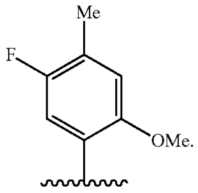 [SMILES: *c1cc(F)c(C)cc1OC]

In some embodiments, the semi-synthetic organism further comprises a heterologous tRNA. In some embodiments, the heterologous tRNA comprises at least one unnatural base selected from

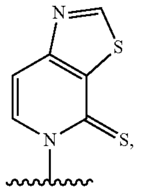
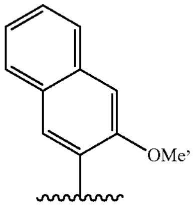
and
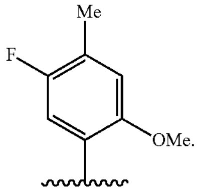

In some embodiments, the heterologous tRNA comprises at least one unnatural base which is

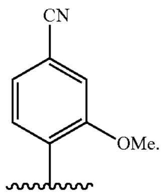

In some embodiments, the heterologous tRNA comprises at least one unnatural base which is

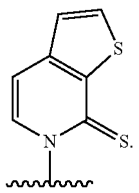

In some embodiments, the heterologous tRNA comprises at least one unnatural base which is

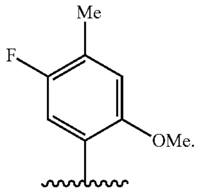

In some embodiments, the semi-synthetic organism disclosed herein further comprises a heterologous mRNA and a heterologous tRNA. In some embodiments, the semi-synthetic organism further comprises (a) a heterologous nucleoside triphosphate transporter, (b) a heterologous mRNA, (c) a heterologous tRNA, (d) a heterologous tRNA synthetase, and (e) a heterologous RNA polymerase, and wherein the organism does not express a protein having the function of DNA recombinational repair. In some embodiments, the nucleoside triphosphate transporter is PtNTT2, the tRNA synthetase is *M. barkeri* pyrrolysyl-tRNA synthetase (Mb PylRS), and the RNA polymerase is T7 RNAP.

In some embodiments, the semi-synthetic organism is *E. coli* and the organism does not express RecA. In some embodiments, the semi-synthetic organism overexpresses one or more DNA polymerases. In some embodiments, the organism overexpresses DNA Pol II.

Natural and Unnatural Amino Acids

As used herein, an amino acid residue can refer to a molecule containing both an amino group and a carboxyl group. Suitable amino acids include, without limitation, both the D- and L-isomers of the naturally-occurring amino acids, as well as non-naturally occurring amino acids prepared by organic synthesis or any other method. The term amino acid, as used herein, includes, without limitation, α-amino acids, β-amino acids, naturally occurring amino acids, non-canonical amino acids, non-natural amino acids, and amino acid analogs.

The term "α-amino acid" can refer to a molecule containing both an amino group and a carboxyl group bound to a carbon which is designated the α-carbon. For example:

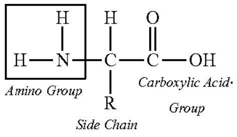

The term "β-amino acid" can refer to a molecule containing both an amino group and a carboxyl group in a β configuration.

"Naturally occurring amino acid" can refer to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of naturally occurring amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamine acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive(10%) neutral(90%) | −3.2 |
| Isolencine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acid" can be glycine, alanine, proline, and analogs thereof. "Large hydrophobic amino acids" can be valine, leucine, isoleucine, phenylalanine, methionine, tryptophan, and analogs thereof "Polar amino acids" can be serine, threonine, asparagine, glutamine, cysteine, tyrosine, and analogs thereof. "Charged amino acids" can be lysine, arginine, histidine, aspartate, glutamate, and analogs thereof.

An "amino acid analog" can be a molecule which is structurally similar to an amino acid and which can be substituted for an amino acid in the formation of a peptidomimetic macrocycle Amino acid analogs include, without limitation, j-amino acids and amino acids where the amino or carboxy group is substituted by a similarly reactive group (e.g., substitution of the primary amine with a secondary or tertiary amine, or substitution of the carboxy group with an ester).

A "non-canonical amino acid (ncAA)" or "non-natural amino acid" or "unnatural amino acid" can be an amino acid which is not one of the twenty amino acids commonly found in peptides synthesized in nature, and known by the one letter abbreviations A, R, N, C, D, Q, E, G, H, I, L, K, M, F, P, S, T, W, Y and V. In some instances, non-natural amino acids are a subset of non-canonical amino acids.

Amino acid analogs can include β-amino acid analogs. Examples of β-amino acid analogs include, but are not limited to, the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid;

(S)-3-amino-4-(4-chlorophenyl) butyric acid; (S)-3-amino-4-(4-cyanophenyl)-butyric acid; (S)-3-amino-4-(4-fluorophenyl) butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogs can include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanine; β-cyclohexyl-D-alanine; β-cyclohexyl-L-alanine; β-cyclopenten-1-yl-alanine; β-cyclopentyl-alanine; β-cyclopropyl-L-Ala-OH·dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH·dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH·dicyclohexylammonium salt; cyclopentyl-Gly-OH·dicyclohexylammonium salt; D-α,β-diaminopropionic acid; D-α-aminobutyric acid; D-α-t-butylglycine; D-(2-thienyl)glycine; D-β-thienyl)glycine; D-2-aminocaproic acid; D-2-indanylglycine; D-allylglycine-dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl) glycine; L-2-amino-3-(dimethylamino)-propionic acid; L-2-aminocaproic acid dicyclohexyl-ammonium salt; L-2-indanylglycine; L-allylglycine dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene) ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs can include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; $Lys(Me)_2$-OH; $Lys(N_3)$ OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (N-1-(4,4-dimethyl-2,6-dioxo-cyclohex-1-ylidene)ethyl)-D-ornithine; (Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg $(Me)_2$-OH (asymmetrical); Arg(Me)2-OH (symmetrical); Lys(ivDde)-OH; Lys(Me)2-OH·HCl; Lys(Me3)-OH chloride; No-nitro-D-arginine; and No-nitro-L-arginine.

Amino acid analogs can include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-p-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Amino acid analogs can include analogs of cysteine and methionine. Examples of amino acid analogs of cysteine and methionine include, but are not limited to, the following: Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Amino acid analogs can include analogs of phenylalanine and tyrosine. Examples of amino acid analogs of phenylalanine and tyrosine include, but are not limited to, the following: 3-methyl-phenylalanine, O-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2; 4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogs can include analogs of proline. Examples of amino acid analogs of proline include, but are not limited to, the following: 3,4-dehydro-proline, 4-fluoro-proline, cis-4-hydroxy-proline, thiazolidine-2-carboxylic acid, and trans-4-fluoro-proline.

Amino acid analogs can include analogs of serine and threonine. Examples of amino acid analogs of serine and threonine include, but are not limited to, the following: 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogs can include analogs of tryptophan. Examples of amino acid analogs of tryptophan include, but are not limited to, the following: α-methyl-tryptophan; β-(3-benzothienyl)-D-alanine; 0-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

Amino acid analogs can be racemic. In some instances, the D isomer of the amino acid analog is used. In some cases, the L isomer of the amino acid analog is used. In some instances, the amino acid analog comprises chiral centers that are in the R or S configuration. Sometimes, the amino group(s) of a β-amino acid analog is substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

In some embodiments, an unnatural amino acid is an unnatural amino acid described in Liu C. C., Schultz, P. G. *Annu. Rev. Biochem.* 2010, 79, 413, the disclosures of which is hereby incorporated by reference in its entirety. In some embodiments, an unnatural amino acid comprises N6(2-azidoethoxy)-carbonyl-L-lysine.

In some embodiments, an amino acid residue described herein (e.g., within a protein) is mutated to an unnatural amino acid prior to binding to a conjugating moiety. In some cases, the mutation to an unnatural amino acid prevents or minimizes a self-antigen response of the immune system. As used herein, the term "unnatural amino acid" refers to an amino acid other than the 20 amino acids that occur naturally in protein. Non-limiting examples of unnatural amino acids include: p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GcNAcp-serine, L-Dopa, fluorinated phenylalanine, isopropyl-L-phenylalanine, p-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, azido-lysine (N6-azidoethoxy-carbonyl-L-lysine, AzK), an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynyl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof, an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an α, α disubstituted amino acid; a β-amino acid; a cyclic amino acid other than proline or histidine, and an aromatic amino acid other than phenylalanine, tyrosine or tryptophan.

In some embodiments, the unnatural amino acid comprises a selective reactive group, or a reactive group for site-selective labeling of a target protein or polypeptide. In some instances, the chemistry is a biorthogonal reaction (e.g., biocompatible and selective reactions). In some cases, the chemistry is a Cu(I)-catalyzed or "copper-free" alkyne-azide triazole-forming reaction, the Staudinger ligation, inverse-electron-demand Diels-Alder (IEDDA) reaction, "photo-click" chemistry, or a metal-mediated process such as olefin metathesis and Suzuki-Miyaura or Sonogashira cross-coupling. In some embodiments, the unnatural amino acid comprises a photoreactive group, which crosslinks, upon irradiation with, e.g., UV. In some embodiments, the unnatural amino acid comprises a photo-caged amino acid. In some instances, the unnatural amino acid is a para-substituted, meta-substituted, or an ortho-substituted amino acid derivative.

In some instances, the unnatural amino acid comprises p-acetyl-L-phenylalanine, p-azidomethyl-L-phenylalanine (pAMF), p-iodo-L-phenylalanine, O-methyl-L-tyrosine, p-methoxyphenylalanine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, or isopropyl-L-phenylalanine.

In some cases, the unnatural amino acid is 3-aminotyrosine, 3-nitrotyrosine, 3,4-dihydroxy-phenylalanine, or 3-iodotyrosine. In some cases, the unnatural amino acid is phenylselenocysteine. In some instances, the unnatural amino acid is a benzophenone, ketone, iodide, methoxy, acetyl, benzoyl, or azide containing phenylalanine derivative. In some instances, the unnatural amino acid is a benzophenone, ketone, iodide, methoxy, acetyl, benzoyl, or azide containing lysine derivative. In some instances, the unnatural amino acid comprises an aromatic side chain. In some instances, the unnatural amino acid does not comprise an aromatic side chain. In some instances, the unnatural amino acid comprises an azido group. In some instances, the unnatural amino acid comprises a Michael-acceptor group. In some instances, Michael-acceptor groups comprise an unsaturated moiety capable of forming a covalent bond through a 1,2-addition reaction. In some instances, Michael-acceptor groups comprise electron-deficient alkenes or alkynes. In some instances, Michael-acceptor groups include but are not limited to alpha,beta unsaturated: ketones, aldehydes, sulfoxides, sulfones, nitriles, imines, or aromatics. In some instances, the unnatural amino acid is dehydroalanine. In some instances, the unnatural amino acid comprises an aldehyde or ketone group. In some instances, the unnatural amino acid is a lysine derivative comprising an aldehyde or ketone group. In some instances, the unnatural amino acid is a lysine derivative comprising one or more O, N, Se, or S atoms at the beta, gamma, or delta position. In some instances, the unnatural amino acid is a lysine derivative comprising O, N, Se, or S atoms at the gamma position. In some instances, the unnatural amino acid is a lysine derivative wherein the epsilon N atom is replaced with an oxygen atom. In some instances, the unnatural amino acid is a lysine derivative that is not naturally-occurring post-translationally modified lysine.

In some instances, the unnatural amino acid is an amino acid comprising a side chain, wherein the sixth atom from the alpha position comprises a carbonyl group. In some instances, the unnatural amino acid is an amino acid comprising a side chain, wherein the sixth atom from the alpha position comprises a carbonyl group, and the fifth atom from the alpha position is nitrogen. In some instances, the unnatural amino acid is an amino acid comprising a side chain, wherein the seventh atom from the alpha position is an oxygen atom.

In some instances, the unnatural amino acid is a serine derivative comprising selenium. In some instances, the unnatural amino acid is selenoserine (2-amino-3-hydroselenopropanoic acid). In some instances, the unnatural amino acid is 2-amino-3-((2-((3-(benzyloxy)-3-oxopropyl)amino)ethyl)selanyl)propanoic acid. In some instances, the unnatural amino acid is 2-amino-3-(phenylselanyl)propanoic acid. In some instances, the unnatural amino acid comprises selenium, wherein oxidation of the selenium results in the formation of an unnatural amino acid comprising an alkene.

In some instances, the unnatural amino acid comprises a cyclooctynyl group. In some instances, the unnatural amino acid comprises a transcycloctenyl group. In some instances, the unnatural amino acid comprises a norbornenyl group. In some instances, the unnatural amino acid comprises a cyclopropenyl group. In some instances, the unnatural amino acid comprises a diazirine group. In some instances, the unnatural amino acid comprises a tetrazine group.

In some instances, the unnatural amino acid is a lysine derivative, wherein the side-chain nitrogen is carbamylated. In some instances, the unnatural amino acid is a lysine derivative, wherein the side-chain nitrogen is acylated. In some instances, the unnatural amino acid is 2-amino-6-{[(tert-butoxy)carbonyl]amino}hexanoic acid. In some instances, the unnatural amino acid is 2-amino-6-{[(tert-butoxy)carbonyl]amino}hexanoic acid. In some instances, the unnatural amino acid is N6-Boc-N6-methyllysine. In some instances, the unnatural amino acid is N6-acetyllysine. In some instances, the unnatural amino acid is pyrrolysine. In some instances, the unnatural amino acid is N6-trifluoroacetyllysine. In some instances, the unnatural amino acid is 2-amino-6-{[(benzyloxy)carbonyl]amino}hexanoic acid. In some instances, the unnatural amino acid is 2-amino-6-{[(p-iodobenzyloxy)carbonyl]amino}hexanoic acid. In some instances, the unnatural amino acid is 2-amino-6-{[(p-nitrobenzyloxy)carbonyl]amino}hexanoic acid. In some instances, the unnatural amino acid is N6-prolyllysine. In some instances, the unnatural amino acid is 2-amino-6-{[(cyclopentyloxy)carbonyl]amino}hexanoic acid. In some instances, the unnatural amino acid is N6-(cyclopentanecarbonyl)lysine. In some instances, the unnatural amino acid is N6-(tetrahydrofuran-2-carbonyl)lysine. In some instances, the unnatural amino acid is N6-(3-ethynyltetrahydrofuran-2-carbonyl)lysine. In some instances, the unnatural amino acid is N6-((prop-2-yn-1-yloxy)carbonyl)lysine. In some instances, the unnatural amino acid is 2-amino-6-{[(2-azidocyclopentyloxy)carbonyl]amino}hexanoic acid. In some instances, the unnatural amino acid is N6-((2-azidoethoxy)carbonyl)lysine. In some instances, the unnatural amino acid is 2-amino-6-{[(2-nitrobenzyloxy)carbonyl]amino}hexanoic acid. In some instances, the unnatural amino acid is 2-amino-6-{[(2-cyclooctynyloxy)carbonyl]amino}hexanoic acid. In some instances, the unnatural amino acid is N6-(2-aminobut-3-ynoyl)lysine. In some instances, the unnatural amino acid is 2-amino-6-((2-aminobut-3-ynoyl)oxy)hexanoic acid. In some instances, the unnatural amino acid is N6-(allyloxycarbonyl)lysine. In some instances, the unnatural amino acid is N6-(butenyl-4-oxycarbonyl)lysine. In some instances, the unnatural amino acid is N6-(pentenyl-5-oxycarbonyl)lysine. In some instances, the unnatural amino acid is N6-((but-3-yn-1-yloxy)carbonyl)-lysine. In some instances, the unnatural amino acid is N6-((pent-4-yn-1-yloxy)carbonyl)-lysine. In some instances, the unnatural amino acid is N6-(thiazolidine-4-carbonyl)lysine. In some instances, the unnatural amino acid is 2-amino-8-oxononanoic acid. In some instances, the unnatural amino acid is 2-amino-8-oxooctanoic acid. In some instances, the unnatural amino acid is N6-(2-oxoacetyl)lysine.

In some instances, the unnatural amino acid is N6-propionyllysine. In some instances, the unnatural amino acid is N6-butyryllysine. In some instances, the unnatural amino acid is N6-(but-2-enoyl)lysine. In some instances, the unnatural amino acid is N6-((bicyclo[2.2.1]hept-5-en-2-yloxy)carbonyl)lysine. In some instances, the unnatural amino acid is N6-((spiro[2.3]hex-1-en-5-ylmethoxy)carbonyl)lysine. In some instances, the unnatural amino acid is N6-(((4-(1-(trifluoromethyl)cycloprop-2-en-1-yl)benzyl)oxy)carbonyl)lysine. In some instances, the unnatural amino acid is N6-((bicyclo[2.2.1]hept-5-en-2-ylmethoxy)carbonyl)lysine. In some instances, the unnatural amino acid is cysteinyllysine. In some instances, the unnatural amino acid is N6-((1-(6-nitrobenzo[d][1,3]dioxol-5-yl)ethoxy)carbonyl)lysine. In some instances, the unnatural amino acid is N6-((2-(3-methyl-3H-diazirin-3-yl)ethoxy)carbonyl)lysine. In some instances, the unnatural amino acid is N6-((3-(3-methyl-3H-diazirin-3-yl)propoxy)carbonyl)lysine. In some instances, the unnatural amino acid is N6-((meta nitrobenzyloxy)N6-methylcarbonyl)lysine. In some instances, the unnatural amino acid is N6-((bicyclo[6.1.0]non-4-yn-9-ylmethoxy)carbonyl)-lysine. In some instances, the unnatural amino acid is N6-((cyclohept-3-en-1-yloxy)carbonyl)-L-lysine.

In some instances, the unnatural amino acid is 2-amino-3-(((((benzyloxy)carbonyl)amino)methyl)selanyl)propanoic acid. In some embodiments, the unnatural amino acid is incorporated into a protein by a repurposed amber, opal, or ochre stop codon. In some embodiments, the unnatural amino acid is incorporated into a protein by a 4-base codon. In some embodiments, the unnatural amino acid is incorporated into the protein by a repurposed rare sense codon.

In some embodiments, the unnatural amino acid is incorporated into a protein by an unnatural codon comprising an unnatural nucleotide.

In some embodiments, the protein comprises at least two unnatural amino acids. In some embodiments, the protein comprises at least three unnatural amino acids. In some embodiments, the protein comprises at least two different unnatural amino acids. In some embodiments, the protein comprises at least three different unnatural amino acids. the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-azidoethoxy-carbonyl-L-lysine (AzK) or N6-propargylethoxy-carbonyl-L-lysine (PraK). In some embodiments, the at least one unnatural amino acid comprises N6-azidoethoxy-carbonyl-L-lysine (AzK). In some embodiments, the at least one unnatural amino acid comprises N6-propargylethoxy-carbonyl-L-lysine (PraK).

In some instances, incorporation of the unnatural amino acid into a protein is mediated by an orthogonal, modified synthetase/tRNA pair. Such orthogonal pairs comprise a natural or mutated synthetase that is capable of charging the unnatural tRNA with a specific unnatural amino acid, often while minimizing charging of a) other endogenous amino acids or alternate unnatural amino acids onto the unnatural tRNA and b) any other (including endogenous) tRNAs. Such orthogonal pairs comprise tRNAs that are capable of being charged by the synthetase, while avoiding being charged with other endogenous amino acids by endogenous synthetases. In some embodiments, such pairs are identified from various organisms, such as bacteria, yeast, Archaea, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA. In any of these embodiments, the tRNA can be heterologous tRNA.

In some embodiments, the unnatural amino acid is incorporated into a protein by an aminoacyl (aaRS or RS)-tRNA synthetase-tRNA pair. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophilus* $tRNA_{CUA}$ pairs, *E. coli* LeuRS (Ec-Leu)/*B. stearothermophilus* $tRNA_{CUA}$ pairs, and pyrrolysyl-tRNA pairs. In some instances, the unnatural amino acid is incorporated into a protein by a Mj-TyrRS/tRNA pair. Exemplary unnatural amino acids (UAAs) that can be incorporated by a Mj-TyrRS/tRNA pair include, but are not limited to, para-substituted phenylalanine derivatives such as p-aminophenylalanine and p-methoyphenylalanine; meta-substituted tyrosine derivatives such as 3-aminotyrosine, 3-nitrotyrosine, 3,4-dihydroxyphenylalanine, and 3-iodotyrosine; phenylselenocysteine; p-boronopheylalanine; and o-nitrobenzyltyrosine.

In some instances, the unnatural amino acid is incorporated into a protein by a Ec-Tyr/$tRNA_{CUA}$ or a Ec-Leu/$tRNA_{CUA}$ pair. Exemplary UAAs that can be incorporated by a Ec-Tyr/$tRNA_{CUA}$ or a Ec-Leu/$tRNA_{CUA}$ pair include, but are not limited to, phenylalanine derivatives containing benzophenone, ketone, iodide, or azide substituents; O-propargyltyrosine; α-aminocaprylic acid, O-methyl tyrosine, O-nitrobenzyl cysteine; and 3-(naphthalene-2-ylamino)-2-amino-propanoic acid.

In some instances, the unnatural amino acid is incorporated into a protein by a pyrrolysyl-tRNA pair. In some cases, the PylRS is obtained from an archaebacterial species, e.g., from a methanogenic archaebacterium. In some cases, the PylRS is obtained from *Methanosarcina barkeri, Methanosarcina mazei*, or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-D-prolyl-L-lysine, and N-ε-cyclopentyloxycarbonyl-L-lysine; N-ε-Acryloyl-L-lysine; N-ε-[(1-(6-nitrobenzo[d][1,3]dioxol-5-yl)ethoxy)carbonyl]-L-lysine; and N-ε-(1-methylcyclopro-2-enecarboxamido)lysine.

In some instances, an unnatural amino acid is incorporated into a protein described herein by a synthetase disclosed in U.S. Pat. Nos. 9,988,619 and 9,938,516, the disclosures of each of which are hereby incorporated by reference in their entirety. Exemplary UAAs that can be incorporated by such synthetases include para-methylazido-L-phenylalanine, aralkyl, heterocyclyl, heteroaralkyl unnatural amino acids, and others. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, such synthetases are expressed and used to incorporate UAAs into proteins in vivo. In some embodiments, such synthetases are used to incorporate UAAs into proteins using a cell-free translation system.

In some instances, an unnatural amino acid is incorporated into a protein described herein by a naturally occurring synthetase. In some embodiments, an unnatural amino acid is incorporated into a protein by an organism that is auxotrophic for one or more amino acids. In some embodiments, synthetases corresponding to the auxotrophic amino acid are capable of charging the corresponding tRNA with an unnatural amino acid. In some embodiments, the unnatural amino acid is selenocysteine, or a derivative thereof. In some embodiments, the unnatural amino acid is selenomethionine, or a derivative thereof. In some embodiments, the unnatural amino acid is an aromatic amino acid, wherein the aromatic amino acid comprises an aryl halide, such as an iodide. In embodiments, the unnatural amino acid is structurally similar to the auxotrophic amino acid.

Figure 8A:
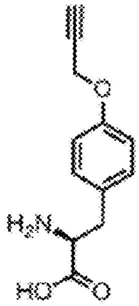
FIG. 8A shows exemplary unnatural amino acids. This figure is adapted from FIG. 2 of Young et al., "Beyond the canonical 20 amino acids: expanding the genetic lexicon," *J. of Biological Chemistry* 285(15): 11039-11044 (2010).
Figure 8A:
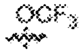
Figure 8A:
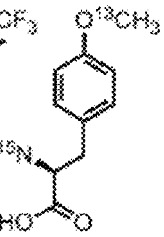
Figure 8A:
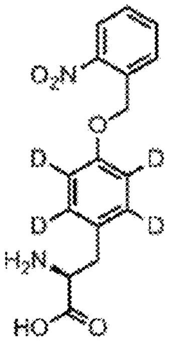
Figure 8A:
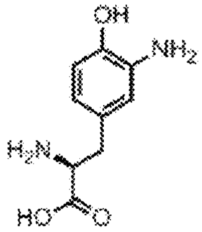
Figure 8A:
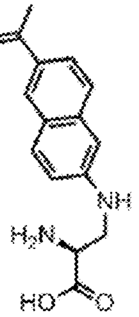
Figure 8A:
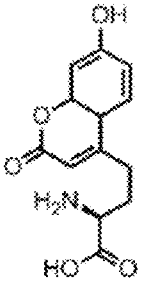
Figure 8A:
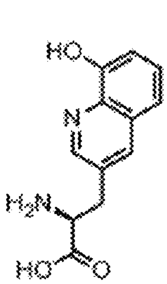
Figure 8A:
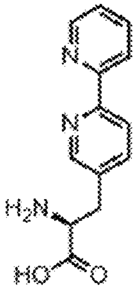
Figure 8A:
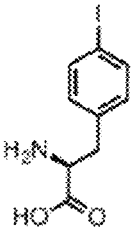
Figure 8A:
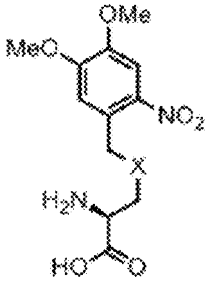
Figure 8A:
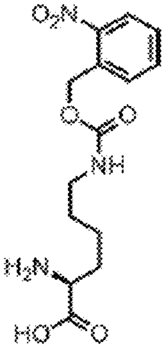
Figure 8A:
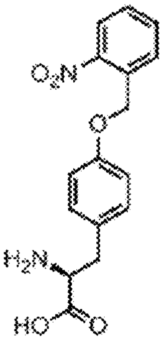
Figure 8A:
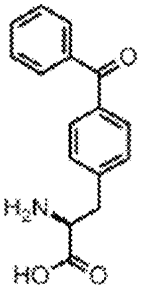
Figure 8A:
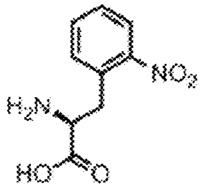
Figure 8A:
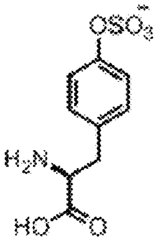
Figure 8A:
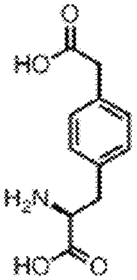
Figure 8A:
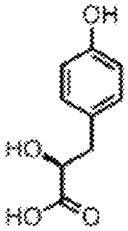
Figure 8A:
Figure 8A:
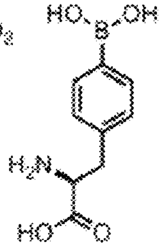

In some instances, the unnatural amino acid comprises an unnatural amino acid illustrated in FIG. 8A.

Figure 8B:
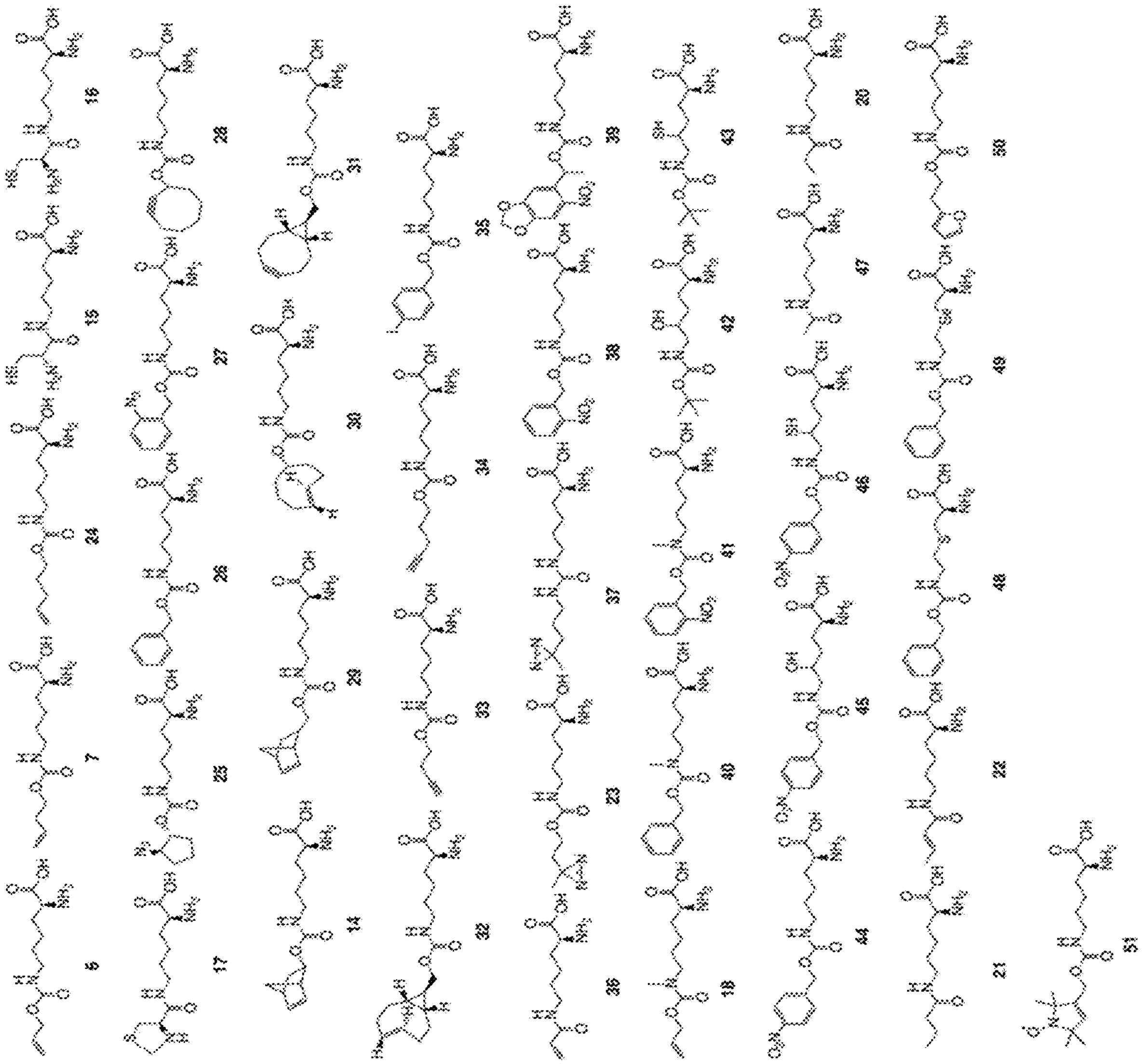
FIG. 8B illustrates exemplary unnatural amino acid lysine derivatives.
Figure 8C:
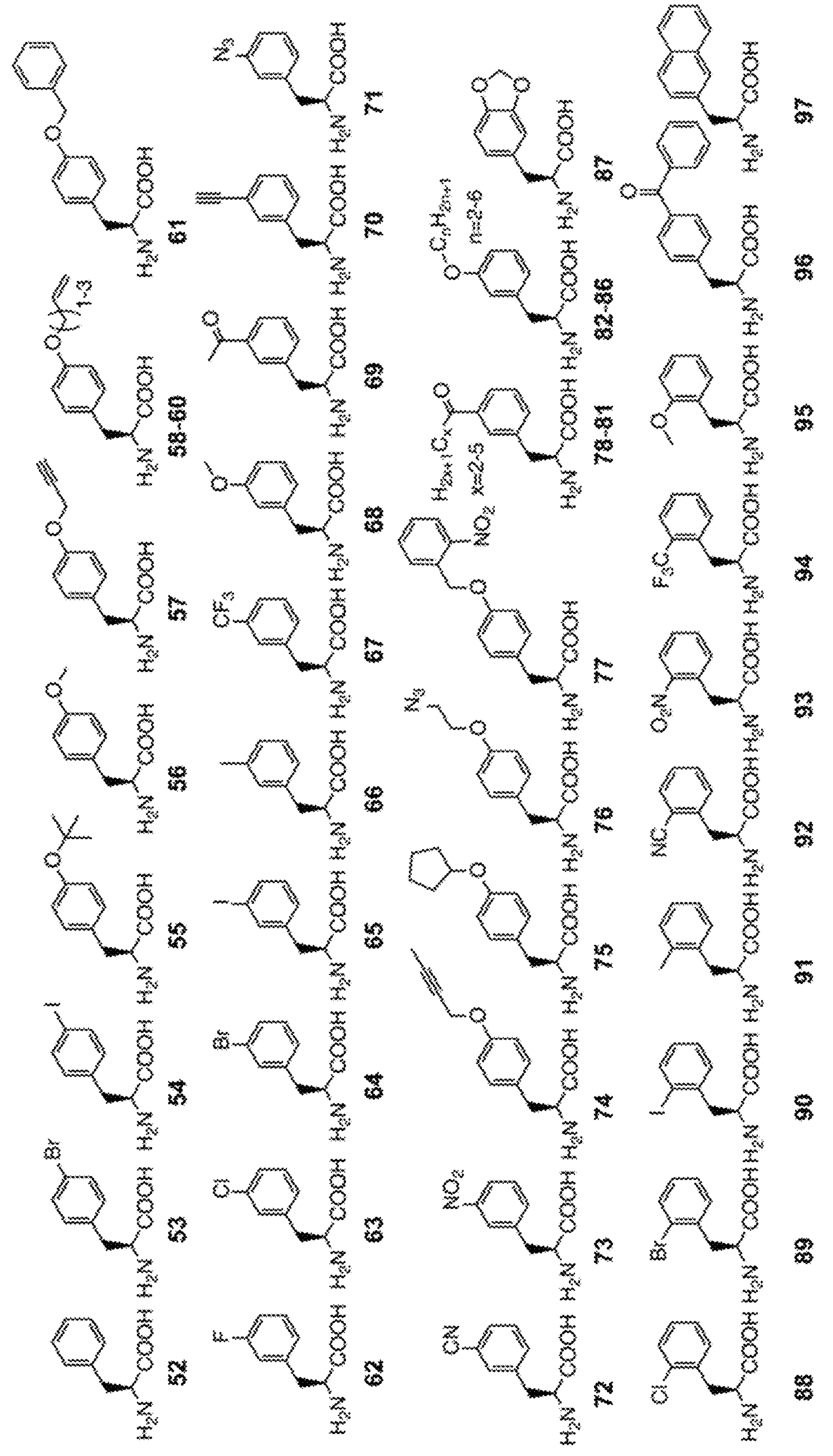
FIG. 8C illustrates exemplary unnatural amino acid phenylalanine derivatives.
Figure 8D:
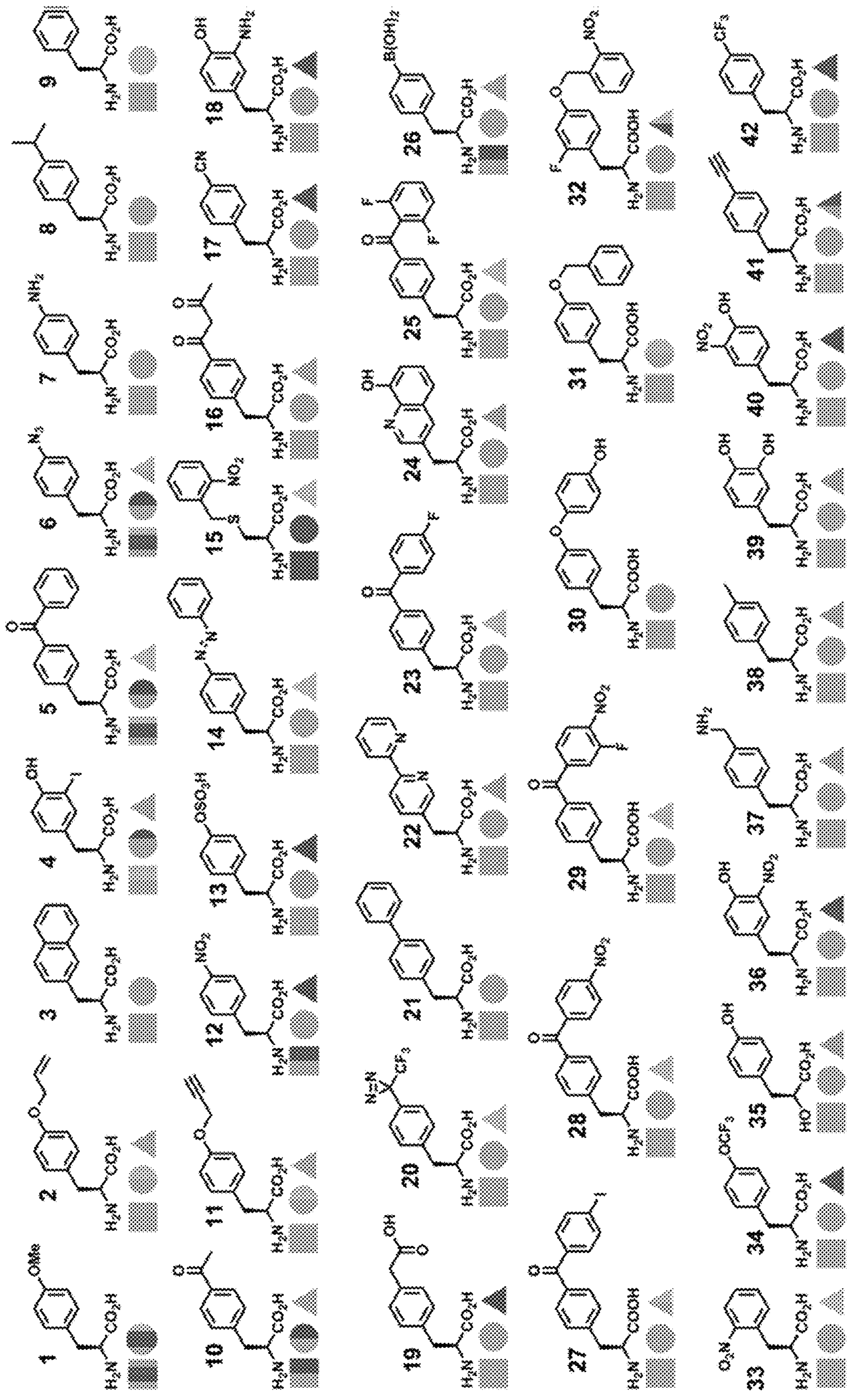
FIGS. 8D-8G illustrate exemplary unnatural amino acids. These unnatural amino acids (UAAs) have been genetically encoded in proteins (FIG. 8D—UAA #1-42.
Figure 8E:
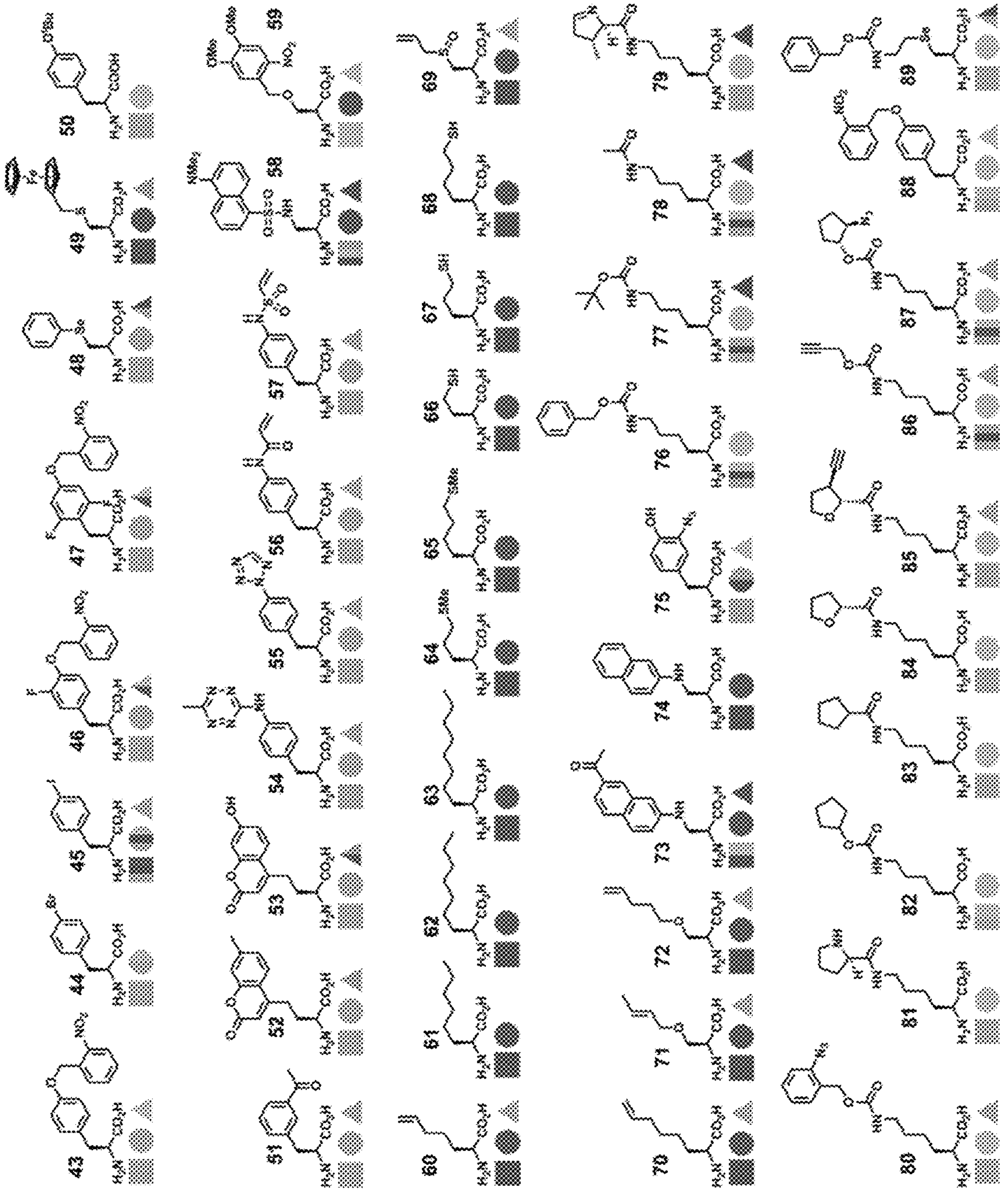
Figure 8F:
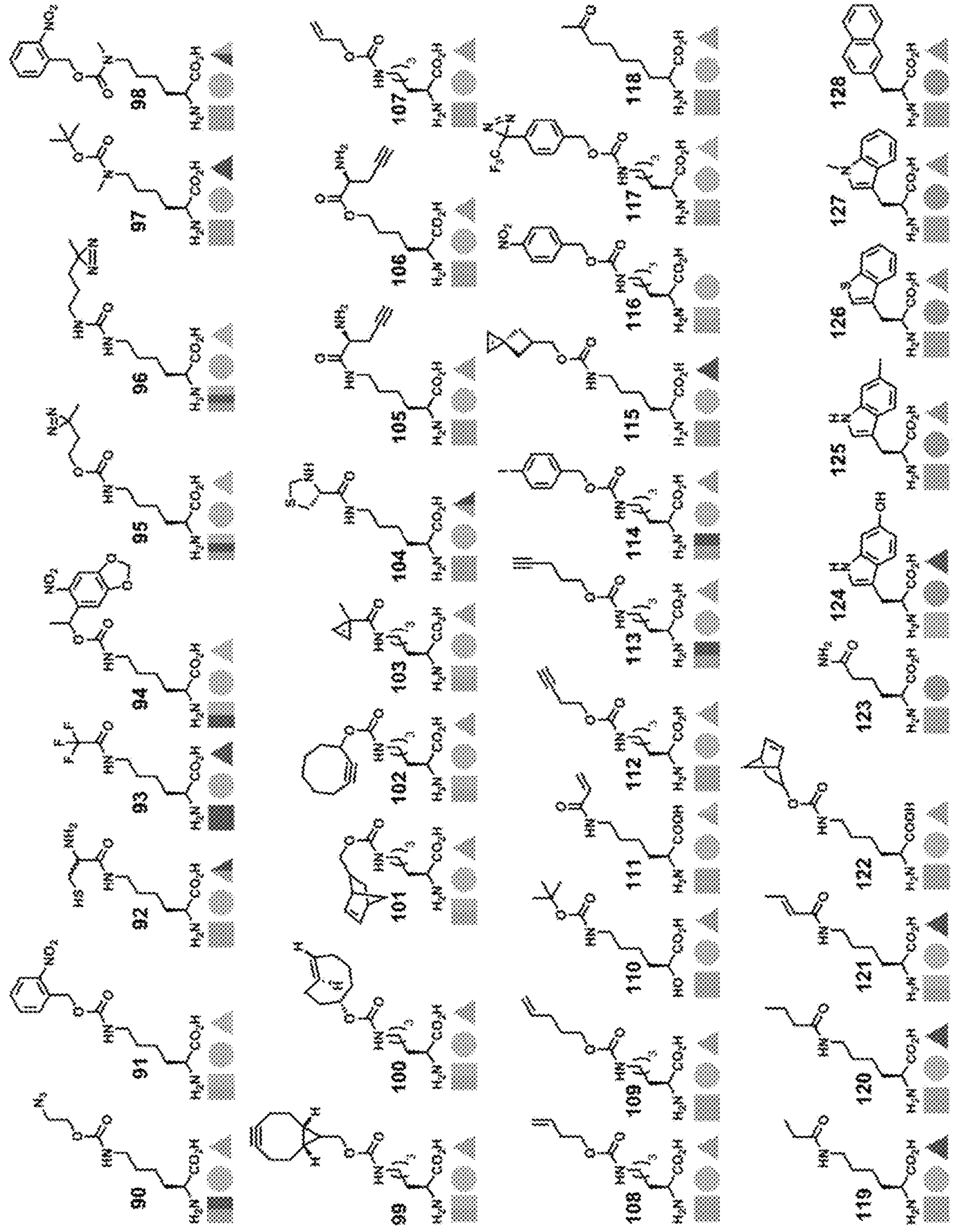
Figure 8G:
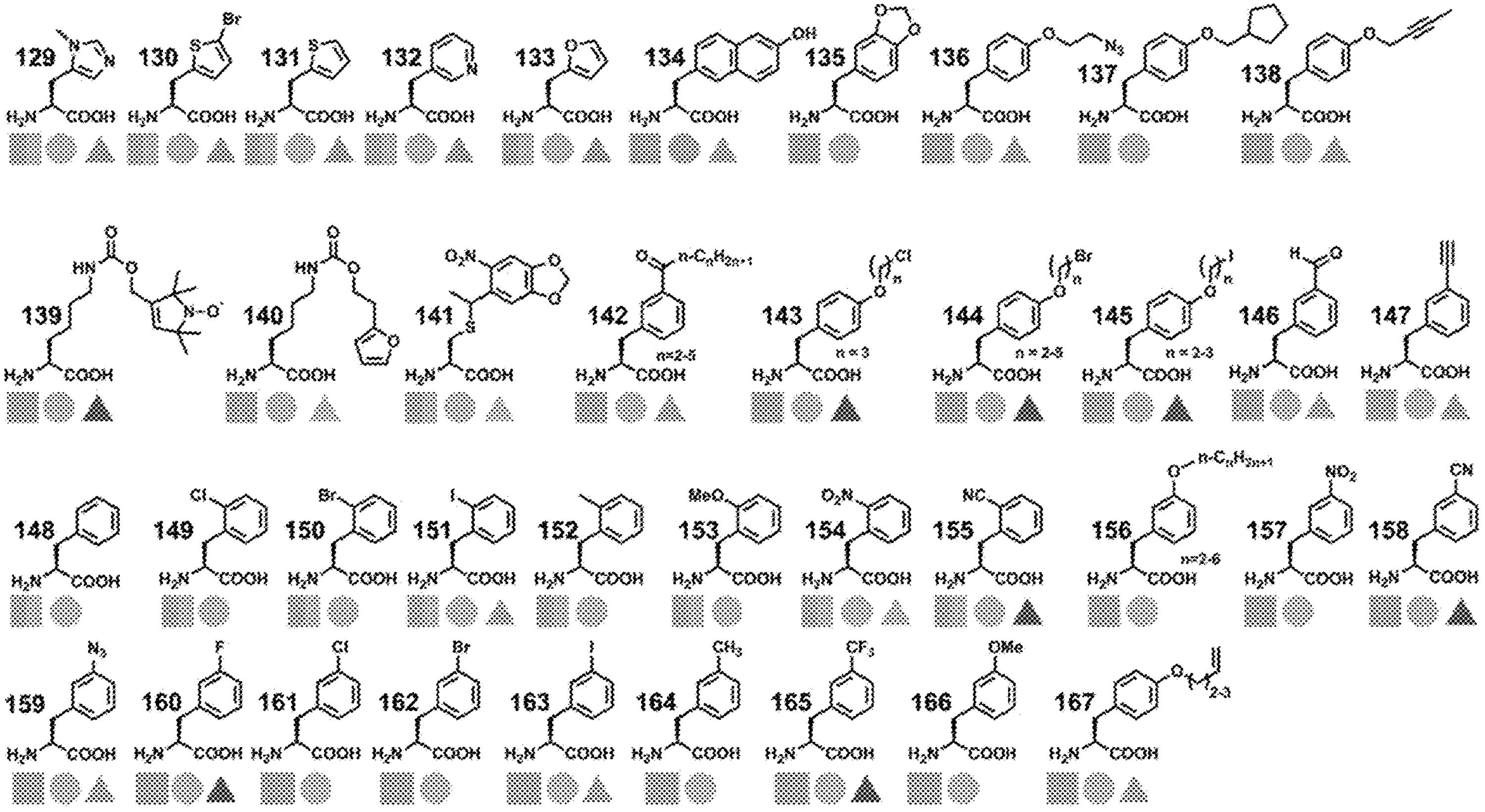

In some instances, the unnatural amino acid comprises a lysine or phenylalanine derivative or analogue. In some instances, the unnatural amino acid comprises a lysine derivative or a lysine analogue. In some instances, the unnatural amino acid comprises a pyrrolysine (Pyl). In some instances, the unnatural amino acid comprises a phenylalanine derivative or a phenylalanine analogue. In some instances, the unnatural amino acid is an unnatural amino acid described in Wan, et al., "Pyrrolysyl-tRNA synthetase: an ordinary enzyme but an outstanding genetic code expansion tool," Biocheim Biophys Aceta 1844(6): 1059-4070 (2014). In some instances, the unnatural amino acid comprises an unnatural amino acid illustrated in FIG. 8B and FIG. 8C.

In some embodiments, the unnatural amino acid comprises an unnatural amino acid illustrated in FIG. 8D-FIG. 8G (adopted from Table 1 of Dumas et al., *Chemical Science* 2015, 6, 50-69).

In some embodiments, an unnatural amino acid incorporated into a protein described herein is disclosed in U.S. Pat. Nos. 9,840,493; 9,682,934; US 2017/0260137; U.S. Pat. No. 9,938,516; or US 2018/0086734; the disclosures of each of which are hereby incorporated by reference in their entirety. Exemplary UAAs that can be incorporated by such synthetases include para-methylazido-L-phenylalanine, aralkyl, heterocyclyl, and heteroaralkyl, and lysine derivative unnatural amino acids. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water-soluble moiety. In some embodiments, a UAA comprises an azide attached to an aromatic moiety via an alkyl linker. In some embodiments, an alkyl linker is a $C_1$-$C_{10}$ linker. In some embodiments, a UAA comprises a tetrazine attached to an aromatic moiety via an alkyl linker. In some embodiments, a UAA comprises a tetrazine attached to an aromatic moiety via an amino group. In some embodiments, a UAA comprises a tetrazine attached to an aromatic moiety via an alkylamino group. In some embodiments, a UAA comprises an azide attached to the terminal nitrogen (e.g., N6 of a lysine derivative, or N5, N4, or N3 of a derivative comprising a shorter alkyl side chain) of an amino acid side chain via an alkyl chain. In some embodiments, a UAA comprises a tetrazine attached to the terminal nitrogen of an amino acid side chain via an alkyl chain. In some embodiments, a UAA comprises an azide or tetrazine attached to an amide via an alkyl linker. In some embodiments, the UAA is an azide or tetrazine-containing carbamate or amide of 3-aminoalanine, serine, lysine, or derivative thereof. In some embodiments, such UAAs are incorporated into proteins in vivo. In some embodiments, such UAAs are incorporated into proteins in a cell-free system.

Cell Types

In some embodiments, many types of cells/microorganisms are used, e.g., for transforming or genetically engineering. In some embodiments, a cell is a prokaryotic or eukaryotic cell. In some embodiments, the prokaryotic cell is a bacterial cell. In some embodiments, the eukaryotic cell is a fungal cell or unicellular protozoan. In some embodiments, the fungal cell is a yeast cell. In other cases, the eukaryotic cell is a cultured animal, plant, or human cell. In additional cases, the eukaryotic cell is present in an organism such as a plant, multicellular fungus, or animal.

In some embodiments, an engineered microorganism is a single cell organism, often capable of dividing and proliferating. As used herein, an "engineered microorganism" is a microorganism whose genetic material has been altered using genetic engineering techniques (i.e., recombinant DNA technology). A microorganism can include one or more of the following features: aerobe, anaerobe, filamentous, non-filamentous, monoploid, diploid, auxotrophic and/or non-auxotrophic. In certain embodiments, an engineered microorganism is a prokaryotic microorganism (e.g., bacterium), and in certain embodiments, an engineered microorganism is a non-prokaryotic microorganism, such as a eukaryotic microorganism. In some embodiments, an engineered microorganism is a eukaryotic microorganism (e.g., yeast, other fungus, amoeba). In some embodiments, an engineered microorganism is a fungus. In some embodiments, an engineered organism is a yeast.

Any suitable yeast may be selected as a host microorganism, engineered microorganism, genetically modified organism or source for a heterologous or modified polynucleotide. Yeast include, but are not limited to, *Yarrowia* yeast (e.g., *Y. lipolytica* (formerly classified as *Candida lipolytica*)), *Candida* yeast (e.g., *C. revkaufi, C. viswanathii, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris, K. phaffii*) and *Lipomyces* yeast (e.g., *L. starkeyii, L. lipoferus*). In some embodiments, a suitable yeast is of the genus *Arachniotus, Aspergillus, Aureobasidium, Auxarthron, Blastomyces, Candida, Chrysosporuim, Chrysosporium, Debaryomyces, Coccidiodes, Cryptococcus, Gymnoascus, Hansenula, Histoplasma, Issatchenkia, Kluyveromyces, Lipomyces, Lssatchenkia, Microsporum, Myxotrichum, Myxozyma, Oidiodendron, Pachysolen, Penicillium, Pichia, Rhodosporidium, Rhodotorula, Rhodotorula, Saccharomyces, Schizosaccharomyces, Scopulariopsis, Sepedonium, Trichosporon*, or *Yarrowia*. In some embodiments, a suitable yeast is of the species *Arachniotus flavoluteus, Aspergillus flavus, Aspergillus fumigatus, Aspergillus niger, Aureobasidium pullulans, Auxarthron thaxteri, Blastomyces dermatitidis, Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii, Chrysosporuim keratinophilum, Coccidiodes immitis, Cryptococcus albidus* var. *diffluens, Cryptococcus laurentii, Cryptococcus neofomans, Debaryomyces hansenii, Gymnoascus dugwayensis, Hansenula anomala, Histoplasma capsulatum, Issatchenkia occidentalis, Isstachenkia orientalis, Kluyveromyces lactis, Kluyveromyces marxianus, Kluyveromyces thermotolerans, Kluyveromyces waltii, Lipomyces lipoferus, Lipomyces starkeyii, Microsporum gypseum, Myxotrichum deflexum, Oidiodendron echinulatum, Pachysolen tannophilis, Penicillium notatum, Pichia anomala, Pichia pastoris, Pichia stipitis, Rhodosporidium toruloides, Rhodotorula glutinus, Rhodotorula graminis, Saccharomyces cerevisiae, Saccharomyces kluyveri, Schizosaccharomyces pombe, Scopulariopsis acremonium, Sepedonium chrysospermum, Trichosporon cutaneum, Trichosporon pullans, Yarrowia lipolytica*, or *Yarrowia lipolytica* (formerly classified as *Candida lipolytica*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *Candida* species (i.e., *Candida* spp.) yeast. Any suitable *Candida* species can be used and/or genetically modified for production of a fatty dicarboxylic acid (e.g., octanedioic acid, decanedioic acid, dodecanedioic acid, tetradecanedioic acid, hexadecanedioic acid, octadecanedioic acid, eicosanedioic acid). In some embodiments, suitable *Candida* species include, but are not limited to *Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii* and any other *Candida* spp. yeast described herein. Non-limiting examples of *Candida* spp. strains include, but are not limited to, sAA001 (ATCC20336), sAA002 (ATCC20913), sAA003 (ATCC20962), sAA496 (US2012/0077252), sAA106 (US2012/0077252), SU-2 (ura3-/ura3-), H5343 (beta oxidation blocked; U.S. Pat. No. 5,648,247) strains. Any suitable strains from *Candida* spp. yeast may be utilized as parental strains for genetic modification.

Yeast genera, species and strains are often so closely related in genetic content that they can be difficult to distinguish, classify and/or name. In some cases strains of *C. lipolytica* and *Y. lipolytica* can be difficult to distinguish, classify and/or name and can be, in some cases, considered the same organism. In some cases, various strains of *C. tropicalis* and *C. viswanathii* can be difficult to distinguish, classify and/or name (for example see Arie et. al., J. Gen. Appl. Microbiol., 46, 257-262 (2000). Some *C. tropicalis* and *C. viswanathii* strains obtained from ATCC as well as from other commercial or academic sources can be considered equivalent and equally suitable for the embodiments described herein. In some embodiments, some parental strains of *C. tropicalis* and *C. viswanathii* are considered to differ in name only.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), *Thraustochytrium* fungi, *Schizochytrium* fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, Norcardia baceteria, Xanthobacter bacteria, *Escherichia* bacteria (e.g., *E. coli* (e.g., strains DH10B, Stbl2, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), *Megasphaera* bacteria (e.g., *Megasphaera elsdenii*). Bacteria also include, but are not limited to, photosynthetic bacteria (e.g., green non-sulfur bacteria (e.g., Choroflexus bacteria (e.g., *C. aurantiacus*), Chloronema bacteria (e.g., *C. gigateum*)), green sulfur bacteria (e.g., *Chlorobium* bacteria (e.g., *C. limicola*), Pelodictyon bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., *R. sphaeroides, R. capsulatus*), and Rhodomicrobium bacteria (e.g., *R. vanellii*)).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and Trichoplusa (e.g., High-Five cells); nematode cells (e.g., *C. elegans* cells); avian cells; amphibian cells (e.g., *Xenopus laevis* cells); reptilian cells; mammalian cells (e.g., NIH3T3, 293, CHO, COS, VERO, C127, BHK, Per-C6, Bowes melanoma and HeLa cells); and plant cells (e.g., *Arabidopsis thaliana, Nicotania tabacum, Cuphea acinifolia, Cuphea aequipetala, Cuphea angustifolia, Cuphea appendiculata, Cuphea avigera, Cuphea avigera* var. *pulcherrima, Cuphea axilliflora, Cuphea bahiensis, Cuphea baillonis, Cuphea brachypoda, Cuphea bustamanta, Cuphea calcarata, Cuphea calophylla, Cuphea calophylla* subsp. *mesostemon, Cuphea carthagenensis, Cuphea circaeoides, Cuphea confertiflora, Cuphea cordata, Cuphea crassiflora, Cuphea cyanea, Cuphea decandra, Cuphea denticulata, Cuphea disperma, Cuphea epilobiifolia, Cuphea ericoides, Cuphea flava, Cuphea flavisetula, Cuphea fuchsiifolia, Cuphea gaumeri, Cuphea glutinosa, Cuphea heterophylla, Cuphea hookeriana, Cuphea hyssopifolia* (Mexican-heather), *Cuphea hyssopoides, Cuphea ignea, Cuphea ingrata, Cuphea jorullensis, Cuphea lanceolata, Cuphea linarioides, Cuphea llavea, Cuphea lophostoma, Cuphea lutea, Cuphea lutescens, Cuphea melanium, Cuphea melvilla, Cuphea micrantha, Cuphea micropetala, Cuphea mimuloides, Cuphea nitidula, Cuphea palustris, Cuphea parsonsia, Cuphea pascuorum, Cuphea paucipetala, Cuphea procumbens, Cuphea pseudosilene, Cuphea pseudovaccinium, Cuphea pulchra, Cuphea racemosa, Cuphea repens, Cuphea salicifolia, Cuphea salvadorensis, Cuphea schumannii, Cuphea sessiliflora, Cuphea sessilifolia, Cuphea setosa, Cuphea spectabilis, Cuphea spermacoce, Cuphea splendida, Cuphea* splendida var. *viridiflava, Cuphea strigulosa, Cuphea subuligera, Cuphea teleandra, Cuphea thymoides, Cuphea tolucana, Cuphea urens, Cuphea utriculosa, Cuphea viscosissima, Cuphea watsoniana, Cuphea wrightii, Cuphea lanceolata*).

Microorganisms or cells used as host organisms or source for a heterologous polynucleotide are commercially available. Microorganisms and cells described herein, and other suitable microorganisms and cells are available, for example, from Invitrogen Corporation, (Carlsbad, CA), American Type Culture Collection (Manassas, Virginia), and Agricultural Research Culture Collection (NRRL; Peoria, Illinois). Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Polymerases

A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases.

The ability to improve specificity, processivity, or other features of polymerases unnatural nucleic acids would be highly desirable in a variety of contexts where, e.g., unnatural nucleic acid incorporation is desired, including amplification, sequencing, labeling, detection, cloning, and many others In some instances, disclosed herein includes polymerases that incorporate unnatural nucleic acids into a growing template copy, e.g., during DNA amplification. In some embodiments, polymerases can be modified such that the active site of the polymerase is modified to reduce steric entry inhibition of the unnatural nucleic acid into the active site. In some embodiments, polymerases can be modified to provide complementarity with one or more unnatural features of the unnatural nucleic acids. Such polymerases can be expressed or engineered in cells for stably incorporating a UBP into the cells. Accordingly, the invention includes compositions that include a heterologous or recombinant polymerase and methods of use thereof.

Polymerases can be modified using methods pertaining to protein engineering. For example, molecular modeling can be carried out based on crystal structures to identify the locations of the polymerases where mutations can be made to modify a target activity. A residue identified as a target for replacement can be replaced with a residue selected using energy minimization modeling, homology modeling, and/or conservative amino acid substitutions, such as described in Bordo, et al. J Mol Biol 217: 721-729 (1991) and Hayes, et al. Proc Natl Acad Sci, USA 99: 15926-15931 (2002), the disclosures of each of which are hereby incorporated by reference in their entirety.

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. In some embodiments, a polymerase is a wild type polymerase. In some embodiments, a polymerase is a modified, or mutant, polymerase. In some embodiments, the polymerase can be a heterologous polymerase.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified polymerase has a specificity for an unnatural nucleic acid that is at least about 10%, 20%, 30%, 40%, 50%, 60%, 70%, 80%, 90%, 95%, 97%, 98%, 99%, 99.5%, or 99.99% of the specificity of the wild type polymerase toward the unnatural nucleic acid. In some embodiments, a modified or wild type polymerase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, or 99.99% of the specificity of the wild type polymerase toward a natural nucleic acid and/or the unnatural nucleic acid without the modified sugar. In some embodiments, a modified or wild type polymerase has a specificity for an unnatural nucleic acid comprising a modified base that is at least about 10%, 20%, 30%, 40%, 50%, 60%, 70%, 80%, 90%, 95%, 97%, 98%, 99%, 99.5%, or 99.99% of the specificity of the wild type polymerase toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, or 99.99% of the specificity of the wild type polymerase toward a nucleic acid comprising a triphosphate and/or the unnatural nucleic acid without the triphosphate. For example, a modified or wild type polymerase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, or 99.99% of the specificity of the wild type polymerase toward the unnatural nucleic acid with a diphosphate or monophosphate, or no phosphate, or a combination thereof.

In some embodiments, a modified or wild type polymerase has a relaxed specificity for an unnatural nucleic acid. In some embodiments, a modified or wild type polymerase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, or 99.99% of the specificity of the wild type polymerase toward the natural nucleic acid. In some embodiments, a modified or wild type polymerase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, or 99.99% of the specificity of the wild type polymerase toward the natural nucleic acid. In some embodiments, a modified or wild type polymerase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, or 99.99% of the specificity of the wild type polymerase toward the natural nucleic acid.

Absence of exonuclease activity can be a wild type characteristic or a characteristic imparted by a variant or engineered polymerase. For example, an exo minus Klenow fragment is a mutated version of Klenow fragment that lacks 3' to 5' proofreading exonuclease activity.

The method of the invention may be used to expand the substrate range of any DNA polymerase which lacks an intrinsic 3 to 5' exonuclease proofreading activity or where a 3 to 5' exonuclease proofreading activity has been disabled, e.g. through mutation. Examples of DNA polymerases include polA, polB (see e.g. Parrel & Loeb, Nature Struc Biol 2001) polC, poD, polY, polX and reverse transcriptases (RT) but preferably are processive, high-fidelity polymerases (PCT/GB2004/004643). In some embodiments a modified or wild type polymerase substantially lacks 3' to 5' proofreading exonuclease activity. In some embodiments a modified or wild type polymerase substantially lacks 3' to 5' proofreading exonuclease activity for an unnatural nucleic acid. In some embodiments, a modified or wild type polymerase has a 3' to 5' proofreading exonuclease activity. In some embodiments, a modified or wild type polymerase has a 3' to 5' proofreading exonuclease activity for a natural nucleic acid and substantially lacks 3' to 5' proofreading exonuclease activity for an unnatural nucleic acid.

In some embodiments, a modified polymerase has a 3' to 5' proofreading exonuclease activity that is at least about 60%, 70%, 80%, 90%, 95%, 97%, 98%, 99%, 99.5%, or 99.99% of the proofreading exonuclease activity of the wild type polymerase. In some embodiments, a modified polymerase has a 3' to 5' proofreading exonuclease activity for an unnatural nucleic acid that is at least about 60%, 70%, 80%, 90%, 95%, 97%, 98%, 99%, 99.5%, 99.99% of the proofreading exonuclease activity of the wild type polymerase to a natural nucleic acid. In some embodiments, a modified polymerase has a 3' to 5' proofreading exonuclease activity for an unnatural nucleic acid and a 3' to 5' proofreading exonuclease activity for a natural nucleic acid that is at least about 60%, 70%, 80%, 90%, 95%, 97%, 98%, 99%, 99.5%, or 99.99% of the proofreading exonuclease activity of the wild type polymerase to a natural nucleic acid. In some embodiments, a modified polymerase has a 3' to 5' proofreading exonuclease activity for a natural nucleic acid that is at least about 60%, 70%, 80%, 90%, 95%, 97%, 98%, 99%, 99.5%, or 99.99% of the proofreading exonuclease activity of the wild type polymerase to the natural nucleic acid.

In some embodiments, polymerases are characterized according to their rate of dissociation from nucleic acids. In some embodiments a polymerase has a relatively low dissociation rate for one or more natural and unnatural nucleic acids. In some embodiments a polymerase has a relatively high dissociation rate for one or more natural and unnatural nucleic acids. The dissociation rate is an activity of a polymerase that can be adjusted to tune reaction rates in methods set forth herein.

In some embodiments, polymerases are characterized according to their fidelity when used with a particular natural and/or unnatural nucleic acid or collections of natural and/or unnatural nucleic acid. Fidelity generally refers to the accuracy with which a polymerase incorporates correct nucleic acids into a growing nucleic acid chain when making a copy of a nucleic acid template. DNA polymerase fidelity can be measured as the ratio of correct to incorrect natural and unnatural nucleic acid incorporations when the natural and unnatural nucleic acid are present, e.g., at equal concentrations, to compete for strand synthesis at the same site in the polymerase-strand-template nucleic acid binary complex. DNA polymerase fidelity can be calculated as the ratio of ($k_{cat}/K_m$) for the natural and unnatural nucleic acid and ($k_{cat}/K_m$) for the incorrect natural and unnatural nucleic acid; where $k_{cat}$ and $K_m$ are Michaelis-Menten parameters in steady state enzyme kinetics (Fersht, A. R. (1985) Enzyme Structure and Mechanism, 2nd ed., p 350, W. H. Freeman & Co., New York., incorporated herein by reference). In some embodiments, a polymerase has a fidelity value of at least about 100, 1000, 10,000, 100,000, or $1\times10^6$, with or without a proofreading activity.

In some embodiments, polymerases from native sources or variants thereof are screened using an assay that detects incorporation of an unnatural nucleic acid having a particular structure. In one example, polymerases can be screened for the ability to incorporate an unnatural nucleic acid or UBP; e.g., d5SICSTP, dCNMOTP, dTPT3TP, dNaMTP, dCNMOTP-dTPT3TP, or d5SICSTP-dNaMTP UBP. A polymerase, e.g., a heterologous polymerase, can be used that displays a modified property for the unnatural nucleic acid as compared to the wild-type polymerase. For example, the modified property can be, e.g., $K_m$, $k_{cat}$, $V_{max}$, polymerase processivity in the presence of an unnatural nucleic acid (or of a naturally occurring nucleotide), average template read-length by the polymerase in the presence of an unnatural nucleic acid, specificity of the polymerase for an unnatural nucleic acid, rate of binding of an unnatural nucleic acid, rate of product (pyrophosphate, triphosphate, etc.) release, branching rate, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the polymerase optionally has an increased rate of binding of an unnatural nucleic acid, an increased rate of product release, and/or a decreased branching rate, as compared to a wild-type polymerase.

At the same time, a polymerase can incorporate natural nucleic acids, e.g., A, C, G, and T, into a growing nucleic acid copy. For example, a polymerase optionally displays a specific activity for a natural nucleic acid that is at least about 5% as high (e.g., 5%, 10%, 25%, 50%, 75%, 100% or higher), as a corresponding wild-type polymerase and a processivity with natural nucleic acids in the presence of a template that is at least 5% as high (e.g., 5%, 10%, 25%, 50%, 75%, 100% or higher) as the wild-type polymerase in the presence of the natural nucleic acid. Optionally, the polymerase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type polymerase.

Polymerases used herein that can have the ability to incorporate an unnatural nucleic acid of a particular structure can also be produced using a directed evolution approach. A nucleic acid synthesis assay can be used to screen for polymerase variants having specificity for any of a variety of unnatural nucleic acids. For example, polymerase variants can be screened for the ability to incorporate an unnatural nucleoside triphosphate opposite an unnatural nucleotide in a DNA template; e.g., dTPT3TP opposite dCNMO, dCNMOTP opposite dTPT3, NaMTP opposite dTPT3, or TAT1TP opposite dCNMO or dNaM. In some embodiments, such an assay is an in vitro assay, e.g., using a recombinant polymerase variant. In some embodiments, such an assay is an in vivo assay, e.g., expressing a polymerase variant in a cell. Such directed evolution techniques can be used to screen variants of any suitable polymerase for activity toward any of the unnatural nucleic acids set forth herein. In some instances, polymerases used herein have the ability to incorporate unnatural ribonucleotides into a nucleic acid, such as RNA. For example, NaM or TAT1 ribonucleotides are incorporated into nucleic acids using the polymerases described herein.

Modified polymerases of the compositions described can optionally be a modified and/or recombinant Φ29-type DNA polymerase. Optionally, the polymerase can be a modified and/or recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase.

Modified polymerases of the compositions described can optionally be modified and/or recombinant prokaryotic DNA polymerase, e.g., DNA polymerase II (Pol II), DNA polymerase III (Pol III), DNA polymerase IV (Pol IV), DNA polymerase V (Pol V). In some embodiments, the modified polymerases comprise polymerases that mediate DNA synthesis across non-instructional damaged nucleotides. In some embodiments, the genes encoding Pol I, Pol II (polB), Poll IV (dinB), and/or Pol V (umuCD) are constitutively expressed, or overexpressed, in the engineered cell, or SSO. In some embodiments, an increase in expression or overexpression of Pol II contributes to an increased retention of unnatural base pairs (UBPs) in an engineered cell, or SSO.

Nucleic acid polymerases generally useful in the invention include DNA polymerases, RNA polymerases, reverse transcriptases, and mutant or altered forms thereof. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al, 1991, Polynucleotides Res, 19: 4193, New England Biolabs), 9° Nm™ DNA polymerase (New England Biolabs), Stoffel fragment, Thermo Sequenase© (Amersham Pharmacia Biotech UK), Therminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al, 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al, 1981, J Biol. Chem. 256:3112), and archaeal DP1I/DP2 DNA polymerase II (Cann et al, 1998, Proc. Natl. Acad. Sci. USA 95:14250). Both mesophilic polymerases and thermophilic polymerases are contemplated. Thermophilic DNA polymerases include, but are not limited to, ThermoSequenase®, 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A polymerase that is a 3' exonuclease-deficient mutant is also contemplated. Reverse transcriptases useful in the invention include, but are not limited to, reverse transcriptases from HIV, HTLV-I, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al, CRC Crit Rev Biochem. 3:289-347(1975)). Further examples of polymerases include, but are not limited to 9°N DNA Polymerase, Taq DNA polymerase, Phusion® DNA polymerase, Pfu DNA polymerase, RB69 DNA polymerase, KOD DNA polymerase, and VentR® DNA polymerase Gardner et al. (2004) "Comparative Kinetics of Nucleotide Analog Incorporation by Vent DNA Polymerase (J. Biol. Chem., 279(12), 11834-11842; Gardner and Jack "Determinants of nucleotide sugar recognition in an archaeon DNA polymerase" Nucleic Acids Research, 27(12) 2545-2553.) Polymerases isolated from non-thermophilic organisms can be heat inactivatable. Examples are DNA polymerases from phage. It will be understood that polymerases from any of a variety of sources can be modified to increase or decrease their tolerance to high temperature conditions. In some embodiments, a polymerase can be thermophilic. In some embodiments, a thermophilic polymerase can be heat inactivatable. Thermophilic polymerases are typically useful for high temperature conditions or in thermocycling conditions such as those employed for polymerase chain reaction (PCR) techniques.

In some embodiments, the polymerase comprises Φ29, B103, GA-1, PZA, Φ15, BS32, M2Y, Nf, G1, Cp-1, PRD1, PZE, SF5, Cp-5, Cp-7, PR4, PR5, PR722, L17, ThermoSequenase®, 9° Nm™, Therminator™ DNA polymerase, Tne, Tma, TfI, Tth, TIi, Stoffel fragment, Vent™ and Deep Vent™ DNA polymerase, KOD DNA polymerase, Tgo, JDF-3, Pfu, Taq, T7 DNA polymerase, T7 RNA polymerase, PGB-D, UlTma DNA polymerase, *E. coli* DNA polymerase I, *E. coli* DNA polymerase III, archaeal DP1I/DP2 DNA polymerase II, 9° N DNA Polymerase, Taq DNA polymerase, Phusion® DNA polymerase, Pfu DNA polymerase, SP6 RNA polymerase, RB69 DNA polymerase, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase.

In some embodiments, the polymerase is DNA polymerase I (or Klenow fragment), Vent polymerase, Phusion® DNA polymerase, KOD DNA polymerase, Taq polymerase, T7 DNA polymerase, T7 RNA polymerase, Therminator™ DNA polymerase, POLB polymerase, SP6 RNA polymerase, *E. coli* DNA polymerase I, *E. coli* DNA polymerase III, Avian Myeloblastosis Virus (AMV) reverse transcriptase, Moloney Murine Leukemia Virus (MMLV) reverse transcriptase, SuperScript® II reverse transcriptase, or SuperScript® III reverse transcriptase.

Nucleotide Transporter

Nucleotide transporters (NTs) are a group of membrane transport proteins that facilitate the transfer of nucleotide substrates across cell membranes and vesicles. In some embodiments, there are two types of NTs, concentrative nucleoside transporters and equilibrative nucleoside transporters. In some instances, NTs also encompass the organic anion transporters ('OAT) and the organic cation transporters (OCT). In some instances, nucleotide transporter is a nucleoside triphosphate transporter (NTT).

In some embodiments, a nucleoside triphosphate transporter (NTT) is from bacteria, plant, or algae. In some embodiments, a nucleotide nucleoside triphosphate transporter is TpNTT1, TpNTT2, TpNTT3, TpNTT4, TpNTT5, TpNTT6, TpNTT7, TpNTT8 (*T. pseudonana*), PtNTT1, PtNTT2, PtNTT3, PtNTT4, PtNTT5, PtNTT6 (*P. tricornutum*), GsNTT (*Galdieria sulphuraria*), AtNTT 1, AtNTT2 (*Arabidopsis thaliana*), CtNTT1, CtNTT2 (*Chlamydia trachomatis*), PamNTT 1, PamNTT2 (*Protochlamydia amoebophila*), CcNTT (*Caedibacter caryophilus*), or RpNTT1 (*Rickettsia prowazekii*).

In some embodiments, the NTT is CNT1, CNT2, CNT3, ENT1, ENT2, OAT1, OAT3, or OCT1.

In some embodiments, NTT imports unnatural nucleic acids into an organism, e.g. a cell. In some embodiments, NTTs can be modified such that the nucleotide binding site of the NTT is modified to reduce steric entry inhibition of the unnatural nucleic acid into the nucleotide biding site. In some embodiments, NTTs can be modified to provide increased interaction with one or more natural or unnatural features of the unnatural nucleic acids. Such NTTs can be expressed or engineered in cells for stably importing a UBP into the cells. Accordingly, the invention includes compositions that include a heterologous or recombinant NTT and methods of use thereof.

NTTs can be modified using methods pertaining to protein engineering. For example, molecular modeling can be carried out based on crystal structures to identify the locations of the NTTs where mutations can be made to modify a target activity or binding site. A residue identified as a target for replacement can be replaced with a residue selected using energy minimization modeling, homology modeling, and/or conservative amino acid substitutions, such as described in Bordo, et al. J Mol Biol 217: 721-729 (1991) and Hayes, et al. Proc Natl Acad Sci, USA 99: 15926-15931 (2002), the disclosures of each of which are hereby incorporated by reference in their entirety.

Any of a variety of NTTs can be used in a method or composition set forth herein including, for example, protein-based enzymes isolated from biological systems and functional variants thereof. Reference to a particular NTT, such as those exemplified below, will be understood to include functional variants thereof unless indicated otherwise. In some embodiments, a NTT is a wild type NTT. In some embodiments, a NTT is a modified, or mutant, NTT.

NTTs, with features for improving entry of unnatural nucleic acids into cells and for coordinating with unnatural nucleotides in the nucleotide biding region, can also be used. In some embodiments, a modified NTT has a modified nucleotide binding site. In some embodiments, a modified or wild type NTT has a relaxed specificity for an unnatural nucleic acid. For example, a NTT optionally displays a specific importation activity for an unnatural nucleotide that is at least about 0.1% as high (e.g., about 0.1%, 0.2%, 0.5%, 0.8%, 1%, 1.1%, 1.2%, 1.5%, 1.8%, 2%, 3%, 4%, 5%, 10%, 25%, 50%, 75%, 100% or higher), as a corresponding wild-type NTT. Optionally, the NTT displays a $k_{cat}/K_m$ or $V_{max}/K_m$ for an unnatural nucleotide that is at least about 0.1% as high (e.g., about 0.1%, 0.2%, 0.5%, 0.8%, 1%, 1.1%, 1.2%, 1.5%, 1.8%, 2%, 3%, 4%, 5%, 10%, 25%, 50%, 75% or 100% or higher) as the wild-type NTT.

NTTs can be characterized according to their affinity for a triphosphate (i.e. Km) and/or the rate of import (i.e. Vmax). In some embodiments a NTT has a relatively Km or Vmax for one or more natural and unnatural triphosphates. In some embodiments a NTT has a relatively high Km or Vmax for one or more natural and unnatural triphosphates.

NTTs from native sources or variants thereof can be screened using an assay that detects the amount of triphosphate (either using mass spec, or radioactivity, if the triphosphate is suitably labeled). In one example, NTTs can be screened for the ability to import an unnatural triphosphate; e.g., dTPT3TP, dCNMOTP, d5SICSTP, dNaMTP, NaMTP, and/or TPT1TP. A NTT, e.g., a heterologous NTT, can be used that displays a modified property for the unnatural nucleic acid as compared to the wild-type NTT. For example, the modified property can be, e.g., $K_m$, $k_{cat}$, $V_{max}$, for triphosphate import. In one embodiment, the modified property is a reduced $K_m$ for an unnatural triphosphate and/or an increased $k_{cat}/K_m$ or $V_{max}/K_m$ for an unnatural triphosphate. Similarly, the NTT optionally has an increased rate of binding of an unnatural triphosphate, an increased rate of intracellular release, and/or an increased cell importation rate, as compared to a wild-type NTT.

At the same time, a NTT can import natural triphosphates, e.g., dATP, dCTP, dGTP, dTTP, ATP, CTP, GTP, and/or TTP, into cell. In some instances, a NTT optionally displays a specific importation activity for a natural nucleic acid that is able to support replication and transcription. In some embodiments, a NTT optionally displays a $k_{cat}/K_m$ or $V_{max}/K_m$ for a natural nucleic acid that is able to support replication and transcription.

NTTs used herein that can have the ability to import an unnatural triphosphate of a particular structure can also be produced using a directed evolution approach. A nucleic acid synthesis assay can be used to screen for NTT variants having specificity for any of a variety of unnatural triphosphates. For example, NTT variants can be screened for the ability to import an unnatural triphosphate; e.g., d5SICSTP, dNaMTP, dCNMOTP, dTPT3TP, NaMTP, and/or TPT1TP. In some embodiments, such an assay is an in vitro assay, e.g., using a recombinant NTT variant. In some embodiments, such an assay is an in vivo assay, e.g., expressing a NTT variant in a cell. Such techniques can be used to screen variants of any suitable NTT for activity toward any of the unnatural triphosphate set forth herein.

Nucleic Acid Reagents & Tools

A nucleotide and/or nucleic acid reagent (or polynucleotide) for use with a method, cell, or engineered microorganism described herein comprises one or more ORFs with or without an unnatural nucleotide. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example. In some embodiments, a nucleotide and/or nucleic acid reagent or other reagent described herein is isolated or purified. ORFs may be created that include unnatural nucleotides via published in vitro methods. In some cases, a nucleotide or nucleic acid reagent comprises an unnatural nucleobase.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media. In some instances, libraries of nucleic acid reagents are used with the methods and compositions described herein. For example, a library of at least 100, 1000, 2000, 5000, 10,000, or more than 50,000 unique polynucleotides are present in a library, wherein each polynucleotide comprises at least one unnatural nucleobase.

A nucleic acid or nucleic acid reagent, with or without an unnatural nucleotide, can comprise certain elements, e.g., regulatory elements, often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element(s) and 3'UTR; and (4) promoter element, 5'UTR, target nucleotide sequence and 3'UTR. In some embodiments, the UTR can be optimized to alter or increase transcription or translation of the ORF that are either fully natural or that contain unnatural nucleotides.

Nucleic acid reagents, e.g., expression cassettes and/or expression vectors, can include a variety of regulatory elements, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleotide triphosphate transporter nucleic acid segment. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3" to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression and can be used to alter or optimize ORF expression, including ORFs that are fully natural or that contain unnatural nucleotides.

As noted above, nucleic acid reagents may also comprise one or more 5' UTR's, and one or more 3'UTR's. For example, expression vectors used in eukaryotic host cells (e.g., yeast, fungi, insect, plant, animal, human or nucleated cells) and prokaryotic host cells (e.g., virus, bacterium) can contain sequences that signal for the termination of transcription which can affect mRNA expression. These regions can be transcribed as polyadenylated segments in the untranslated portion of the mRNA encoding tissue factor protein. The 3" untranslated regions also include transcription termination sites. In some preferred embodiments, a transcription unit comprises a polyadenylation region. One benefit of this region is that it increases the likelihood that the transcribed unit will be processed and transported like mRNA. The identification and use of polyadenylation signals in expression constructs is well established. In some preferred embodiments, homologous polyadenylation signals can be used in the transgene constructs.

A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, −35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., DOI: 10.1002/bit.20267; and Gallie et al., Nucleic Acids Research 15: 3257-3273 (1987); the disclosures of each of which are hereby incorporated by reference in their entirety).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR is used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

Expression of a nucleotide triphosphate transporter from an expression cassette or expression vector can be controlled by any promoter capable of expression in prokaryotic cells or eukaryotic cells. A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments. In some embodiments, a promoter element can be isolated from a gene or organism and inserted in functional connection with a polynucleotide sequence to allow altered and/or regulated expression. A non-native promoter (e.g., promoter not normally associated with a given nucleic acid sequence) used for expression of a nucleic acid often is referred to as a heterologous promoter. In certain embodiments, a heterologous promoter and/or a 5'UTR can be inserted in functional connection with a polynucleotide that encodes a polypeptide having a desired activity as described herein. The terms “operably linked” and “in functional connection with” as used herein with respect to promoters, refer to a relationship between a coding sequence and a promoter element. The promoter is operably linked or in functional connection with the coding sequence when expression from the coding sequence via transcription is regulated, or controlled by, the promoter element. The terms “operably linked” and “in functional connection with” are utilized interchangeably herein with respect to promoter elements.

A promoter often interacts with a RNA polymerase. A polymerase is an enzyme that catalyzes synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions. As with all methods disclosed herein, the inclusion of natural or modified promoters can be used to alter or optimize expression of a fully natural ORF (e.g. a NTT or aaRS) or an ORF containing an unnatural nucleotide (e.g. an mRNA or a tRNA).

Non-limiting examples of selective or regulatory agents that influence transcription from a promoter element used in embodiments described herein include, without limitation: (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., 3-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; (13) nucleic acid segments that encode conditional replication functions, e.g., replication in certain hosts or host cell strains or under certain environmental conditions (e.g., temperature, nutritional conditions, and the like); and/or (14) nucleic acids that encode one or more mRNAs or tRNA that comprise unnatural nucleotides. In some embodiments, the regulatory or selective agent can be added to change the existing growth conditions to which the organism is subjected (e.g., growth in liquid culture, growth in a fermenter, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

Nucleic acids encoding heterologous proteins, e.g., nucleotide triphosphate transporters, can be inserted into or employed with any suitable expression system. In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids).

Recombinant expression is usefully accomplished using an expression cassette that can be part of a vector, such as a plasmid. A vector can include a promoter operably linked to nucleic acid encoding a nucleotide triphosphate transporter. A vector can also include other elements required for transcription and translation as described herein. An expression cassette, expression vector, and sequences in a cassette or vector can be heterologous to the cell to which the unnatural nucleotides are contacted. For example, a nucleotide triphosphate transporter sequence can be heterologous to the cell.

A variety of prokaryotic and eukaryotic expression vectors suitable for carrying, encoding and/or expressing nucleotide triphosphate transporters can be produced. Such expression vectors include, for example, pET, pET3d, pCR2.1, pBAD, pUC, and yeast vectors. The vectors can be used, for example, in a variety of in vivo and in vitro situations. Non-limiting examples of prokaryotic promoters that can be used include SP6, T7, T5, tac, bla, trp, gal, lac, or maltose promoters. Non-limiting examples of eukaryotic promoters that can be used include constitutive promoters, e.g., viral promoters such as CMV, SV40 and RSV promoters, as well as regulatable promoters, e.g., an inducible or repressible promoter such as a tet promoter, a hsp70 promoter, and a synthetic promoter regulated by CRE. Vectors for bacterial expression include pGEX-5X-3, and for eukaryotic expression include pCIneo-CMV. Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in Verma, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid.

Cloning

Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described herein. In some embodiments, a cloning strategy can be combined with genetic manipulation such as recombination (e.g., recombination of a nucleic acid reagent with a nucleic acid sequence of interest into the genome of the organism to be modified, as described further herein). In some embodiments, the cloned ORF(s) can produce (directly or indirectly) modified or wild type nucleotide triphosphate transporters and/or polymerases), by engineering a microorganism with one or more ORFs of interest, which microorganism comprises altered activities of nucleotide triphosphate transporter activity or polymerase activity.

A nucleic acid may be specifically cleaved by contacting the nucleic acid with one or more specific cleavage agents. Specific cleavage agents often will cleave specifically according to a particular nucleotide sequence at a particular site. Examples of enzyme specific cleavage agents include, without limitation, endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, BsaI, Bsm I, BsmBI, BssH II, BstE II, Cfo I, CIa I, Dde I, Dpn I, Dra I, EcIX I, EcoR I, EcoR I, EcoR II, EcoR V, Hae II, Hae II, Hind II, Hind III, Hpa I, Hpa II, Kpn I, KspI, MluI, MIuNI, MspI, NciI, NcoI, NdeI, NdeII, NheI, NotI, NruI, NsiI, PstI, PvuI, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes; and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., Sauer, Curr. Opin. Biotech. 5:521-527 (1994)). Other examples of recombination sites include attB, attP, attL, and attR sequences, and mutants, fragments, variants and derivatives thereof, which are recognized by the recombination protein λ Int and by the auxiliary proteins integration host factor (IFF), FIS and excisionase (Xis) (e.g., U.S. Pat. Nos. 5,888,732; 6,143,557; 6,171,861; 6,270,969; 6,277,608; and 6,720,140; U.S. patent application Ser. Nos. 09/517,466, and 09/732,914; U.S. Patent Publication No. US2002/0007051; and Landy, Curr. Opin. Biotech. 3:699-707 (1993); the disclosures of each of which are hereby incorporated by reference in their entirety).

Examples of recombinase cloning nucleic acids are in Gateway® systems (Invitrogen, California), which include at least one recombination site for cloning desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A nucleic acid reagent sometimes contains one or more origin of replication (ORI) elements. In some embodiments, a template comprises two or more ORIs, where one functions efficiently in one organism (e.g., a bacterium) and another function efficiently in another organism (e.g., a eukaryote, like yeast for example). In some embodiments, an ORI may function efficiently in one species (e.g., *S. cerevisiae*, for example) and another ORI may function efficiently in a different species (e.g., *S. pombe*, for example). A nucleic acid reagent also sometimes includes one or more transcription regulation sites.

A nucleic acid reagent, e.g., an expression cassette or vector, can include nucleic acid sequence encoding a marker product. A marker product is used to determine if a gene has been delivered to the cell and once delivered is being expressed. Example marker genes include the *E. coli* lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern et al., J. Molec. Appl. Genet. 1: 327 (1982)), mycophenolic acid, (Mulligan et al., Science 209: 1422 (1980)) or hygromycin, (Sugden, et al., Mol. Cell. Biol. 5: 410-413 (1985); the disclosures of each of which are hereby incorporated by reference in their entirety).

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism, and another functions efficiently in another organism. Examples of selection elements include, but are not limited to: (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent can be of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (e.g., Biochemistry 1996 Jun. 25; 35(25):8429-38). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

Cloning strategies analogous to those described above may be employed to produce DNA containing unnatural nucleotides. For example, oligonucleotides containing the unnatural nucleotides at desired positions are synthesized using standard solid-phase synthesis and purified by HPLC. The oligonucleotides are then inserted into the plasmid containing required sequence context (i.e. UTRs and coding sequence) using a cloning method (such as Golden Gate Assembly) with cloning sites, such as BsaI sites (although others discussed above may be used).

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In some embodiments, a kit includes a suitable packaging material to house the contents of the kit. In some cases, the packaging material is constructed by well-known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for a method of synthesizing a polynucleotide or for a method of determining the sequence of a nucleic acid.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

In some embodiments, a kit is provided that is useful for stably incorporating an unnatural nucleic acid into a cellular nucleic acid, e.g., using the methods provided by the present invention for preparing genetically engineered cells. In one embodiment, a kit described herein includes a genetically engineered cell and one or more unnatural nucleic acids. In another embodiment, a kit described herein includes an isolated and purified plasmid comprising a sequence selected from SEQ ID NOS: 1-2. In a further embodiment, a kit described herein includes a primer comprising a sequence selected from SEQ ID NOS: 3-20.

In additional embodiments, the kit described herein provides a cell and a nucleic acid molecule containing a heterologous gene for introduction into the cell to thereby provide a genetically engineered cell, such as expression vectors comprising the nucleic acid of any of the embodiments hereinabove described in this paragraph.

Exemplary Embodiments

The present disclosure is further described by the following embodiments. The features of each of the embodiments are combinable with any of the other embodiments where appropriate and practical.

Embodiment 1. An in vivo method of producing a protein comprising an unnatural amino acid, the method comprising:

- transcribing a DNA template comprising a first unnatural base and a complementary second unnatural base to incorporate a third unnatural base into a mRNA, the third unnatural base configured to form a first unnatural base pair with the first unnatural base;
- transcribing the DNA template to incorporate a fourth unnatural base into a tRNA, wherein the fourth unnatural base is configured to form a second unnatural base pair with the second unnatural base, wherein the first unnatural base pair and the second unnatural base pair are not the same; and
- translating a protein from the mRNA and tRNA, wherein said protein comprises an unnatural amino acid.

Embodiment 2. The method of embodiment 1, wherein the in vivo method comprises use of a semi-synthetic organism.

Embodiment 3. The method of embodiment 32, wherein the organism comprises a microorganism.

Embodiment 4. The method of embodiment [0042], wherein the organism comprises a bacterium.

Embodiment 5. The method of embodiment [0043], wherein the organism comprises a Gram-positive bacterium.

Embodiment 6. The method of embodiment [0043], wherein the organism comprises a Gram-negative bacterium.

Embodiment 7. The method of any one of embodiments 2-[0043], wherein the organism comprises an *Escherichia coli.*

Embodiment 8. The method of any one of embodiments 1-[0046], wherein at least one unnatural base is selected from the group consisting of (i) 2-thiouracil, 2-thio-thymine, 2'-deoxyuridine, 4-thio-uracil, 4-thio-thymine, uracil-5-yl, hypoxanthin-9-yl (I), 5-halouracil; 5-propynyl-uracil, 6-azo-thymine, 6-azo-uracil, 5-methylaminomethyluracil, 5-methoxyaminomethyl-2-thiouracil, pseudouracil, uracil-5-oxacetic acid methylester, uracil-5-oxacetic acid, 5-methyl-2-thiouracil, 3-(3-amino-3-N-2-carboxypropyl) uracil, 5-methyl-2-thiouracil, 4-thiouracil, 5-methyluracil, 5'-methoxycarboxymethyluracil, 5-methoxyuracil, uracil-5-oxyacetic acid, 5-(carboxyhydroxylmethyl)uracil, 5-carboxymethylaminomethyl-2-thiouridine, 5-carboxymethylaminomethyluracil, or dihydrouracil;

(ii) 5-hydroxymethyl cytosine, 5-trifluoromethyl cytosine, 5-halocytosine, 5-propynyl cytosine, 5-hydroxycytosine, cyclocytosine, cytosine arabinoside, 5,6-dihydrocytosine, 5-nitrocytosine, 6-azo cytosine, azacytosine, N4-ethylcytosine, 3-methylcytosine, 5-methylcytosine, 4-acetylcytosine, 2-thiocytosine, phenoxazine cytidine([5,4-b][1,4]benzoxazin-2(3H)-one), phenothiazine cytidine (1H-pyrimido[5,4-b][1,4] benzothiazin-2(3H)-one), phenoxazine cytidine (9-(2-aminoethoxy)-H-pyrimido[5,4-b][1,4]benzoxazin-2 (3H)-one), carbazole cytidine (2H-pyrimido[4,5-b] indol-2-one), or pyridoindole cytidine (H-pyrido [3',2': 4,5]pyrrolo [2,3-d]pyrimidin-2-one);

(iii) 2-aminoadenine, 2-propyl adenine, 2-amino-adenine, 2-F-adenine, 2-amino-propyl-adenine, 2-amino-2'-deoxyadenosine, 3-deazaadenine, 7-methyladenine, 7-deaza-adenine, 8-azaadenine, 8-halo, 8-amino, 8-thiol, 8-thioalkyl, and 8-hydroxyl substituted adenines, N6-isopentenyladenine, 2-methyladenine, 2,6-diaminopurine, 2-methythio-N6-isopentenyladenine, or 6-aza-adenine;

(iv) 2-methylguanine, 2-propyl and alkyl derivatives of guanine, 3-deazaguanine, 6-thio-guanine, 7-methylguanine, 7-deazaguanine, 7-deazaguanosine, 7-deaza-8-azaguanine, 8-azaguanine, 8-halo, 8-amino, 8-thiol, 8-thioalkyl, and 8-hydroxyl substituted guanines, 1-methylguanine, 2,2-dimethylguanine, 7-methylguanine, or 6-aza-guanine; and (v) hypoxanthine, xanthine, 1-methylinosine, queosine, beta-D-galactosylqueosine, inosine, beta-D-mannosylqueosine, wybutoxosine, hydroxyurea, (acp3)w, 2-aminopyridine, or 2-pyridone.

Embodiment 9. The method of any one of embodiments 1-[0046], wherein at least one of the first unnatural base, the second unnatural base, the third unnatural base, or the fourth unnatural base is selected from the group consisting of:

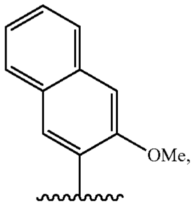, 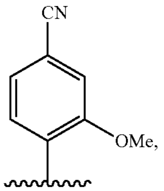,
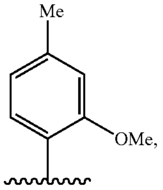, 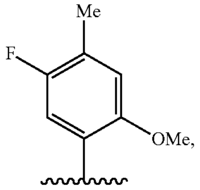,
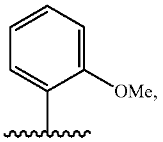, 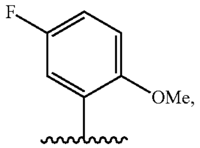,
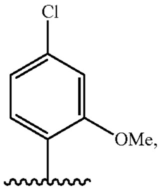, 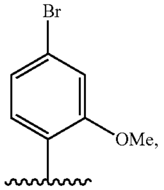,
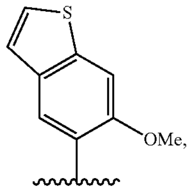, 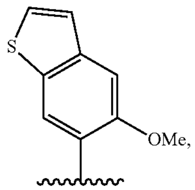,
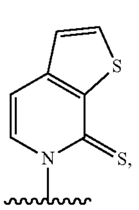, 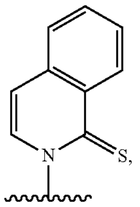, 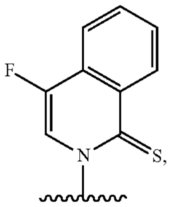, -continued

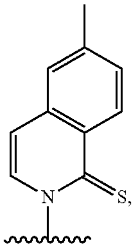, and 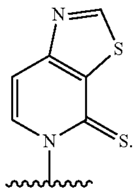.

Embodiment 10. The method of any one of embodiments 1-[0046], wherein at least one of the first unnatural base, the second unnatural base, the third unnatural base, or the fourth unnatural base is selected from the group consisting of:

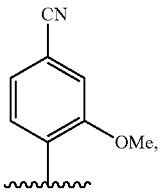,
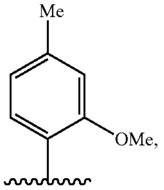, 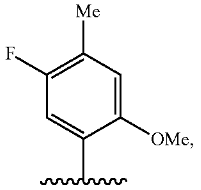,
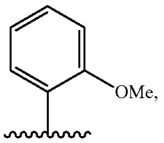, 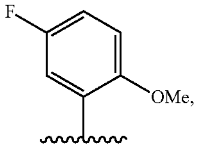,
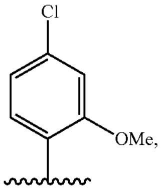, 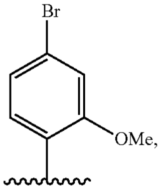,
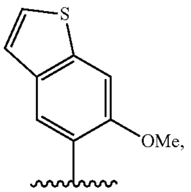, 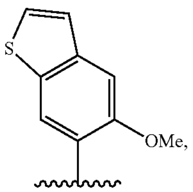,
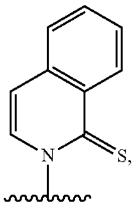, 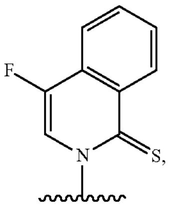, -continued

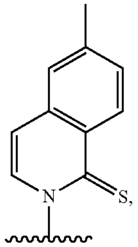, and 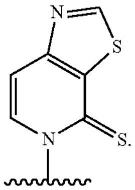 [SMILES: *n1ccc2ncsc2c1=S].

Embodiment 11. The method of embodiment 33, wherein at least one of the first unnatural base, the second unnatural base, the third unnatural base, or the fourth unnatural base is selected from the group consisting of:

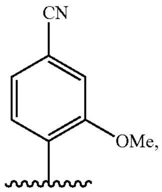, 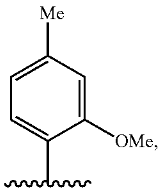, 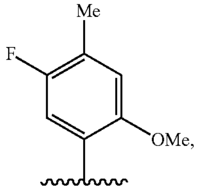, 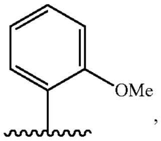, 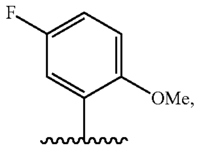, 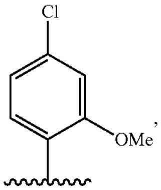, 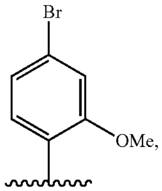, 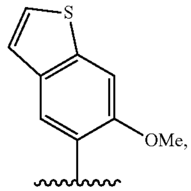, and 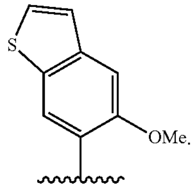.

Embodiment 12. The method of embodiment 33, wherein at least one of the first unnatural base, the second unnatural base, the third unnatural base, or the fourth unnatural base is selected from the group consisting of:

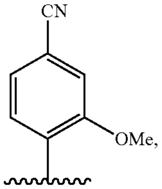, 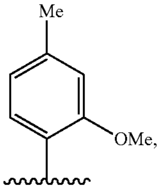, 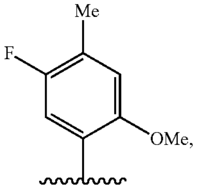, 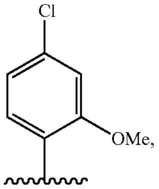, 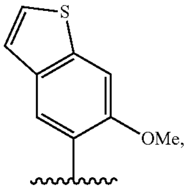, and 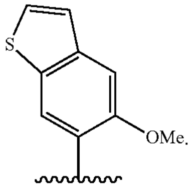.

Embodiment 13. The method of embodiment 33, wherein at least one of the first unnatural base, the second unnatural base, the third unnatural base, or the fourth unnatural base is selected from the group consisting of:

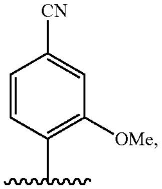, 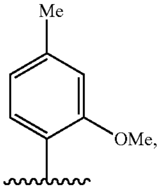, 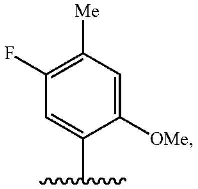, 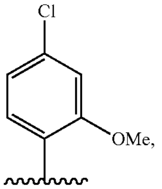, and 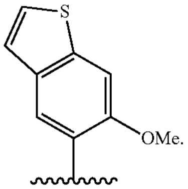.

Embodiment 14. The method of embodiment 33, wherein at least one of the first unnatural base, the second unnatural base, the third unnatural base, or the fourth unnatural base is selected from the group consisting of:

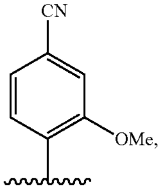, 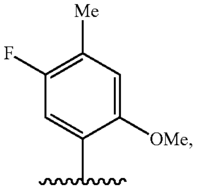, and

-continued

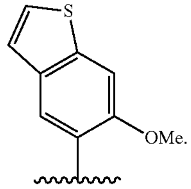

Embodiment 15. The method of embodiment 33, wherein at least one of the first unnatural base, the second unnatural base, the third unnatural base, or the fourth unnatural base is selected from the group consisting of:

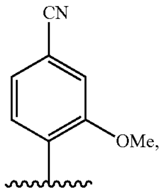

and

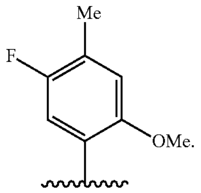

Embodiment 16. The method of embodiment 33, wherein at least one of the first unnatural base, the second unnatural base, the third unnatural base, or the fourth unnatural base is selected from the group consisting of

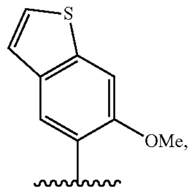

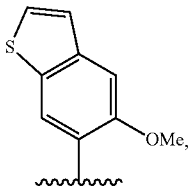

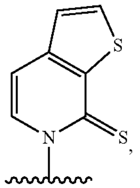

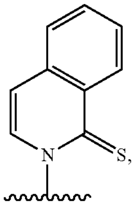

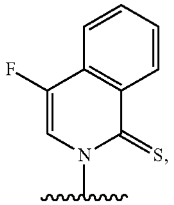

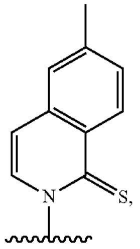

and

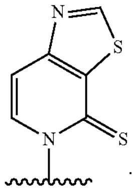

.

Embodiment 17. The method of embodiment 33, wherein at least one of the first unnatural base, the second unnatural base, the third unnatural base, or the fourth unnatural base is selected from the group consisting of:

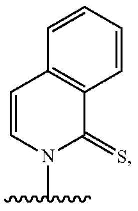

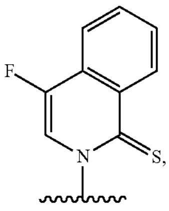

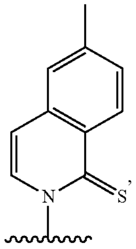

and

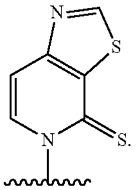

Embodiment 18. The method of embodiment 33, wherein at least one of the first unnatural base, the second unnatural base, the third unnatural base, or the fourth unnatural base is selected from:

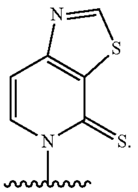

Embodiment 19. The method of embodiment 33, wherein at least one of the first unnatural base, the second unnatural base, the third unnatural base, or the fourth unnatural base is selected from:

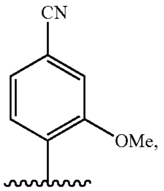

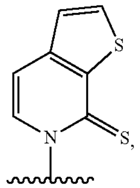

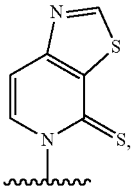

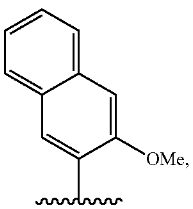

and

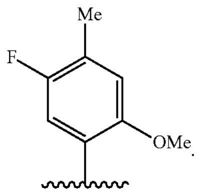

Embodiment 20. The method of embodiment 33, wherein the first or second unnatural base is

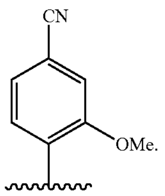 [SMILES: *c1ccc(C#N)cc1OC]

Embodiment 21. The method of embodiment 33, wherein the first or second unnatural base is

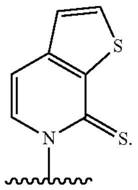 [SMILES: *n1ccc2ccsc2c1=S]

Embodiment 22. The method of embodiment 33, wherein the first unnatural base is

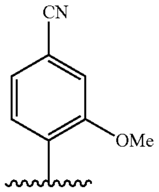 [SMILES: *c1ccc(C#N)cc1OC]

and the second unnatural base is

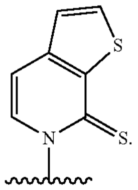 [SMILES: *n1ccc2ccsc2c1=S]

Embodiment 23. The method of embodiment 33, wherein the first unnatural base is

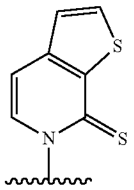 [SMILES: *n1ccc2ccsc2c1=S]

and the second unnatural base is

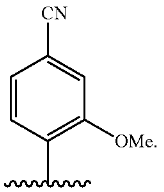 [SMILES: *c1ccc(C#N)cc1OC]

Embodiment 24. The method of embodiment 33, wherein the third or fourth unnatural base is

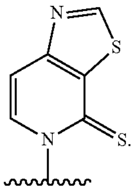 [SMILES: *n1ccc2ncsc2c1=S]

Embodiment 25. The method of embodiment 33, wherein the third unnatural base is

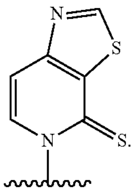 [SMILES: *n1ccc2ncsc2c1=S]

Embodiment 26. The method of embodiment 33, wherein the fourth unnatural base is

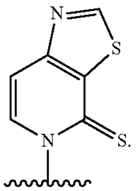 [SMILES: *n1ccc2ncsc2c1=S]

Embodiment 27. The method of embodiment 33, wherein the third or fourth unnatural base is

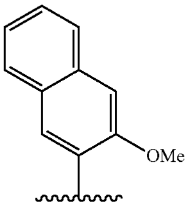

or

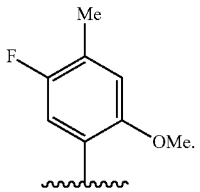

Embodiment 28. The method of embodiment 33, wherein the third unnatural base is

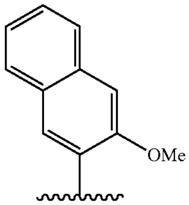 or 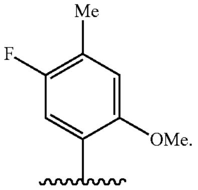

Embodiment 29. The method of embodiment 33, wherein the fourth unnatural base is

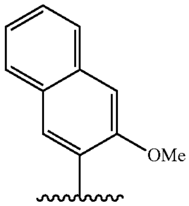 or 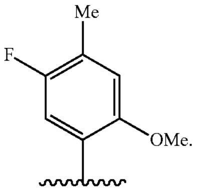

Embodiment 30. The method of embodiment 33, wherein the first unnatural base is

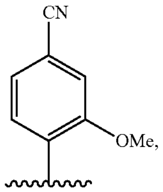 [SMILES: *c1ccc(C#N)cc1OC]

the second unnatural base is

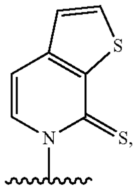

the third unnatural base is

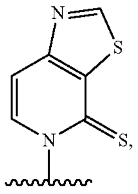 [SMILES: *n1ccc2ncsc2c1=S]

and the fourth unnatural base is

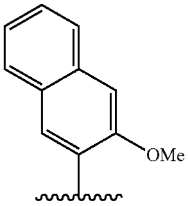 or 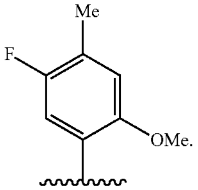

Embodiment 31. The method of embodiment 33, wherein the first unnatural base is

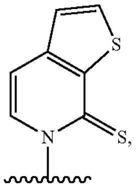 [SMILES: *n1ccc2ccsc2c1=S]

the second unnatural base is

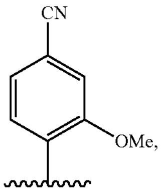 [SMILES: *c1ccc(C#N)cc1OC]

the third unnatural base is

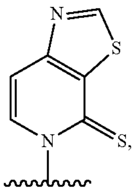 [SMILES: *n1ccc2ncsc2c1=S]

and the fourth unnatural base is or

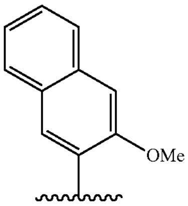 or 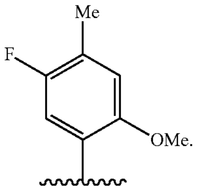

Embodiment 32. The method of embodiment 33, wherein the first unnatural base is

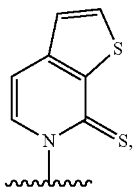

the second unnatural base is

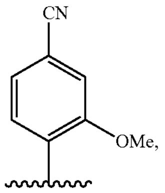 [SMILES: *c1ccc(C#N)cc1OC]

the third unnatural base is

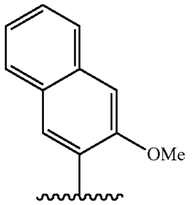

or

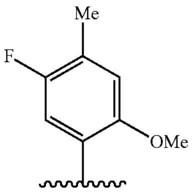

and the fourth unnatural base is

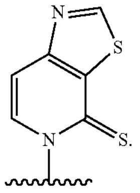 [SMILES: *n1ccc2ncsc2c1=S]

Embodiment 33. The method of embodiment 33, wherein the third unnatural base is

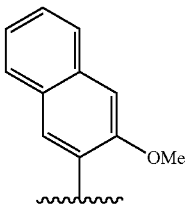

or

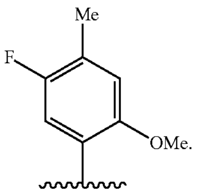

Embodiment 34. The method of embodiment 33, wherein the fourth unnatural base is

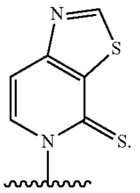 [SMILES: *n1ccc2ncsc2c1=S]

Embodiment 35. The method of embodiment 33, wherein the first unnatural base is

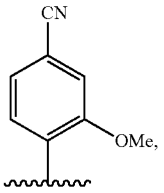 [SMILES: *c1ccc(C#N)cc1OC]

the second unnatural base is

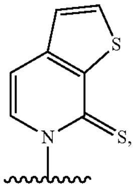 [SMILES: *n1ccc2ccsc2c1=S]

the third unnatural base is

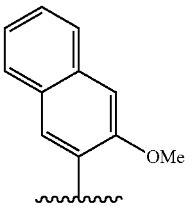

or

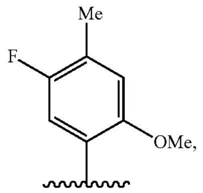

and the fourth unnatural base is

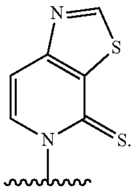 [SMILES: *n1ccc2ncsc2c1=S]

Embodiment 36. The method of any one of embodiments 33 to 49, wherein the third unnatural base and the fourth unnatural base comprise ribose.

Embodiment 37. The method of any one of embodiments 33 to 49, wherein the third unnatural base and the fourth unnatural base comprise deoxyribose.

Embodiment 38. The method of any one of embodiments 33 to 49, wherein the first and second unnatural bases comprise deoxyribose.

Embodiment 39. The method of any one of embodiments 33 to 49, wherein the first and second unnatural bases comprise deoxyribose and the third unnatural base and the fourth unnatural base comprise ribose.
Embodiment 40. The method of embodiment 33, wherein the DNA template comprises at least one unnatural base pair (UBP) selected from the group consisting of
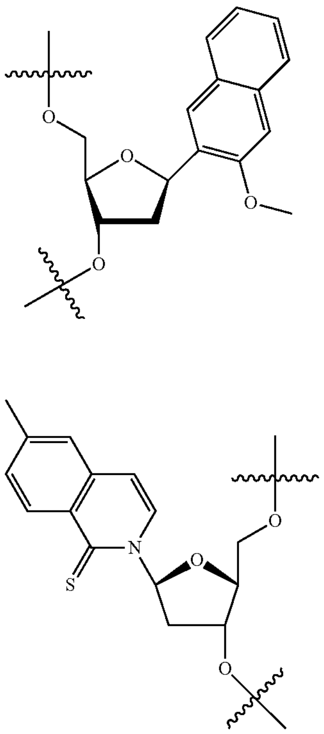
dNaM-d5SICS
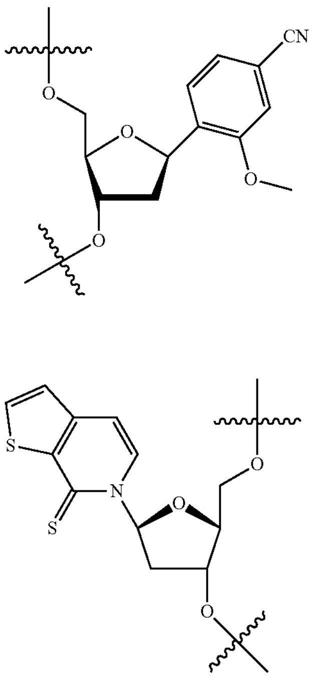
dCNMO-dTPT3
-continued
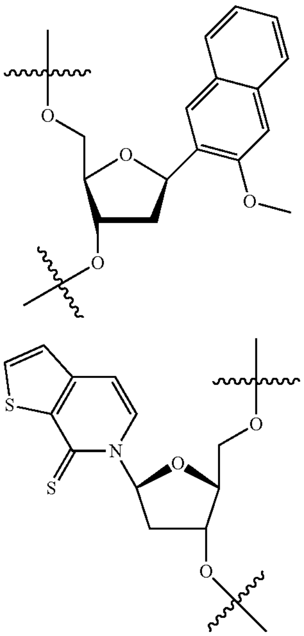
dNaM-dTPT3
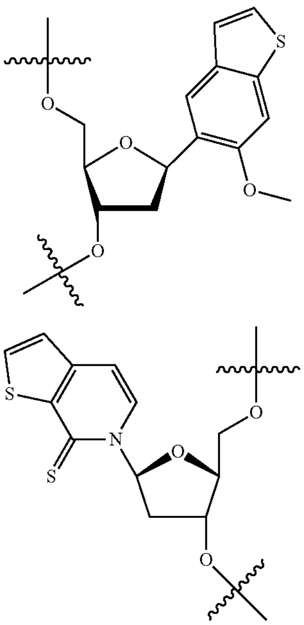
dPTMO-dTPT3
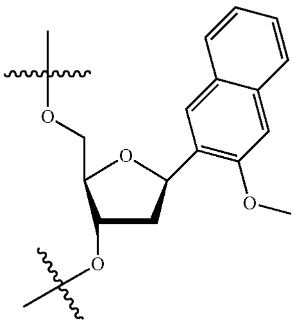

-continued

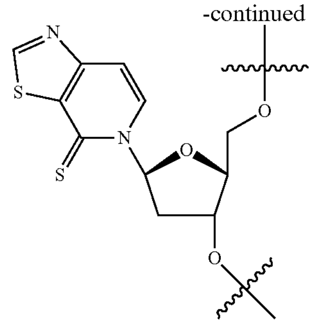

dNaM-dTAT1

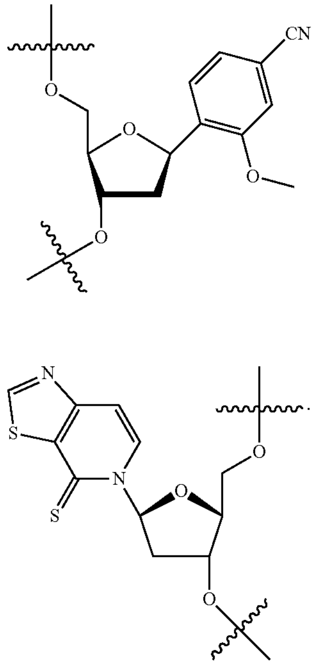

dCNMO-dTAT1

Embodiment 41. The method of embodiment 50, wherein the DNA template comprises at least one unnatural base pair (UBP) which is dNaM-d5SICS.

Embodiment 42. The method of embodiment 50, wherein the DNA template comprises at least one unnatural base pair (UBP) which is dCNMO-dTPT3.

Embodiment 43. The method of embodiment 50, wherein the DNA template comprises at least one unnatural base pair (UBP) which is dNaM-dTPT3.

Embodiment 44. The method of embodiment 50, wherein the DNA template comprises at least one unnatural base pair (UBP) which is dPTMO-dTPT3.

Embodiment 45. The method of embodiment 50, wherein the DNA template comprises at least one unnatural base pair (UBP) which is dNaM-dTAT1.

Embodiment 46. The method of embodiment 50, wherein the DNA template comprises at least one unnatural base pair (UBP) which is dCNMO-dTAT1.

Embodiment 47. The method of embodiment 1, wherein the DNA template comprises at least one unnatural base pair (UBP) selected from the group consisting of

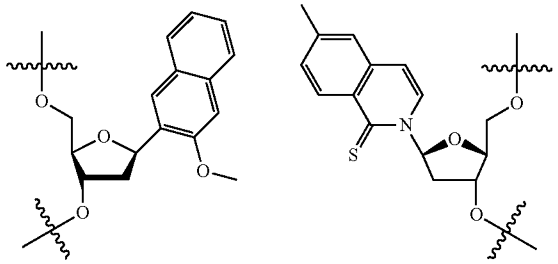

dNaM-d5SICS

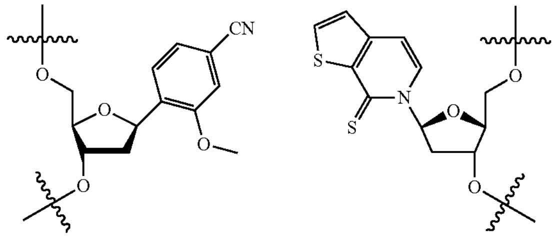

dCNMO-dTPT3

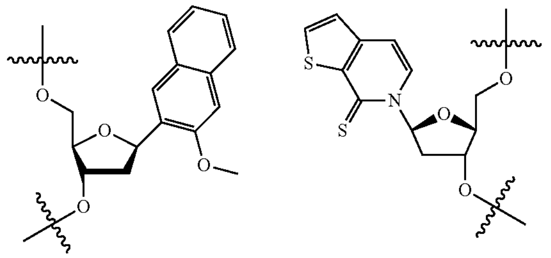

dNaM-dTPT3

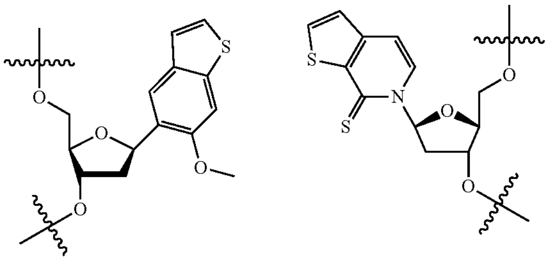

dPTMO-dTPT3

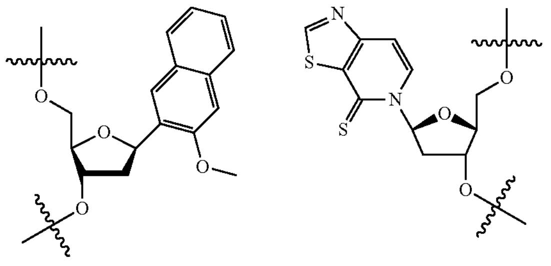

dNaM-dTAT1

-continued

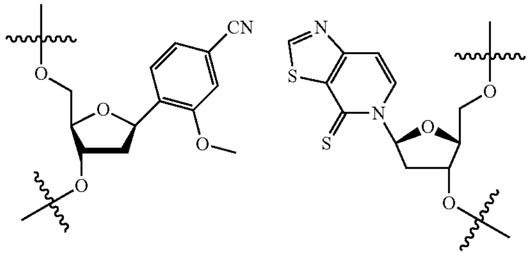

;

dCNMO-dTAT1 and wherein the mRNA and the tRNA comprise at least one unnatural base selected from:

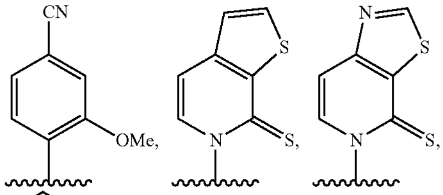

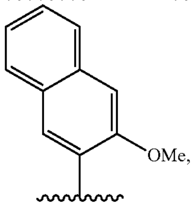

and

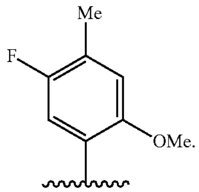

Embodiment 48. The method according to embodiment 51, wherein the DNA template comprises at least one unnatural base pair (UBP) which is dNaM-d5SICS.

Embodiment 49. The method of embodiment 51, wherein the DNA template comprises at least one unnatural base pair (UBP) which is dCNMO-dTPT3.

Embodiment 50. The method of embodiment 51, wherein the DNA template comprises at least one unnatural base pair (UBP) which is dNaM-dTPT3.

Embodiment 51. The method of embodiment 51, wherein the DNA template comprises at least one unnatural base pair (UBP) which is dPTMO-dTPT3.

Embodiment 52. The method of embodiment 51, wherein the DNA template comprises at least one unnatural base pair (UBP) which is dNaM-dTAT1.

Embodiment 53. The method of embodiment 51, wherein the DNA template comprises at least one unnatural base pair (UBP) which is dCNMO-dTAT1.

Embodiment 54. The method of any one of embodiments 51 to [0091], wherein the mRNA and the tRNA comprise an unnatural base selected from

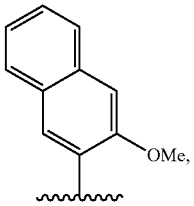

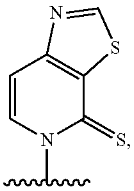

and

-continued

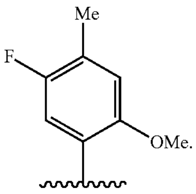

Embodiment 55. The method of embodiment [0092], wherein the mRNA and the tRNA comprise an unnatural base selected from

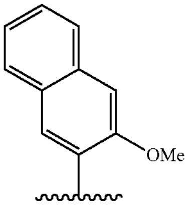 [SMILES: *c1cc2ccccc2cc1OC]

and

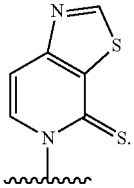 [SMILES: *n1ccc2ncsc2c1=S]

Embodiment 56. The method of embodiment [0092], wherein the mRNA comprises an unnatural base which is

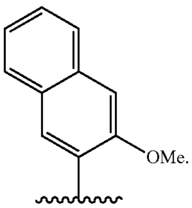

Embodiment 57. The method of embodiment [0092], wherein the mRNA comprises an unnatural base which is

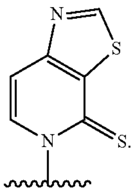

Embodiment 58. The method of embodiment [0092], wherein the mRNA comprises an unnatural base which is

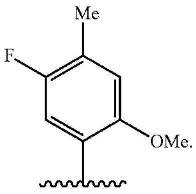 [SMILES: *c1cc(F)c(C)cc1OC]

Embodiment 59. The method of embodiment [0092], wherein the tRNA comprises an unnatural base selected from and

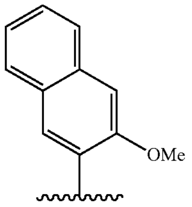 and 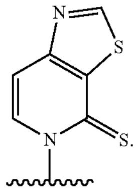

Embodiment 60. The method of embodiment [0092], wherein the tRNA comprises an unnatural base which is

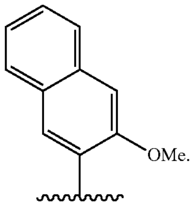 [SMILES: *c1cc2ccccc2cc1OC]

Embodiment 61. The method of embodiment [0092], wherein the tRNA comprises an unnatural base which is

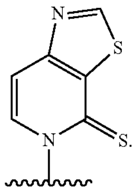 [SMILES: *n1ccc2ncsc2c1=S]

Embodiment 62. The method of embodiment [0092], wherein the tRNA comprises an unnatural base which is

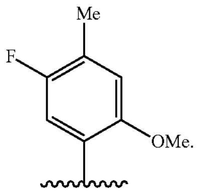 [SMILES: *c1cc(F)c(C)cc1OC]

Embodiment 63. The method of any one of embodiments 1-[0046], wherein the first unnatural base comprises dCNMO, and the second unnatural base comprises dTPT3.

Embodiment 64. The method of any one of embodiments 1-[0046] or 51, wherein the third unnatural base comprises NaM, and the second unnatural base comprises TAT1.

Embodiment 65. The method of any one of embodiments 1-53, wherein the first unnatural base or the second unnatural base is recognized by a DNA polymerase.

Embodiment 66. The method of any one of embodiments 1-[00103], wherein the third unnatural base or the fourth unnatural base is recognized by an RNA polymerase.

Embodiment 67. The method of any one of embodiments 1-[00104], wherein the protein comprises at least two unnatural amino acids.

Embodiment 68. The method of any one of embodiments 1-[00104], wherein the protein comprises at least three unnatural amino acids.

Embodiment 69. The method of any one of embodiments 1-[00104], wherein the protein comprises at least two different unnatural amino acids.

Embodiment 70. The method of any one of embodiments 1-[00104], wherein the protein comprises at least three different unnatural amino acids.

Embodiment 71. The method of any one of embodiments 1-58, wherein the at least one unnatural amino acid:

is a lysine analogue;

comprises an aromatic side chain;

comprises an azido group;

comprises an alkyne group; or comprises an aldehyde or ketone group.

Embodiment 72. The method of any one of embodiments 1-58, wherein the at least one unnatural amino acid does not comprise an aromatic side chain.

Embodiment 73. The method of any one of embodiments 1-58, wherein the at least one unnatural amino acid comprises N6-azidoethoxy-carbonyl-L-lysine (AzK), N6-propargylethoxy-carbonyl-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine.

Embodiment 74. The method of embodiment [00112], wherein the at least one unnatural amino acid comprises N6-azidoethoxy-carbonyl-L-lysine (AzK) and N6-propargylethoxy-carbonyl-L-lysine (PraK).

Embodiment 75. The method of embodiment 60, wherein the at least one unnatural amino acid comprises N6-azidoethoxy-carbonyl-L-lysine (AzK).

Embodiment 76. The method of embodiment 60, wherein the at least one unnatural amino acid comprises N6-propargylethoxy-carbonyl-L-lysine (PraK).

Embodiment 77. A semi-synthetic organism comprising an expanded genetic alphabet, wherein the genetic alphabet comprises at least two unique unnatural bases.

Embodiment 78. The semi-synthetic organism of embodiment 64, wherein the organism comprises a microorganism.

Embodiment 79. The semi-synthetic organism of any one of embodiments 64-68, wherein the organism comprises a bacterium.

Embodiment 80. The semi-synthetic organism of embodiment 79, wherein the organism comprises a Gram-positive bacterium.

Embodiment 81. The semi-synthetic organism of embodiment 79, wherein the organism comprises a Gram-positive bacterium.

Embodiment 82. The semi-synthetic organism of any one of embodiments 64-79, wherein the organism comprises an *Escherichia coli*.

Embodiment 83. The semi-synthetic organism of any one of embodiments 64-68, wherein at least one of the unnatural bases is selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chorouracil, 5-fluorouracil, and 5-iodouracil, 6-alkyl derivatives of adenine and guanine, 6-azapyrimidines, 6-azo-uracil, 6-azocytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, 5-methoxyaminomethyl-2-thiouracil, beta-D-mannosylqueosine, 5'-methoxycarboxymethyluracil, 5-methoxyuracil, 2-methythio-N6-isopentenyladenine, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

Embodiment 84. The semi-synthetic organism of any one of embodiments 64-68, wherein the organism comprises DNA comprising at least one unnatural nucleobase selected from the group consisting of:

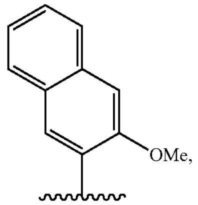
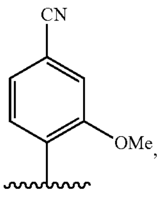

-continued

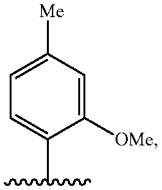
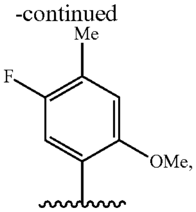
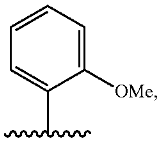
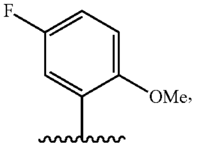
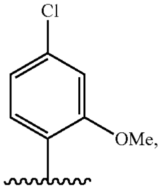
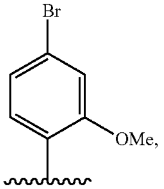
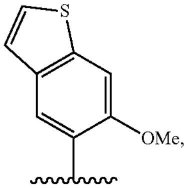
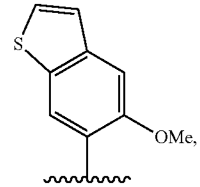
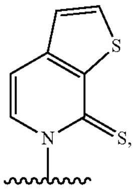
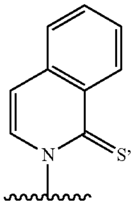
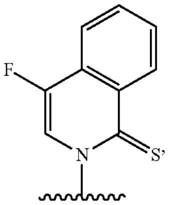
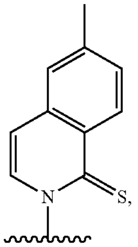
and
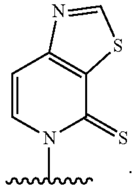

Embodiment 85. The semi-synthetic organism of any one of embodiments 64-69, wherein the DNA comprising at least one of the unnatural bases forms an unnatural base pair (UBP).

Embodiment 86. The semi-synthetic organism of embodiment 70, wherein the unnatural base pair (UBP) is dCNMO-dTPT3, dNaM-dTPT3, dCNMO-dTAT1, or dNaM-dTAT1.

Embodiment 87. The semi-synthetic organism of embodiment 69, wherein the DNA comprises at least one unnatural nucleobase selected from the group consisting of:

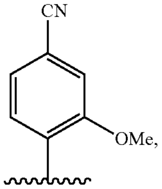
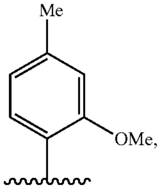

-continued

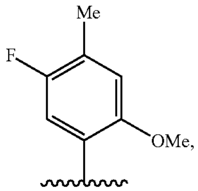 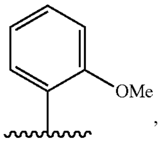 ,

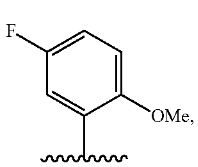 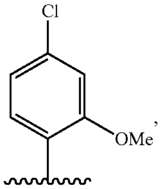

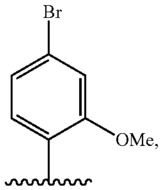 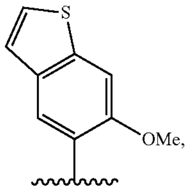

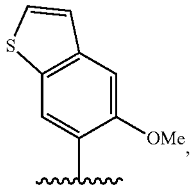 , 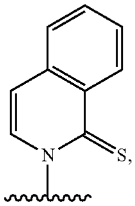 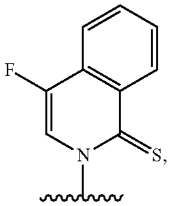

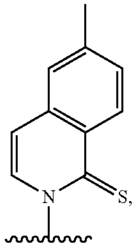 and 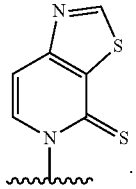 .

Embodiment 88. The semi-synthetic organism of embodiment 87, wherein the DNA comprises at least one unnatural nucleobase selected from the group consisting of:

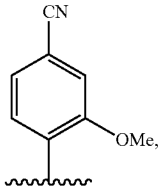 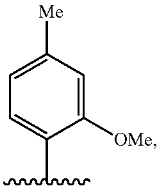

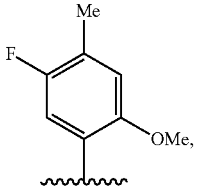 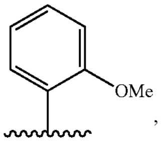 ,

-continued

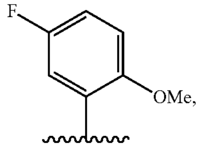 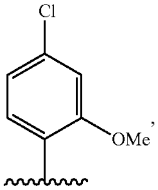

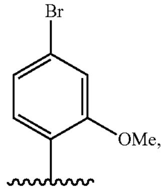 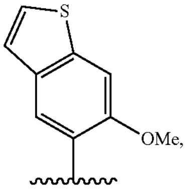 and

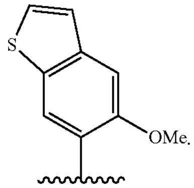

Embodiment 89. The semi-synthetic organism of embodiment 88, wherein the DNA comprises at least one unnatural nucleobase selected from the group consisting of:

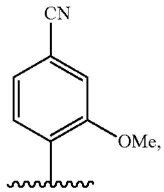 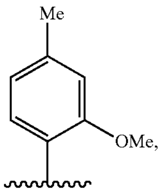

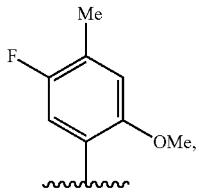 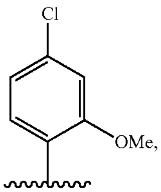

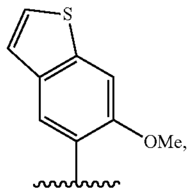 and 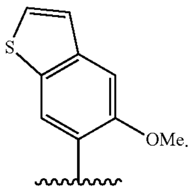

Embodiment 90. The semi-synthetic organism of embodiment 88, wherein the DNA comprises at least one unnatural nucleobase selected from the group consisting of:

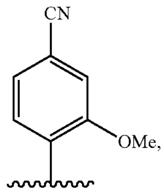 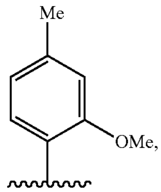

-continued

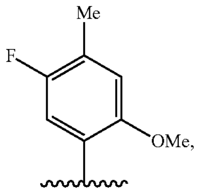

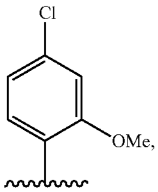

and

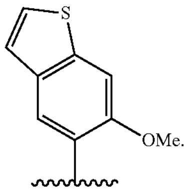

Embodiment 91. The semi-synthetic organism of embodiment 88, wherein the DNA comprises at least one unnatural nucleobase selected from the group consisting of:

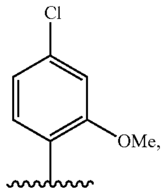

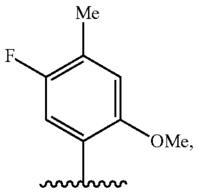

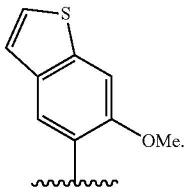

Embodiment 92. The semi-synthetic organism of embodiment 88, wherein the DNA comprises at least one unnatural nucleobase selected from the group consisting of:

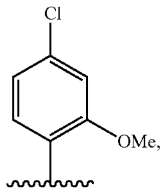

and

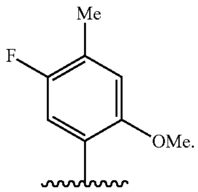

Embodiment 93. The semi-synthetic organism of embodiment 88, wherein the DNA comprises at least one unnatural nucleobase selected from the group consisting of:

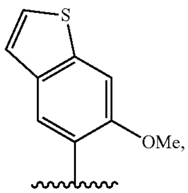

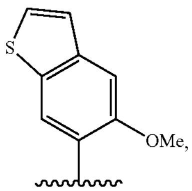

-continued

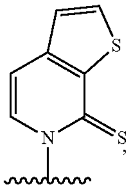

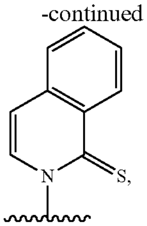

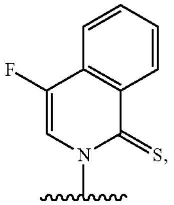

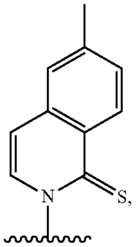

and

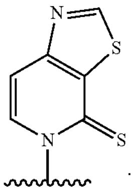

Embodiment 94. The semi-synthetic organism of embodiment 88, wherein the DNA comprises at least one unnatural nucleobase selected from the group consisting of:

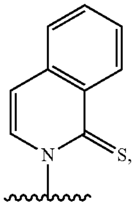

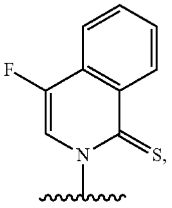

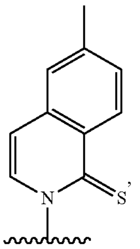

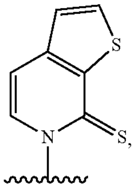

and

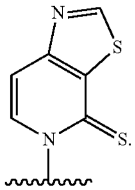

Embodiment 95. The semi-synthetic organism of embodiment 88, wherein the DNA comprises at least one unnatural nucleobase selected from

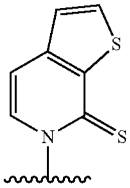

and

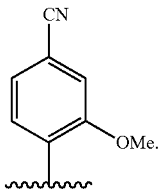

Embodiment 96. The semi-synthetic organism of embodiment 88, wherein the DNA comprises at least two unnatural nucleobases selected from

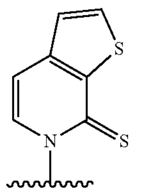

and

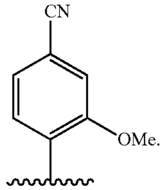

Embodiment 97. The semi-synthetic organism of embodiment 88, wherein the DNA comprises two strands, the first strand comprising at least one nucleobase which is

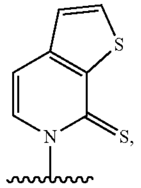

and the second strand comprising at least one nucleobase which is

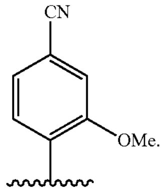 [SMILES: *c1ccc(C#N)cc1OC]

Embodiment 98. The semi-synthetic organism of embodiment 88, wherein the DNA comprises at least one unnatural nucleobase which is

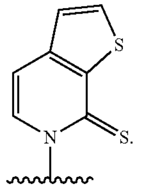

Embodiment 99. The semi-synthetic organism of any one of embodiments 64 to 71, wherein the organism expresses a nucleoside triphosphate transporter.

Embodiment 100. The semi-synthetic organism of embodiment 72, wherein the organism expresses the nucleoside triphosphate transporter is PtNTT2.

Embodiment 101. The semi-synthetic organism of any one of embodiments 64 to 73, wherein the organism further expresses a tRNA synthetase.

Embodiment 102. The semi-synthetic organism of embodiment 74, wherein the tRNA synthetase is *M. barkeri* pyrrolysyl-tRNA synthetase (Mb PylRS).

Embodiment 103. The semi-synthetic organism of embodiment 72, wherein the organism expresses the nucleoside triphosphate transporter PtNTT2 and further expresses the tRNA synthetase *M. barkeri* pyrrolysyl-tRNA synthetase (Mb PylRS).

Embodiment 104. The semi-synthetic organism of any one of embodiments 64 to 103, wherein the organism further expresses an RNA polymerase.

Embodiment 105. The semi-synthetic organism of embodiment 76, wherein the RNA polymerase is T7 RNAP.

Embodiment 106. The semi-synthetic organism of any one of embodiments 64 to 77, wherein the organism does not express a protein having the function of DNA recombinational repair.

Embodiment 107. The semi-synthetic organism of any one of embodiments 64 to 77, wherein the organism is *E. coli* and the organism does not express RecA.

Embodiment 108. The semi-synthetic organism of any one of embodiments 64 to 79, further comprising a mRNA.

Embodiment 109. The semi-synthetic organism of embodiment 80, wherein the mRNA comprises at least one unnatural base selected from

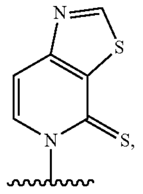

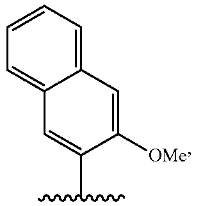

and

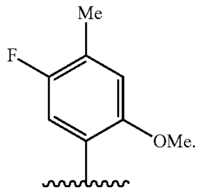

Embodiment 110. The semi-synthetic organism of embodiment 80, wherein the mRNA comprises at least one unnatural base which is

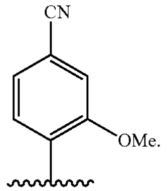 [SMILES: *c1ccc(C#N)cc1OC]

Embodiment 111. The semi-synthetic organism of embodiment 80, wherein the mRNA comprises at least one unnatural base which is

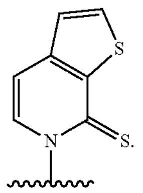

Embodiment 112. The semi-synthetic organism of embodiment 80, wherein the mRNA comprises at least one unnatural base which is

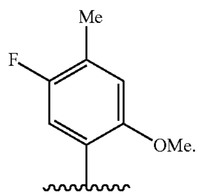 [SMILES: *c1cc(F)c(C)cc1OC]

Embodiment 113. The semi-synthetic organism of any one of embodiments 64 to 112, further comprising a tRNA.

Embodiment 114. The semi-synthetic organism of embodiment 82, wherein the tRNA comprises at least one unnatural base selected from

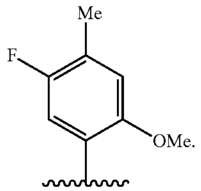

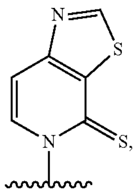

and

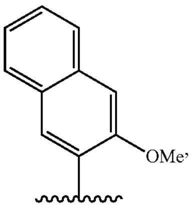

Embodiment 115. The semi-synthetic organism of embodiment 82, wherein the tRNA comprises at least one unnatural base which is

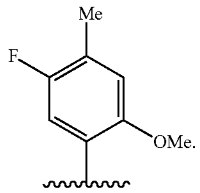

Embodiment 116. The semi-synthetic organism of embodiment 82, wherein the tRNA comprises at least one unnatural base which is

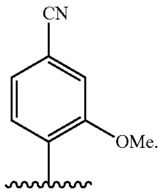 [SMILES: *c1ccc(C#N)cc1OC]

Embodiment 117. The semi-synthetic organism of embodiment 82, wherein the tRNA comprises at least one unnatural base which is

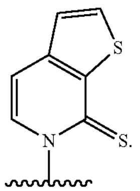

Embodiment 118. The semi-synthetic organism of any one of embodiments 64 to 79, further comprising a mRNA and a tRNA.

Embodiment 119. The semi-synthetic organism of any one of embodiments 64 to 71, wherein the organism further comprises (a) a nucleoside triphosphate transporter, (b) a mRNA, (c) a tRNA, (d) a tRNA synthetase, and (e) an RNA polymerase, and wherein the organism does not express a protein having the function of DNA recombinational repair.

Embodiment 120. The semi-synthetic organism of embodiment 119, wherein the nucleoside triphosphate transporter is PtNTT2, the tRNA synthetase is *M barkeri* pyrrolysyl-tRNA synthetase (Mb PylRS), and the RNA polymerase is T7 RNAP.

Embodiment 121. The semi-synthetic organism of embodiment 119, wherein the organism is *E. coli* and the organism does not express RecA.

Embodiment 122. The semi-synthetic organism of embodiment 118 or 119, wherein the organism overexpresses one or more DNA polymerases.

Embodiment 123. The semi-synthetic organism of embodiment 122, wherein the organism overexpresses DNA Pol II.

Embodiment 124. The semi-synthetic organism of any one of embodiments 64 to 123, wherein at least one unnatural base further comprises an unnatural sugar moiety.

Embodiment 125. The semi-synthetic organism of embodiment 124, wherein the unnatural sugar moiety is selected from the group consisting of:

a modification at the 2' position:

OH, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2F$;

O-alkyl, S-alkyl, N-alkyl;

O-alkenyl, S-alkenyl, N-alkenyl;

O-alkynyl, S-alkynyl, N-alkynyl;

O-alkyl-O-alkyl, 2'-F, 2'-$OCH_3$, 2'-$O(CH_2)_2OCH_3$ wherein the alkyl, alkenyl and alkynyl may be substituted or unsubstituted $C_1$-$C_{10}$, alkyl, $C_2$-$C_{10}$ alkenyl, $C_2$-$C_{10}$ alkynyl, $—O[(CH_2)_nO]_mCH_3$, $—O(CH_2)_nOCH_3$, $—O(CH_2)_nNH_2$, $—O(CH_2)_nCH_3$, $—O(CH_2)_n—NH_2$, and $—O(CH_2)_nON[(CH_2)_nCH_3)]_2$, wherein n and m are from 1 to about 10;

and/or a modification at the 5' position:

5'-vinyl, 5'-methyl (R or S);

a modification at the 4' position:

4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof.

Embodiment 126. The semi-synthetic organism of any one of embodiments 64-125, wherein at least one unnatural base is recognized by a DNA polymerase.

Embodiment 127. The semi-synthetic organism of any one of embodiments 73-126, wherein at least one unnatural base is recognized by an RNA polymerase.

Embodiment 128. A composition comprising a nucleobase analog of the structure:

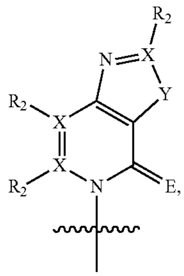

wherein each X is independently carbon or nitrogen;

$R_2$ is optional and when present is independently hydrogen, alkyl, alkenyl, alkynyl, methoxy, methanethiol, methaneseleno, halogen, cyano, or azide group;

wherein each Y is independently sulfur, oxygen, selenium, or secondary amine;

wherein each E is independently oxygen, sulfur, or selenium; and wherein the wavy line indicates a point of bonding to a ribosyl, deoxyribosyl, or dideoxyribosyl moiety or an analog thereof, wherein the ribosyl, deoxyribosyl, or dideoxyribosyl moiety or analog thereof is in free form, connected to a mono-phosphate, diphosphate, or triphosphate group, optionally comprising an α-thiotriphosphate, β-thiotriphosphate, or γ-thiotriphosphate group, or is included in an RNA or a DNA or in an RNA analog or a DNA analog.

Embodiment 129. The compound of embodiment 128, wherein the ribosyl or deoxyribosyl moiety bears a triphosphate or an a-thiotriphosphate group bonded to a 5'-hydroxyl thereof.

Embodiment 130. The compound of any one of embodiments 128 or 129, wherein the ribosyl or deoxyribosyl moiety is incorporated into a RNA or DNA oligonucleotide chain, respectively, or the ribosyl or deoxyribosyl moiety or analog thereof is incorporated into polynucleotide.

Embodiment 131. The compound of any one of embodiments 128 to 130, wherein X is carbon.

Embodiment 132. The compound of any one of embodiments 128 to 131, wherein E is sulfur.

Embodiment 133. The compound of any one of embodiments 128 to 132, wherein Y is sulfur.

Embodiment 134. The compound of embodiment 128, wherein the nucleobase comprises the structure

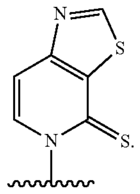

Embodiment 135. The compound of any one of embodiments 128 to 134, wherein the nucleobase is bound to a complementary base-pairing nucleobase to form an unnatural base pair (UBP).

Embodiment 136. The compound of embodiment 135, wherein the complementary base-pairing nucleobase is selected from:

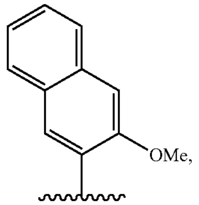
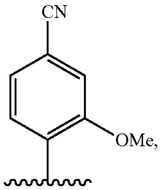
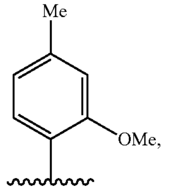
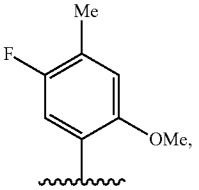
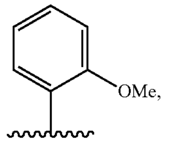
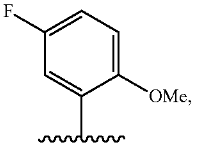
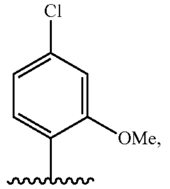
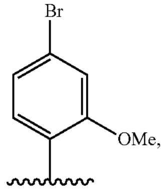
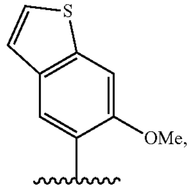
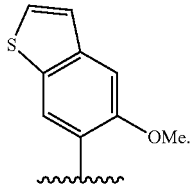

Embodiment 137. A double stranded oligonucleotide duplex wherein a first oligonucleotide strand comprises a compound of any one of embodiments 128 to 134, and a second complementary oligonucleotide strand comprises a complementary base-pairing nucleobase in a complementary base-pairing site thereof.

Embodiment 138. The double stranded oligonucleotide duplex of embodiment 137, wherein the first oligonucleotide strand comprises

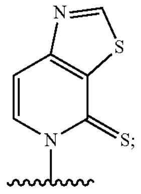

and the second strand comprises a complementary base pairing nucleobase selected from the group consisting of

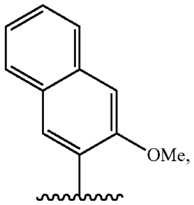,
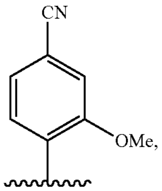,
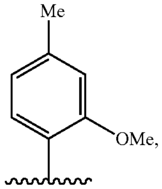,
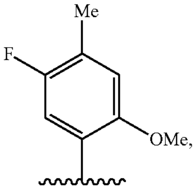,
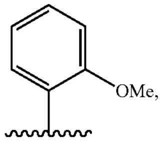,
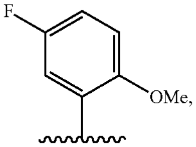,
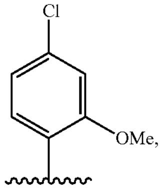,
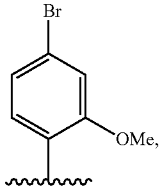,
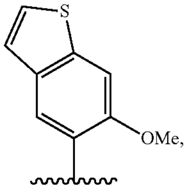,
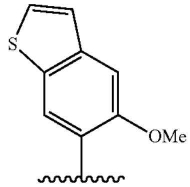

in a complementary base-pairing site thereof.

Embodiment 139. A transfer RNA (tRNA) comprising the nucleobase analog of any one of embodiments 128 to 36, comprising:

an anticodon, wherein the anticodon comprises the nucleobase analog; and a recognition element, wherein the recognition element promotes selective charging of the tRNA with an unnatural amino acid by an aminoacyl tRNA synthetase.

Embodiment 140. The tRNA of embodiment 139, wherein the nucleobase analog is located in an anticodon region of the tRNA.

Embodiment 141. The tRNA of embodiment 140, wherein the nucleobase analog is located in the first position of the anticodon.

Embodiment 142. The tRNA of embodiment 140, wherein the nucleobase analog is located in the second position of the anticodon.

Embodiment 143. The tRNA of embodiment 140, wherein the nucleobase analog is located in the third position of the anticodon.

Embodiment 144. The tRNA of embodiment 139, wherein the aminoacyl tRNA synthetase is derived from a thermophile.

Embodiment 145. The tRNA of embodiment 139, wherein the aminoacyl tRNA synthetase is derived from *Methanosarcina*, or a variant thereof.

Embodiment 146. The tRNA of embodiment 139, wherein the aminoacyl tRNA synthetase is derived from *Methanococcus* (*Methanocaldococcus*) or a variant thereof.

Embodiment 147. The tRNA of embodiment 139, wherein the unnatural amino acid comprises an aromatic moiety.

Embodiment 148. The tRNA of embodiment 139, wherein the unnatural amino acid is a lysine derivative.

Embodiment 149. The tRNA of embodiment 139, wherein the unnatural amino acid is a phenylalanine derivative.

Embodiment 150. The tRNA of embodiment 139, wherein the unnatural amino acid is selected from the group consisting of: N6-azidoethoxy-carbonyl-L-lysine (AzK), N6-propargylethoxy-carbonyl-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, and selenocysteine.

Embodiment 151. A structure comprising the formula:

N1-Zx-N2 wherein N1 is a nucleotide or analog thereof, or terminal phosphate group; wherein N2 is a nucleotide or analog thereof, or terminal hydroxyl group; wherein Z is a compound of any one of embodiments 128-136, and wherein x is an integer from 1 to 20.

Embodiment 152. The structure of embodiment 151, wherein the structure encodes for a gene.

Embodiment 153. The structure of embodiment 151, wherein Zx is located in a translated region of the gene.

Embodiment 154. The structure of embodiment 151, wherein Zx is located in an untranslated region of the gene.

Embodiment 155. The structure of embodiment 151, wherein the structure further comprises a 5' or 3' untranslated region (UTR).

Embodiment 156. The structure of embodiment 151, wherein the structure further comprises a terminator region.

Embodiment 157. The structure of embodiment 151, wherein the structure further comprises a promoter region.

Embodiment 158. A polynucleotide library, wherein the library comprises at least 5000 unique polynucleotides, and wherein each polynucleotide comprises at least one compound of any one of embodiments 128-136.

Embodiment 159. The library of embodiment 158, wherein the polynucleotide library encodes for at least one gene.

Embodiment 160. A nucleoside triphosphate, wherein the nucleobase is selected from

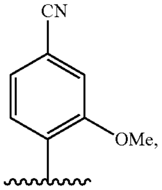,

-continued

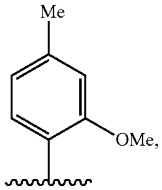, 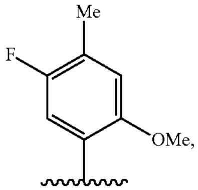,

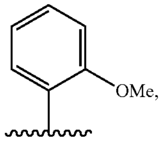, 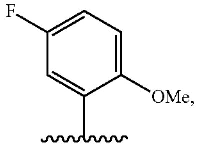,

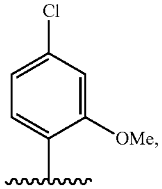, 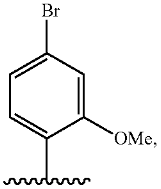,

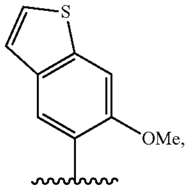, 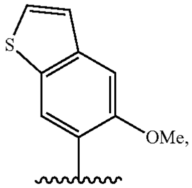,

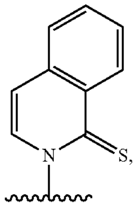, 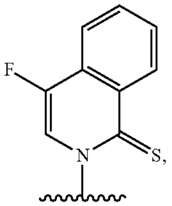,

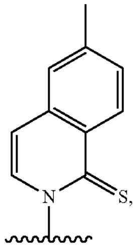, and 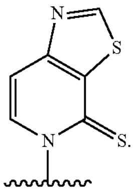.

Embodiment 161. The nucleoside triphosphate of embodiment 160, wherein the nucleoside comprises ribose.

Embodiment 162. The nucleoside triphosphate of embodiment 160, wherein the nucleoside comprises deoxyribose.

Embodiment 163. The nucleoside triphosphate of any one of embodiments 160 to 162, wherein the nucleobase is selected from

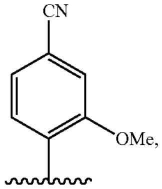, 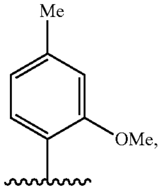,

-continued

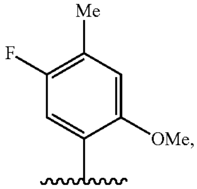 [SMILES: *c1cc(F)c(C)cc1OC], 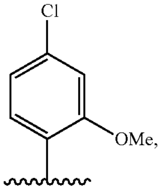,

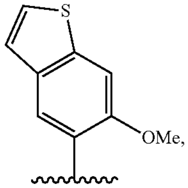, 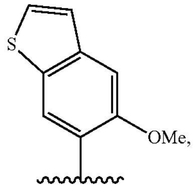,

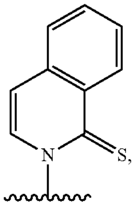, 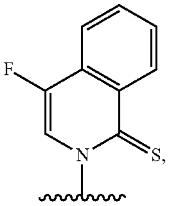,

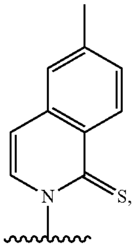, and 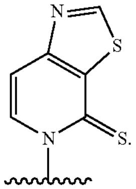 [SMILES: *n1ccc2ncsc2c1=S].

Embodiment 164. The nucleoside triphosphate of embodiment 163, wherein the nucleobase is selected from

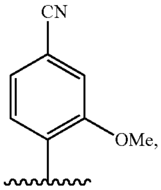, 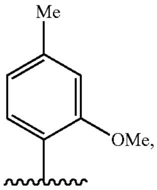,

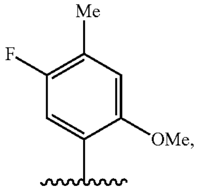, 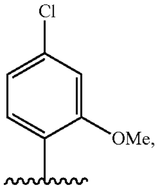,

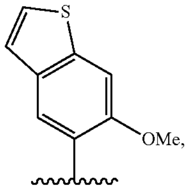, 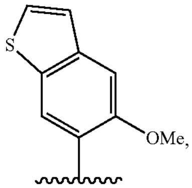, and

-continued

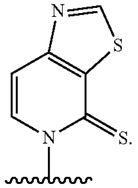

Embodiment 165. The nucleoside triphosphate of embodiment 163, wherein the nucleobase is selected from

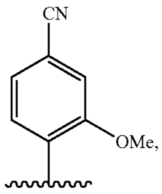

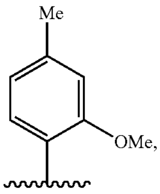

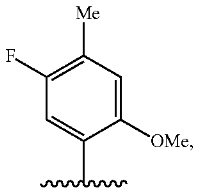

and

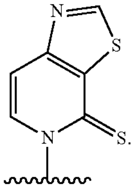 [SMILES: *n1ccc2ncsc2c1=S]

Embodiment 166. The nucleoside triphosphate of embodiment 163, wherein the nucleobase is selected from

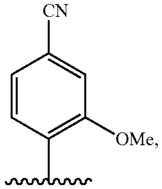 [SMILES: *c1ccc(C#N)cc1OC]

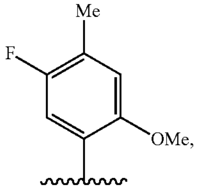 [SMILES: *c1cc(F)c(C)cc1OC]

and

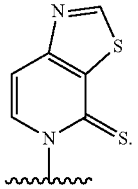

Embodiment 167. The nucleoside triphosphate of embodiment 165, wherein the nucleobase is

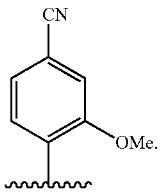

Embodiment 168. The nucleoside triphosphate of embodiment 167, wherein the nucleoside comprises ribose.

Embodiment 169. The nucleoside triphosphate of embodiment 167, wherein the nucleoside comprises deoxyribose.

Embodiment 170. The nucleoside triphosphate of embodiment 165, wherein the nucleobase is

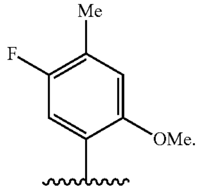

Embodiment 171. The nucleoside triphosphate of embodiment 170, wherein the nucleoside comprises ribose.

Embodiment 172. The nucleoside triphosphate of embodiment 170, wherein the nucleoside comprises deoxyribose.

Embodiment 173. The nucleoside triphosphate of embodiment 165, wherein the nucleobase is

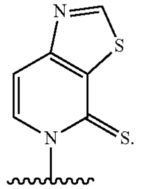 [SMILES: *n1ccc2ncsc2c1=S]

Embodiment 174. The nucleoside triphosphate of embodiment 173, wherein the nucleoside comprises ribose.

Embodiment 175. The nucleoside triphosphate of embodiment 173, wherein the nucleoside comprises deoxyribose.

Described herein are in vivo methods of producing a protein comprising an unnatural amino acid, the method comprising: transcribing a DNA template comprising a first unnatural base and a complementary second unnatural base to incorporate a third unnatural base into a mRNA, the third unnatural base configured to form a first unnatural base pair with the first unnatural base; transcribing the DNA template to incorporate a fourth unnatural base into a tRNA, wherein the fourth unnatural base is configured to form a second unnatural base pair with the second unnatural base, wherein the first unnatural base pair and the second unnatural base pair are not the same; and translating a protein from the mRNA and tRNA, wherein said protein comprises an unnatural amino acid. In some embodiments, the in vivo method comprises use of a semi-synthetic organism. In some embodiments, the organism comprises a microorganism. In some embodiments, the organism comprises a bacterium. In some embodiments, the organism comprises a Gram-positive bacterium. In some embodiments, the organism comprises a Gram-negative bacterium. In some embodiments, the organism comprises an *Escherichia coli*. In some embodiments, the at least one unnatural base is selected from the group consisting of (i) 2-thiouracil, 2-thio-thymine, 2'-deoxyuridine, 4-thio-uracil, 4-thio-thymine, uracil-5-yl, hypoxanthin-9-yl (I), 5-halouracil; 5-propynyl-uracil, 6-azo-thymine, 6-azo-uracil, 5-methylaminomethyluracil, 5-methoxyaminomethyl-2-thiouracil, pseudouracil, uracil-5-oxacetic acid methylester, uracil-5-oxacetic acid, 5-methyl-2-thiouracil, 3-(3-amino-3-N-2-carboxypropyl) uracil, 5-methyl-2-thiouracil, 4-thiouracil, 5-methyluracil, 5'-methoxycarboxymethyluracil, 5-methoxyuracil, uracil-5-oxyacetic acid, 5-(carboxyhydroxylmethyl) uracil, 5-carboxymethylaminomethyl-2-thiouridine, 5-carboxymethylaminomethyluracil, or dihydrouracil; (ii) 5-hydroxymethyl cytosine, 5-trifluoromethyl cytosine, 5-halocytosine, 5-propynyl cytosine, 5-hydroxycytosine, cyclocytosine, cytosine arabinoside, 5,6-dihydrocytosine, 5-nitrocytosine, 6-azo cytosine, azacytosine, N4-ethylcytosine, 3-methylcytosine, 5-methylcytosine, 4-acetylcytosine, 2-thiocytosine, phenoxazine cytidine([5,4-b][1,4]benzoxazin-2(3H)-one), phenothiazine cytidine (1H-pyrimido[5,4-b][1,4]benzothiazin-2 (3H)-one), phenoxazine cytidine (9-(2-aminoethoxy)-H-pyrimido[5,4-b][1,4]benzoxazin-2(3H)-one), carbazole cytidine (2H-pyrimido[4,5-b]indol-2-one), or pyridoindole cytidine (H-pyrido [3',2':4,5]pyrrolo [2,3-d]pyrimidin-2-one); (iii) 2-aminoadenine, 2-propyl adenine, 2-amino-adenine, 2-F-adenine, 2-amino-propyl-adenine, 2-amino-2'-deoxyadenosine, 3-deazaadenine, 7-methyladenine, 7-deaza-adenine, 8-azaadenine, 8-halo, 8-amino, 8-thiol, 8-thioalkyl, and 8-hydroxyl substituted adenines, N6-isopentenyladenine, 2-methyladenine, 2,6-diaminopurine, 2-methythio-N6-isopentenyladenine, or 6-aza-adenine; (iv) 2-methylguanine, 2-propyl and alkyl derivatives of guanine, 3-deazaguanine, 6-thio-guanine, 7-methylguanine, 7-deazaguanine, 7-deazaguanosine, 7-deaza-8-azaguanine, 8-azaguanine, 8-halo, 8-amino, 8-thiol, 8-thioalkyl, and 8-hydroxyl substituted guanines, 1-methylguanine, 2,2-dimethylguanine, 7-methylguanine, or 6-aza-guanine; and (v) hypoxanthine, xanthine, 1-methylinosine, queosine, beta-D-galactosylqueosine, inosine, beta-D-mannosylqueosine, wybutoxosine, hydroxyurea, (acp3)w, 2-aminopyridine, or 2-pyridone. In some embodiments, at least one of the first unnatural base, the second unnatural base, the third unnatural base, or the fourth unnatural base is selected from the group consisting of:

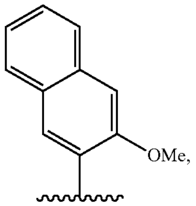
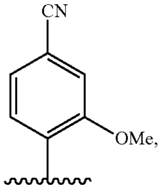 [SMILES: *c1ccc(C#N)cc1OC]
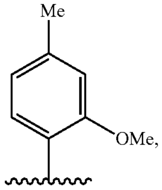
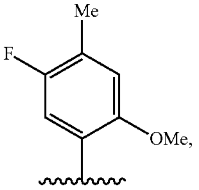
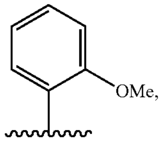
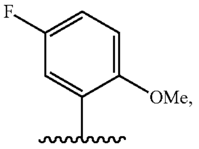
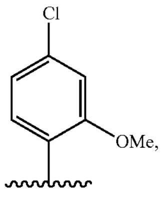
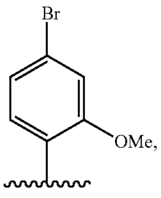

-continued

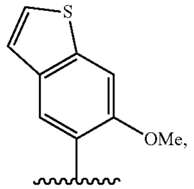
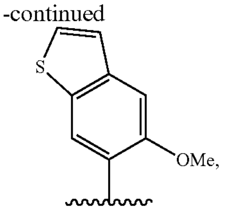
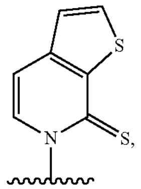
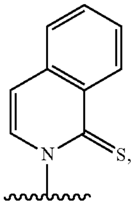
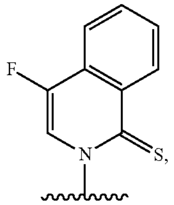
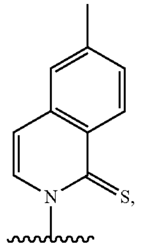
and
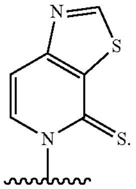

In some embodiments, at least one of the first unnatural base, the second unnatural base, the third unnatural base, or the fourth unnatural base is selected from the group consisting of

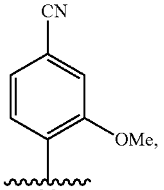
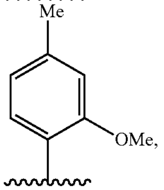
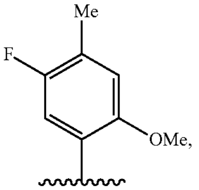
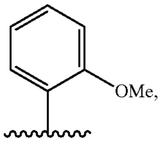
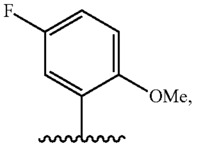
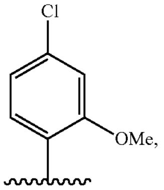
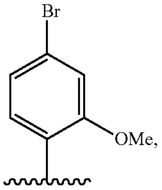
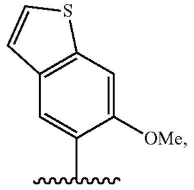
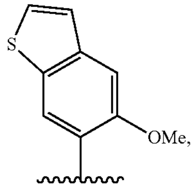

-continued

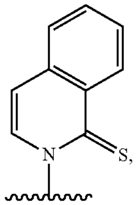,
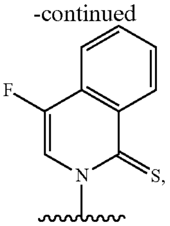,
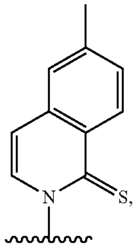, and
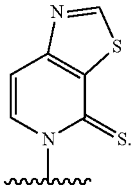.

In some embodiments, at least one of the first unnatural base, the second unnatural base, the third unnatural base, or the fourth unnatural base is selected from the group consisting of:

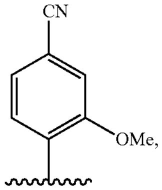,
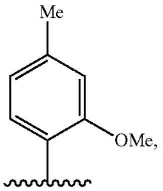,
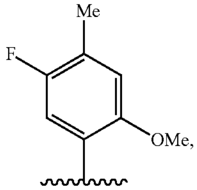,
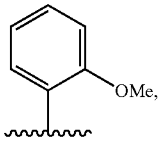,
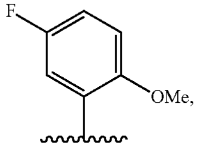,
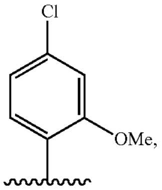,
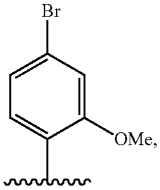,
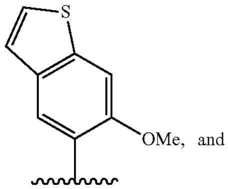, and
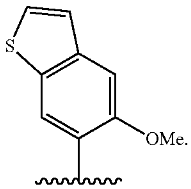.

In some embodiments, at least one of the first unnatural base, the second unnatural base, the third unnatural base, or the fourth unnatural base is selected from the group consisting of:

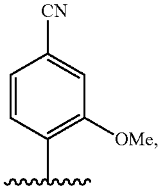,
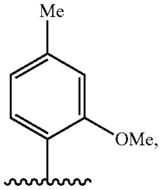,
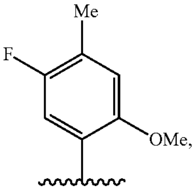,
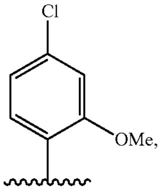,
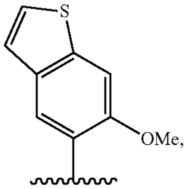, and
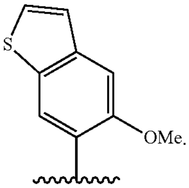.

In some embodiments, at least one of the first unnatural base, the second unnatural base, the third unnatural base, or the fourth unnatural base is selected from the group consisting of:

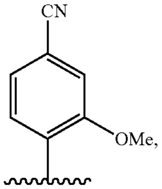,
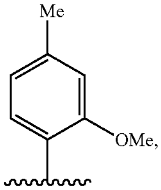,
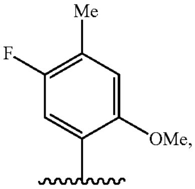,
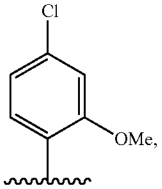, and
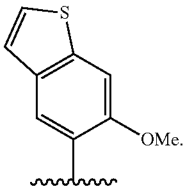.

Only the base of the nucleoside or nucleotide is shown, with the sugar moiety and, optionally, any phosphate(s) residues omitted for clarity. Here and throughout, the wavy line represents connection to a deoxy- or ribonucleoside or nucleotide, in which the sugar portion of the nucleotide may be further modified. In some embodiments, at least one of the first unnatural base, the second unnatural base, the third unnatural base, or the fourth unnatural base is selected from the group consisting of:

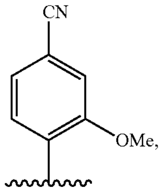

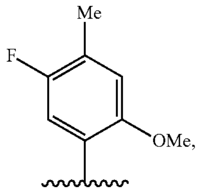

and

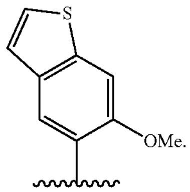

In some embodiments, at least one of the first unnatural base, the second unnatural base, the third unnatural base, or the fourth unnatural base is selected from the group consisting of:

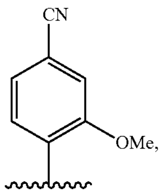

and

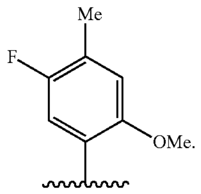

In some embodiments, at least one of the first unnatural base, the second unnatural base, the third unnatural base, or the fourth unnatural base is selected from the group consisting of

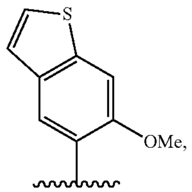

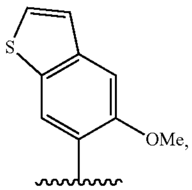

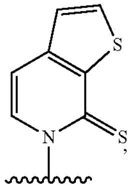

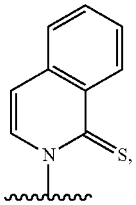

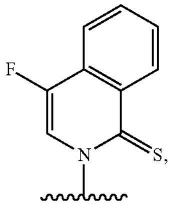

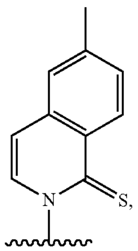

and

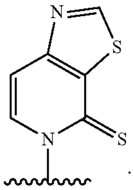

In some embodiments, at least one of the first unnatural base, the second unnatural base, the third unnatural base, or the fourth unnatural base is selected from the group consisting of:

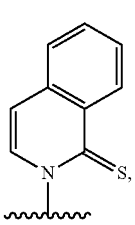

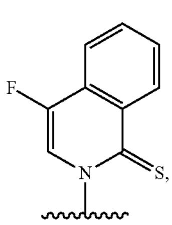

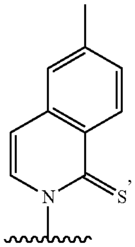

and

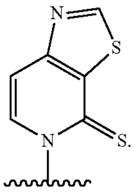

In some embodiments, at least one of the first unnatural base, the second unnatural base, the third unnatural base, or the fourth unnatural base is

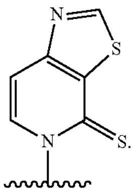

In some embodiments, at least one of the first unnatural base, the second unnatural base, the third unnatural base, or the fourth unnatural base is selected from:

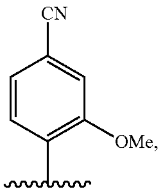

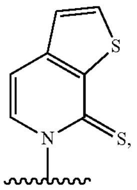

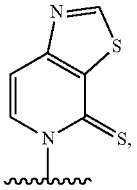

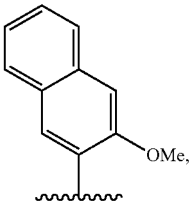

and

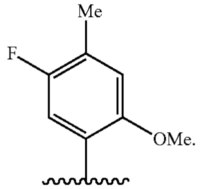

In some embodiments, the first or second unnatural base is

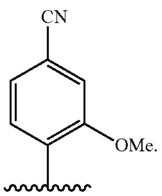

In some embodiments, the first or second unnatural base is

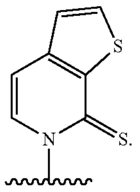

In some embodiments, the first unnatural base is

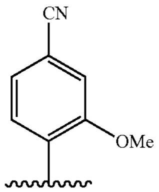 [SMILES: *c1ccc(C#N)cc1OC]

and the second unnatural base is

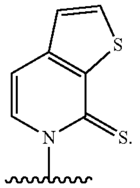 [SMILES: *n1ccc2ccsc2c1=S]

In some embodiments, the first unnatural base is

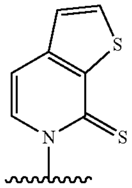 [SMILES: *n1ccc2ccsc2c1=S]

and the second unnatural base is

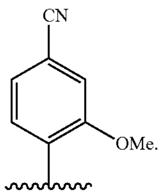 [SMILES: *c1ccc(C#N)cc1OC]

In some embodiments, the third or fourth unnatural base is

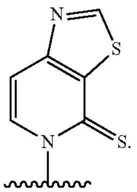 [SMILES: *n1ccc2ncsc2c1=S]

In some embodiments, the third unnatural base is

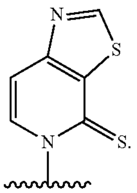 [SMILES: *n1ccc2ncsc2c1=S]

In some embodiments, the fourth unnatural base is

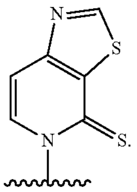

In some embodiments, the third or fourth unnatural base is

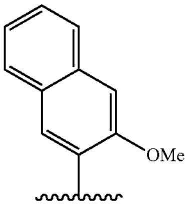

or

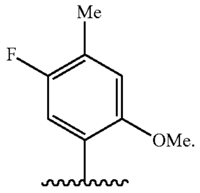

In some embodiments, the third unnatural base is or

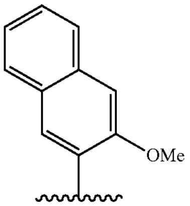

or

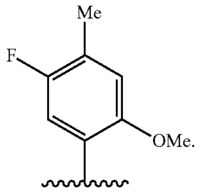

In some embodiments, the fourth unnatural base is

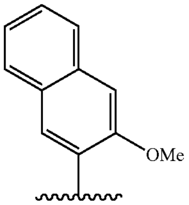
or
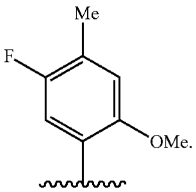

In some embodiments, the first unnatural base is

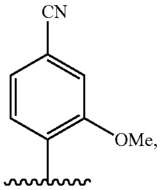 [SMILES: *c1ccc(C#N)cc1OC]

the second unnatural base is

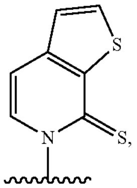

the third unnatural base is

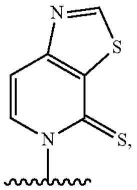 [SMILES: *n1ccc2ncsc2c1=S]

and the fourth unnatural base is

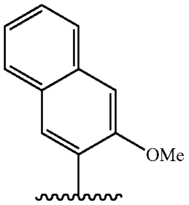
or
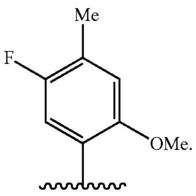

In some embodiments, the first unnatural base is

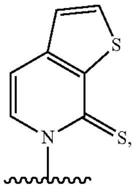 [SMILES: *n1ccc2ccsc2c1=S]

the second unnatural base is

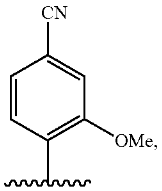 [SMILES: *c1ccc(C#N)cc1OC]

the third unnatural base is

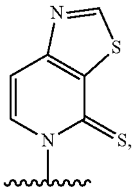 [SMILES: *n1ccc2ncsc2c1=S]

and the fourth unnatural base is

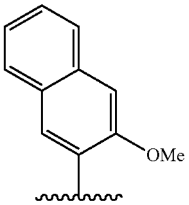
or
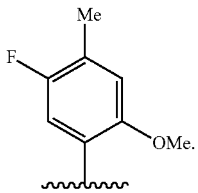

In some embodiments, the first unnatural base is

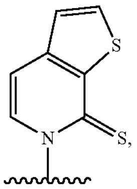

the second unnatural base is

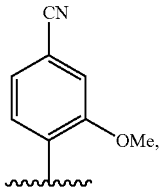 [SMILES: *c1ccc(C#N)cc1OC]

the third unnatural base is

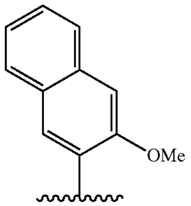

or

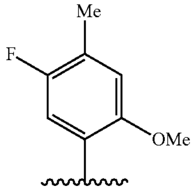

and the fourth unnatural base is

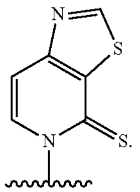

In some embodiments, the third unnatural base is

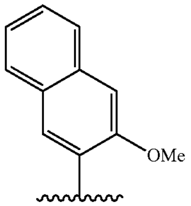

or

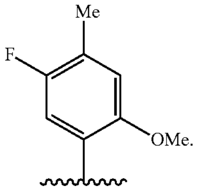

In some embodiments, the fourth unnatural base is

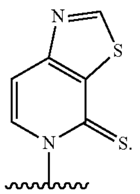 [SMILES: *n1ccc2ncsc2c1=S]

In some embodiments, the first unnatural base is

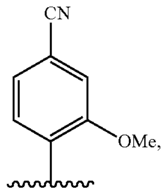

the second unnatural base is

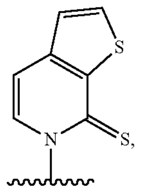

the third unnatural base is

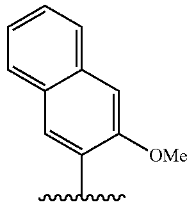

or

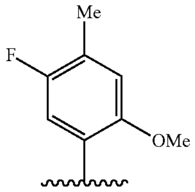

, and the fourth unnatural base is

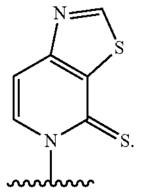

In some embodiments, the third unnatural base and the fourth unnatural base comprise ribose. In some embodiments, the third unnatural base and the fourth unnatural base comprise deoxyribose. In some embodiments, the first and second unnatural bases comprise deoxyribose. In some embodiments, the first and second unnatural bases comprise deoxyribose and the third unnatural base and the fourth unnatural base comprise ribose. In some embodiments, the DNA template comprises at least one unnatural base pair (UBP) selected from the group consisting of

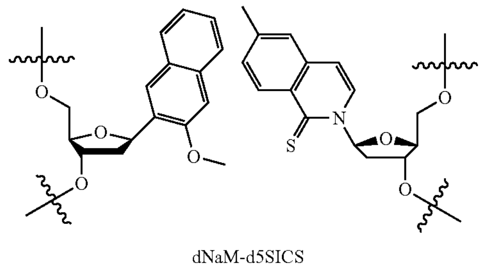

dNaM-d5SICS

-continued

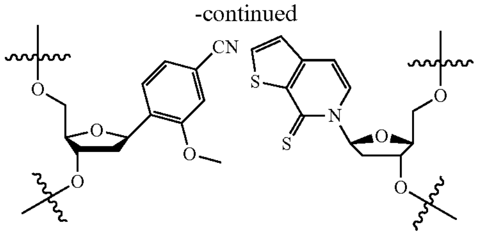

dCNMO-dTPT3

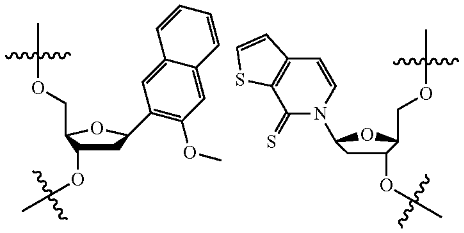

dNaM-dTPT3

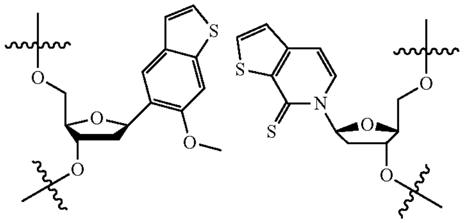

dPTMO-dTPT3

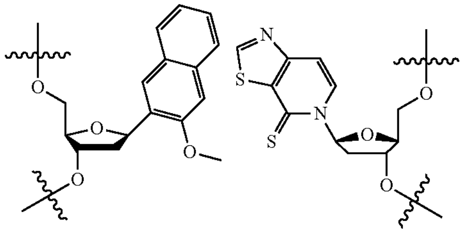

dNaM-dTAT1

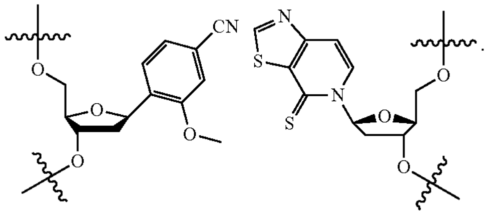

dCNMO-dTAT1

In some embodiments, the DNA template comprises at least one unnatural base pair (UBP) which is dNaM-d5SICS. In some embodiments, the DNA template comprises at least one unnatural base pair (UBP) which is dCNMO-dTPT3. In some embodiments, the DNA template comprises at least one unnatural base pair (UBP) which is dNaM-dTPT3. In some embodiments, the DNA template comprises at least one unnatural base pair (UBP) which is dPTMO-dTPT3. In some embodiments, the DNA template comprises at least one unnatural base pair (UBP) selected from the group consisting of

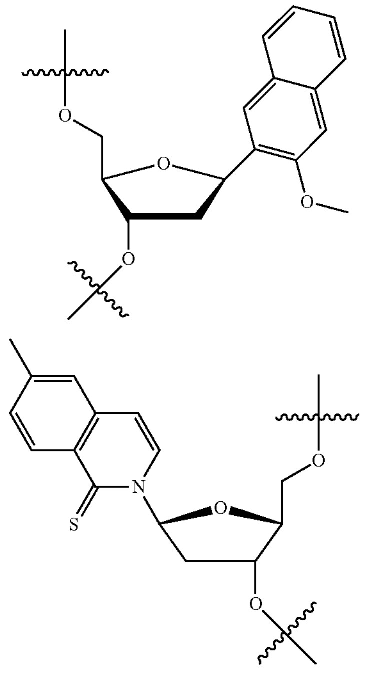

dNaM-d5SICS

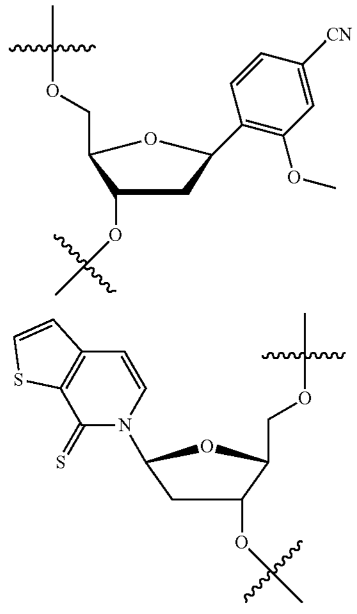

dCNMO-dTPT3

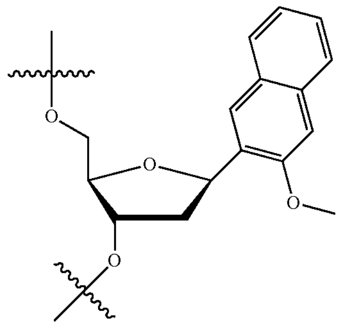

-continued

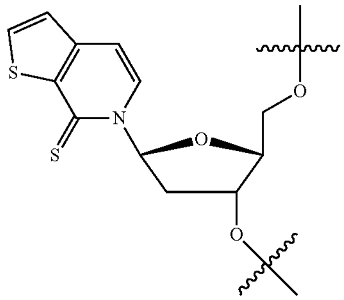

dNaM-dTPT3

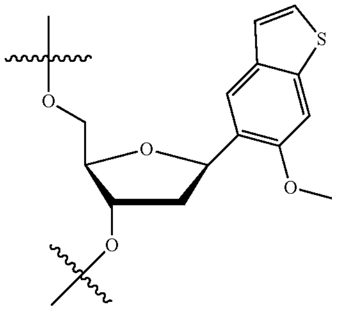

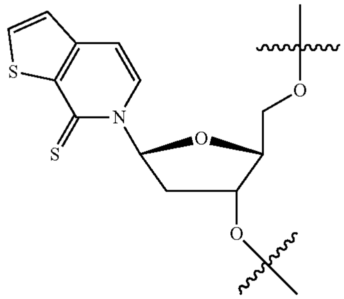

dPTMO-dTPT3

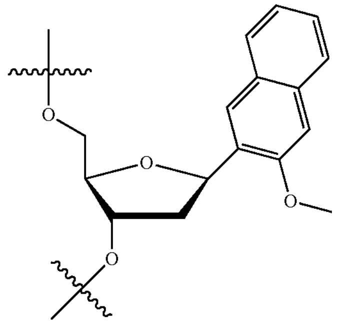

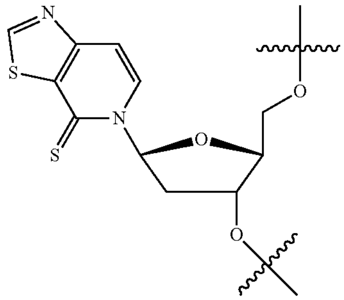

dNaM-dTAT1

-continued

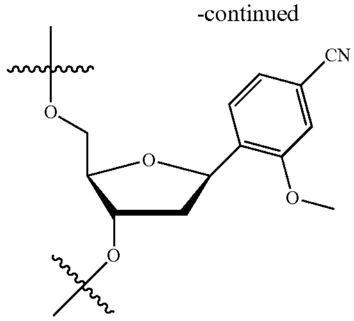

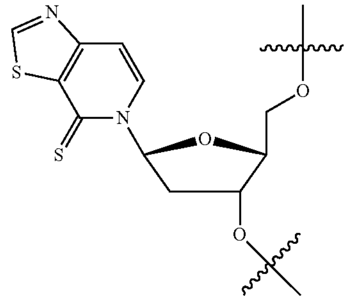

;

dCNMO-dTAT1 and wherein the mRNA and the tRNA comprise at least one unnatural ribonucleotide with an unnatural base selected from:

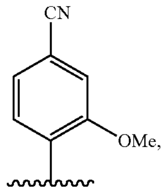 [SMILES: *c1ccc(C#N)cc1OC]

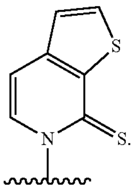

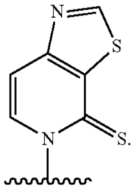 [SMILES: *n1ccc2ncsc2c1=S]

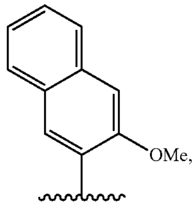

and

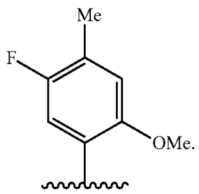

In some embodiments, the DNA template comprises at least one unnatural base pair (UBP) which is dNaM-d5SICS. In some embodiments, the DNA template comprises at least one unnatural base pair (UBP) which is dCNMO-dTPT3. In some embodiments, the DNA template comprises at least one unnatural base pair (UBP) which is dNaM-dTPT3. In some embodiments, the DNA template comprises at least one unnatural base pair (UBP) which is dPTMO-dTPT3. In some embodiments, the mRNA and the tRNA comprise an unnatural base selected from

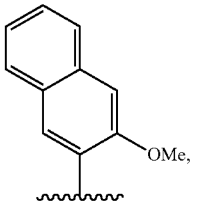 [SMILES: *c1cc2ccccc2cc1OC]

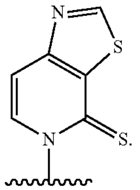 [SMILES: *n1ccc2ncsc2c1=S]

and

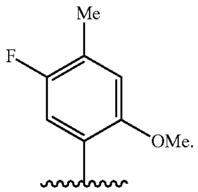 [SMILES: *c1cc(F)c(C)cc1OC]

In some embodiments, the mRNA and the tRNA comprise an unnatural base selected from

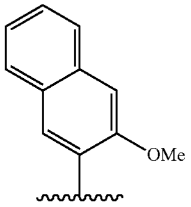 [SMILES: *c1cc2ccccc2cc1OC]

and

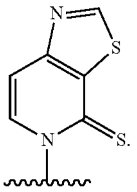 [SMILES: *n1ccc2ncsc2c1=S]

In some embodiments, the mRNA comprises an unnatural base which is

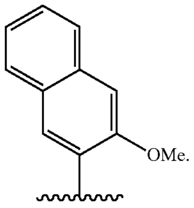

In some embodiments, the mRNA comprises an unnatural base which is

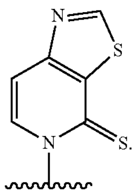

In some embodiments, the mRNA comprises an unnatural base which is

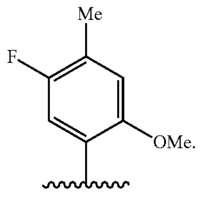 [SMILES: *c1cc(F)c(C)cc1OC]

In some embodiments, the tRNA comprises an unnatural base selected from

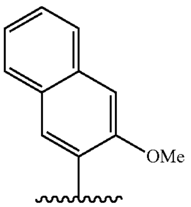

and

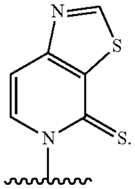

In some embodiments, the tRNA comprises an unnatural base which is

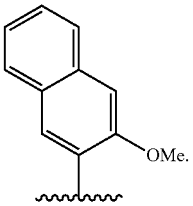

In some embodiments, the tRNA comprises an unnatural base which is

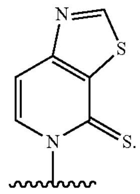

In some embodiments, the tRNA comprises an unnatural base which is

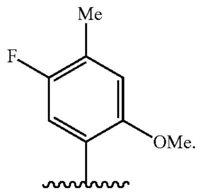

In some embodiments, the first unnatural base comprises dCNMO, and the second unnatural base comprises dTPT3. In some embodiments, the third unnatural base comprises NaM, and the second unnatural base comprises TAT1. In some embodiments, the first unnatural base or the second unnatural base is recognized by a DNA polymerase. In some embodiments, the third unnatural base or the fourth unnatural base is recognized by an RNA polymerase. In some embodiments, the protein comprises at least two unnatural amino acids. In some embodiments, the protein comprises at least three unnatural amino acids. In some embodiments, the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-azidoethoxy-carbonyl-L-lysine (AzK), N6-propargylethoxy-carbonyl-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid comprises N6-azidoethoxy-carbonyl-L-lysine (AzK) and N6-propargylethoxy-carbonyl-L-lysine (PraK). In some embodiments, the at least one unnatural amino acid comprises N6-azidoethoxy-carbonyl-L-lysine (AzK). In some embodiments, the at least one unnatural amino acid comprises N6-propargylethoxy-carbonyl-L-lysine (PraK).

Described herein are semi-synthetic organisms comprising an expanded genetic alphabet, wherein the genetic alphabet comprises at least three unique unnatural bases. In some embodiments, the organism comprises a microorganism. In some embodiments, the organism comprises a bacterium. In some embodiments, the organism comprises a Gram-positive bacterium. In some embodiments, the organism comprises a Gram-positive bacterium. In some embodiments, the organism comprises an *Escherichia coli*. In some embodiments, at least one of the unnatural bases is selected from the group consisting of 2-aminoadenin-9-yl, 2-amino-adenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methylcytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azocytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido [5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido [4,5-b]indol-2-one), pyridoindole cytidine (H-pyrido [3',2':4,5]pyrrolo [2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladenine, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle. In some embodiments, the organism comprises DNA comprising at least one unnatural nucleobase selected from the group consisting of:

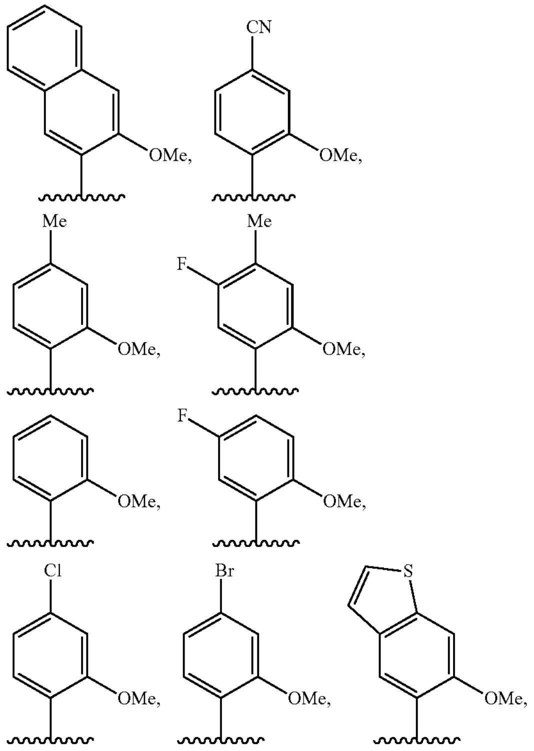

-continued

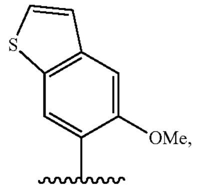, 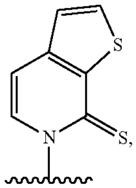, 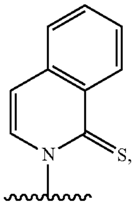,

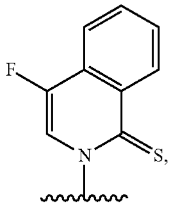, 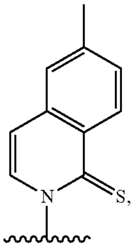, and 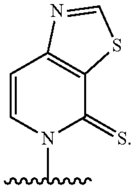.

In some embodiments, the DNA comprising at least one of the unnatural bases forms an unnatural base pair (UBP). In some embodiments, the unnatural base pair (UBP) is dCNMO-dTPT3, dNaM-dTPT3, dCNMO-dTAT1, or dNaM-dTAT1. In some embodiments, the DNA comprises at least one unnatural nucleobase selected from the group consisting of:

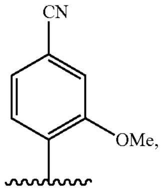, 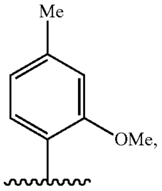,

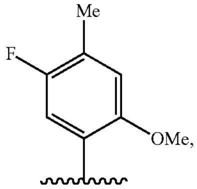, 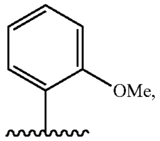,

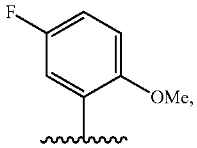, 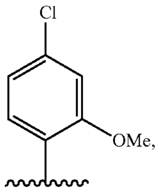,

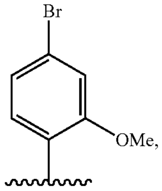, 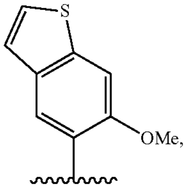,

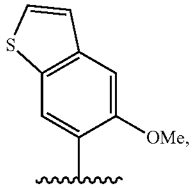, 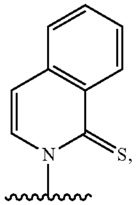, 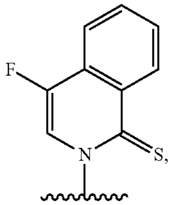,

-continued

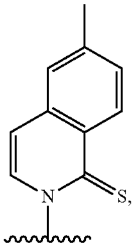, and 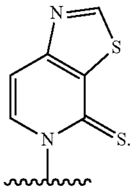.

In some embodiments, the DNA comprises at least one unnatural nucleobase selected from the group consisting of:

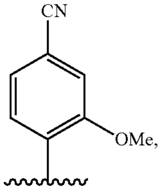, 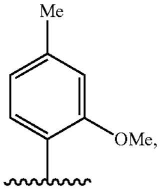,

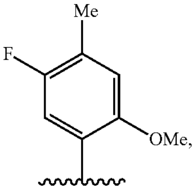, 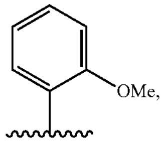,

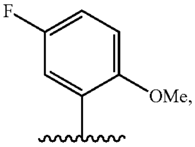, 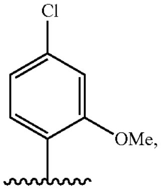,

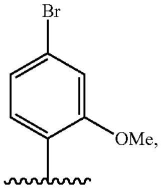, 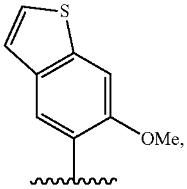, and

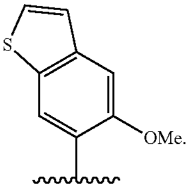.

In some embodiments, the DNA comprises at least one unnatural nucleobase selected from the group consisting of:

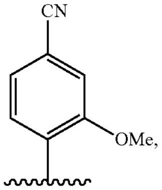, 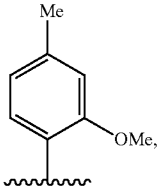,

-continued

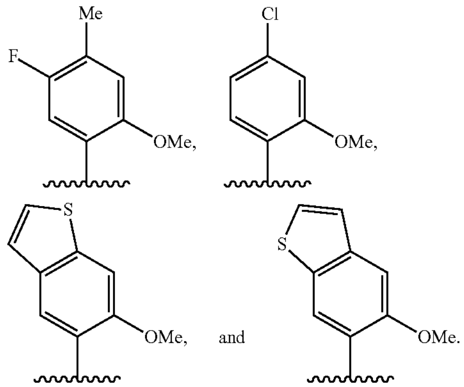

and

In some embodiments, the DNA comprises at least one unnatural nucleobase selected from the group consisting of:

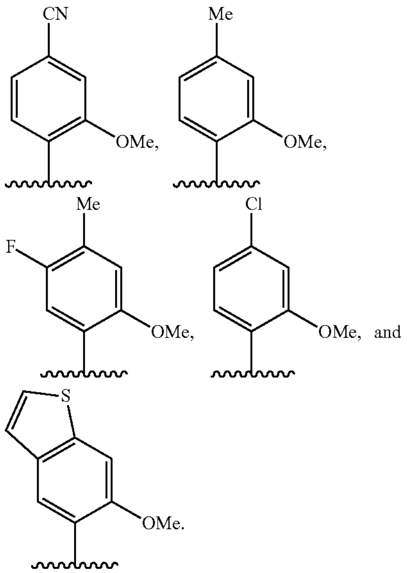

and

In some embodiments, the DNA comprises at least one unnatural nucleobase selected from the group consisting of:

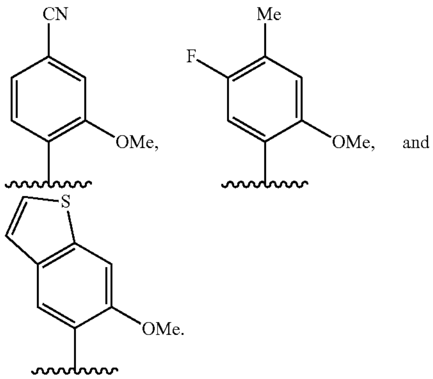

and

In some embodiments, the DNA comprises at least one unnatural nucleobase selected from the group consisting of:

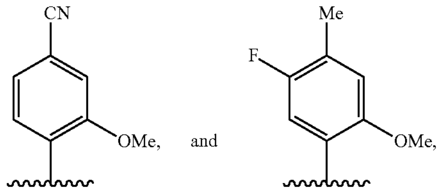 [SMILES: *c1ccc(C#N)cc1OC ; *c1cc(F)c(C)cc1OC]

and

In some embodiments, the DNA comprises at least one unnatural nucleobase selected from the group consisting of:

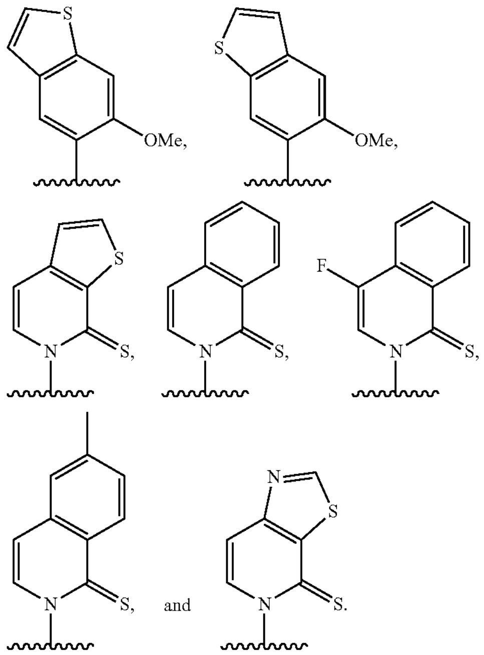

and

In some embodiments, the DNA comprises at least one unnatural nucleobase selected from the group consisting of:

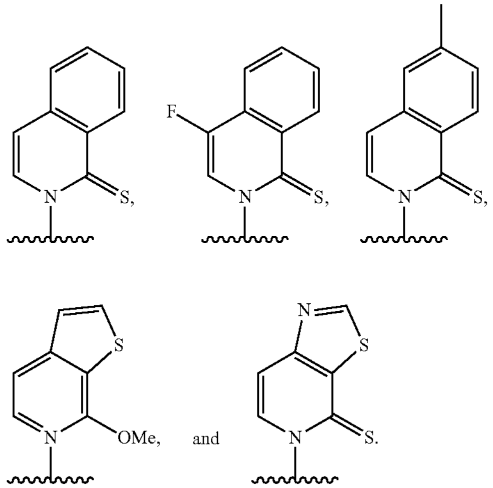

and

In some embodiments, the DNA comprises at least one unnatural nucleobase selected from

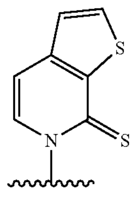 and 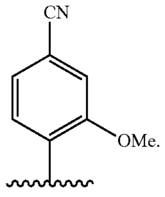

In some embodiments, the DNA comprises at least two unnatural nucleobases selected from

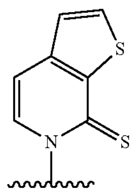 and 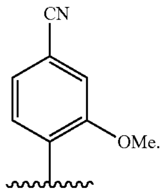

In some embodiments the DNA comprises two strands, the first strand comprising at least one nucleobase which is

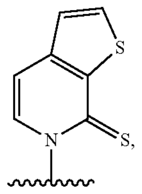 [SMILES: *n1ccc2ccsc2c1=S]

and the second strand comprising at least one nucleobase which is

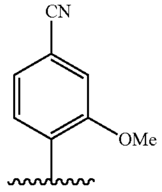 [SMILES: *c1ccc(C#N)cc1OC]

In some embodiments, the DNA comprises at least one unnatural nucleobase which is

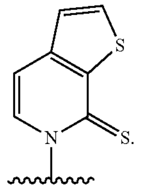

In some embodiments, the organism expresses a nucleoside triphosphate transporter. In some embodiments, the organism expresses the nucleoside triphosphate transporter is PtNTT2. In some embodiments, the organism further expresses a tRNA synthetase. In some embodiments, the tRNA synthetase is *M. barkeri* pyrrolysyl-tRNA synthetase (Mb PylRS). In some embodiments, the organism expresses the nucleoside triphosphate transporter PtNTT2 and further expresses the tRNA synthetase *M. barkeri* pyrrolysyl-tRNA synthetase (Mb PylRS). In some embodiments, the organism further expresses an RNA polymerase. In some embodiments, the RNA polymerase is T7 RNAP. In some embodiments, the organism does not express a protein having the function of DNA recombinational repair. In some embodiments, the organism is *E. coli* and the organism does not express RecA. In some embodiments, the organism overexpresses a DNA polymerase. In some embodiments, the organism overexpresses DNA Polymerase II. In some embodiments, the semi-synthetic organism further comprises a mRNA. In some embodiments, the mRNA comprises at least one unnatural base selected from

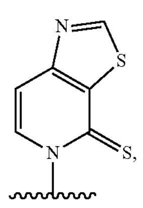 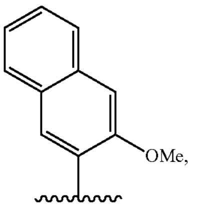 and

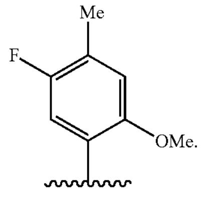

In some embodiments, the mRNA comprises at least one unnatural base which is

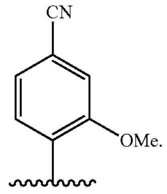 [SMILES: *c1ccc(C#N)cc1OC]

In some embodiments, the mRNA comprises at least one unnatural base which is

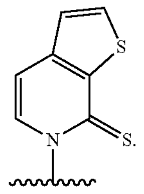 [SMILES: *n1ccc2ccsc2c1=S]

In some embodiments, the mRNA comprises at least one unnatural base which is

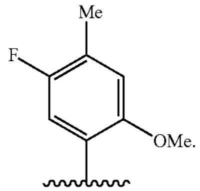 [SMILES: *c1cc(F)c(C)cc1OC]

In some embodiments, the semi-synthetic organism further comprises a tRNA. In some embodiments, the tRNA comprises at least one unnatural base selected from

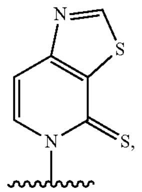

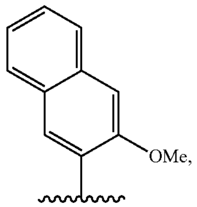

and

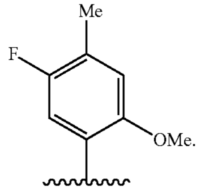

In some embodiments, the tRNA comprises at least one unnatural base which is

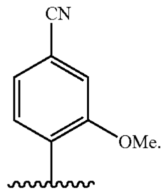 [SMILES: *c1ccc(C#N)cc1OC]

In some embodiments, the tRNA comprises at least one unnatural base which is

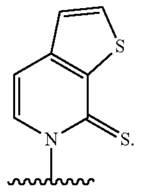

In some embodiments, the tRNA comprises at least one unnatural base which is

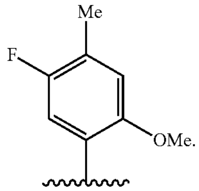 [SMILES: *c1cc(F)c(C)cc1OC]

In some embodiments, the semi-synthetic organism further comprises a mRNA and/or a tRNA. In some embodiments, the organism further comprises (a) a nucleoside triphosphate transporter, (b) a mRNA, (c) a tRNA, (d) a tRNA synthetase, and (e) an RNA polymerase, and wherein the organism does not express a protein having the function of DNA recombinational repair. In some embodiments, the nucleoside triphosphate transporter is PtNTT2, the tRNA synthetase is *M. barkeri* pyrrolysyl-tRNA synthetase (Mb PylRS), and the RNA polymerase is T7 RNAP. In some embodiments, the organism is *E. coli* and the organism does not express RecA. In some embodiments, the organism overexpresses one or more DNA polymerases. In some embodiments, the organism overexpresses one DNA Pol II. In some embodiments, at least one unnatural base further comprises an unnatural sugar moiety. In some embodiments, the unnatural sugar moiety is selected from the group consisting of: a modification at the 2' position: OH, substituted lower alkyl, alkaryl, aralkyl, O-alkaryl or O-aralkyl, SH, $SCH_3$, OCN, $C_1$, Br, CN, $CF_3$, $OCF_3$, $SOCH_3$, $SO_2CH_3$, $ONO_2$, $NO_2$, $N_3$, $NH_2F$; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-$OCH_3$, 2'-$O(CH_2)_2OCH_3$ wherein the alkyl, alkenyl and alkynyl may be substituted or unsubstituted $C_1$-$C_{10}$, alkyl, $C_2$-$C_{10}$ alkenyl, $C_2$-$C_{10}$ alkynyl, $—O[(CH_2)_nO]_mCH_3$, $—O(CH_2)_nOCH_3$, $—O(CH_2)_nNH_2$, $—O(CH_2)_nCH_3$, $—O(CH_2)_n—NH_2$, and $—O(CH_2)_nON[(CH_2)_nCH_3)]2$, wherein n and m are from 1 to about 10; and/or a modification at the 5' position: 5'-vinyl, 5'-methyl (R or S); a modification at the 4' position: 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof. In some embodiments, at least one unnatural base is recognized by a DNA polymerase. In some embodiments, at least one unnatural base is recognized by an RNA polymerase.

Described herein are compositions comprising a nucleobase analog of the structure:

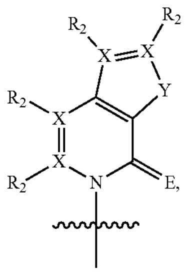

wherein each X is independently carbon or nitrogen; $R_2$ is optional and when present is independently a hydrogen, alkyl, alkenyl, alkynyl, methoxy, methanethiol, methaneseleno, halogen, cyano, or azide group; wherein each Y is independently sulfur, oxygen, selenium, or secondary amine; wherein each E is independently oxygen, sulfur, or selenium; and wherein the wavy line indicates a point of bonding to a ribosyl, deoxyribosyl, or dideoxyribosyl moiety or an analog thereof, wherein the ribosyl, deoxyribosyl, or dideoxyribosyl moiety or analog thereof is in free form, connected to a mono-phosphate, diphosphate, or triphosphate group, optionally comprising an α-thiotriphosphate, β-thiotriphosphate, or γ-thiotriphosphate group, or is included in an RNA or a DNA or in an RNA analog or a DNA analog. In some embodiments, the ribosyl or deoxyribosyl moiety bears a triphosphate or an α-thiotriphosphate group bonded to a 5'-hydroxyl thereof. In some embodiments, the ribosyl or deoxyribosyl moiety is incorporated into a RNA or DNA oligonucleotide chain, respectively, or the ribosyl or deoxyribosyl moiety or analog thereof is incorporated into an RNA or a DNA analog. In some embodiments, X is carbon. In some embodiments, E is sulfur. In some embodiments, Y is sulfur. In some embodiments, the nucleobase comprises the structure

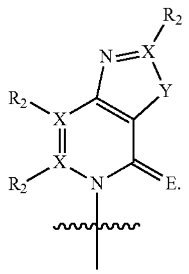

In some embodiments, the nucleobase comprises the structure

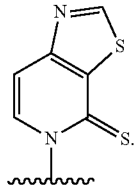 [SMILES: *n1ccc2ncsc2c1=S]

In some embodiments, the nucleobase pairs with a complementary nucleobase to form an unnatural base pair (UBP). In some embodiments, the complementary base-pairing nucleobase is selected from:

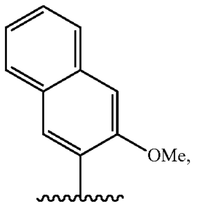

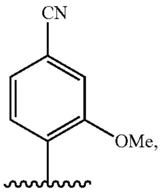

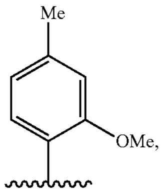

-continued

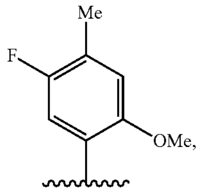

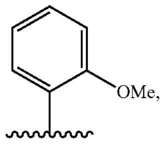

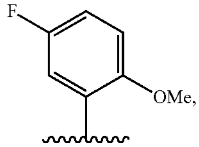

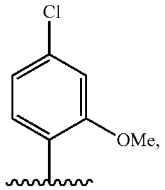

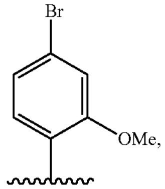

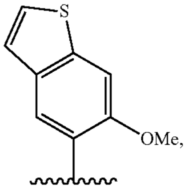

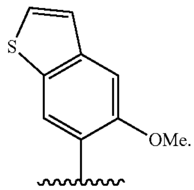

Described herein are double stranded oligonucleotide duplexes wherein a first oligonucleotide strand comprises a compound described herein, and a second complementary oligonucleotide strand comprises a complementary base-pairing nucleobase in a complementary base-pairing site thereof. In some embodiments, the first oligonucleotide strand comprises

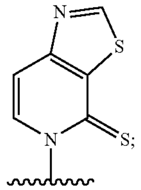 [SMILES: *n1ccc2ncsc2c1=S]

and the second strand comprises a complementary base pairing nucleobase selected from the group consisting of

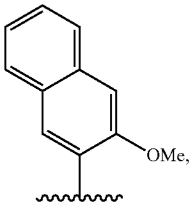

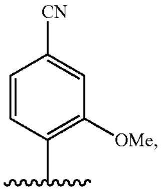 [SMILES: *c1ccc(C#N)cc1OC]

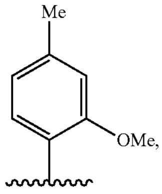

-continued

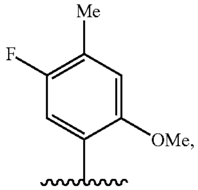, 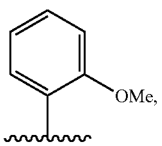, 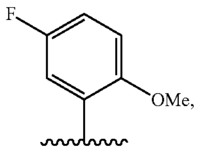, 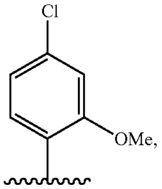, 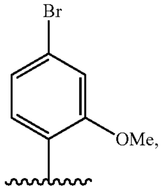, 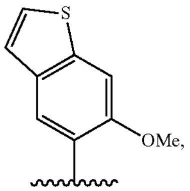, 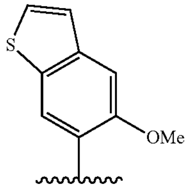

in a complementary base-pairing site thereof.

Described herein are transfer RNA (tRNA) comprising a ribonucleobase analog described herein, comprising: an anticodon, wherein the anticodon comprises the ribonucleobase analog; and a recognition element, wherein the recognition element promotes selective charging of the tRNA with an unnatural amino acid by an aminoacyl tRNA synthetase. In some embodiments of a tRNA, the nucleobase analog is located in an anticodon region of the tRNA. In some embodiments of a tRNA, the nucleobase analog is located in the first position of the anticodon. In some embodiments of a tRNA, the nucleobase analog is located in the second position of the anticodon. In some embodiments of a tRNA, the nucleobase analog is located in the third position of the anticodon. In some embodiments of a tRNA, the aminoacyl tRNA synthetase is derived from a thermophile. In some embodiments of a tRNA, the aminoacyl tRNA synthetase is derived from *Methanosarcina*, or a variant thereof. In some embodiments of a tRNA, the aminoacyl tRNA synthetase is derived from *Methanococcus* (*Methanocaldococcus*) or a variant thereof. In some embodiments of a tRNA, the unnatural amino acid comprises an aromatic moiety. In some embodiments of a tRNA, the unnatural amino acid is a lysine derivative. In some embodiments of a tRNA, the unnatural amino acid is a phenylalanine derivative. In some embodiments of a tRNA, the unnatural amino acid is selected from the group consisting of: N6-azidoethoxy-carbonyl-L-lysine (AzK), N6-propargylethoxy-carbonyl-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, and selenocysteine.

Described herein are structures comprising the formula: N1-Zx-N2 wherein N1 is a nucleotide or analog thereof, or terminal phosphate group; wherein N2 is a nucleotide or analog thereof, or terminal hydroxyl group; wherein Z is a compound described herein, and wherein x is an integer from 1 to 20. In some embodiments, the structure encodes for a gene. In some embodiments, Zx is located in a coding region of the gene. In some embodiments, Zx is located in a codon. In some embodiments, the structure further comprises a 5' or 3' untranslated region (UTR). In some embodiments, the structure further comprises a terminator region. In some embodiments, the structure further comprises a promoter region.

Described herein are polynucleotide libraries, wherein the libraries comprises at least 5000 unique polynucleotides, and wherein each polynucleotide comprises at least one unnatural nucleobase described herein. In some embodiments, the polynucleotide library encodes for at least one gene.

Described herein are nucleoside triphosphates, wherein the nucleobase is selected from

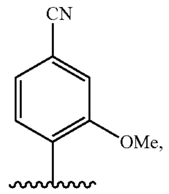, 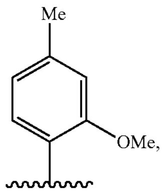, 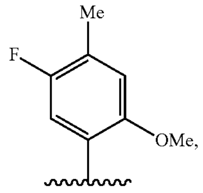 [SMILES: *c1cc(F)c(C)cc1OC], 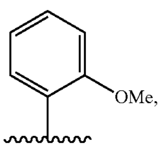, 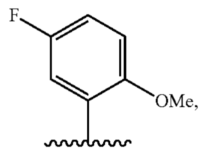, 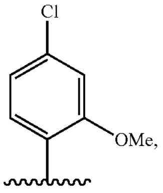, 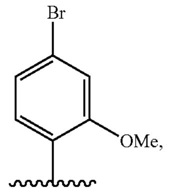, 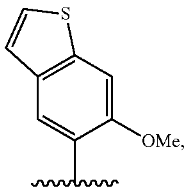, -continued

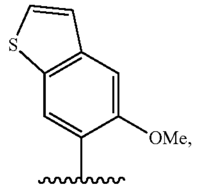
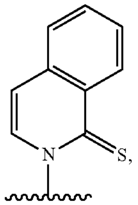
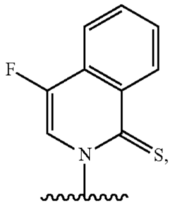
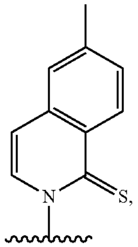
and
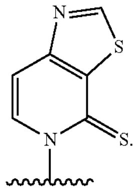 [SMILES: *n1ccc2ncsc2c1=S]

In some embodiments, the nucleoside comprises ribose. In some embodiments, the nucleoside comprises deoxyribose. In some embodiments, the nucleobase is selected from

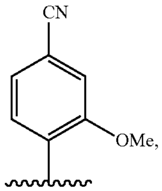
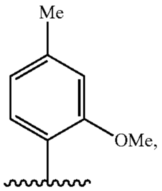
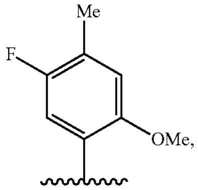
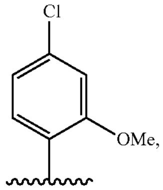
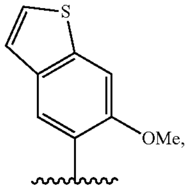
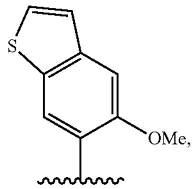
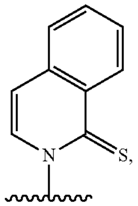
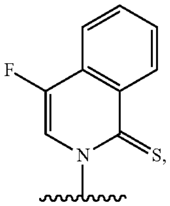
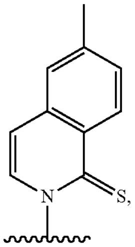
and
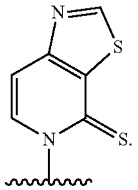

In some embodiments, the nucleobase is selected from

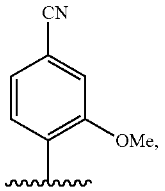
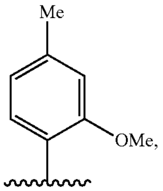
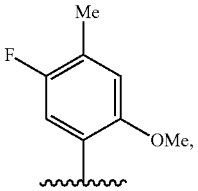
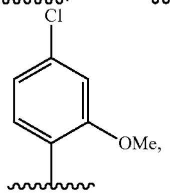
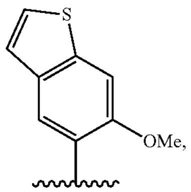
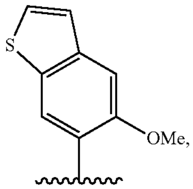
and
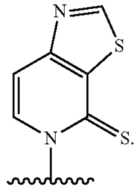

In some embodiments, the nucleobase is selected from

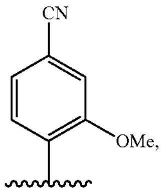
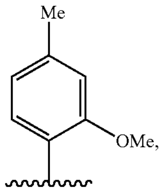
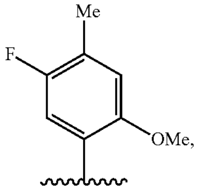
and
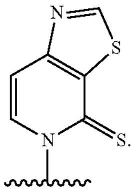

In some embodiments, the nucleobase is selected from

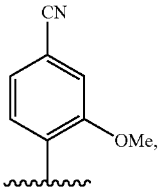
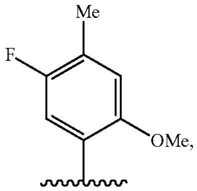
and
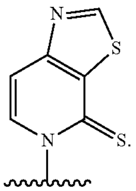

In some embodiments, the nucleobase is

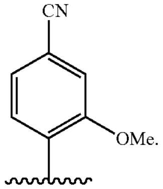

In some embodiments, the nucleoside comprises ribose. In some embodiments, the nucleoside comprises deoxyribose. In some embodiments, the nucleobase is

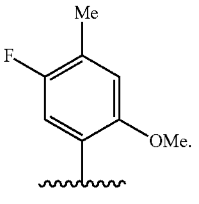

In some embodiments, the nucleoside comprises ribose. In some embodiments, the nucleoside comprises deoxyribose. In some embodiments, the nucleobase is

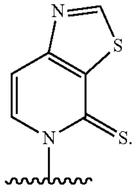

In some embodiments, the nucleoside comprises ribose. In some embodiments, the nucleoside comprises deoxyribose.

EXAMPLES

These examples are provided for illustrative purposes only and not to limit the scope of the claims provided herein.

Example 1A: Overview of Replication and Templating of Transcription

Plasmids were constructed with two dNaM-dTPT3 UBPs, such that the sequence AXC (here and throughout X refers to (d)NaM or a (d)NaM analog) was positioned to template codon 151 of sfGFP mRNA (sfGFP$^{151}$(AXC)) and with the sequence GYT (here and throughout Y refers to (d)TPT3 or a (d)TPT3 analog) positioned to template the anticodon of the *M. mazei* Pyl tRNA (tRNA$^{Pyl}$(GYT)), which is selectively charged with the ncAA N6-(2-azidoethoxy)-carbonyl-L-lysine (AzK) by the *M. barkeri* pyrrolysyl-tRNA synthetase (Mb PylRS). These plasmids were used to transform *E. coli* expressing the nucleoside triphosphate transporter PtNTT2 (strain YZ38) and harboring a plasmid encoding Mb PylRS. After transformation, colonies were selected and grown to an OD600~1.0 in liquid media supplemented with dTPT3TP (10 μM) and one of seven different dXTPs (FIG. 2) added at varying concentrations (150 μM, 10 μM, or 5 μM). Cells were then diluted into fresh expression media containing the same unnatural deoxyribonucleotides as well as NaMTP (250 μM), TPT3TP (30 μM), and AzK (10 mM). After a brief incubation, T7 RNAP and tRNAPyl(GYT) expression was induced by the addition of isopropyl-β-d-thiogalactoside (IPTG, 1 mM). After an additional 1 h of incubation, the expression of sfGFP$^{151}$(AXC) was initiated by the addition of anhydrotetracycline (aTc, 100 ng/mL).

Figure 3A:
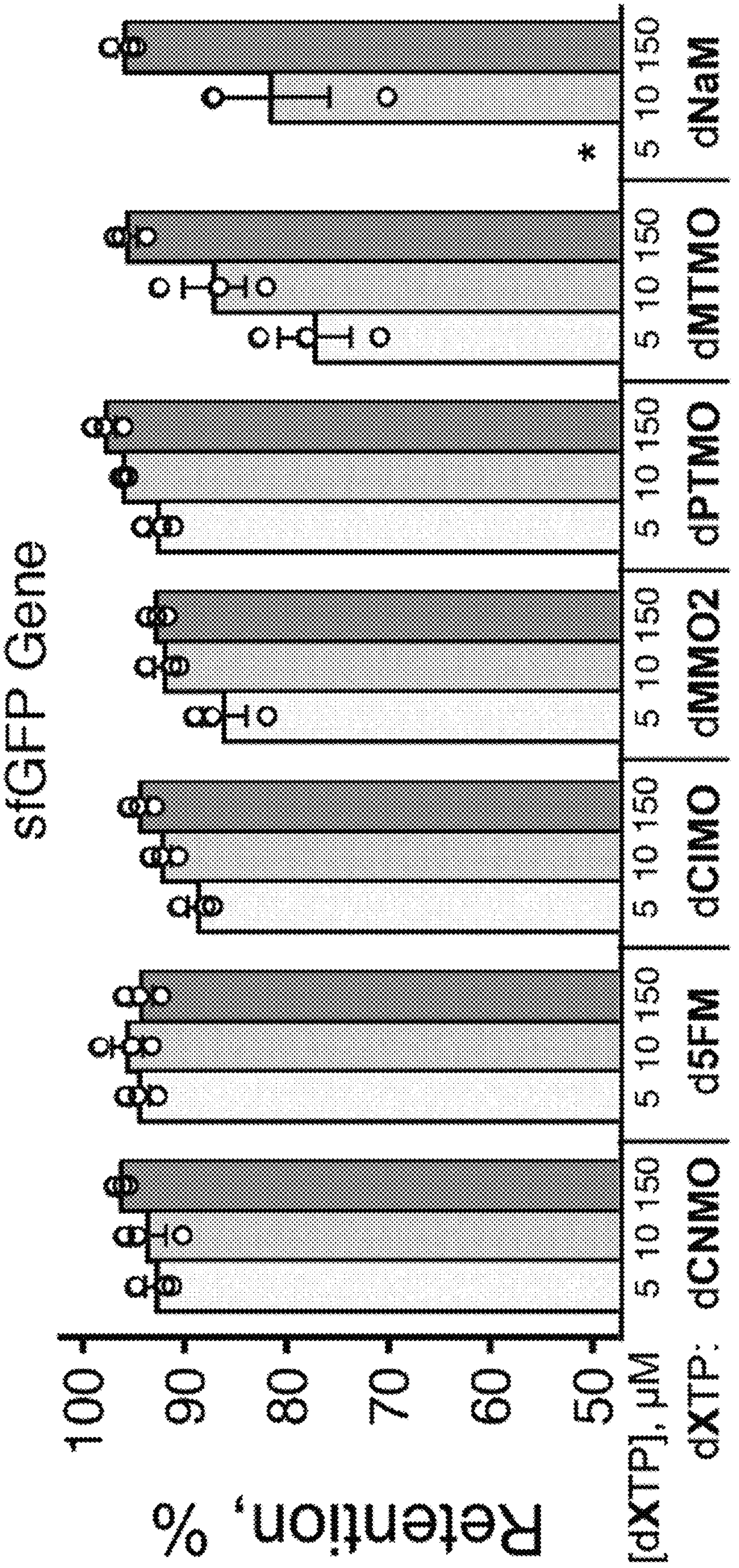
FIG. 3A illustrates a plot of UBP retention (%) in the sfGFP gene to optimize incorporation of AzK into sfGFP using various dXTPs. Each bar represents the mean, with error bars indicating standard error (n=3). Open circles represent data for each independent trial. Asterisk indicates that cells were unable to grow under the condition indicated.
Figure 3B:
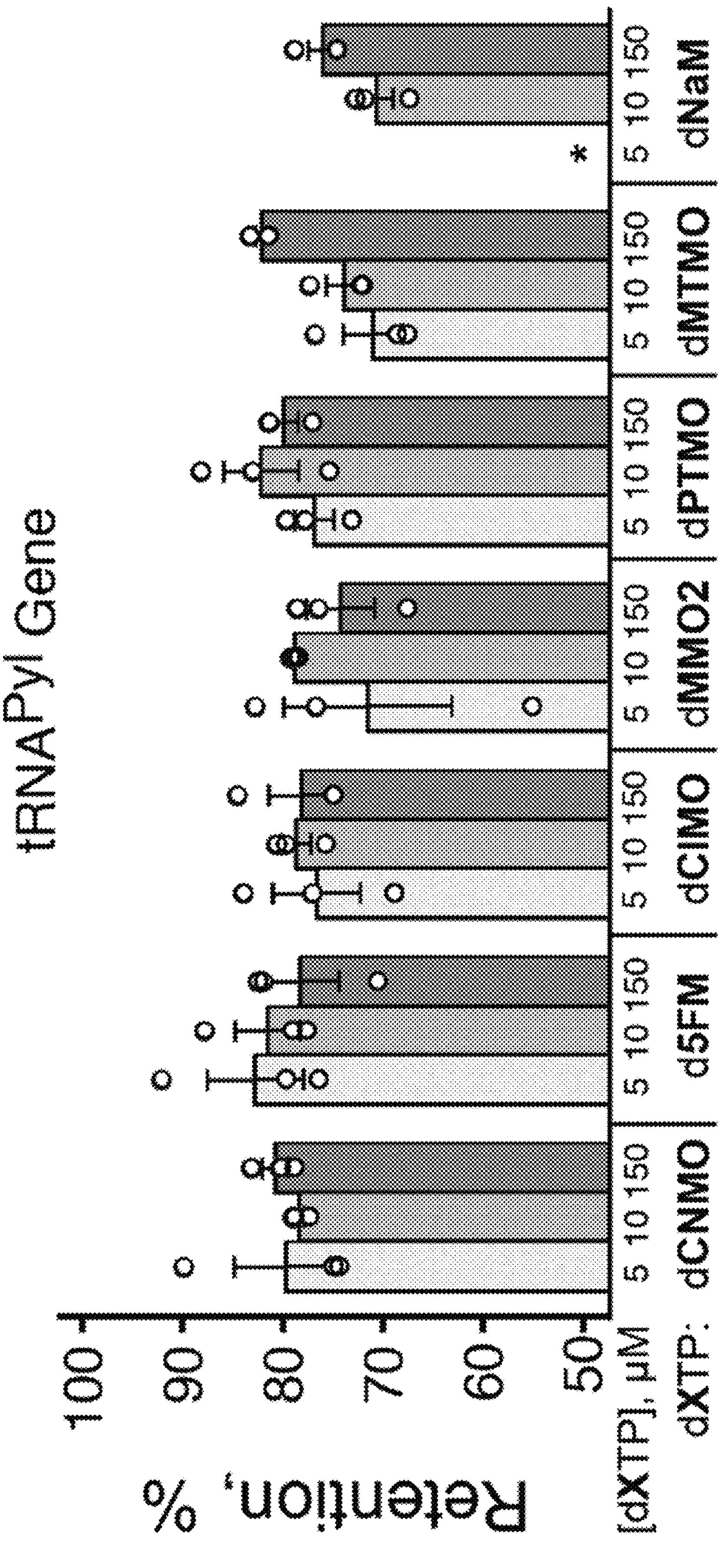
FIG. 3B illustrates a plot of UBP retention (%) in the tRNAPyl gene to optimize incorporation of AzK into sfGFP using various dXTPs. Each bar represents the mean, with error bars indicating standard error (n=3). Open circles represent data for each independent trial. Asterisk indicates that cells were unable to grow under the condition indicated.

Analysis of PCR products. After 2.5 h, plasmids were isolated and then the genes of interest were independently PCR amplified using d5SICSTP and a biotinylated analog of dNaMTP7. The resulting PCR product was analyzed via a gel mobility shift assay using streptavidin to quantify the UBP retained as a percent shift of the total amplified product (hereafter referred to as the streptavidin gel shift assay) (FIG. 3A and FIG. 3B). At the highest dXTP concentration examined (150 μM), retention in the sfGFP$^{151}$(AXC) gene was similar for each dXTP analog, varying from 99% for dNaMTP to 92% for dMTMOTP. Retention within the tRNA$^{Pyl}$(GYT) gene was slightly lower, ranging from 82% for dMTMOTP to 74% for dMMO2TP. With the addition of 10 μM of each dXTP, retention in the sfGFP$^{151}$(AXC) gene ranged from 96% for d5FMTP to 73% for dNaMTP. With the tRNA$^{Pyl}$(GYT) gene, retentions were again generally slightly lower, ranging from 82% for d5FMTP and dPTMOTP to 71% for dNaMTP. At the lowest concentration (5 μM), retention ranged from 94% for d5FMTP to 64% for dMTMOTP in the sfGFP$^{151}$(AXC) gene, and from 83% for d5FMTP to 71% for dMTMOTP in the tRNA$^{Pyl}$(GYT) gene. Generally, at the highest concentration, all dXTPs performed with nearly quantitative retention of the UBP within the sfGFP gene. However, at lower concentrations dCNMO-dTPT3, d5FM-dTPT3, and dPTMO-dTPT3 were replicated with significantly higher retention. Retention in the tRNA gene was significantly less dependent on dXTP concentration.

Figure 3C:
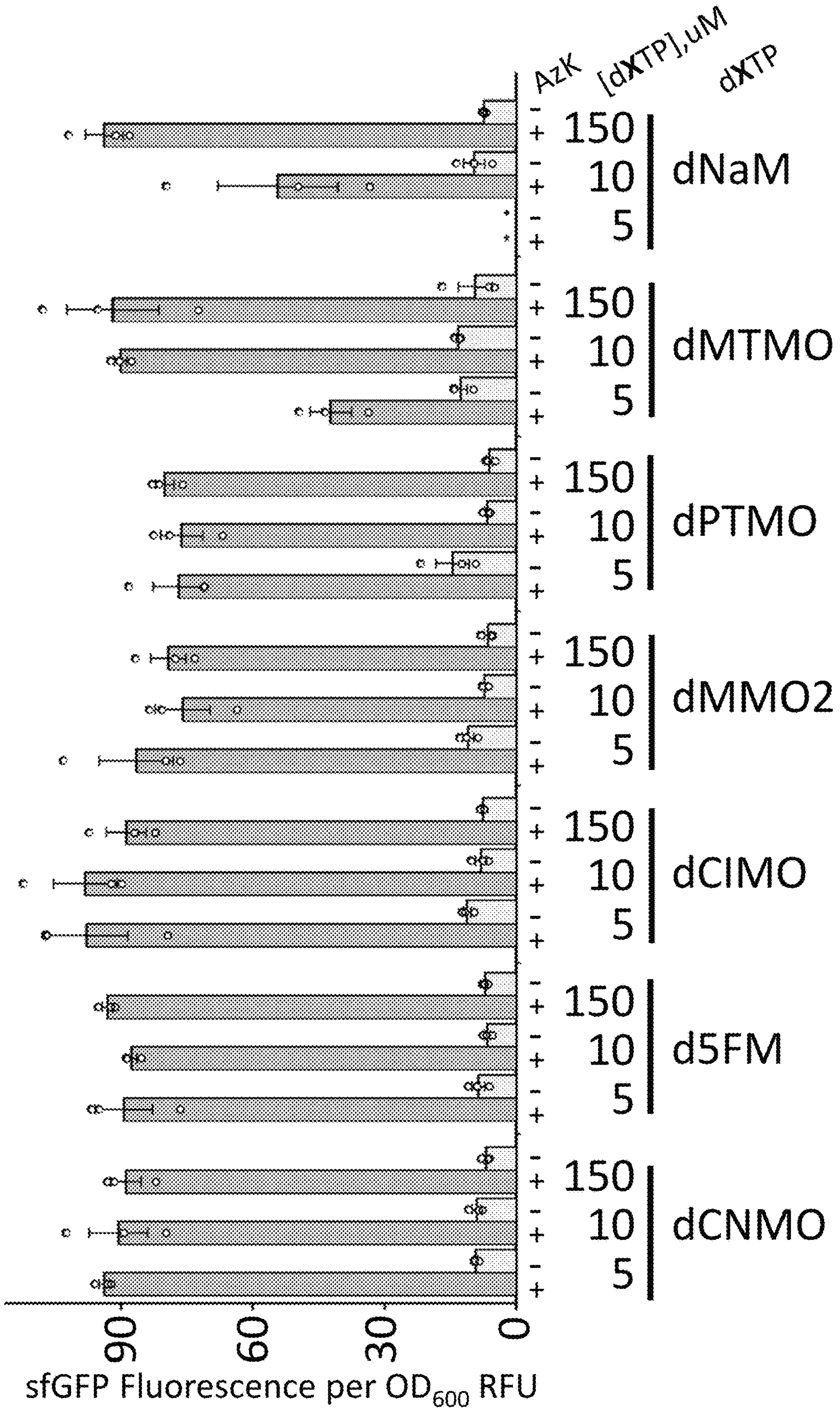
FIG. 3C illustrates a plot of relative sfGFP fluorescence observed, normalized to cell growth (Relative Fluorescence Units (RFU) per OD600) in the presence or absence of AzK to optimize incorporation of AzK into sfGFP using various dXTPs. Each bar represents the mean, with error bars indicating standard error (n=3). Open circles represent data for each independent trial. Asterisk indicates that cells were unable to grow under the condition indicated.

Analysis of reporter protein production. To characterize the amount of protein produced, bulk culture fluorescence normalized to cell growth was measured 2.5 h after the induction of protein expression (FIG. 3C). In the absence of AzK, fluorescence was generally low, with the exceptions of dPTMOTP and dMTMOTP at the lower concentrations, which appeared slightly higher. When AzK was added to the media, cells grown with each dXTP at either 150 or 10 μM generally showed significant and similar levels of fluorescence, with the exceptions of dNaMTP, which showed significantly less fluorescence at 10 μM than at 150 μM. At the lowest concentration (5 μM), the addition of AzK resulted in less fluorescence observed with dMTMOTP while it remained the same with dCNMOTP, d5FMTP, dClMOTP, dMMO2TP, or dPTMOTP. Cells growth was not observed when provided with only 5 μM dNaMTP. While similar at high concentrations, at lower concentrations the use of each dXTP analog results in a greater AzK-dependent increase in fluorescence than does the use of dNaMTP. In particular, dCNMOTP, d5FMTP, and dClMOTP showed the largest AzK-dependent increase in fluorescence.

Figure 3D:
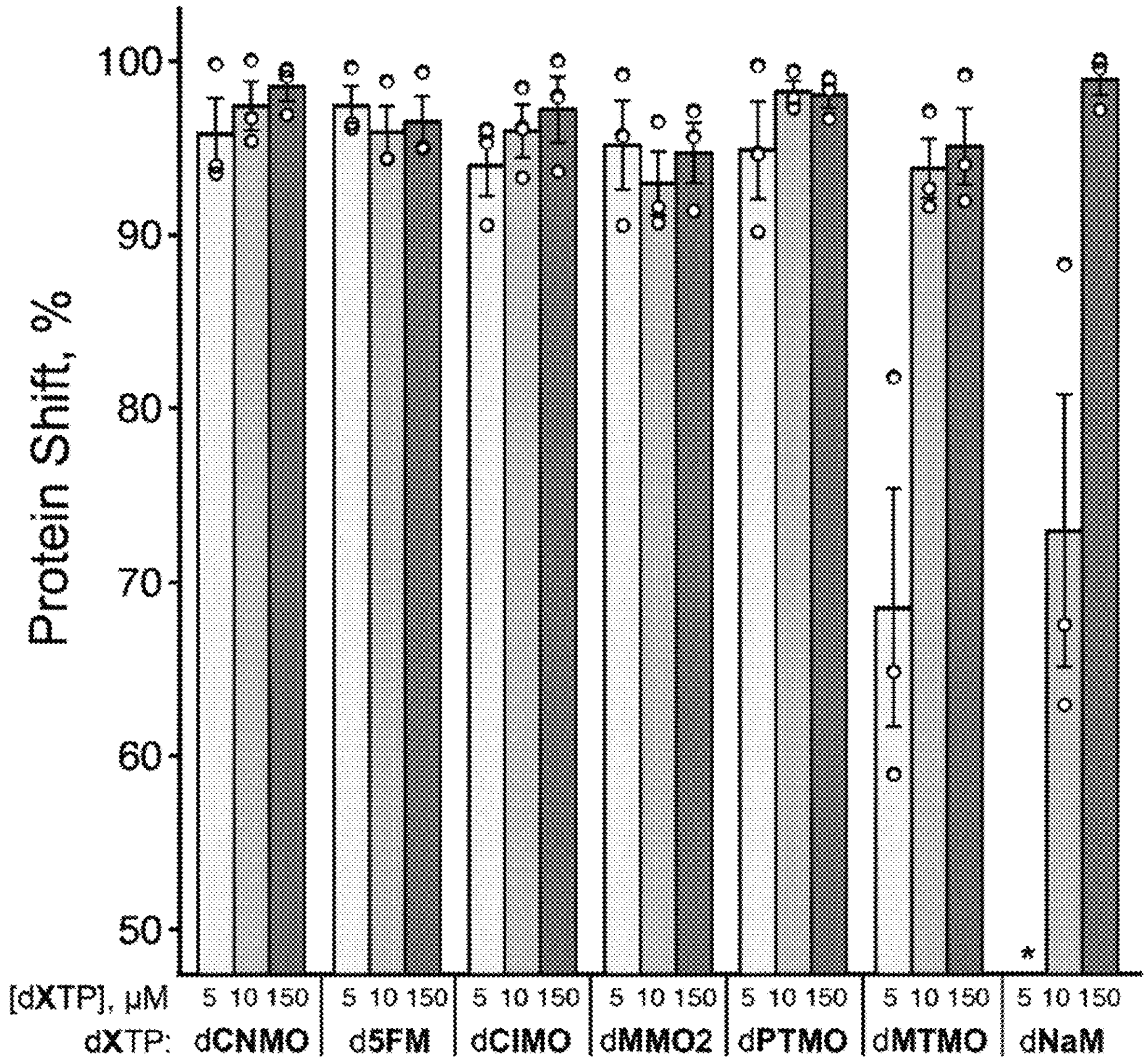
FIG. 3D illustrates a plot of relative protein shift (%) measured by western blot to optimize incorporation of AzK into sfGFP using various dXTPs. Each bar represents the mean, with error bars indicating standard error (n=3). Open circles represent data for each independent trial. Asterisk indicates that cells were unable to grow under the condition indicated.

Analysis of reporter protein fidelity. To directly assess the fidelity of unnatural protein production, cells were harvested 2.5 h after the induction of protein expression and the sfGFP produced was purified and subjected to a strain-promoted azide-alkyne cycloaddition reaction with dibenzocyclooctyne (DBCO) linked to a TAMRA dye by four PEG units. In addition to tagging the proteins containing the ncAA with a detectable fluorophore, conjugation produces a shift in electrophoretic migration, allowing quantification of protein containing AzK as a percentage of the total protein produced (i.e. fidelity of ncAA incorporation; FIG. 3D). As with dNaM, use of each dXTP at the highest concentration (150 μM) resulted in virtually complete shifts of the purified protein, reflecting high fidelity incorporation of the ncAA. When grown in the presence of 10 μM of the dXTP, the fidelity of ncAA incorporation remained high for dCNMOTP, d5FMTP, dCMOTP, dMMO2TP, dPTMOTP, and dMTMOTP, but dropped precipitously for dNaMTP. Finally, at a concentration of 5 μM dXTP, the fidelity of ncAA incorporation remained similar to that observed at 10 μM for dCNMOTP, d5FMTP, dClMOTP, dMMO2TP, and dPT- MOTP, but dropped for dMTMOTP (again due to viability, fidelity with dNaMTP could not be measured at this concentration).

Results. The unnatural bases that produced the greatest quantity of pure unnatural protein, especially at lower concentrations, are dCNMOTP and d5FMTP. However, relative to d5FMTP, the use of dCNMOTP has been previously shown to result in higher UBP retention in more difficult to replicate sequences. The dCNMO-dTPT3 UBP is competent for the storage and retrieval of increased information. The previously reported SSOs stored information with the UBPs dNaM-dTPT3, dPTMO-dTPT3, or dMTMO-dTPT3, and retrieved that information using NaMTP and TPT3TP. To explore the optimization of the SSO, retention of the UBP, transcription into sfGFP mRNA and tRNA$^{Pyl}$, and decoding at the ribosome, was examined using a collection of previously and newly reported deoxy- and ribonucleotide triphosphate analogs. The ability to store information with seven different dX-dTPT3 UBPs was examined. In each case, the strand context of the UBP was the same, with dTPT3 and dX positioned in the corresponding antisense (template) strands of the sfGFP and tRNA$^{Pyl}$ genes, respectively. With high concentrations of each dXTP provided, each dX-dTPT3 UBP is retained at a high level in the mRNA gene, with variation between 92% for dMTMOTP and 96% to 99% for dCNMOTP, dPTMOTP, and dNaMTP. Retentions in the tRNA gene were somewhat reduced, varying between 74% to 82%. As the concentrations of dXTP decreased, retentions remained roughly constant in the tRNA gene, but decreased in a dXTP specific manner in the mRNA gene, decreasing to 64% for dMTMOTP, but remaining relatively high, at ~94%, for dCNMOTP and d5FMTP. Without being bound by theory, the different concentration dependencies for retention in the tRNA and mRNA genes likely result from sequence context effects causing nucleotide insertion to be rate limiting in the mRNA and continued extension to be rate limiting in the tRNA gene. Exceptions were observed with dNaMTP, where at 10 μM retention decreased to 73%, and the cells did not survive when dNaMTP was provided at 5 μM. In addition, with dCNMOTP and d5FMTP, retentions remained high in the mRNA (~93%) at even the lowest concentration examined. Without being bound by theory, loss of retention in the tRNA gene could result in less unnatural protein production, and perhaps more problematically, reduced fidelity of ncAA incorporation due to increased competition for decoding of the unnatural codon by "near-cognate" natural tRNAs. However, the fidelity of ncAA incorporation was correlated with retention in the mRNA gene (data not shown). Thus, the data demonstrates that each dX templates transcription of tRNA with sufficient efficiency and fidelity to not limit the fidelity of unnatural protein production. Based on these results, d5FM-dTPT3, and dCNMO-dTPT3 are UBPs capable of increased information storage, with their utility relative to dNaM-dTPT3 deriving principally from their higher retention and protein production at lower unnatural triphosphate concentrations.

Example 1B: Detailed Procedures for Replication and Templating of Transcription Golden Gate assembly of plasmids. Inserts containing the UBP (and if necessary, genes encoding sfGFP or tRNA$^{Pyl}$) were generated by PCR of unnatural-containing oligonucleotides O3 and O6-12 (see Table S4 for oligo sequences) either synthesized manually (see Oligonucleotide Synthesis) or gifted from Synthorx, using dTPT3TP and dNaMTP, and primers P1-2 (when amplifying O3 or O7-12) and P3-4 (when amplifying O6) (see Table S for primer sequences) to create terminal BsaI recognition sites that, once digested, introduce overhangs compatible with the appropriate destination plasmid p[sfGFP(gg)151 tRNA$^{Pyl}$(gg)] GG destination plasmid for sfGFP translation, sequence as shown below (SEQ ID NO: 2). PCR amplifications were performed in a PTC-200 Peltier Thermal Cycler (MJ Research). Template oligonucleotides (0.025 ng per 50 μL reaction) were PCR-amplified using the following reagent concentrations: OneTaq Standard Reaction Buffer (1×, New England BioLabs), dNTPs (0.2 mM), dTPT3TP (0.1 mM), dNaMTP (0.1 mM), MgSO4 (1.2 mM), primers (1 μM each), and OneTaq polymerase (1.25 U). Natural oligonucleotides were amplified in the absence of unnatural triphosphates. These were amplified under the following thermocycling conditions (times denoted as mm:ss): [94° C. 0:30|20×(94° C. 0:30|54° C. 0:30|68° C. 4:00)]. The remaining solution was purified by spin-column (DNA Clean and Concentrator-5; Zymo Research) then quantified by absorption at 280 nm using an Infinite M200 Pro Multimode Microplate Reader (Tecan).

TABLE S1

Sequences of oligonucleotides and primers used in this study, where X denotes dNaM and Y denotes dTPT3.

| SEQ ID NO. | Name | Code | Description | Sequence (5'-3') |
|---|---|---|---|---|
| 3 | O1 | GFP151 (TAG) | sfGFP position 151 amber codon | CTCGAGTACAACTTTAACTCACACAATGTATAGATCACGGCAGACAAACAAAAGAATGGAATC |
| 4 | O2 | GFP151 (TAC) | sfGFP position 151 natural (Tyr) codon | CTCGAGTACAACTTTAACTCACACAATGTATACATCACGGCAGACAAACAAAAGAATGGAATC |
| 5 | O3 | GFP151 (AXC) | sfGFP position 151 unnatural codon | CTCGAGTACAACTTTAACTCACACAATGTAAXCATCACGGCAGACAAACAAAAGAATGGAATC |
| 6 | O4 | Mm (CTA) | *M. mazei* tRNA$^{Pyl}$ amber anticodon | GAATCTAACCCGGCTGAACGGATTTAGAGTCCGTTCGATCTACATGATCAGG |
| 7 | O5 | Mm (GTA) | *M. mazei* tRNA$^{Pyl}$ natural (Tyr) anticodon | GAATCTAACCCGGCTGAACGGATTTACAGTCCGTTCGATCTACATGATCAGG |
| 8 | O6 | Mm (GYT) | *M. mazei* tRNA$^{Pyl}$ unnatural anticodon | GAATCTAACCCGGCTGAACGGATTAXCAGTCCGTTCGATCTACATGATCAGG |

TABLE S1-continued

Sequences of oligonucleotides and primers used in this study, where X denotes dNaM and Y denotes dTPT3.

| SEQ ID NO. | Name | Code | Description | Sequence (5'-3') |
|---|---|---|---|---|
| 9 | O7 | GFP149 (AXC) | sfGFP position 149 unnatural codon | CTCGAGTACAACTTTAACTCACACAXCGTATA CATCACGGCAGACAAACAAAAGAATGGAATC |
| 10 | O8 | GFP153 (AXC) | sfGFP position 153 unnatural codon | CTCGAGTACAACTTTAACTCACACAATGTATA CATCAXCGCAGACAAACAAAAGAATGGAATC |
| 11 | O9 | GFP149 + 151 (AXC x 2) | sfGFP position 149 + 151 double unnatural codons | CTCGAGTACAACTTTAACTCACACAXCGTAAX CATCACGGCAGACAAACAAAAGAATGGAATC |
| 12 | O10 | GFP151 + 153 (AXC x 2) | sfGFP position 151 + 153 double unnatural codons | CTCGAGTACAACTTTAACTCACACAATGTAAX CATCAXCGCAGACAAACAAAAGAATGGAATC |
| 13 | O11 | GFP149 + 153 (AXC x 2) | sfGFP position 149 + 153 double unnatural codons | CTCGAGTACAACTTTAACTCACACAXCGTATA CATCAXCGCAGACAAACAAAAGAATGGAATC |
| 14 | O12 | GFP149 + 151 + 153 (AXC x 3) | sfGFP position 149 + 151 + 153 triple unnatural codons | CTCGAGTACAACTTTAACTCACACAXCGTAAX CATCAXCGCAGACAAACAAAAGAATGGAATC |
| 15 | P1 | YZ73 | Insert PCR primer for sfGFP F | ATGGGTCTCACACAAACTCGAGTACAACTTTA ACTCACAC |
| 16 | P2 | YZ74 | Insert PCR primer for sfGFP R | ATGGGTCTCGATTCCATTCTTTTGTTTGTCTG C |
| 17 | P3 | YZ435 | Insert PCR + Streptavidin Gel Shift primer for *M. mazei* $tRNA^{Pyl}$ F | ATGGGTCTCGAAACCTGATCATGTAGATCGAA CGG |
| 18 | P4 | YZ436 | Insert PCR + Streptavidin Gel Shift primer for *M. mazei* $tRNA^{Pyl}$ R | ATGGGTCTCATCTAACCCGGCTGAACGG |
| 19 | P5 | YZ351 | Streptavidin Gel Shift primer for sfGFP F | CTCGAGTACAACTTTAACTCACAC |
| 20 | P6 | YZ352 | Streptavidin Gel Shift primer for sfGFP R | GATTCCATTCTTTTGTTTGTCTGC |

Oligonucleotide synthesis. Modified oligonucleotides were synthesized on a 0.2 μmol scale using an Expedite 8909 gene synthesizer, succinyl linked LCAA-CPG (long chain alkyl amine-controlled pore glass) columns with a pore size of 1,000 Å, and standard protocols for incorporation of dABz, dCBz, dGiBu and dT DNA phosphoramidites. The following hand-coupling conditions were used for incorporation of monomer dNaM (15 min; Tetrazole in $CH_3CN$; >95%). Modified phosphoramidites were used at 50-fold molar excess and 0.05 M concentration in anhydrous $CH_3CN$. Cleavage from solid support and removal of protecting groups was accomplished using ~30% aq. ammonia (55° C., 16 h). Purification of the DMT-on crude oligonucleotides was performed using a Vanquish UHPLC system equipped with a Hypersil Gold C18 column (5 m, 4.6×150 mm) using 0-50% B over 25 min (Buffer A=0.05 M TEAA, pH 7; Buffer B=25% H2O in $CH_3CN$; flow rate=1.0 mL/min). Appropriate fractions were pooled, evaporated to dryness, followed by detritylation (80% aq. AcOH) and precipitation (NaOAc/NaClO4/acetone, −80° C. for 3 h). Purity was verified by ion-pair reverse phase HPLC running in analytical mode (>90%).

The plasmids were assembled in an 80 μL reaction volume, under the following conditions: destination plasmid (1 μg), PCR insert(s) (4:1 insert: plasmid molar ratio), T4 DNA ligase (532 U), BsaI-HF (53.4 U), and ATP (1 mM) were combined in CutSmart buffer (1×, New England BioLabs) and thermocycled under the following conditions (times denoted as mm:ss): [37° C. 20:00|40×(37° C. 5:00|16° C. 10:00|22° C. 5:00)|37° C. 20:00|50° C. 15:00|70° C. 30:00]. After the Golden Gate reaction, T5 exonuclease (13.3 U) and BsaI-HF (26.6 U) were added, and the reaction was incubated at 37° C. for 1 h to digest remaining DNA fragments and unincorporated destination plasmid. The assembled plasmids were purified on Zymo-Spin I columns and quantified using the Qubit dsDNA HS Assay Kit (Thermo Fisher Scientific).

Transformation of YZ3/ML2 with pGEX-MbPyRS TetR. An overnight culture of the SSO strain YZ3 or ML2 was grown in 2×YT supplemented with 50 mM potassium phosphate and 5 g/mL chloramphenicol (herein referred to in this section as "media"), then diluted back to an OD600 of 0.03 in the same media and grown to an OD600 of 0.4 to 0.6. The culture was then chilled with shaking over ice-water for 5 min then pelleted by centrifugation at 3,200×g for 10 min. Cells were then resuspended and washed with ice-cold $ddH_2O$ twice then resuspended in ice-cold ddH2 to an OD600 of 50-60. The electrocompetent cells (50 μL) and 2 ng of pGEX-MbPyRS TetR plasmid (SEQ ID NO: 1) were transferred to a pre-chilled electroporation cuvette (0.2-cm-gap) and then electroporated (Gene Pulser II; Bio-Rad) according to manufacturer's recommendations (voltage 25 kV, capacitor 2.5 μF, resistor 200Ω), then immediately diluted with 950 μL of media. An aliquot of this electroporation reaction (40 μL) was then diluted five-fold with media to a final volume of 200 μL and then allowed to recover at 37° C. for 1 h. Two-fold dilutions of the recovery were plated on solid 2×YT media supplemented with 50 mM potassium phosphate, 5 μg/mL chloramphenicol, 100 μg/mL carbenicillin, and 2% w/v agar and then allowed to grow at 37° C. overnight. Single colonies were picked to inoculate cultures of liquid media supplemented with 100 μg/mL carbenicillin and then stored in glycerol (25% v/v) at −80° C.

In vivo Translation Screen of dXTPs. An overnight culture of the SSO strain YZ3 carrying the pGEX-MbPylRS TetR plasmid was grown in 2×YT supplemented with 50 mM potassium phosphate, 5 g/mL chloramphenicol and 100 μg/mL carbenicillin (herein referred to in this section as "media"), then diluted back to an $OD_{600}$ of 0.03 in the same media and grown to an $OD_{600}$ of 0.4 to 0.6. The culture was then chilled with shaking over ice-water for 15 minutes then pelleted by centrifugation at 3,200×g for 10 min. Cells were then resuspended and washed with ice-cold ddH2O twice then resuspended in ice-cold $ddH_2O$ to an OD600 of 55-65. The electrocompetent cells (50 μL) and 1 ng of Golden Gate assembled plasmid with the UBP within the sfGFP and tRNAPyl genes (see Golden Gate Assembly of Plasmids) were transferred to a pre-chilled electroporation cuvette (0.2-cm-gap), then electroporated (Gene Pulser II; Bio-Rad) according to manufacturer's recommendations (voltage 25 kV, capacitor 2.5 μF, resistor 200Ω), and then immediately diluted with 950 μL of media. An aliquot (40 μL) of the transformation was then diluted five-fold in media supplemented with dNaMTP (150 μM) and dTPT3TP (10 μM) for a final volume of 200 μL then allowed to recover for 1 h shaking at 37° C. Two-fold dilutions of the recovery were plated onto solid media supplemented with zeocin (50 μg/mL), dNaMTP (150 μM), dTPT3TP (10 μM), and agar (2% w/v), then grown at 37° C. overnight. Single colonies were picked and grown in media (300 μL) supplemented with 50 μg/mL zeocin (herein afterward referred to in this section as "growth media") and provided dNaMTP (150 μM), and dTPT3TP (10 μM). The culture was monitored for cell growth (Envision 2103 Multilabel Plate Reader with a 590/20 nm filter) and then collected at an OD600~1.0. An aliquot (50 μL) was subjected to plasmid isolation using the ZR Plasmid Prep Kit (Zymo Research). Isolated plasmids were then subjected to the streptavidin gel shift assay described below (using primers P3-4 and P5-6, Table S1) to determine UBP retention. Colonies with excellent UBP retention were then stored in glycerol (25% v/v) at −80° C.

Ten-fold dilutions of the glycerol stock were re-plated onto solid growth media supplemented with dNaMTP (150 μM), dTPT3TP (10 μM), and 2% w/v agar, then grown at 37° C. overnight. Single colonies were picked and grown in growth media (300 μL) supplemented with corresponding dXTP (various concentrations), and dTPT3TP (10 μM), then monitored for cell growth and collected at an OD600~1.0. Once all samples were collected, samples were left on ice overnight. The samples were then re-diluted to OD600~0.1, to a final volume of 300 μL and provided with the corresponding dXTP (various concentrations), and dTPT3TP (10 μM). The remaining culture not used was pelleted and stored at −80° C. for subsequent plasmid isolation using the ZR Plasmid Prep Kit (Zymo Research) to determine UBP retention. When cultures reached an OD600~0.4-0.6, they were provided with NaMTP (250 μM) and TPT3TP (30 μM), and AzK (10 mM) (or $ddH_2O$ for cultures grown in the absence of AzK). Samples were shielded from light after addition of AzK to prevent photodegradation. These samples were then grown at 37° C. for 20 min before adding 1 mM IPTG and grown at 37° C. for an additional 1 h to induce T7 RNAP and transcription of tRNAPyl and PylRS. From this point on, cells were monitored for growth and fluorescence. Expression of sfGFP was then induced with anhydrotetracycline (100 ng/mL). After an additional 2.5 h of growth at 37° C., cells were collected (50 μL for plasmid isolation to determine UBP retention, 230 μL for affinity purification of sfGFP), cooled, and then pelleted and stored at −80° C. before assessment of UBP retention and protein purification.

In vivo Translation Screen of XTPs/YTPs. An overnight culture of the SSO strain ML2 carrying the pGEX-MbPylRS TetR plasmid was grown in 2×YT supplemented with 50 mM potassium phosphate, 5 g/mL chloramphenicol and 100 μg/mL carbenicillin (herein referred to in this section as "media"), then diluted back to an $OD_{600}$ of 0.03 in the same media and grown to an OD600 of 0.4 to 0.6. The culture was then chilled with shaking over ice-water for 15 minutes then pelleted by centrifugation at 3,200×g for 10 min. Cells were then resuspended and washed with ice-cold $ddH_2O$ twice then resuspended in ice-cold $ddH_2O$ to OD600 of 55-65. The electrocompetent cells (50 μL) and 1 ng of Golden Gate assembled plasmid with the UBP within the sfGFP and tRNAPyl genes (see Golden Gate Assembly of Plasmids) were transferred to a pre-chilled electroporation cuvette (0.2-cm-gap), then electroporated (Gene Pulser II; Bio-Rad) according to manufacturer's recommendations (voltage 25 kV, capacitor 2.5 μF, resistor 200Ω), and then immediately diluted with 950 μL of media. An aliquot (40 μL) of the transformation was then diluted five-fold in media supplemented with dCNMOTP (25 μM) and dTPT3TP (10 μM) for a final volume of 200 μL then allowed to recover for 1 h shaking at 37° C. Two-fold dilutions of the recovery were plated onto solid media supplemented with zeocin (50 μg/mL), dCNMOTP (10 μM), dTPT3TP (10 μM), and agar (2% w/v), then grown at 37° C. for 18 h. Single colonies were picked and grown in media (300 μL) supplemented with 50 μg/mL zeocin and provided dCNMOTP (25 μM) and dTPT3TP (10 μM) (herein afterward referred to in this section as "growth media"). The culture was monitored for cell growth (Envision 2103 Multilabel Plate Reader with a 590/20 nm filter) and then collected at an OD600~1.0. An aliquot (50 μL) was subjected to plasmid isolation using the ZR Plasmid Prep Kit (Zymo Research). Isolated plasmids were then subjected to the streptavidin gel shift assay described below (using primers P3-4 and P5-6, Table S1) to determine UBP retention.

A colony with excellent UBP retention was then diluted to an $OD_{600}$~0.01 in growth media and grown to $OD_{600}$~0.4-0.6. This culture was then divided into multiple 300 μL cultures and for the screen of XTP analogs, each was provided with the corresponding XTP (at either 25 μM or 250 μM) or $ddH_2O$ for "−XTP" samples, TPT3TP (30 μM), and AzK (10 mM). For the screen of YTP analogs, each 300 μL culture was provided with the corresponding YTP (at either 25 μM or 250 μM) or $ddH_2O$ for "−YTP" samples, NaMTP (250 μM), and AzK (10 mM). Samples were shielded from light after addition of AzK to prevent photodegradation. These samples were then grown at 37° C. for 20 min before adding 1 mM IPTG and grown at 37° C. for an additional 1 h to induce T7 RNAP and transcription of tRNAPyl and PylRS. From this point on, cells were monitored for growth and fluorescence. Expression of sfGFP was then induced with anhydrotetracycline (100 ng/mL). After an additional 3 h of growth at 37° C., cells were collected (230 μL for affinity purification of sfGFP), cooled, and then pelleted and stored at −80° C. before protein purification.

TABLE S2

OD600 values observed for each unnatural ribonucleotide after 3 h of protein induction under the conditions described for ribonucleotide screening, with toxicity apparent through comparing the high concentration of provided triphosphate to the low concentration.

| | | Triphosphate | $OD_{600}$ |
|---|---|---|---|
| | | no XTP added | 1.10 ± 0.03 |
| XTP | 250 μM | NaM | 1.06 ± 0.06 |
| | | CNMO | 1.07 ± 0.05 |
| | | MMO2 | 0.86 ± 0.05 |
| | | SFM | 1.05 ± 0.04 |
| | | CIMO | 1.01 ± 0.05 |
| | | BrMO | 1.09 ± 0.05 |
| | | PTMO | 1.09 ± 0.04 |
| | | MTMO | 1.13 ± 0.07 |

TABLE S2-continued

OD600 values observed for each unnatural ribonucleotide after 3 h of protein induction under the conditions described for ribonucleotide screening, with toxicity apparent through comparing the high concentration of provided triphosphate to the low concentration.

| | | Triphosphate | $OD_{600}$ |
|---|---|---|---|
| | | 2OMe | 1.04 ± 0.09 |
| | | 5F2OMe | 1.16 ± 0.07 |
| | 25 μM | NaM | 1.16 ± 0.07 |
| | | CNMO | 1.17 ± 0.07 |
| | | MMO2 | 1.16 ± 0.09 |
| | | 5FM | 1.16 ± 0.07 |

TABLE S2-continued

OD600 values observed for each unnatural ribonucleotide after 3 h of protein induction under the conditions described for ribonucleotide screening, with toxicity apparent through comparing the high concentration of provided triphosphate to the low concentration.

| | | Triphosphate | $OD_{600}$ |
|---|---|---|---|
| | | CIMO | 1.16 ± 0.05 |
| | | BrMO | 1.12 ± 0.04 |
| | | PTMO | 1.21 ± 0.07 |
| | | MTMO | 1.21 ± 0.07 |
| | | 5F2OMe | 1.14 ± 0.05 |
| | | no YTP added | 1.26 ± 0.16 |
| YTP | 250 μM | TPT3 | 0.73 ± 0.05 |
| | | SICS | 0.90 ± 0.04 |
| | | FSICS | 0.86 ± 0.04 |
| | | 5SICS | 1.06 ± 0.07 |
| | | TAT1 | 1.28 ± 0.11 |
| | 25 μM | TPTS | 1.11 ± 0.05 |
| | | SICS | 1.25 ± 0.10 |
| | | FSICS | 1.15 ± 0.08 |
| | | 5SICS | 1.16 ± 0.09 |
| | | TAT1 | 1.68 ± 0.12 |

Steptavidin Gel Shift Assay. PCR amplifications were performed in a CFX Connect Real-Time PCR Detection System (Bio-Rad). Plasmid minipreps, or Golden Gate assembled plasmids (0.5 μL to 2 μL, 0.5 ng/μL to 5 ng/μL), or dNaM-containing oligonucleotides (0.025 ng) were PCR amplified in total reaction volumes of 15 μL under the following conditions: OneTaq Standard Reaction Buffer (1×, New England BioLabs), dNTPs (400 μM), SYBR Green I (1×, Life Technologies), MgSO4 (2.2 mM), primers P3-4 or P5-6 (1 μM each, see Table S4 for primer sequences), d5SICSTP (65 μM), $dMMO2^{BIO}TP$ (65 μM; structure shown below with sugar and phosphate omitted for clarity), OneTaq DNA polymerase (0.27 U, New England BioLabs), DeepVent DNA polymerase (0.105 U, New England BioLabs).

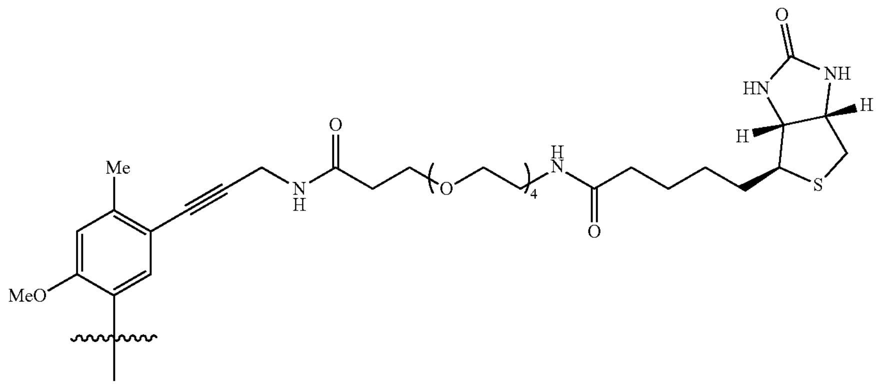

$dMMO2^{BIO}TP$

Plasmids isolated from translation experiments were amplified using the following thermocycling conditions (times denoted as mm:ss): [96° C. 5:00|20×(95° C. 00:15|54° C. 00:15|68° C. 4:00]. Afterward, streptavidin (2.5 μL, 2 μg/μL; Promega) was mixed with each reaction (1 μL) and incubated for 5 min at room temperature. Samples with (3.5 μL) and without (1 μL) streptavidin were each mixed with loading buffer and separated on a 6% (wt/vol) polyacrylamide (29:1 acrylamide:bis-acrylamide) Tris/borate/EDTA (TBE) gel, at 120 V for ~30 min. Gels were then stained with 1×SYBR Gold dye (Thermo Fisher) and imaged using a Molecular Imager Gel Doc XR+ (Bio-Rad) equipped with a 520DF30 filter (Bio-Rad). UBP retention could then be determined by comparing the ratio of the shifted to unshifted bands in each lane relative to that obtained for the input plasmid (plasmid used in the starting transformation). This assay has been previously demonstrated as quantitative.

The streptavidin gel shift assay is sensitive to various factors such as mini-prep purity and may be repeated multiple times, sometimes with higher plasmid concentration, in order to obtain reasonable amplification of the UBP-containing plasmid for detection of the UBP retention. In cases where plasmid concentration is too low, UBP retention appears lower according to the streptavidin gel shift assay and were repeated using more mini-prep plasmid.

TABLE S3

Streptavidin gel shift data (percent UBP retention) for plasmids extracted from cells carrying constructs related to the retrieval of higher density unnatural genetic information.

| AXC codon | dNaM-dTPT3/NaMTP, TPT3TP | | dCNMO-dTPT3/NaMTP, TAT1TP | |
|---|---|---|---|---|
| position | mRNA | tRNA | mRNA | tRNA |
| 149 | 100.2 ± 0.2 | 92.6 ± 0.4 | 100.7 ± 0.2 | 98.1 ± 1.1 |
| 153 | 95.2 ± 1.7 | 92.2 ± 0.6 | 101.4 ± 1.9 | 96.6 ± 1.1 |
| 149, 151 | n.d.[a] | 92.0 ± 0.9 | n.d.[a] | 99.7 ± 0.6 |
| 151, 153 | n.d.[a] | 93.9 ± 1.6 | n.d.[a] | 97.3 ± 0.5 |
| 149, 153 | n.d.[a] | 90.5 ± 0.7 | n.d.[a] | 96.7 ± 0.7 |
| 149, 151, 153 | n.d.[a] | 87.7 ± 0.9 | n.d.[a] | 99.4 ± 0.6 |

[a]n.d. Value could not be determined

Affinity Purification of sfGFP. Cell pellets collected from translation experiments were resuspended in BugBuster (100 μL 1×, EMD Millipore) and shaken at room temperature for 15 min. The cell lysate was then diluted with Buffer W (380 μL; 50 mM HEPES pH 8, 150 mM NaCl, 1 mM EDTA) and magnetic Strep-Tactin beads (20 μL, 5% (v/v) suspension of MagStrep 'type3' XT beads, IBA Lifesciences) equilibrated in Buffer W, were added. The mixture was gently inverted at 4° C. for 30 min. Beads were then pulled down with a magnetic rack and washed with Buffer W (2×500 μL), and then 25 μL BXT Buffer (100 mM Tris-HCl pH 8, 50 mM D-biotin) was added and the suspension was allowed to incubate at room temperature for 10 min with occasional mixing. Beads were pulled down again for collection of eluents. Purified proteins were quantified using the Qubit Protein Assay Kit (Thermo Fisher Scientific) .

Copper-Free Click Conjugation of TAMRA. Purified protein (300 ng) was mixed with TAMRA-DBCO (0.1 mM, Click Chemistry Tools; product #A131) and water was added to a final reaction volume of 6 μL and incubated overnight at room temperature and shielded from light. Following conjugation, measures were taken to minimize light exposure of samples, gels, and blots to minimize photobleaching of TAMRA.

Western Blotting of sfGFP. Purified protein (300 ng), conjugated to TAMRA-DBCO was mixed (2:1 v:v) with loading buffer/dye (250 mM Tris-HCl, 30% (v/v) glycerol, 2% (w/v) SDS, pH 6.8) then heated at 95° C. for 5 mins. Protein ladder (Color Prestained Protein Standard, Broad Range, New England BioLabs) and a portion of each click reaction (60 ng protein) was loaded to a SDS-PAGE gel (stacking gel: 5% (w/v) acrylamide:bis-acrylamide 29:1 (Fisher), 0.125 M Tris-HCl and 0.1% SDS, pH 6.8 (ProtoGel Stacking Buffer, National Diagnostics); resolving gel: 15% (w/v) acrylamide:bis-acrylamide 29:1 (Fisher), 0.375 M Tris-HCl and 0.1% SDS, pH 8.8 (ProtoGel Resolving Buffer, National Diagnostics)) and then run at 50 V for 15 min, then 120 V for another 4.5 h in SDS-PAGE buffer (25 mM Tris-Base, 200 mM glycine, 0.1% (w/v) SDS). The samples were then transferred to low-fluorescence PVDF (0.2 μM, Bio-Rad) by semi-dry transfer in the appropriate buffer (20% (v/v) MeOH, 50 mM Tris-Base, 400 mM glycine, 0.0373% (w/v) SDS), run at 15V for ~30-45 min. The membrane was then rocked overnight at 4° C. in blocking solution (5% (w/v) nonfat milk (Carnation) in PBS-T (PBS pH 7.4, 0.01% (v/v) Tween-20), solubilized at 37° C. for 1 h). The membrane was then rinsed 2× with PBS-T then shaken in rabbit anti-GFP antibody (1:3000 in PBS-T, product #G1544, lot 046M4871V, SigmaAldrich) for 1 h at room temperature. The membrane was then washed for 5 min with PBS-T and then shaken in goat anti-rabbit Alexa Fluor 647-conjugated antibody (1:20,000 in PBS-T, product #A32733, lot #SD250298, Thermo Fisher Scientific) at room temperature for 45 min. The membrane was then washed (3×5 min) with PBS-T and imaged with a flatbed laser scanner (Typhoon 9410, GE Amersham Biosciences) set with the following preferences: 50 μM resolution, 532 nm laser excitation and 580/30 nm emission filter with 400 V PMT for TAMRA, and 633 nm laser excitation and 670/30 nm emission filter with 500 V PMT for AlexaFluor 647.

In order to assess incorporation of AzK, purified protein was conjugated to DBCO-TAMRA to produce a gel shift by SDS-PAGE. The different band sizes correspond to native sfGFP and sfGFP conjugated TAMRA. These bands were then quantified using Image Studio Lite 5.2.5 software (LI-COR Biosciences) by densiometric quantification of bands to produce a ratio of the shifted (conjugated) band to the total signal produced by both shifted (conjugated) and unshifted (native) sfGFP bands. This can be interpreted as percent protein shift or percent of sfGFP in a sample that has been incorporated the ncAA AzK.

Quantitative High-Resolution Mass Spectrometry of Intact Proteins. Sample preparation and acquisition of data. Purified protein (4 μg) were diluted with 450 μL mass spec grade water and applied to a centrifugal filter device (Amicon Ultra-0.5—Millipore) for desalting. The device was centrifuged at 14,000×g for 10 min, and the resulting concentrated solution was diluted with mass spec grade water back to a total volume of 500 μL. This process was repeated for a total of four centrifugations, with the final spin lasting for 18 minutes. Following the final spin, samples were recovered by inversion of the filter device into a fresh microcentrifuge tube and centrifugation at 1,000×g for 2 min. The desalted protein was then injected (6 μL, ~250 ng) into a Waters I-Class LC connected to a Waters G2-XS TOF. Flow conditions were 0.4 mL/min of 50:50 water:acetonitrile plus 0.1% formic acid. Ionization was by ESI+, with data collected between m/z 500 and m/z 2000. A spectral combine was performed over the main portion of the peak, and combined spectrum was deconvoluted using Waters MaxEnt1.

Validating quantification. Authentic protein samples in which the 151 position of sfGFP contained either a tyrosine residue or an AzK residue were prepared using identical plasmid preparation and protein expression conditions as described above, but using sfGFP151(TAC) and sfGFP151 (TAG), respectively, and without supplementing with unnatural triphosphates. Using these authentic proteins, mixtures of Y151 and AzK151 sfGFP were prepared in defined ratios spanning the range from 100:0 to 0:100 of AzK to Y. These mixtures were than prepared and quantified by HRMS as described above. The observed data was very linear throughout the whole range of samples, and accurately matched the expected ratios, validating this method as highly quantitative.

Examining the Toxicity of Ribonucleoside Triphosphates. An overnight culture of ML2 was grown in 2×YT media supplemented with 50 mM potassium phosphate and chloramphenicol (5 μg/mL), referred to throughout this section as "media". This culture was diluted back to an OD600 of 0.01 split into multiple 300 μL cultures, each supplemented with varying concentrations of TPT3TP, TAT1TP, NaMTP, or 5FMTP, along with a no triphosphate control. The cultures were then incubated at 37° C. with shaking at 230 rpm. Cells were then monitored for cell growth (Envision 2103 Multilabel Plate Reader with a 590/20 nm filter) every hour for a total of eight hours. OD600 was then plotted as a function of time for each nucleotide at each concentration to visualize differences in growth rates.

Example 2: Synthesis and First SAR Analysis of Ribonucleotide Candidates

Retrieval of the information made available by the UBP has only previously been explored using NaMTP and TPT3TP. To begin to elucidate the SARs governing efficient transcription and translation in the SSO, nine novel NaMTP analogs (FIG. 4A) and four novel TPT3TP analogs (FIG. 4B) were designed and synthesized. These analogs were designed to explore the role of nucleobase shape, aromatic surface area, and heteroatom derivatization. Generally, the synthesis of the XTP analogs proceeded via lithiation of the corresponding aryl halide, followed by coupling of the lithiated species to either the benzyl- or TBS-protected ribolactone. Reduction of the resulting hemi-acetal intermediate in the presence of boron trifluoride diethyl etherate and triethylsilane afforded the desired protected nucleoside in each case. Following deprotection, the resulting X nucleoside analogs were converted to triphosphates using standard Ludwig phosphorylation conditions. NaMTP and MMO2TP were synthesized as reported previously. The synthesis of the YTP analogs generally proceeded via intramolecular Curtius rearrangement of the corresponding acyl azide, followed by Lewis-acid mediated coupling to 1-Oacetyl-2, 3,5-tri-O-benzoyl-b-D-ribofuranose, resulting in pure β-anomer of the desired protected nucleoside. Following conversion of the pyridine to the corresponding thio-pyridone and subsequent benzoyl deprotection, the corresponding free nucleosides were converted to triphosphates using standard Ludwig phosphorylation conditions. 5SICSTP was synthesized as reported previously.

Figure 5A:
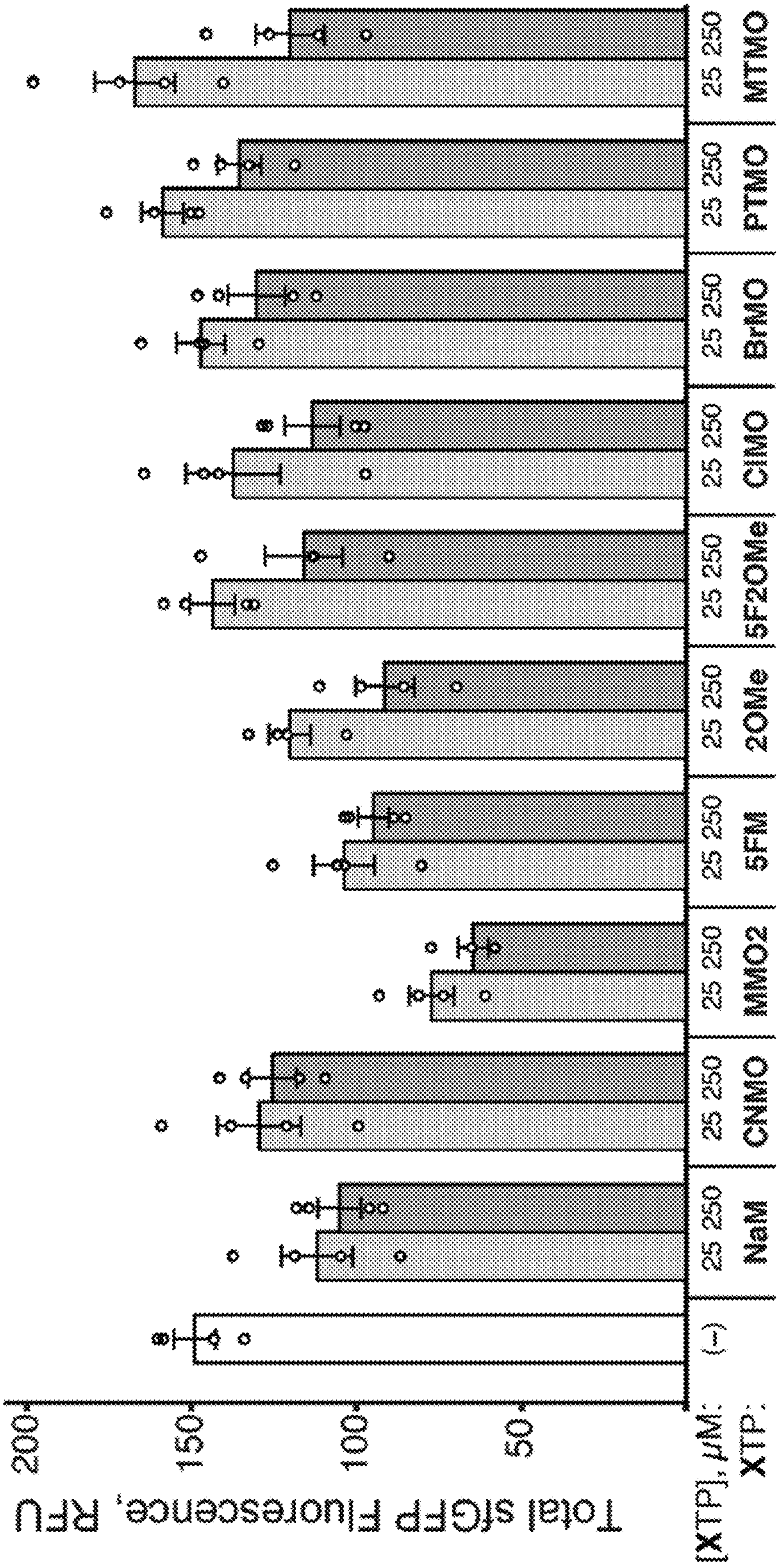
FIG. 5A illustrates a plot of an SAR analysis of translation using various unnatural ribonucleotides to incorporate AzK into sfGFP, with total sfGFP fluorescence (RFU) observed in the presence of AzK for XTP analogs on the y-axis. Each bar represents the mean, with error bars indicating standard error (n=4). Open circles represent data for each independent trial.
Figure 5B:
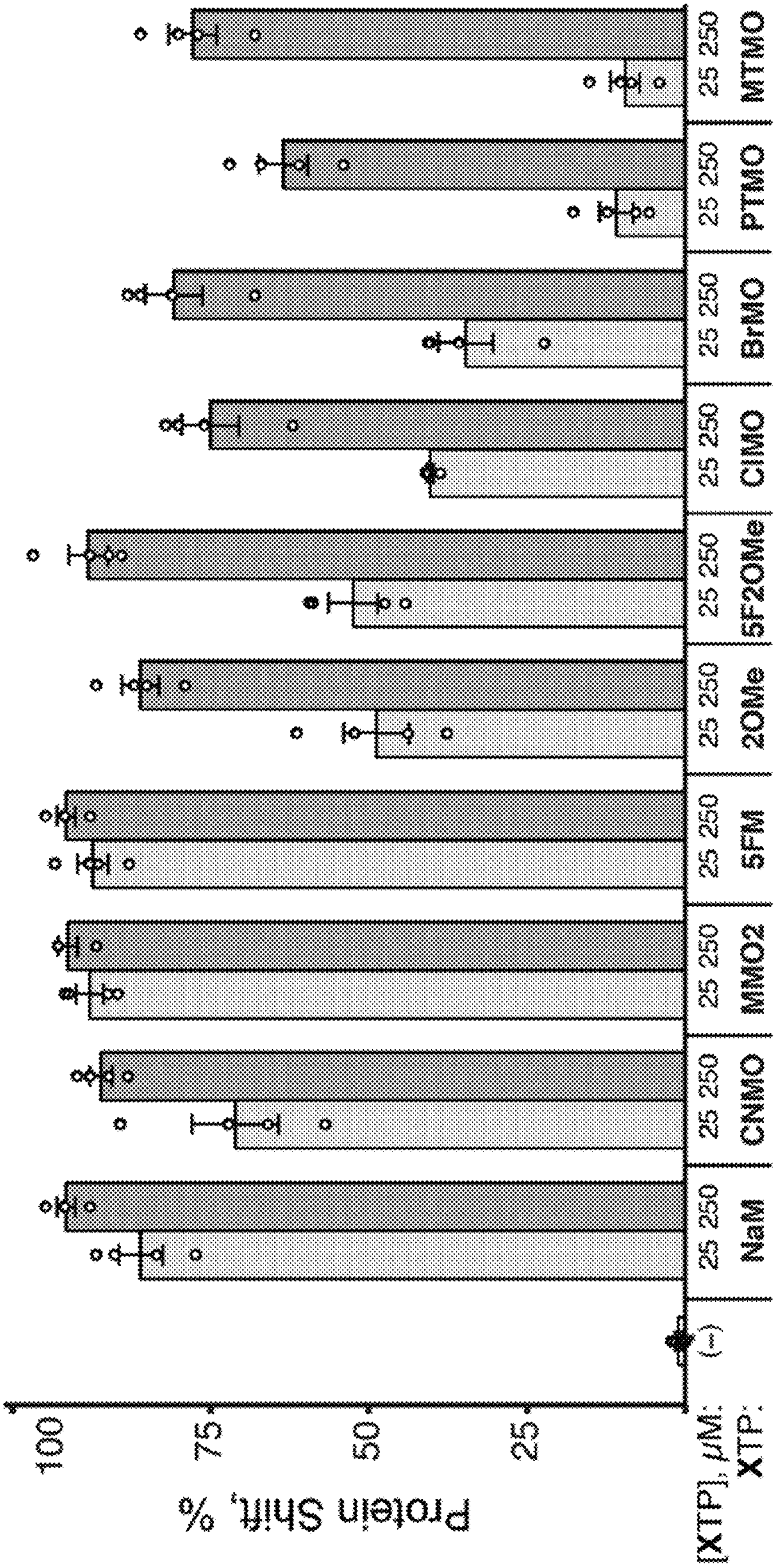
FIG. 5B illustrates a plot of an SAR analysis of translation using various unnatural ribonucleotides to incorporate AzK into sfGFP, with protein shift (%) measured by western blot for XTP analogs on the y-axis. Each bar represents the mean, with error bars indicating standard error (n=4). Open circles represent data for each independent trial.

An SAR analysis was initiated with NaMTP and the nine XTP analogs. Based on performance in the dXTP screen described above, and to eliminate variable loss at the DNA level as a complicating factor, the unnatural information was encoded with the dCNMO-dTPT3 UBP. Additionally, the *E. coli* strain ML2, which expresses the nucleoside triphosphate transporter PtNTT2, but has also been genetically engineered for higher fidelity replication of the UBP by deletion of the gene encoding RecA (as is common in cloning strains) and overexpression of DNA Pol II was used. The same plasmid described above in Examples 1A and 1, harboring $sfGFP^{151}$(AXC) and $tRNA^{Pyl}$(GYT), was used, and to focus the screen to a single unnatural ribonucleotide, the *M. mazei* Pyl tRNA was transcribed in the presence of 30 μM TPT3TP. Cells were grown and induced to produce protein as described above, except that the various XTPs were provided at either high (250 μM) or low (25 μM) concentration in the expression media (FIGS. 5A-5D). Expressed sfGFP was purified 3 h after induction and ncAA content analyzed using the DBCO mediated gel shift assay described above (FIG. 5B). Use of each XTP at 250 μM resulted in sfGFP gel shifts of at least 63%. Along with the lack of observable shift in the absence of an XTP, XTP is imported by PtNTT2 and participates in transcription and translation at the ribosome with at least reasonable efficiency. While CNMOTP and 5F2OMeTP each performed well, resulting in gel shifts of 92% and 94%, respectively, NaMTP, MMO2TP, and 5FMTP performed the best, with protein gel shifts of 98%, 97%, and 98%, respectively. With similarly high levels of protein purity, the relative fluorescence produced using these three XTPs was compared in the absence of any complications resulting from significant levels of natural sfGFP contaminant. Cells grown with 250 μM of either MMO2TP or 5FMTP produced 63% and 90% bulk fluorescence, respectively, compared to cells grown with NaMTP at the same concentration (FIG. 5A).

Figure 5C:
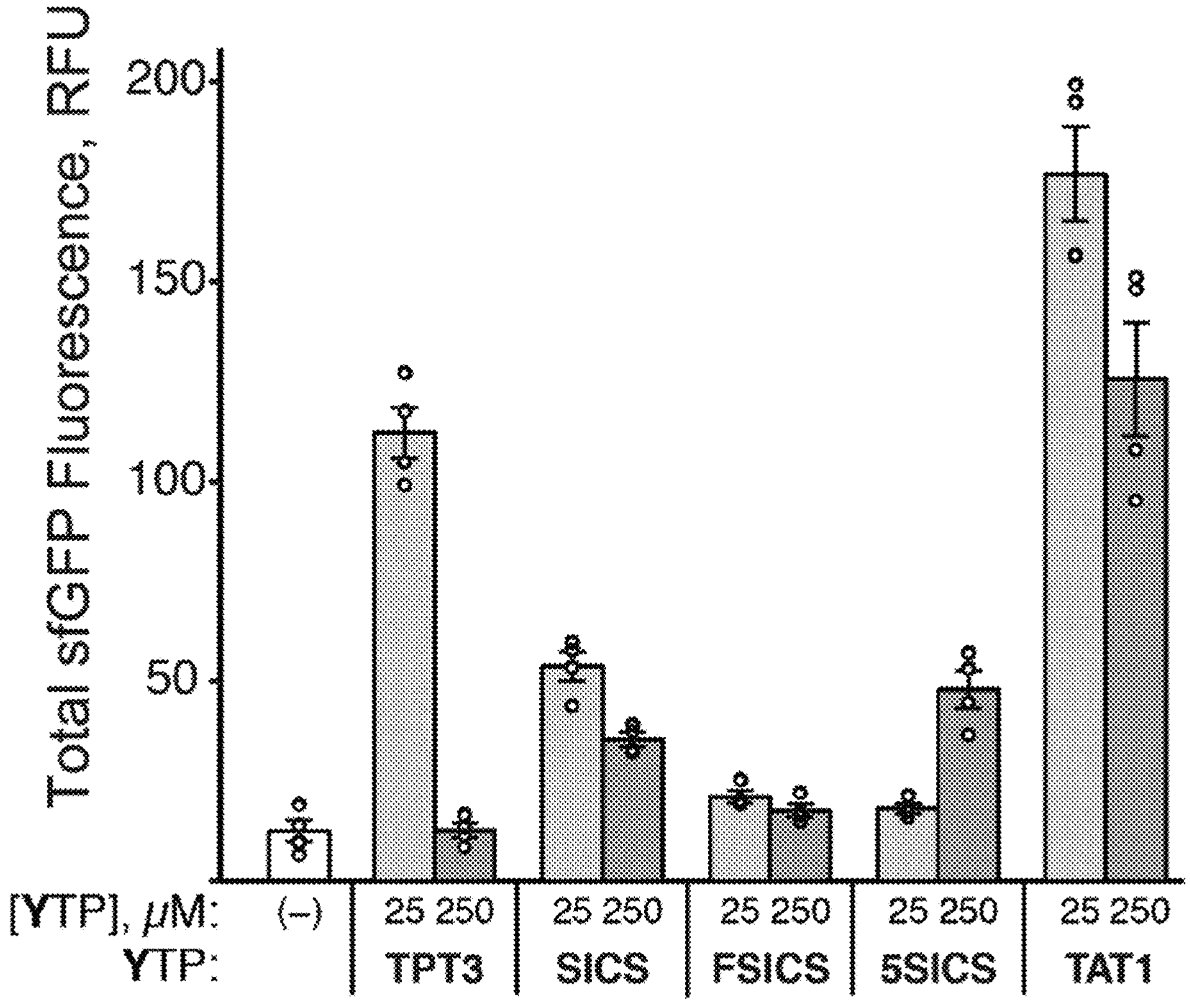
FIG. 5C illustrates a plot of an SAR analysis of translation using various unnatural ribonucleotides to incorporate AzK into sfGFP, with total sfGFP fluorescence (RFU) observed in the presence of AzK for YTP analogs on the y-axis. Each bar represents the mean, with error bars indicating standard error (n=4). Open circles represent data for each independent trial.
Figure 5D:
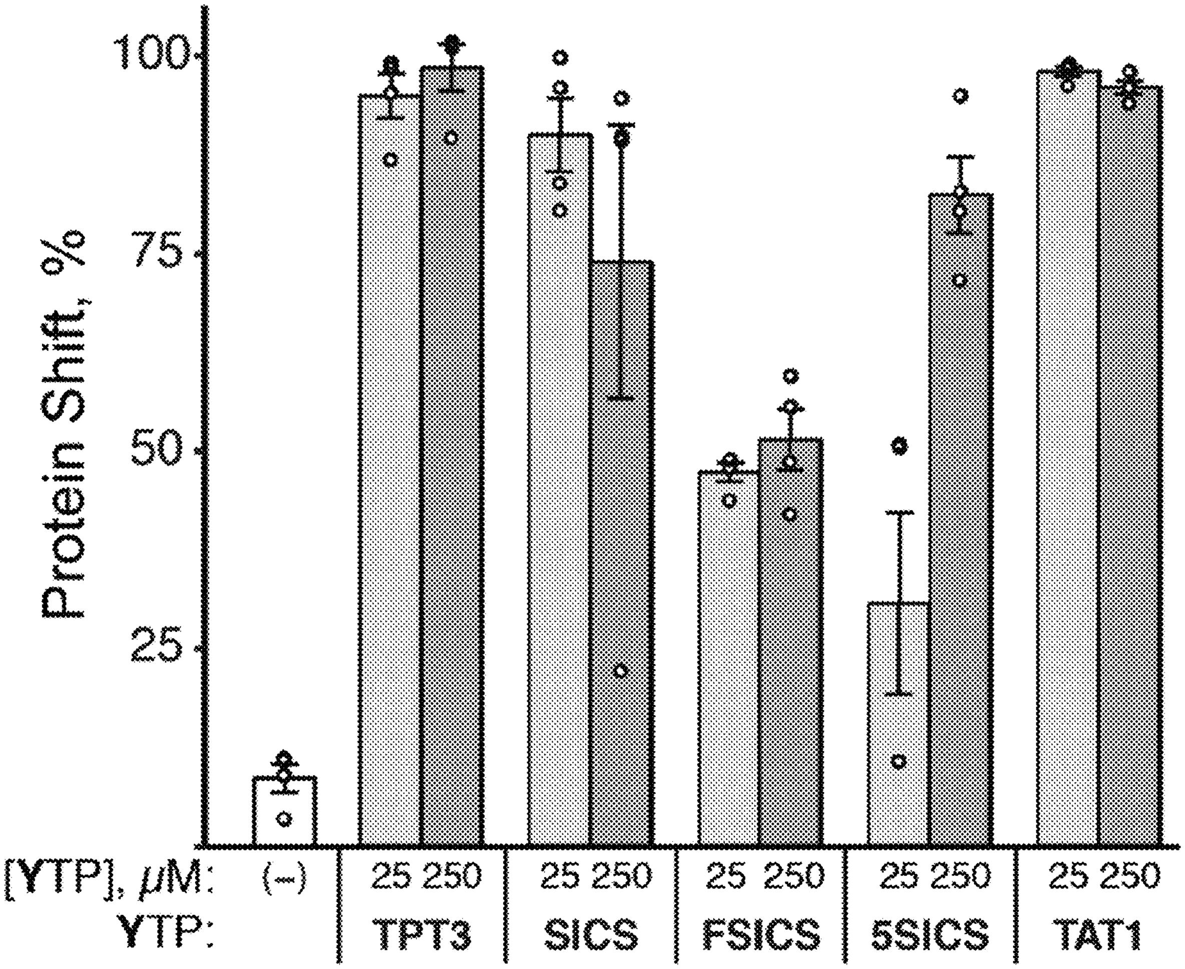
FIG. 5D illustrates a plot of an SAR analysis of translation using various unnatural ribonucleotides to incorporate AzK into sfGFP, with protein shift (%) measured by western blot for YTP analogs on the y-axis. Each bar represents the mean, with error bars indicating standard error (n=4). Open circles represent data for each independent trial.

At the lower concentration tested (25 μM), the use of NaMTP resulted in a lower fidelity of ncAA incorporation, with a protein shift that dropped to 86%. While 7 of the 9 NaMTP analogs also showed significant decreases in fidelity, the use of MMO2TP and 5FMTP each yielded protein shifts of 94%. Comparing the relative fluorescence of cells grown with these ribonucleotides (again possible due to the similar and high fidelity of unnatural protein produced), 5FMTP produced 34% more fluorescence than MMO2TP at this lower concentration. Similar experiments were conducted wherein a constant amount of NaMTP (250 μM) and either a high (250 μM) or low (25 μM) concentration of a YTP analog was supplied. Consistent with previous reports, the addition of TPT3TP at the higher concentration resulted in significantly reduced cell growth and little fluorescence relative to the control sample that did not receive a YTP (FIG. 5C). In contrast, each of the other YTP analogs produced fluorescence above background, and protein shifts of at least 51% (FIG. 5D). Use of TAT1TP resulted in at least 2.6-fold more fluorescence than any other YTP, while maintaining a protein shift of 96%. The addition of TAT1TP at this concentration resulted in a modest level of reduced cell growth (data not shown). TPT3TP is somewhat less toxic when provided at lower concentrations, and correspondingly, when provided at 25 μM, cells produce significant quantities of pure protein. Under these conditions, TPT3TP produced 2-, 5-, and 6-fold greater fluorescence than SICSTP, FSICSTP, and 5SICSTP, respectively. Toxicity observed with TAT1TP at the higher concentrations was almost completely eliminated at lower concentrations (data not shown), and its use resulted in greater fluorescence than at the higher concentration. When provided at 25 μM, TAT1TP produces 41% more fluorescence than when provided at 250 μM, and interestingly, it produced 57% more fluorescence than when TPT3TP is provided at 25 μM. Use of TAT1TP at these concentrations resulted in the production of protein with 98% ncAA incorporation.

Synthetic Protocols.

General materials and methods. For synthetic procedures all reactions were carried out in oven-dried glassware under an inert atmosphere. Solvents were distilled and/or dried over 4 Å molecular sieves. Unless otherwise noted, all other chemical reagents were used without further purification. 1H, 13C, and 31P spectra were taken on a Bruker NMR spectrometer (AV-600, DRX-500, or DPX-400). Mass spectroscopic data were obtained from the core facilities at The Scripps Research Institute. Unnatural deoxyribonucleoside triphosphates were synthesized as reported previously (see Dien, V. T. et al. *J. Am. Chem. Soc.* 2018, 140, 16115-16123; Lavergne, T. et al. *J. Am. Chem. Soc.* 2013, 135, 5408-5419; Matsuda, S. et al. *J. Am. Chem. Soc.* 2007, 129, 5551-5557;

Seo, Y. J. et al. *J. Am. Chem. Soc.* 2009, 131, 3246-3252, the disclosures of each of which are hereby incorporated by reference in their entirety). The nucleoside triphosphates dNaMTP, dTPT3TP, dCNMOTP, and TPT3TP were kindly gifted by Synthorx Inc.

Synthesis of nucleobase 13a. The TAT1 nucleobase (compound 13a) was synthesized based on literature methods (see New, J. S. et al. *J. Med. Chem.* 1989, 32, 1147-1156; Asagarasu, A. et al. *Chem. Pharm. Bull.* 2009, 57, 34-42, the disclosures of each of which are hereby incorporated by reference in their entirety). Briefly, condensation of thiazole-4-carboxaldehyde (1 eq) with malonic acid at 100° C. using pyridine as a solvent and piperidine as a catalyst (2:1 pyridine to piperidine, 2.75 M final reaction concentration) for 13 h, followed by reflux for 1 h, yielded the corresponding acrylic acid intermediate (compound 11). Chlorination of this acid (1 eq) with thionyl chloride (1.1 eq) in chloroform (1.3 M reaction concentration) in the presence of catalytic DMF (0.2 eq) afforded the acyl chloride. Without further purification, the acyl chloride was converted to the corresponding azide (compound 12) in a 1:1 biphasic mixture of 1,4-dioxane and water at 5° C. with sodium azide (2 eq). Crude acyl azide was dissolved in chloroform and added dropwise to diphenyl ether to 0.2 M. The resulting mixture was then heated to 230° C. for 2 h. Upon cooling to room temperature, hexanes were added and the reaction mixture was filtered, using additional hexanes to wash. The resulting crude was purified by flash chromatography using silica gel as the stationary phase to give the desired nucleobase (compound 13a).

Scheme S1.

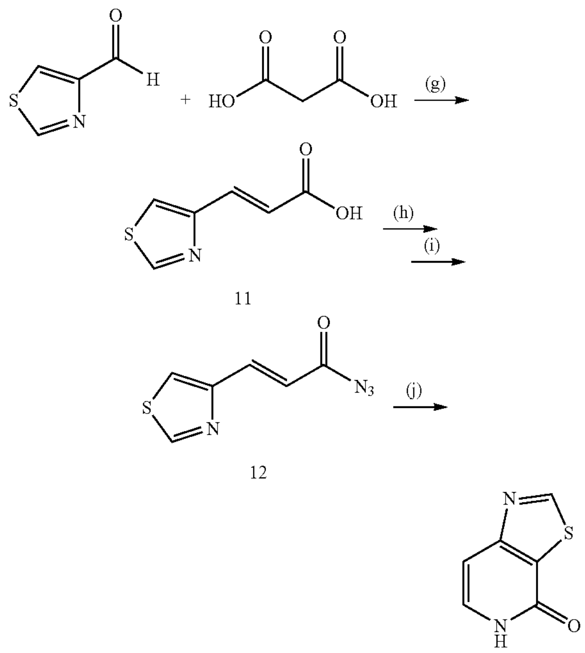

11

12

13a (g) Piperidine, pyridine, 100° C., 12 h, then reflux for 1 h,
(h) $SOCl_2$, DMF, $CHCl_3$, reflux, 3 h,
(i) $NaN_3$, 1,4-dioxane, $H_2O$, 5° C., 0.5 h,
(j) diphenyl ether, 230° C., 1 h Nucleobase coupling and deprotection of TBS-protected ribolactone 2. Aryl halide (1.0 eq) was dissolved in anhydrous THE to 0.1 M and cooled to −78° C. Once cooled, a solution of n-BuLi (1.6 eq, 1.6 M in hexanes) was added dropwise to the reaction flask. After 30 min of stirring this mixture at −78° C., a solution of TBS-protected ribolactone (compound 2, 1.6 eq) in anhydrous THF at ~0.8 M was added dropwise. The reaction was then allowed to stir for an additional 1 h at −78° C. before quenching with saturated aqueous solution of ammonium chloride. Upon warming to room temperature, volatiles were removed in vacuo, and the resulting residues were extracted with ethyl acetate and water. Organics were dried over sodium sulfate, filtered, and volatiles were again removed in vacuo.

Residual solvent was removed on high vacuum for 1 h at room temperature before re-dissolving in anhydrous DCM to 0.1 M. The solution was cooled to −78° C., before the dropwise addition of triethylsilane (3 eq), followed by the dropwise addition of a 48% solution of boron trifluoride diethyl etherate (3 eq). The reaction was then allowed to stir at −78° C. for 15-20 min before quenching with a 1:1 solution of methanol and triethylamine (add a volume 30% the volume of the reaction). This mixture was allowed to stir for 3 min at −78° C. before the addition of saturated sodium bicarbonate (50% the original reaction volume). The mixture was then diluted 2-fold with DCM, and the organic layer was separated. The aqueous layer was extracted two more times with DCM, and combined organics were dried over sodium sulfate, filtered, and concentrated in vacuo.

Any residual solvents were removed from the remaining residue on high vacuum for 1 h at room temperature. At this time, the residue was dissolved in THE to 0.1 M, and a solution of tetrabutylammonium fluoride was added (3.3 eq, 1.0 M in THF). The reaction was allowed to stir for 1 h before diluting with ethyl acetate and extracting with water. Combined organics were dried with sodium sulfate, filtered, and concentrated in vacuo. The resulting residue was then purified by flash chromatography on silica gel using 5-10% ethanol in DCM as the mobile phase.

Nucleobase coupling and deprotection of benzyl-protected ribolactone 10. Aryl halide (1.0 eq) was dissolved in anhydrous THE to 0.1 M and cooled to −78° C. Once cooled, a solution of n-BuLi (1.6 eq, 1.6 M in hexanes) was added dropwise to the reaction flask. After 30 min of stirring this mixture at −78° C., a solution of benzyl-protected ribolactone (compound 10, 1.6 eq) in anhydrous THE at −0.8 M was added dropwise. The reaction was then allowed to stir for an additional 1 h at −78° C. before quenching with saturated aqueous solution of ammonium chloride. Upon warming to room temperature, volatiles were removed in vacuo, and the resulting residues were extracted with ethyl acetate and water. Organics were dried over sodium sulfate, filtered, and volatiles were again removed in vacuo.

Residual solvent was removed on high vacuum for 1 h at room temperature before re-dissolving in anhydrous DCM to 0.1 M. The solution was cooled to −78° C., before the dropwise addition of triethylsilane (3 eq), followed by the dropwise addition of a 48% solution of boron trifluoride diethyl etherate (3 eq). The reaction was then allowed to stir at −78° C. for 15-20 min before quenching with a 1:1 solution of methanol and triethylamine (add a volume 30% the volume of the reaction). This mixture was allowed to stir for 3 min at −78° C. before the addition saturated sodium bicarbonate (50% the original reaction volume). The mixture was then diluted 2-fold with DCM, and the organic layer was separated. The aqueous layer was extracted two more times with DCM, and combined organics were dried over sodium sulfate, filtered, and concentrated in vacuo. The benzyl-protected nucleoside intermediate was then purified by flash chromatography on silica gel using a gradient of 0 to 8-10% ethyl acetate in hexanes as the mobile phase.

The purified benzyl protected nucleoside was diluted in methanol to 0.1 M along with 10% palladium on carbon (0.1 eq). The solution was frozen with liquid nitrogen, and while frozen, the reaction flask was purged three times with hydrogen, leaving the flask under a balloon of hydrogen after the last purge. The reaction was then allowed to thaw and stirred vigorously under hydrogen for 3 h at room temperature. The reaction was then filtered over a patch of silica gel, washing with ethyl acetate. Volatiles were then removed in vacuo, and the resulting crude residue was purified by flash chromatography on silica gel using 5-10% ethanol in DCM as the mobile phase.

Cyanation of aryl bromides. A dry microwave vial was charged with CuCN (8 eq), $Pd_2(dba)_3$(0.1 eq), and DPPF (0.1 eq), and purged three times with argon. Aryl bromide (1 eq) was dissolved in degassed anhydrous DMF to 0.05-0.1M and transferred to the reaction flask. The flask was then sealed under argon and vigorously stirred at 155° C. overnight (~16 h). The reaction was then cooled to room temperature and filtered over a short patch of silica gel, washing with ethyl acetate. Volatiles were removed in vacuo and the resulting crude residue was purified by flash chromatography on silica gel using a gradient from 70-95% ethyl acetate in hexanes as the mobile phase.

General protocol for triphosphorylation of nucleosides. Under inert gas, a dry microwave vial was charged with proton sponge (1.3 eq), and free nucleoside (1 eq). Anhydrous trimethyl phosphate (40 eq) was added to the flask, and the resulting mixture was cooled to −15° C. in a salt ice bath. Freshly distilled phosphorous oxychloride (1.3 eq) was added dropwise to the cooled flask, and the reaction was allowed to stir at −15° C. for 3 h. At this time, tributylammonium pyrophosphate (5 eq) was dissolved in anhydrous DMF at 0.5 M in a separate dry flask, and added dropwise to the reaction flask, followed by the dropwise addition of anhydrous tributylamine (6 eq). The resulting mixture was slowly warmed to 0° C., and was allowed to stir at this temperature for an additional 30 min. The reaction was then quenched by the addition of aqueous triethylammonium bicarbonate (0.5M, pH 7.5, 1:1 with the total reaction volume), and stirred at room temperature for 15 min. This quenched reaction mixture was then purified by anion exchange chromatography using DEAE Sephadex A-25 as the stationary phase and a slow gradient from 0-1.2M TEAB at pH 7.5 as the mobile phase. Fractions containing nucleoside triphosphate were combined and concentrated by SpeedVac to provide the dry, desired product.

Nucleobase coupling and deprotection of benzoyl-protected ribolactone 14. A mixture of nucleobase (1.0 eq) and N,O-bis(trimethylsilyl)acetamide (1.2 eq) in acetonitrile to 0.1 M was stirred under argon atmosphere at room temperature for 30 min. At this time, 1-O-acetyl-2,3,5-tri-O-benzoyl-β-D-ribofuranose (compound 14, 1.2 eq) was added, and the resulting reaction mixture as cooled to 0° C. $SnCl_4$ (1 eq) was then added to the reaction mixture and the solution was stirred overnight at room temperature. The reaction was extracted with ethyl acetate and saturated aqueous $NaHCO_3$, and combined organic layers were dried over anhydrous $Na_2SO_4$. After filtration and evaporation, the residue was purified by flash chromatography on silica gel.

Conversion of pyridones to thio-pyridones. Pyridone (1 eq) was dried by repeated co-evaporation with dry toluene. Lawesson's reagent (3 eq) was added under argon, and the mixture was heated overnight at 120° C. After filtration on cotton, the filtrate was concentrated, and the crude product was purified by flash chromatography on silica gel.

Fluorination of protected nucleosides. Protected nucleoside (1 eq) was dissolved in MeOH—$CH_3CN$ (1:1 v/v) to 0.1 M, and Selectfluor (1.1 eq) was added. The mixture was heated at reflux for 3 h. Volatiles were then removed in vacuo, and the resulting residue was extracted with ethyl acetate and water. Combined organic layers were evaporated, and the resulting crude residue was dried by co-evaporation with anhydrous toluene three times. The residue was dissolved in TfOH-DCM (1:1 v/v) to 0.1 M and the mixture was stirred at room temperature for 1 h. At this time, the reaction was concentrated in vacuo, and the resulting crude product was purified by flash chromatography on silica gel.

Compound characterizations.

Compound 1b. (0.387 mmol, 38% yield, 3 steps). 1H NMR (600 MHz, Chloroform-d) 7.46 (dd, J=8.2, 0.9 Hz, 1H), 7.01 (dd, J=8.2, 1.9 Hz, 1H), 6.87 (d, J=1.9 Hz, 1H), 5.32 (d, J=3.3 Hz, 1H), 4.43 (dd, J=4.6, 3.3 Hz, 1H), 4.37 (dd, J=8.1, 4.6 Hz, 1H), 4.05-4.01 (m, 1H), 3.97 (dd, J=12.0, 3.2 Hz, 1H), 3.83 (s, 3H), 3.77 (dd, J=11.9, 4.1 Hz, 1H). 13C NMR (151 MHz, CDCl3) 156.40, 134.51, 128.81, 124.00, 121.01, 111.03, 82.18, 78.55, 73.31, 72.25, 62.57, 55.85. HRMS (ESI-TOF+) calcd for C12H15ClO5 [M+Na]+ 297.0500; found 297.0501.

Compound 3b. (0.333 mmol, 52% yield, 3 steps). 1H NMR (600 MHz, Methanol-d4) 7.53 (d, J=7.4, 1.5 Hz, 1H), 7.24 (td, J=7.8, 1.8 Hz, 1H), 6.98-6.92 (m, 2H), 5.33 (d, J=2.9 Hz, 1H), 4.35-4.28 (m, 2H), 4.03 (ddd, J=8.2, 4.7, 2.6 Hz, 1H), 3.89 (dd, J=13.1, 3.8 Hz, 1H), 3.84 (s, 3H), 3.70 (dd, J=12.0, 4.7 Hz, 1H). 13C NMR (151 MHz, MeOD) 157.46, 129.07, 129.03, 127.68, 121.09, 110.69, 83.00, 79.66, 74.04, 73.61, 63.32, 55.72. HRMS (ESI-TOF+) calcd for C12H16O5 [M+Na]+ 263.0890; 263.0888.

Compound 4b. (0.765 mmol, 62% yield, 3 steps). 1H NMR (600 MHz, Chloroform-d) 7.23 (dd, J=9.2, 3.1 Hz, 1H), 6.94 (td, J=8.4, 3.2 Hz, 1H), 6.77 (dd, J=8.9, 4.2 Hz, 1H), 5.28 (d, J=3.3 Hz, 1H), 4.43-4.38 (m, 1H), 4.30 (dd, J=8.2, 4.6 Hz, 1H), 3.99 (dt, J=7.8, 3.6 Hz, 1H), 3.90 (dd, J=12.0, 3.2 Hz, 1H), 3.79 (s, 3H), 3.72 (dd, J=12.0, 4.0 Hz, 1H). 13C NMR (151 MHz, CDCl3) 158.28, 156.69, 151.87, 151.86, 127.64, 127.59, 115.09, 114.92, 114.62, 114.46, 110.95, 110.90, 81.92, 78.51, 73.10, 72.30, 62.37, 56.02. HRMS (ESI-TOF+) calcd for C12H15FO5 [M+Na}+ 281.0796; 281.0799.

Compound 5b. (0.366 mmol, 50% yield, 3 steps). 1H NMR (600 MHz, Methanol-d4) δ 7.95 (s, 1H), 7.43 (s, 1H), 7.32 (d, J=5.4 Hz, 1H), 7.26 (d, J=5.4 Hz, 1H), 5.38 (d, J=3.0 Hz, 1H), 4.40-4.35 (m, 1H), 4.32 (dd, J=8.5, 4.4 Hz, 1H), 4.06 (ddd, J=8.2, 4.6, 2.6 Hz, 1H), 3.92 (dd, J=12.0, 2.5 Hz, 1H), 3.90 (s, 3H), 3.71 (dd, J=12.0, 4.7 Hz, 1H). 13C NMR (151 MHz, Methanol-d4) δ 154.39, 139.73, 133.33, 124.79, 123.31, 122.99, 122.24, 102.01, 81.60, 78.62, 72.69, 72.23, 61.98, 54.69. HRMS (ESI-TOF+) calcd for C14H16O5S [M+Na]+ 319.0611; 319.0612.

Compound 6b. (0.160 mmol, 51% yield, 3 steps). 1H NMR (600 MHz, Methanol-d4) δ 7.98 (s, 1H), 7.48 (d, J=5.4 Hz, 1H), 7.34 (s, 1H), 7.29 (d, J=5.4 Hz, 1H), 5.39 (d, J=3.7 Hz, 1H), 4.40-4.35 (m, 1H), 4.32 (dd, J=8.5, 4.4 Hz, 1H), 4.05 (ddd, J=8.4, 4.7, 2.6 Hz, 1H), 3.91 (dd, J=11.9, 2.6 Hz, 1H), 3.89 (s, 3H), 3.71 (dd, J=12.0, 4.7 Hz, 1H). 13C NMR (151 MHz, Methanol-d4) δ 154.41, 139.63, 131.85, 126.26, 125.11, 123.24, 120.94, 102.92, 81.60, 78.66, 72.68, 72.29, 61.95. HRMS (ESI-TOF+) calcd for C14H16O5S [M+Na]+ 319.0611; 319.0609.

Compound 7b. (1.248 mmol, 61% yield, 3 steps). 1H NMR (600 MHz, Chloroform-d) δ 7.41 (dd, J=8.1, 0.9 Hz, 1H), 7.17 (dd, J=8.1, 1.8 Hz, 1H), 7.02 (d, J=1.8 Hz, 1H), 5.32 (d, J=3.3 Hz, 1H), 4.44 (dd, J=4.6, 3.4 Hz, 1H), 4.38 (dd, J=8.1, 4.6 Hz, 1H), 4.04 (dt, J=7.7, 3.6 Hz, 1H), 3.98 (dd, J=11.9, 3.2 Hz, 1H), 3.83 (s, 3H), 3.79 (dd, J=11.9, 4.1 Hz, 1H). 13C NMR (151 MHz, CDCl3) δ 155.82, 128.57, 123.94, 123.44, 121.77, 113.26, 81.62, 78.00, 72.72, 71.60, 61.99, 55.28. HRMS (ESI-TOF−) calcd for C12H15BrO5 [M+Cl]− 352.9797; found 352.9799.

Compound 8a. (0.066 mmol, 42% yield from compound 6b). 1H NMR (600 MHz, Methanol-d4) δ 7.68 (dd, J=7.8, 0.9 Hz, 1H), 7.34 (dd, J=7.8, 1.5 Hz, 1H), 7.28 (d, J=1.5 Hz, 1H), 5.32 (d, J=3.1 Hz, 1H), 4.39 (dd, J=4.5, 3.2 Hz, 1H), 4.30 (dd, J=8.6, 4.5 Hz, 1H), 4.03 (ddd, J=8.6, 4.6, 2.5 Hz, 1H), 3.93-3.89 (m, 4H), 3.70 (dd, J=12.0, 4.6 Hz, 1H). 13C NMR (151 MHz, MeOD) δ 157.65, 134.76, 129.90, 125.39, 120.07, 113.77, 112.30, 83.14, 79.64, 73.80, 73.50, 63.17, 56.31, 50.87. HRMS (ESI-TOF−) calcd for C13H15NO5 [M−H]− 264.0877; found 264.0869.

Compound 9b. (0.288 mmol, 29% yield, 3 steps). 1H NMR (600 MHz, Chloroform-d) δ 7.12 (d, J=9.9 Hz, 1H), 6.73 (d, J=6.1 Hz, 1H), 5.02 (d, J=6.1 Hz, 1H), 4.17 (dd, J=5.9, 4.8 Hz, 1H), 4.13-4.09 (m, 1H), 4.08 (t, J=6.0 Hz, 1H), 3.98 (dd, J=11.9, 3.3 Hz, 1H), 3.87 (s, 3H), 3.85, 3.81 (m, 1H), 2.29 (d, J=2.0 Hz, 3H). 13C NMR (151 MHz, CDCl3) δ 156.19, 154.61, 151.45, 126.24, 124.08, 123.95, 113.10, 83.98, 80.69, 71.56, 62.65, 55.76, 14.22. HRMS (ESI-TOF+) calcd for C13H17FO5 [M+Na]+ 295.0952; 295.0952.

Compound 13a (3.184 mmol, 11% over 4 steps). 1H NMR (500 MHz, DMSO-d6) δ 11.87 (br, 1H, N—H), 9.59 (s, 1H, Ar—H), 7.50 (d, J=5.0 Hz, 1H, Ar—H), 6.98 (d, J=5.0 Hz, 1H, Ar—H). 13C NMR (125 MHz, CDCl3) δ 161.9, 150.3, 159.2, 133.1, 124.3, 102.5. HRMS (ESI-TOF+) calcd for C6H5N2OS+ [M+H]+ 153.0117; found 153.0115.

Compound 13b. (0.530 mmol, 53% yield). 1H NMR (500 MHz, CDCl3) δ 9.13 (s, 1H, Ar—H), 7.36-8.16 (m, 16H, Ar—H), 6.87 (d, J=5.0 Hz, 1H, H-1'), 6.71 (d, J=5.0 Hz, 1H, Ar—H), 5.99-6.01 (m, 1H, H-3'), 5.90-5.92 (m, 1H, H-2'), 4.92 (dd, J1=15 Hz, J2=5 Hz, 1H, H-5'a), 4.80-4.82 (m, 1H, H-4'), 4.72 (dd, J1=15 Hz, J2=5 Hz, 1H, H-5'b). 13C NMR (125 MHz, CDCl3) δ 166.5. 165.7, 165.6, 160.7, 156.7, 134.1, 133.9, 130.9, 130.3, 130.2, 130.1, 130.1, 130.1, 129.8, 129.1, 129.0, 128.9, 128.8, 104.5, 89.2, 80.8, 75.3, 71.4, 64.0. HRMS (ESI-TOF+) calcd for C32H25N2O8S [M+H]+ 597.1326; found 597.1330.

Compound 13c. (0.056 mmol, 56% yield). 1H NMR (500 MHz, CDCl3) δ 9.16 (s, 1H, Ar—H), 7.31-8.24 (m, 17H, Ar—H), 7.12 (d, J=5 Hz, 1H, H-1'), 5.95-5.96 (m, 1H, H-2'), 5.87-5.90 (m, 1H, H-3'), 4.99 (dd, J1=15 Hz, J2=5 Hz, 1H, H-5'a), 4.89-4.91 (m, 1H, H-4'), 4.73 (dd, J1=15 Hz, J2=5 Hz, 1H, H-5'b). 13C NMR (125 MHz, CDCl3) δ 175.7, 166.4, 165.6, 165.3, 163.7, 151.8, 142.1, 134.2, 134.1, 134.0, 132.5, 130.5, 130.3, 130.1, 129.2, 129.2, 128.9, 128.9, 109.7, 92.2, 80.8, 75.9, 69.9, 63.0. HRMS (ESI-TOF+) calcd for C32H25N2O7S2 [M+H]+ 613.1098; found 613.1095.

Compound 13d. (0.043 mmol, 89% yield). 1H NMR (500 MHz, DMSO-d6) δ 9.58 (s, 1H, Ar—H), 8.68 (d, J=10 Hz, 1H, Ar—H), 7.45 (d, J=10 Hz, 1H, Ar—H), 6.81 (d, J=2.5 Hz, 1H, H-1'), 5.48 (d, J=5 Hz, 1H, —OH), 5.39-5.41 (m, 1H, —OH), 5.18 (d, J=5 Hz, 1H, —OH), 4.03-4.05 (m, 2H, H-2', H-3'), 3.98-4.00 (m, 1H, H-4'), 3.78 (dd, J1=10 Hz, J2=2.5 Hz, 1H, H-5'a), 3.64 (dd, J1=10 Hz, J2=2.5 Hz, 1H, H-5'b). 13C NMR (125 MHz, DMSO-d6) δ 174.2, 166.6, 152.2, 135.5, 109.4, 99.9, 95.1, 85.5, 76.6, 69.0, 60.2. HRMS (ESI-TOF+) calcd for C11H13N2O4S2 [M+H]+ 301.0311; found 301.0309.

Compound 15b. (0.931 mmol, 93% yield). 1H NMR (500 MHz, CDCl3) δ 9.05 (d, J=10 Hz, 1H, H—Ar), 7.30-8.16 (m, 20H, Ar—H), 6.72 (d, J=5 Hz, 1H, H-1'), 5.97-5.99 (m, 1H, H-2'), 5.85-5.88 (m, 1H, H-3'), 4.98 (dd, J1=10 Hz, J2=5 Hz, 1H, H-5'a), 4.89-4.90 (m, 1H, H-4'), 4.72 (dd, J1=10 Hz, J2=5 Hz, 1H, H-5'b). 13C NMR (125 MHz, CDCl3) δ 182.1, 179.6, 166.6, 165.5, 165.5, 165.2, 151.1, 143.9, 134.0, 133.9, 133.6, 130.4, 130.3, 130.2, 130.1, 129.6, 129.4, 129.1, 128.9, 128.9, 128.8, 92.8, 80.4, 75.7, 69.7, 62.8. HRMS (ESI-TOF+) calcd for C35H28NO8 [M+H]+ 590.1809; found 590.1811.

Compound 15c. (0.088 mmol, 87% yield). 1H NMR (500 MHz, $CDCl_3$) δ 9.07 (d, J=10 Hz, 1H, Ar—H), 7.30-8.17 (m, 20H, Ar—H, H-1'), 5.98-5.99 (m, 1H, H-2'), 5.82-5.84 (m, 1H, H-3'), 4.89-4.94 (m, 2H, H-5'a, H-4'), 4.80 (dd, J1=15 Hz, J2=5 Hz, 1H, H-5'b). 13C NMR (125 MHz, CDCl3) δ 184.9, 166.5, 165.6, 165.3, 134.0, 133.9, 133.3, 132.7, 130.5, 130.3, 130.2, 129.8, 129.5, 129.1, 128.9, 128.9, 128.8, 127.3, 127.1, 112.8, 92.6, 80.3, 75.9, 70.1, 63.2. HRMS (ESI-TOF+) calcd for C35H28NO7S [M+H]+ 606.1581; found 606.1579.

Compound 15d. (0.044 mmol, 92% yield). 1H NMR (500 MHz, MeOH-d4) δ 8.33 (d, J=10 Hz, 1H, Ar—H), 7.52-7.80 (m, 4H, Ar—H), 6.71 (d, J=5 Hz, 1H, Ar—H), 6.36 (d, J=2.5 Hz, 1H, H-1'), 4.22-4.26 (m, 2H, H-2', H-3'), 4.10-4.11 (m, 1H, H-4'), 3.94 (dd, J1=15 Hz, J2=5 Hz, 1H, H-5'a), 3.82 (dd, J1=15 Hz, J2=5 Hz, 1H, H-5'b). 13C NMR (125 MHz, MeOH-d4) δ 163.0, 137.6, 133.0, 127.5, 127.4, 127.1, 126.3, 125.6, 106.9, 90.1, 85.1, 75.5, 70.3, 61.4. HRMS (ESI-TOF+) calcd for C14H16NO4S [M+H]+ 294.0795; found 294.0799.

Compound 16a. (0.077 mmol, 71% yield). 1H NMR (500 MHz, CDCl3) δ 7.33-8.42 (m, 20H, Ar—H), 6.82 (d, J=5 Hz, 1H, H-1'), 5.94-5.97 (m, 1H, H-2'), 5.83-5.85 (m, 1H, H-3'), 4.87 (d, J=10 Hz, 1H, H-5'a), 4.74-4.79 (m, 2H, H-4', H-5'b). 13C NMR (125 MHz, CDCl3) δ 166.6, 165.7, 165.6, 162.9, 160.8, 134.0, 134.0, 133.9, 133.5, 130.3, 130.2, 130.1, 129.7, 129.1, 129.1, 129.1, 128.9, 128.8, 128.8, 120.3, 111.1, 88.9, 87.8, 85.3, 80.6, 80.4, 74.8, 71.4, 64.1. 19F NMR (376 MHz, CDCl3) δ −145.6. HRMS (ESI-TOF+) calcd for C35H27FNO8 [M+H]+ 608.1715; found 608.1717.

Compound 16b. (0.066 mmol, 65% yield). 1H NMR (500 MHz, CDCl3) δ 9.07 (d, J=10 Hz, 1H, Ar—H), 7.32-8.18 (m, 20H, Ar—H, H-1'), 5.96-5.98 (m, 1H, H-2'), 5.87-5.89 (m, 1H, H-3'), 4.97 (dd, J1=15 Hz, J2=5 Hz, 1H, H-5'a), 4.89-4.91 (m, 1H, H-4'), 4.76 (dd, J1=15 Hz, J2=5 Hz, 1H, H-5'b). 13C NMR (125 MHz, CDCl3) δ 184.3, 166.6, 165.6, 165.3, 134.7, 134.1, 134.0, 133.9, 133.9, 133.3, 133.2, 130.5, 130.3, 130.3, 129.8, 129.7, 129.3, 129.2, 128.9, 128.9, 128.9, 128.8, 128.3, 126.8, 108.4, 100.0, 92.3, 80.7, 75.8, 70.3, 63.2, 56.0. HRMS (ESI-TOF+) calcd for C35H27FNO7S [M+H]+ 624.1487; found 624.1490.

Compound 16c. (0.042 mmol, 90% yield). 1H NMR (500 MHz, MeOH-d4) δ 9.04 (d, J=10 Hz, 1H, H—Ar), 8.73 (d, J=10 Hz, 1H, H—Ar), 7.83-7.87 (m, 2H, Ar—H), 7.65-7.68 (m, 1H, H—Ar), 6.96 (s, 1H, H-1'), 4.23-4.29 (m, 2H, H-2', H-3'), 4.18-4.4.21 (m, 1H, H-4'), 4.11 (dd, J1=10 Hz, J2=5 Hz, H-5'a), 3.91 (dd, J2=10 Hz, J2=5 Hz, H-5'b). 13C NMR (125 MHz, MeOH-d4) δ 180.5, 150.5, 148.6, 134.2, 134.1, 133.2, 132.0, 132.0, 129.2, 126.1, 125.9, 119.6, 119.6, 115.5, 115.1, 96.2, 84.4, 76.1, 68.1, 59.4. HRMS (ESI-TOF)+ calcd for C14H15FNO4S [M+H]+ 312.0700; found 312.0702.

Compound 1c. (0.048, 24% yield). 31P NMR (162 MHz, H2O) δ -8.79--10.99 (m), -21.21--21.58 (m), -21.77--23.23 (m). MS (MALDI-TOF-, matrix: 9-aminoacridine) (m/z) [M-H]- calcd for C12H17ClO14P3-, 512.95; found, 512.7.

Compound 3c. (0.031 mmol, 31% yield). 31P NMR (162 MHz, H2O) δ -11.19--11.91 (m), -22.06--22.73 (m), -23.87--24.46 (m). MS (MALDI-TOF-, matrix: 9-aminoacridine) (m/z) [M-H]- calcd for C12H18O14P3-, 479.00; found, 497.4.

Compound 4c. (0.014 mmol, 14% yield). 31P NMR (162 MHz, H2O) δ -7.31 (d), -11.47 (d), -22.79--23.21 (m). MS (MALDI-TOF-, matrix: 9-aminoacridine) (m/z): [M-H]- calcd for C12H17FO14P3-, 496.97; found, 497.3.

Compound 5c. (0.042 mmol, 23% yield). 31P NMR (162 MHz, D2O) δ -8.48 (d, J=17.8 Hz), -11.21 (d, J=20.7 Hz), -22.96 (t, J=21.6 Hz). MS (MALDI-TOF-, matrix: 9-aminoacridine) (m/z): [M-H]- calcd for C14H18O14P3S—, 534.97; found, 535.4.

Compound 6c. (0.017 mmol, 21% yield). 31P NMR (162 MHz, D2O) δ -9.25 (d, J=21.0 Hz), -10.93 (d, J=19.5 Hz), -22.94 (t, J=20.5 Hz). MS (MALDI-TOF-, matrix: 9-aminoacridine) (m/z): [M-H]- calcd for C14H18O14P3S—, 534.97; found, 535.4.

Compound 7c. (0.009 mmol, 12% yield). 31P NMR (162 MHz, H2O) δ -10.07--11.45 (m), -21.8--22.21 (m), -24.06--24.60 (m). MS (MALDI-TOF-, matrix: 9-aminoacridine) (m/z) [M-H]- calcd for C12H17BrO14P3-, 556.91; found, 556.6.

Compound 8b. (0.023 mmol, 22% yield). 31P NMR (162 MHz, H2O) δ -9.96--12.34 (m), -21.91--22.45 (m), -22.88--24.4 (m). MS (MALDI-TOF-, matrix: 9-aminoacridine) (m/z) [M-H]- calcd for C13H17NO14P3-, 503.99; found, 504.3.

Compound 9c. (0.021 mmol, 21% yield). 31P NMR (162 MHz, H2O) δ -9.77--10.37 (m), -10.8--11.17 (m), -22.0--22.2 (m). MS (MALDI-TOF-, matrix: 9-aminoacridine) (m/z) [M-H]- calcd for C13H19FO14P3-, 511.0; found, 511.0.

Compound 13e. (0.007 mmol, 22% yield). 31P NMR (400 MHz, D2O): δ -10.82-10.94 (m), -11.68-11.74 (m), -23.21-23.45 (m). MS (MALDI-TOF, matrix: 9-aminoacridine) (m/z): [M-H]- calcd for C11H14N2O13P3S2-, 538.9, found, 538.3.

Compound 15e. (0.012 mmol, 35% yield). 31P NMR (400 MHz, D2O): δ -10.74-10.84 (m), -11.55-11.67 (m), -23.17-23.42 (m). MS (MALDI-TOF, matrix: 9-aminoacridine) (m/z): [M-H]- calcd for C14H17NO13P3S—, 532.0, found, 532.5.

Compound 16d. (0.009 mmol, 29% yield). 31P NMR (400 MHz, D2O): δ -10.65-10.79 (m), -11.45-11.54 (m), -22.16-23.40 (m). MS (MALDI-TOF, matrix: 9-aminoacridine) (m/z): [M-H]- calcd for C14H16FNO13P3S—, 550.0, found, 550.6.

Scheme S2.

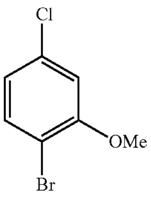

1a

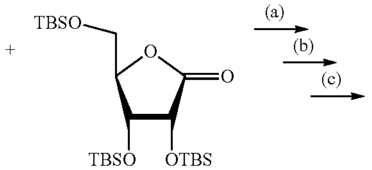

2

-continued

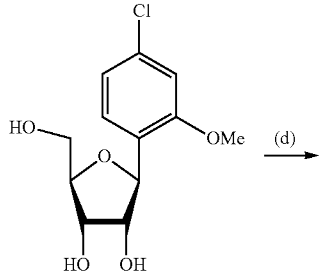

1b

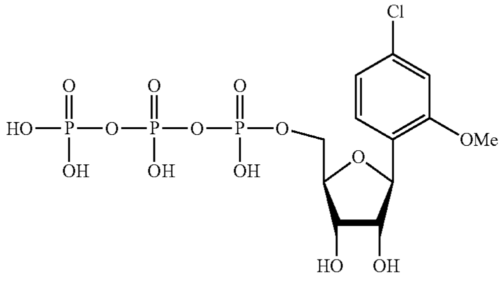

1c (a) 1.6M n-BuLi, THF, -78° C., 1 h,
(b) Triethylsilane, DCM, $BF_3$•$OEt_2$, -78° C., 15-20 min,
(c) 1.0M TBAF, THF, 1 h,
(d) Proton Sponge, $POCl_3$, $Bu_3N$, $Bu_3NPPi$, $(MeO)_3P$, DMF, -15° C., 3 h.

Scheme S3.

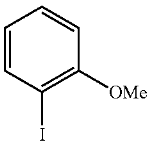

3a

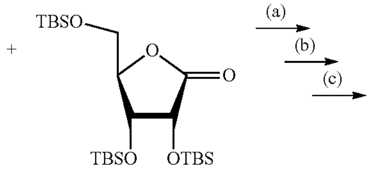

2

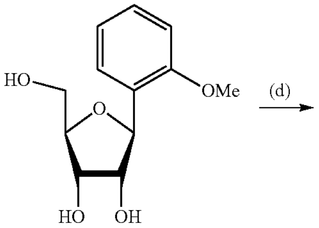

3b

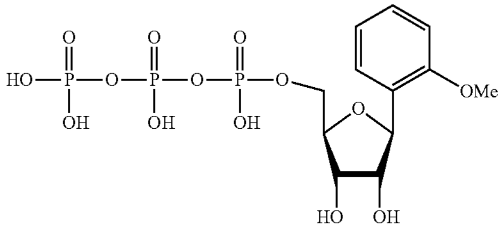

3c (a) 1.6M n-BuLi, THF, -78° C., 1 h,
(b) Triethylsilane, DCM, $BF_3$•$OEt_2$, -78° C., 15-20 min,
(c) 1.0M TBAF, THF, 1 h,
(d) Proton Sponge, $POCl_3$, $Bu_3N$, $Bu_3NPPi$, $(MeO)_3P$, DMF, -15° C., 3 h.

Scheme S4.

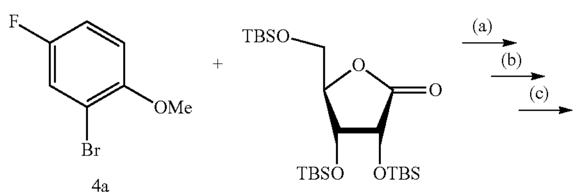

4a

2

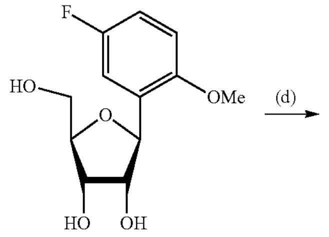

4b

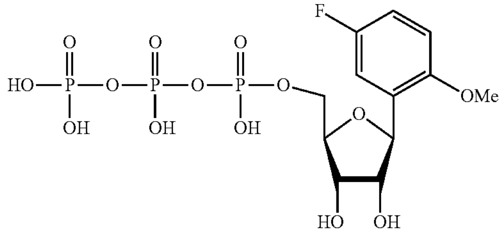

4c (a) 1.6M n-BuLi, THF, -78° C., 1 h,
(b) Triethylsilane, DCM, $BF_3$•$OEt_2$, -78° C., 15-20 min,
(c) 1.0M TBAF, THF, 1 h,
(d) Proton Sponge, $POCl_3$, $Bu_3N$, $Bu_3NPPi$, $(MeO)_3P$, DMF, -15° C., 3 h.

Scheme S5.

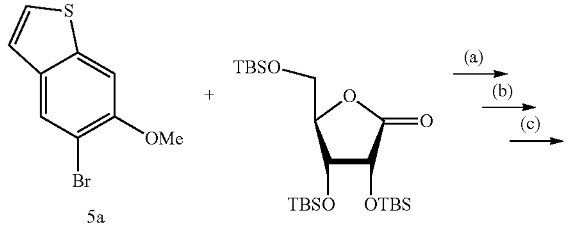

5a

2

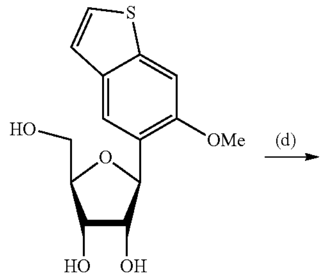

5b

-continued

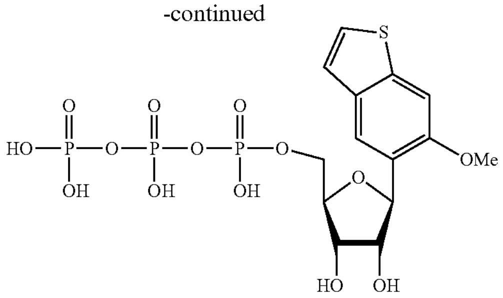

5c (a) 1.6M n-BuLi, THF, -78° C., 1 h,
(b) Triethylsilane, DCM, $BF_3$•$OEt_2$, -78° C., 15-20 min,
(c) 1.0M TBAF, THF, 1 h,
(d) Proton Sponge, $POCl_3$, $Bu_3N$, $Bu_3NPPi$, $(MeO)_3P$, DMF, -15° C., 3 h.

Scheme S6.

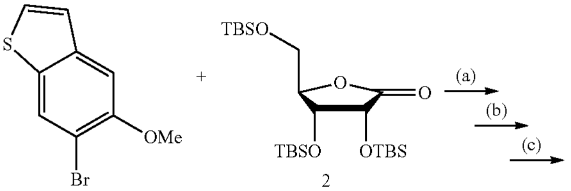

6a

2

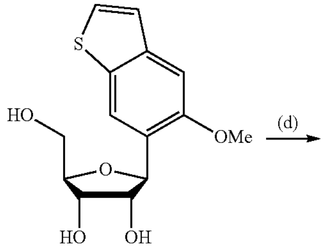

6b

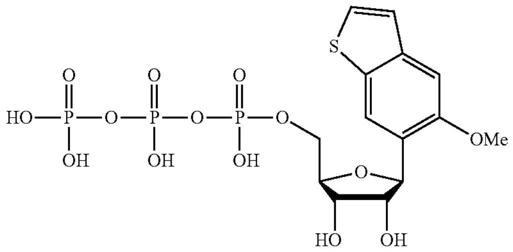

6c (a) 1.6M n-BuLi, THF, -78° C., 1 h, (b) Triethylsilane, DCM, $BF_3$•$OEt_2$, -78° C., 15-20 min, (c) 1.0M TBAF, THF, 1 h, (d) Proton Sponge, $POCl_3$, $Bu_3N$, $Bu_3NPPi$, $(MeO)_3P$, DMF, -15° C., 3 h.

Scheme S7.

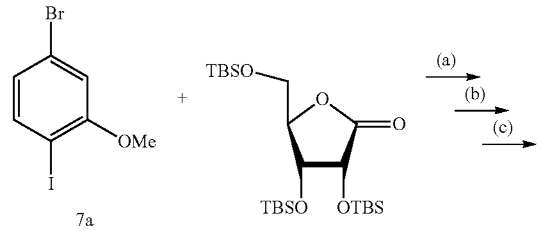

7a 2

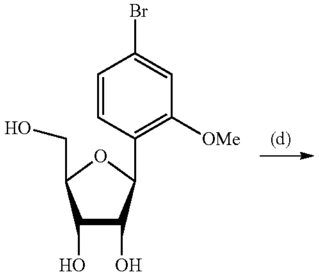

7b

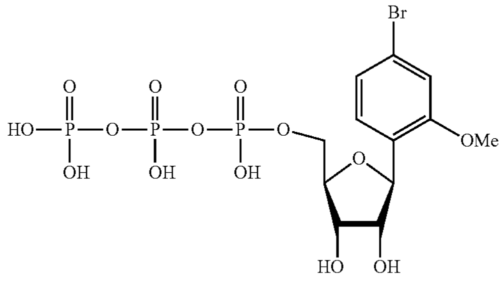

7c (a) 1.6M n-BuLi, THF, -78° C., 1 h,
(b) Triethylsilane, DCM, $BF_3$•$OEt_2$, -78° C., 15-20 min,
(c) 1.0M TBAF, THF, 1 h,
(d) Proton Sponge, $POCl_3$, $Bu_3N$, $Bu_3NPPi$, $(MeO)_3P$, DMF, -15° C., 3 h.

Scheme S8

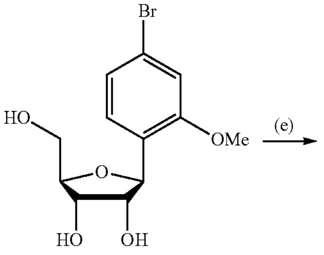

7b

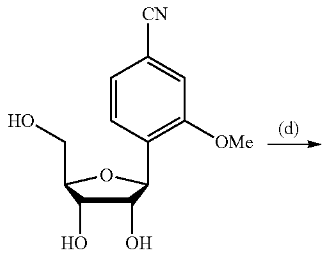

8a

-continued

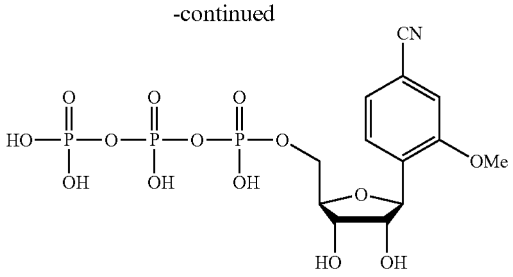

8b (d) Proton Sponge, $POCl_3$, $Bu_3N$, $Bu_3NPPi$, $(MeO)_3P$, DMF, -15° C., 3 h, (e) CuCN, $Pd_2(dba)_3$, DPPF, DMF, 155° C., 16 h Scheme S9.

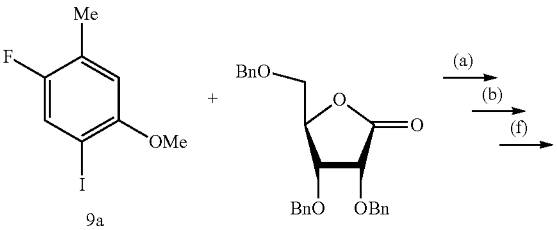

9a 10

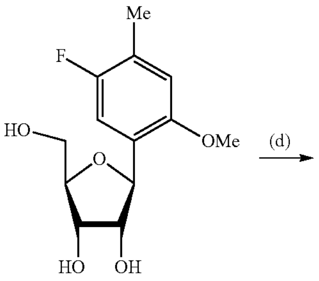

9b

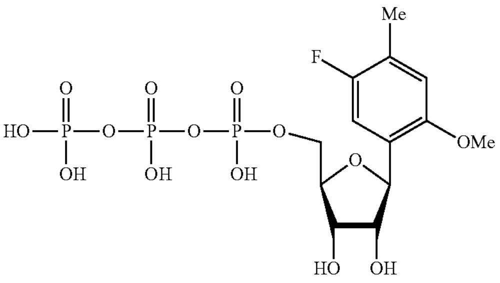

9c (a) 1.6M n-BuLi, THF, -78° C., 1 h,
(b) Triethylsilane, DCM, $BF_3$•$OEt_2$, -78° C., 15-20 min,
(d) Proton Sponge, $POCl_3$, $Bu_3N$, $Bu_3NPPi$, $(MeO)_3P$, DMF, -15° C., 3 h,
(f) $H_2(g)$, Pd/C (10%), MeOH, rt, 3 h Scheme S10.
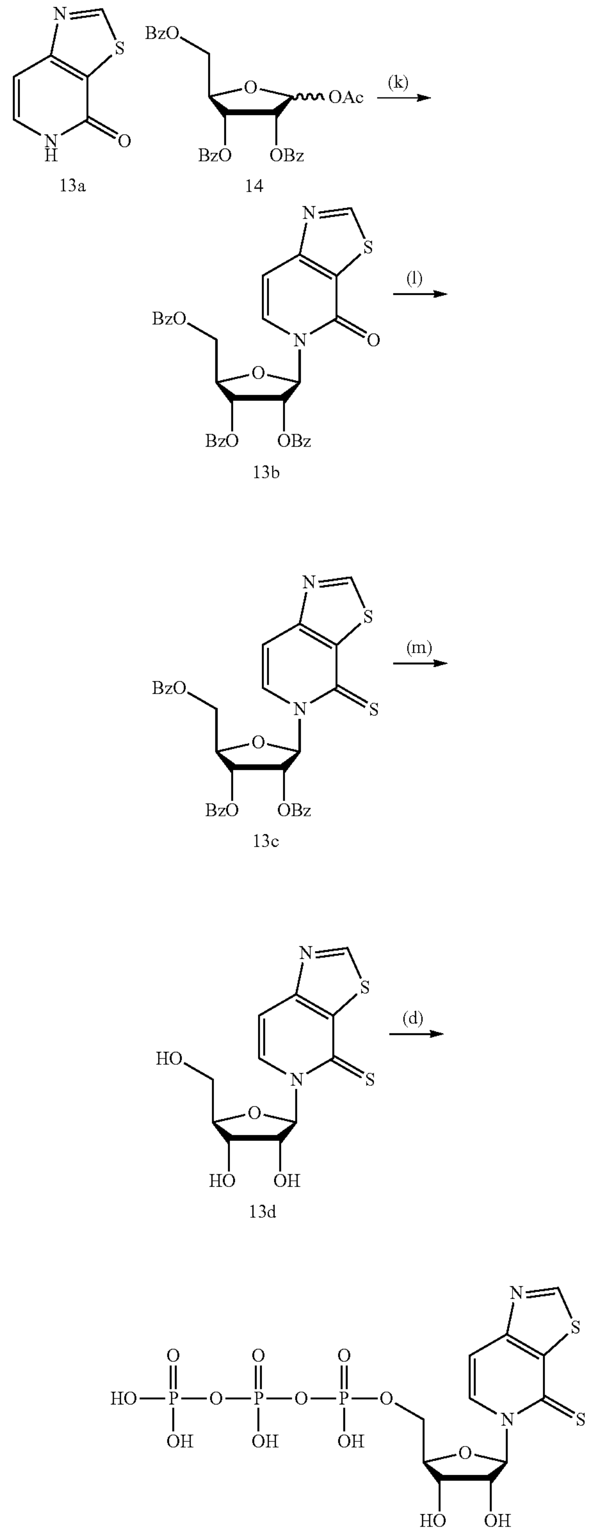
13a 14 13b 13c 13d 13e
(k) N,O-bis(trimethylsily)acetamide, $SnCl_4$, $CH_3CN$, RT, overnight, (l) Lawesson's reagent, 120° C., overnight, (m) 30% NaOMe, DCM, 0° C., 2 h, (d) Proton Sponge, $POCl_3$, $Bu_3N$, $Bu_3NPPI$, $(MeO)_3P$, DMF, -15° C., 3 h
Scheme S11.
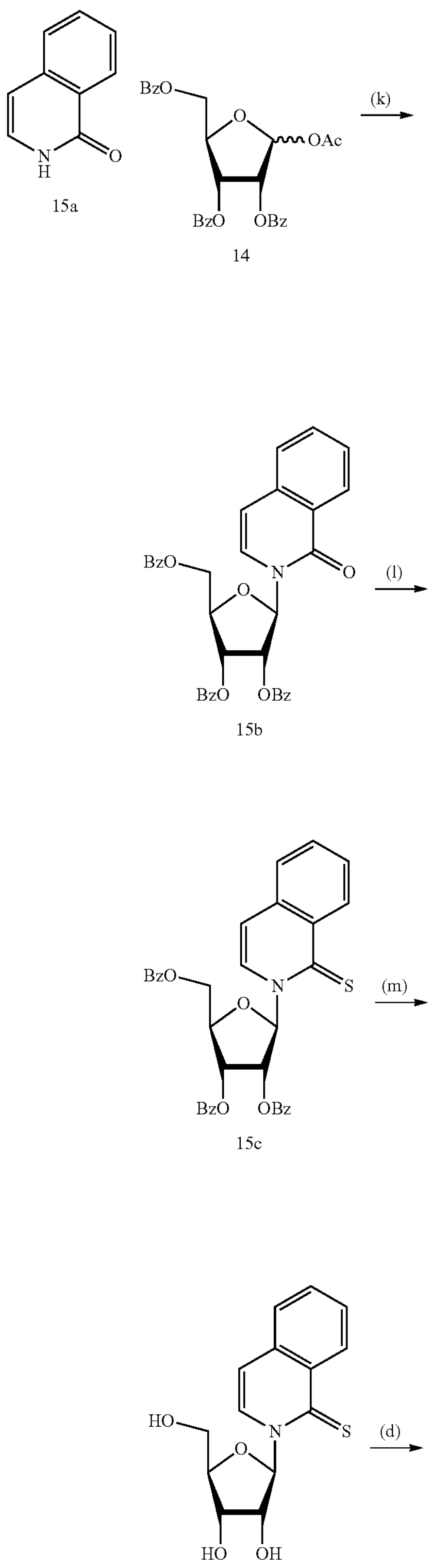
15a 14 15b 15c 15d -continued

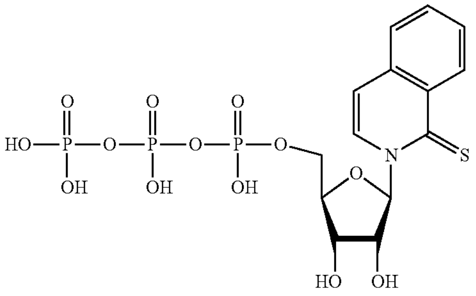

15e (k) N,O-bis(trimethylsilyl)acetamide, $SnCl_4$, $CH_3CN$, RT, overnight,
(l) Lawesson's reagent, 120° C., overnight,
(m) 30% NaOMe, DCM, 0° C., 2 h,
(d) Proton Sponge, $POCl_3$, $Bu_3N$, $Bu_3NPPi$, $(MeO)_3P$, DMF, -15° C., 3 h Scheme S12.

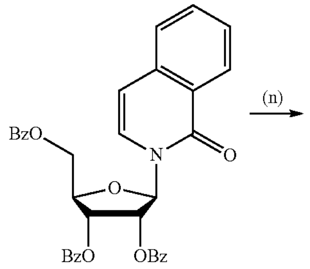

15b

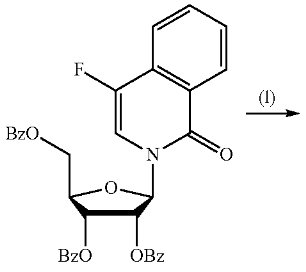

16a

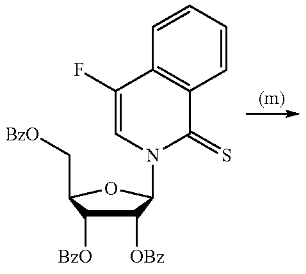

16b

-continued

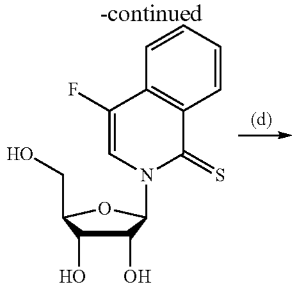

16c

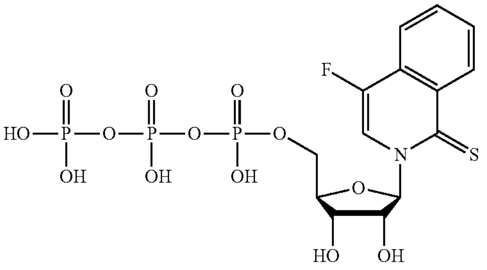

16d (n) i. Selectfluor, $MeOH/CH_3CN$ (1:1 v/v), reflux, 3 h; ii. TfOH/DCM (1:1 v/v), 1 h, (l) Lawesson's reagent, 120° C., overnight, (m) 30% NaOMe, DCM, 0° C., 2 h, (d) Proton Sponge, $POCl_3$, $Bu_3N$, $Bu_3NPPi$, $(MeO)_3P$, DMF, -15° C., 3 h

Example 3: Optimization of Unnatural Protein Production

Figure 6A:
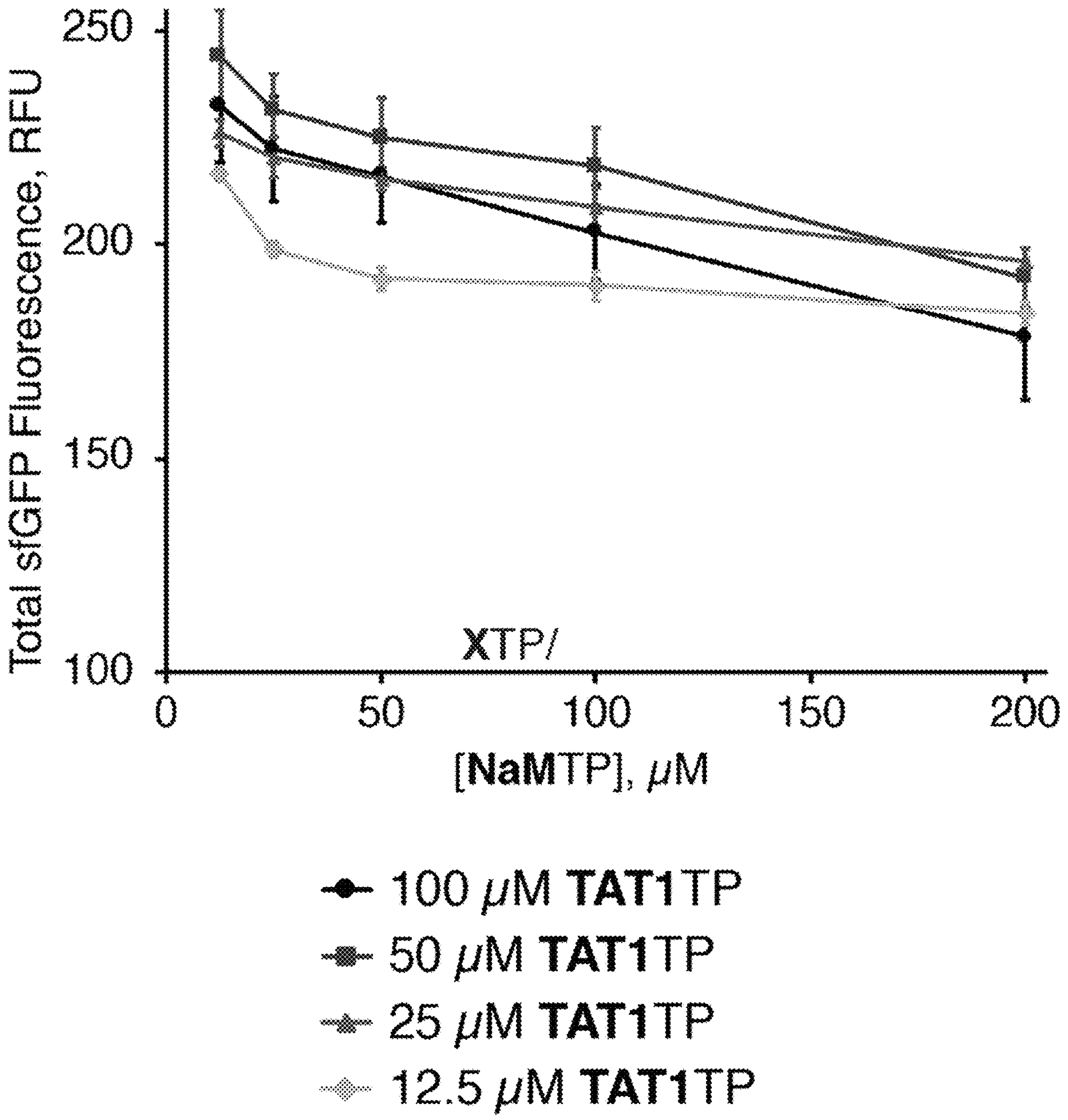
FIG. 6A illustrates a plot of optimization of unnatural ribonucleotide triphosphate concentrations for total sfGFP fluorescence (RFU) as a function of the concentrations of NaMTP and TAT1TP (μM). Error bars indicate standard error of each value (n=3).
Figure 6B:
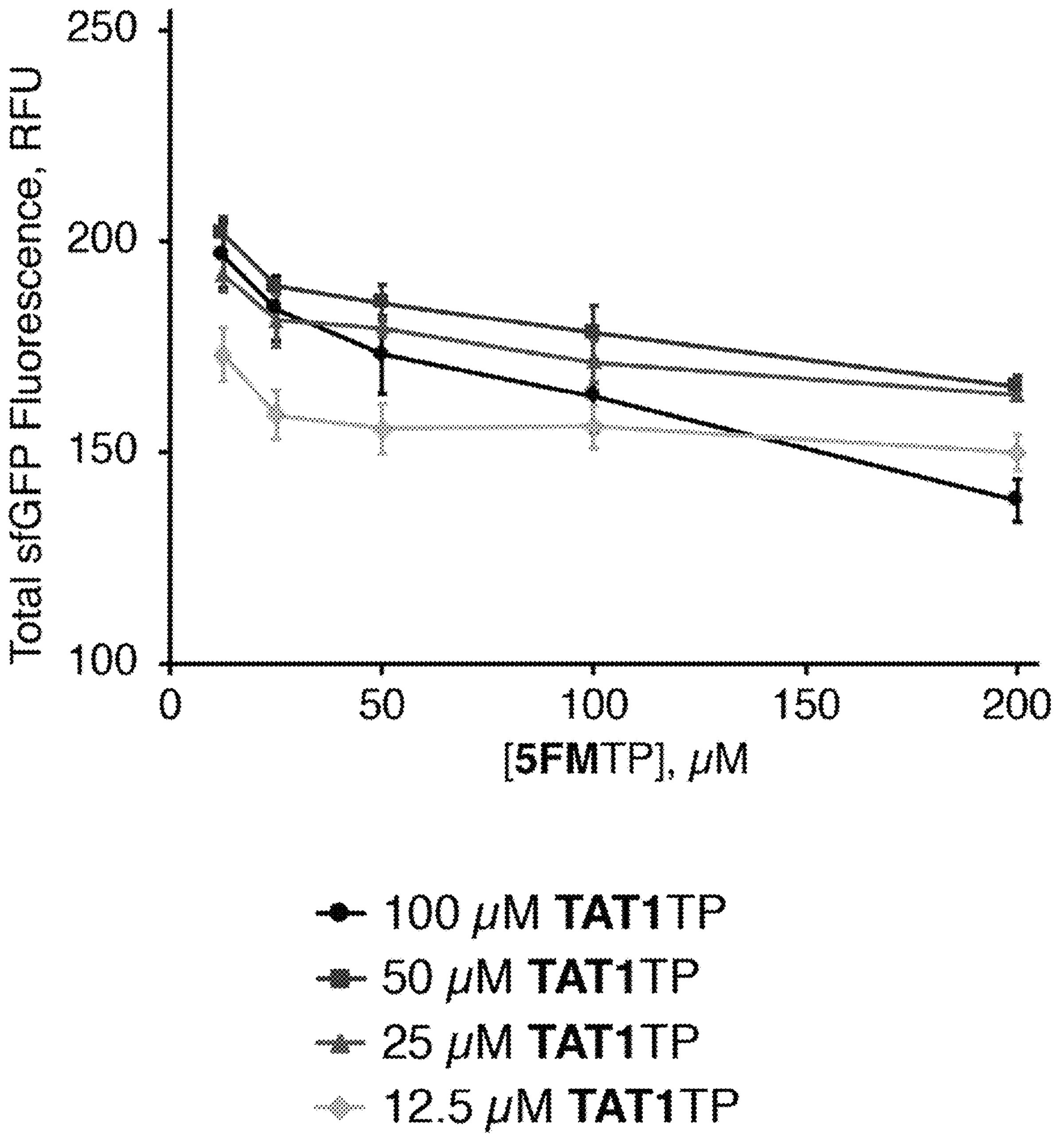
FIG. 6B illustrates a plot of optimization of unnatural ribonucleotide triphosphate concentrations for total sfGFP fluorescence (RFU) as a function of the concentrations of 5FMTP and TAT1TP (μM). Error bars indicate standard error of each value (n=3).
Figure 6C:
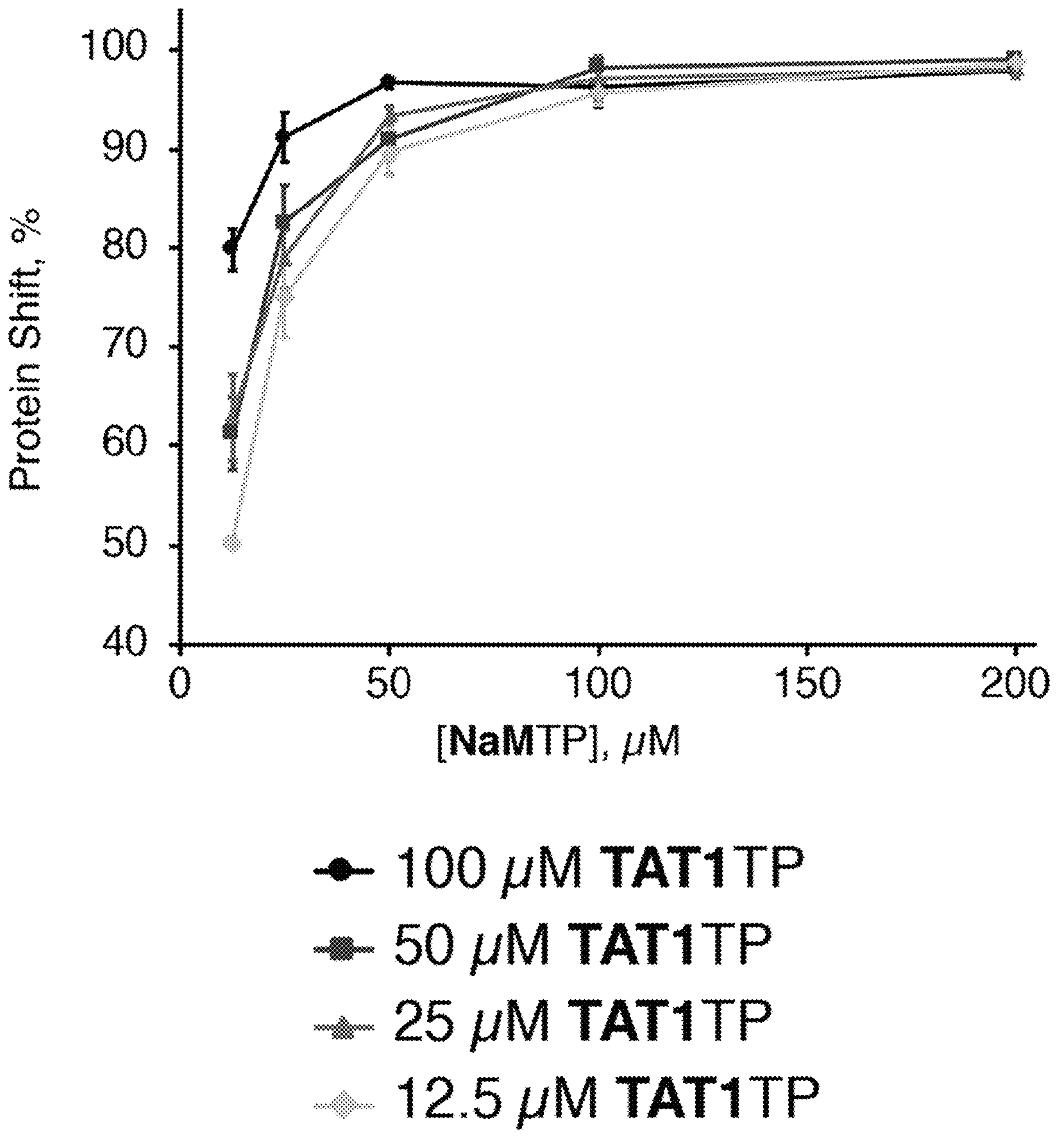
FIG. 6C illustrates a plot of optimization of unnatural ribonucleotide triphosphate concentrations for protein shift (%) as a function of the concentrations of NaMTP and TAT1TP (μM). Error bars indicate standard error of each value (n=3).
Figure 6D:
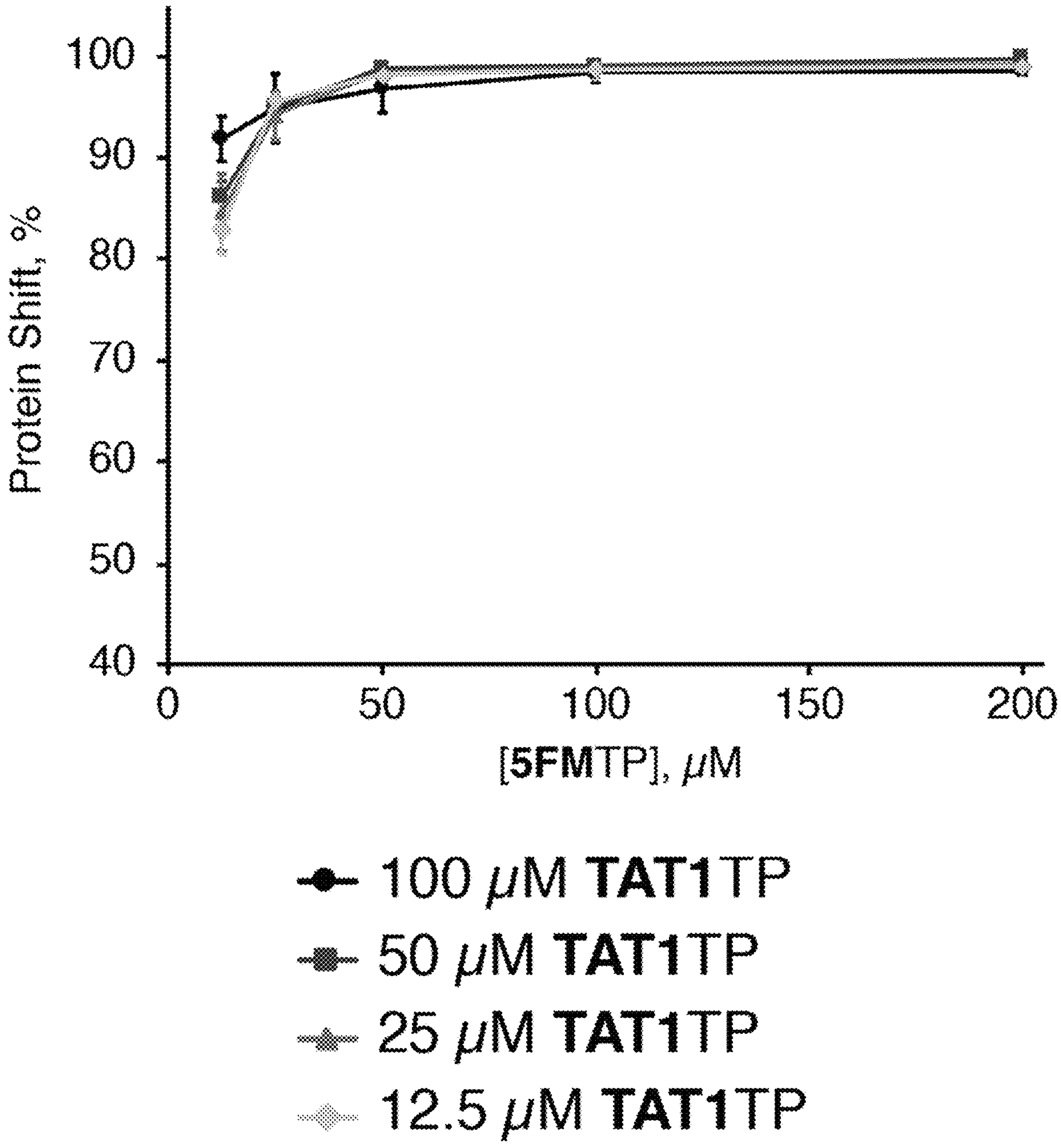
FIG. 6D illustrates a plot of optimization of unnatural ribonucleotide triphosphate concentrations for protein shift (%) as a function of the concentrations of 5FMTP and TAT1TP (μM). Error bars indicate standard error of each value (n=3).

Examples 1A, 1B, and 2 identified dCNMO-dTPT3 as a competent UBP for the storage of information, and TAT1TP and NaMTP or 5FMTP as competent ribonucleoside triphosphates for its retrieval. Upon transformation with the same plasmids used above, 10 μM dTPT3TP and 25 μM dCNMOTP were provided in the growth media, which was then also supplemented with TAT1TP at concentrations ranging from 100 μM to 12.5 μM, and either NaMTP or 5FMTP at concentrations ranging from 200 μM to 12.5 μM, all in series of 2-fold dilutions, and after the addition of 1 mM AzK, the cells were induced to express sfGFP. Total sfGFP fluorescence observed in cells provided with TAT1TP and NaMTP was generally higher than that observed in cells provided with TAT1TP and 5FMTP (FIG. 6A and FIG. 6B). In both cases, fluorescence was higher at lower concentrations of NaMTP or 5FMTP (due to increased production of contaminating natural sfGFP, see below). Additionally, cells generally produced higher fluorescence at higher concentrations of TAT1TP. However, due to a slight reduction in growth, cells provided with 100 μM TAT1TP produced less fluorescence than those provided with 50 μM TAT1TP. Protein production was again quantified via the gel shift assay (FIG. 6C and FIG. 6D). Generally, as the concentration of NaMTP decreased below 200 μM, incrementally lower fidelity of AzK incorporation into sfGFP was observed, while with use of 5FMTP this reduction in fidelity was only observed below a concentration of 50 μM. Clearly lower concentrations of 5FMTP can be used without compromising fidelity. Cells provided with a high concentration of 5FMTP (≥50 M) produced high protein shifts at all concentrations of TAT1TP explored (100 μM, 50 μM, 25 μM, or 12.5 μM). However, when the concentration of 5FMTP was 25 μM or less, decreasing the concentration of TAT1TP resulted in a reduced protein shift. When NaMTP was provided at 200 μM, all concentrations of TAT1TP explored resulted in the production of protein with high fidelity ncAA incorporation, but with lower concentrations of NaMTP, decreasing the concentration of TAT1TP again resulted in a decreased protein shift. In all, these studies revealed that the combined optimization of protein purity and yield is achieved with NaMTP and TAT1TP provided at concentrations of 200 M and 50 μM, respectively, or with 5FMTP and TAT1TP both provided at a concentration of 50 M. In terms of protein production alone, the use of NaMTP and TAT1TP is optimal, whereas the use of 5FMTP and TAT1TP results in slightly lower yields of pure ncAA-labeled protein, but requires significantly lower concentrations of the XTP.

Optimization of in vivo Translation Conditions. An overnight culture of the SSO strain ML2 carrying the pGEX-MbPylRS TetR plasmid was grown in 2×YT supplemented with 50 mM potassium phosphate, 5 g/mL chloramphenicol and 100 μg/mL carbenicillin (herein referred to in this section as "media"), then diluted back to an $OD_{600}$ of 0.03 in the same media and grown to an OD600 of 0.4-0.6. The culture was then chilled with shaking over ice-water for 15 min then pelleted by centrifugation at 3,200×g for 10 min. Cells were then resuspended and washed with ice-cold $ddH_2O$ twice then resuspended in ice-cold $ddH_2O$ to an $OD_{600}$ of 55-65. The electrocompetent cells (50 μL) and ~1 ng of Golden Gate assembled plasmid with the UBP within the sfGFP and tRNAPyl genes (see Golden Gate Assembly of Plasmids) were transferred to a pre-chilled electroporation cuvette (0.2-cm-gap), then electroporated (Gene Pulser II; Bio-Rad) according to manufacturer's recommendations (voltage 25 kV, capacitor 2.5 μF, resistor 200Ω), and then immediately diluted with 950 μL of media. An aliquot (40 μL) of the transformation was then diluted five-fold in media supplemented with dCNMOTP (25 μM) and dTPT3TP (10 μM) for a final volume of 200 μL then allowed to recover for 1 h shaking at 37° C. Two-fold dilutions of the recovery were plated onto solid media supplemented with zeocin (50 μg/mL), dCNMOTP (10 μM), dTPT3TP (10 μM), and agar (2% w/v), then grown at 37° C. for 18 h. Single colonies were picked and grown in media (300 μL) supplemented with 50 μg/mL zeocin and provided dCNMOTP (25 μM) and dTPT3TP (10 μM) (herein afterward referred to in this section as "growth media"). The culture was monitored for cell growth (Envision 2103 Multilabel Plate Reader with a 590/20 nm filter) and then collected at an OD600~1.0. An aliquot (50 μL) was subjected to plasmid isolation using the ZR Plasmid Prep Kit (Zymo Research). Isolated plasmids were then subjected to the streptavidin gel shift assay described below (using primers P3-4 and P5-6, Table S1) to determine UBP retention.

A colony with excellent UBP retention was then diluted to an $OD_{600}$~0.01 in growth media and grown to OD600~0.4-0.6. This culture was then divided into multiple 300 μL cultures and each was provided with either 5FMTP, TAT1TP or NaMTP, TAT1TP at variable concentrations of each XTP (at 12.5 μM, 25 μM, 50 μM, 100 μM, or 200 μM) and TAT1TP (at 12.5 μM, 25 μM, 50 μM, or 100 μM). AzK (10 mM) was also provided to cells at this point. Samples were shielded from light after addition of AzK to prevent photodegradation. These samples were then grown at 37° C. for 20 min before adding 1 mM IPTG and grown at 37° C. for an additional 1 h to induce T7 RNAP and transcription of tRNAPyl and PylRS. From this point on, cells were monitored for growth and fluorescence. Expression of sfGFP was then induced with anhydrotetracycline (100 ng/mL). After an additional 3 h of growth at 37° C., cells were collected (230 μL for affinity purification of sfGFP), cooled, and then pelleted and stored at −80° C. before protein purification.

In vivo Translation of High-Density Unnatural Codons. An overnight culture of the SSO strain ML2 carrying the pGEX-MbPylRS TetR plasmid was grown in 2×YT supplemented with 50 mM potassium phosphate, 5 μg/mL chloramphenicol and 100 μg/mL carbenicillin (herein referred to in this section as "media"), then diluted back to an $OD_{600}$ of 0.03 in the same media and grown to an OD600 of 0.4-0.6. The culture was then chilled with shaking over ice-water for 15 minutes then pelleted by centrifugation at 3,200×g for 10 min. Cells were then resuspended and washed with ice-cold $ddH_2O$ twice then resuspended in ice-cold $ddH_2O$ to $OD_{600}$ of 55-65. The electrocompetent cells (50 μL) and ~1 ng of Golden Gate assembled plasmids with the UBP at either the 149 or 153 codon position of sfGFP, two of the three validated codon positions, or all three positions (sfGFP149(AXC), sfGFP151(AXC), sfGFP149,151(AXC,AXC), sfGFP151,153(AXC,AXC), sfGFP149,153(AXC,AXC), and (sfGFP149,151,153(AXC, AXC,AXC)) (see Golden Gate Assembly of Plasmids), were transferred to a pre-chilled electroporation cuvette (0.2-cm-gap). The cells were then electroporated (Gene Pulser II; Bio-Rad) according to manufacturer's recommendations (voltage 25 kV, capacitor 2.5 μF, resistor 200Ω), and then immediately diluted with 950 μL of media. An aliquot (40 μL) of the transformation was then diluted five-fold in media supplemented with either dNaMTP (150 μM) and dTPT3TP (10 μM) (herein afterward referred to in this section as "old conditions") or dCNMOTP (150 μM) and dTPT3TP (10 μM) (herein afterward referred to in this section as "new conditions") for a final volume of 200 μL then allowed to recover for 1 h shaking at 37° C. Two-fold dilutions of the recovery were plated onto solid media supplemented with zeocin (50 μg/mL), the corresponding unnatural triphosphates, and agar (2% w/v), then grown at 37° C. for ~18 h. Single colonies were picked and grown in media (300 μL) supplemented with 50 μg/mL zeocin (herein afterward referred to in this section as "growth media") and provided the corresponding unnatural triphosphates for old conditions or new conditions. The culture was monitored for cell growth (Envision 2103 Multilabel Plate Reader with a 590/20 nm filter) and then collected at an $OD_{600}$~1.0. Collected cells were chilled on ice overnight.

The cells were then re-diluted to an $OD_{600}$~0.1 in growth media and provided the corresponding unnatural triphosphates for old conditions or new conditions, then grown to $OD_{600}$~0.4-0.6. The cells corresponding to old conditions were then provided with NaMTP (250 μM) and TPT3TP (30 μM) whereas cells corresponding to new conditions were then provided with NaMTP (200 μM) and TAT1TP (50 μM). AzK (10 mM) (or $ddH_2O$ for cultures grown in the absence of AzK) was also provided to cells at this point. Samples were shielded from light after addition of AzK to prevent photodegradation. These samples were then grown at 37° C. for 20 min before adding 1 mM IPTG and grown at 37° C. for an additional 1 h to induce T7 RNAP and transcription of tRNAPyl and PylRS. From this point on, cells were monitored for growth and fluorescence. Expression of sfGFP was then induced with anhydrotetracycline (100 ng/mL). After an additional 3 h of growth at 37° C., cells were cooled, collected (50 μL for plasmid isolation to determine UBP retention, 230 μL for affinity purification of sfGFP), and then pelleted and stored at −80° C. before protein purification and assessment of UBP retention.

Results. All ten XTPs explored at high concentration are capable of mediating the production of proteins with at least moderate ncAA incorporation fidelity (98% to 63%). Generally, as XTP concentrations are decreased, the fidelity of ncAA incorporation decreased, indicating a reduction in the fidelity with which the unnatural mRNA is transcribed. This is consistent with the significant fluorescence observed when XTP was withheld.

This example provided SARs for the transcription and translation of predominantly hydrophobic ribonucleotides. With the XTPs, when considering NaMTP, PTMOTP, and MTMOTP, ring contraction and/or heteroatom derivatization is in some instances deleterious. However, with the monocyclic nucleobase XTPs, with the exception of CIMOTP, higher fidelity protein production is observed, relative to MTMOTP and PTMOTP. In some instances, specific interactions between the unnatural nucleobases or with the polymerase are beneficial for base pairing. For example, substitution at both the 4- and 5-positions of the monocyclic nucleobases in some instances effects base pairing. Compared to 2OMeTP, a Cl or Br substituent at the 4-position (CIMOTP and BrMOTP) is in some instances deleterious, while a methyl group at the 4-position (MMO2TP), reduces overall fluorescence, but with an increase in protein fidelity. A nitrile substituent at the 4-position (CNMOTP) results in the production of the greatest amount of unnatural protein, and also modestly increases the fidelity with which the ncAA is incorporated. Addition of a fluoro substituent at the 5-position (5F2OMeTP) also increases both protein production and fidelity, relative to 2OMeTP. The effects of substitution at the 4- and 5-positions appear in some instances at least approximately additive, as combining the 5-fluoro and 4-methyl substituents (5FMTP) allows for the high yield production of pure unnatural protein at lower concentrations, relative to the other unnatural triphosphates. However, while requiring higher concentrations, NaMTP provides a balanced combination of yield and purity of the XTP analogs examined. In some instances, SARs derived for the XTP analogs are distinctly different from those derived from the replication of dXTP analogs. For example, while dPTMOTP, dCIMOTP, and dCNMO are in some cases more optimal than dNaMTP, CIMOTP and PTMOTP are modestly and significantly less optimal in some cases than NaMTP. Moreover, while dCNMO is the most optimal partner for dTPT3 discovered to date, the use of CNMOTP results in slightly reduced fidelity of ncAA incorporation, relative to NaMTP, although its use does result in the most unnatural protein production. At the highest concentration, all five YTPs explored were effectively incorporated into the anticodon of $tRNA^{Pyl}$ and capable of mediating the production of proteins with at least moderate ncAA incorporation fidelity (98% to 51%). Without being bound by theory, the UBP retention data suggests that the fidelity of protein production is not sensitive to modest loss of unnatural tRNA, implying that for the YTPs that resulted in lower protein gel shifts, transcription of the tRNA was either very inefficient or low fidelity. TPT3TP, SICSTP, FSICSTP, and TAT1TP were all, at least slightly toxic at the highest concentration (data not shown), and bulk cell fluorescence increased with decreasing concentrations. Unlike with XTPs and transcription of the mRNA, fidelity of unnatural protein did not decrease, suggesting that the increased protein production was simply the result of increased cell growth. In contrast, 5SICSTP showed minimal toxicity (data not shown), and both unnatural protein production and fidelity decreased with decreasing concentrations, again presumably due to significantly compromised unnatural tRNA production. When considering this YTP SAR, and using SICSTP as a reference, 7-fluoro substituent (FSICSTP) is in some instances deleterious, and only a small amount of protein is produced and with low fidelity. Addition of a methyl group at the 5-position (5SICSTP) reduces toxicity, but also in some instances reduces unnatural tRNA production. Ring contraction and heteroatom derivatization (TPT3TP) in some instances improves both protein production and fidelity, but at high concentration it is often toxic compared to other YTP analogs. Further heteroatom derivatization of the thiophene ring of TPT3TP, to produce the thioazole of TAT1TP, results in the production of greater unnatural protein than TPT3TP, with a reduction in toxicity. Given both the amount of protein produced and the fidelity of ncAA incorporation, TAT1TP is in some cases used as a YTP.

Example 4: Storage and Retrieval of Higher Density Unnatural Information

Storage and retrieval of information from a gene containing a higher density of UBPs was evaluated. Towards this goal, the ability of the SSO to replicate DNA containing the sfGFP gene with the UBP positioned to encode codons 149 or 153, which are each separated from the codon described above (codon 151) by a single natural codon was validated. Accordingly, expression plasmids were constructed, as described above, but in which the sequence AXC was positioned to encode either codon 149 or 153 ($sfGFP^{149}$(AXC) or $sfGFP^{153}$(AXC), respectively). Upon transformation of ML2, cells were grown in the presence of unnatural nucleoside triphosphates, corresponding to either our previously reported system (the deoxyribonucleotides dNaMTP and dTPT3TP and the ribonucleotides NaMTP and TPT3TP, denoted dNaM-dTPT3/NaMTP, TPT3TP), or the optimized system discovered in the current study (dCNMOdTPT3/NaMTP, TAT1TP). UBP retention was then characterized using the streptavidin gel shift assay, as described above. High retention of the corresponding UBP in both $sfGFP^{149}$(AXC) and $sfGFP^{153}$(AXC) genes (≥95%) as well as in the tRNA gene (≥91%) was observed under both conditions (data not shown).

Figure 7A:
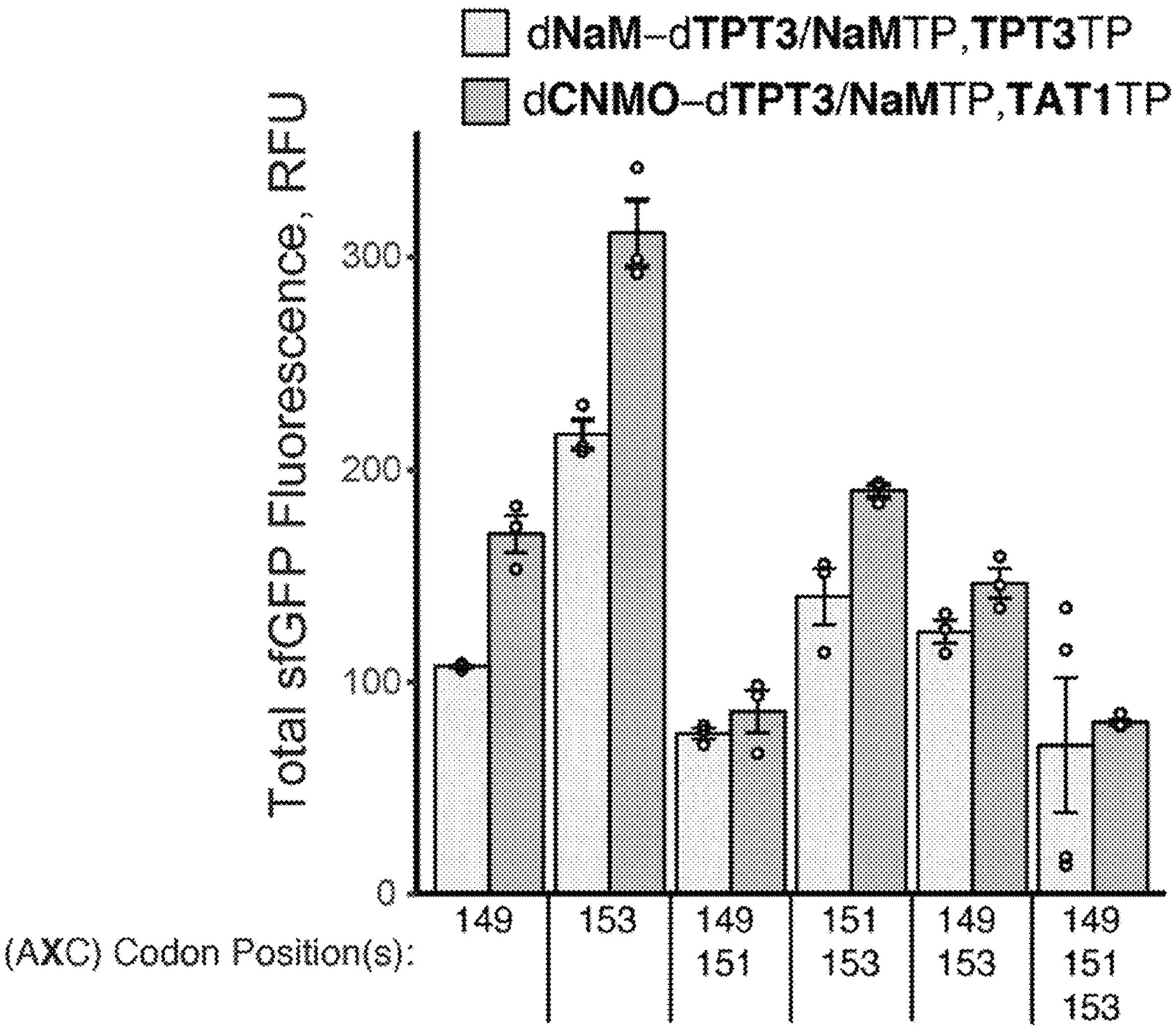
FIG. 7A a plot of storage and retrieval of higher density unnatural information for various unnatural base pairs, codon positions, and total sfGFP fluorescence (RFU) observed in the presence of AzK. For strip charts, each bar represents the mean, with error bars indicating standard error (n=4), and open circles represent data for each independent trial.

Total sfGFP fluorescence observed 3 h after induction revealed significant protein production from both constructs in the presence of AzK under both sets of conditions (FIG. 7A).

However, fluorescence from cells expressing the $sfGFP^{149}$(AXC) construct provided with dCNMOdTPT3/NaM,TAT1 was 58% higher than cells provided with dNaM-dTPT3/NaM,TPT3. In the case of the sfGFP153(AXC) gene, 43% more fluorescence was observed with dCNMOd-TPT3/NaMTP,TAT1TP than with dNaMdTPT3/NaMTP, TPT3TP. Under both sets of conditions, approximately 2-fold more fluorescence was observed with $sfGFP^{153}$(AXC) than with $sfGFP^{149}$(AXC). Protein was purified and AzK incorporation was analyzed as described above (FIG. 7B). With dNaM-dTPT3/NaMTP,TPT3TP, protein shifts of 86% and 94% were observed with $sfGFP^{149}$(AXC) and $sfGFP^{153}$(AXC), respectively. With dCNMOdTPT3/NaMTP,TAT1TP, however, a 96% shift was observed with protein produced from either construct. These results clearly demonstrate that the two additional codon positions are both transcribed and translated efficiently, but again they are transcribed and translated better with the newly identified dCNMO-dTPT3/NaMTP,TAT1TP system. Expression plasmids with an unnatural codon simultaneously encoded at two or all three of the positions examined ($sfGFP^{149,151}$(AXC,AXC), $sfGFP^{151,153}$(AXC,AXC), $sfGFP^{149,153}$(AXC,AXC), and sfGFP149,151,153(AXC,AXC,AXC), respectively) were constructed. ML2 cells were transformed, grown in the presence of either dNaMdTPT3/

Figure 7B:
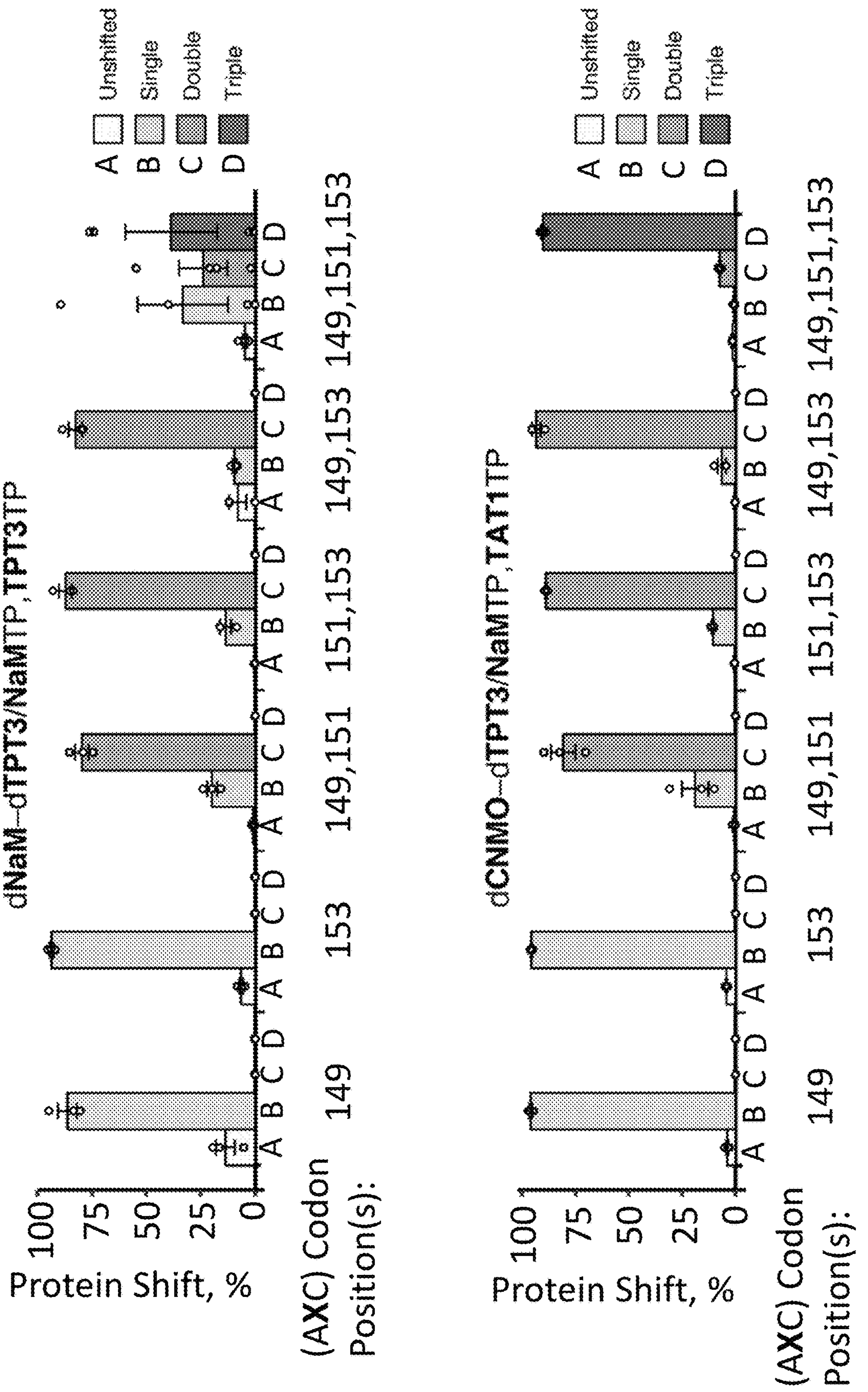
FIG. 7B a plot of storage and retrieval of higher density unnatural information for various unnatural base pairs, codon positions, and protein shift (%) measured by western blot observed in the presence of AzK. For strip charts, each bar represents the mean, with error bars indicating standard error (n=4), and open circles represent data for each independent trial.

NaMTP,TPT3TP or dCNMOdTPT3/NaMTP,TAT1TP, and protein expression was induced as described above. While UBP retention in the tRNA$^{Pyl}$ (GYT) gene remained high (≥88%) in all cases (data not shown), the biotin shift assay with the mRNA genes produced complex and uninterpretable band patterns, likely due to, at least in part, the formation of a mixture of complexes with single PCR products bound to multiple streptavidins. Protein produced via conjugation to DBCO-TAMRA as described above (FIG. 7B) was examined. Gratifyingly, relative to the shift observed with a single ncAA, a significantly further shifted band was observed for proteins expressed from the sfGFP$^{149,151}$(AXC,AXC), sfGFP$^{151,153}$(AXC,AXC), and sfGFP$^{149,153}$(AXC,AXC) constructs, indicating the conjugation of two DBCO-TAMRA molecules to sfGFP bearing two AzK residues. When analyzing purified proteins expressed with dNaM-dTPT3/NaMTP,TPT3TP, quantification of these double shifted bands relative to total sfGFP revealed that 80%, 87%, and 83% of the protein, respectfully, had two AzK residues, and 20%, 13%, or 9%, respectfully, had a single AzK when using the sfGFP$^{149,151}$(AXC, AXC), sfGFP$^{151,153}$(AXC,AXC), or sfGFP$^{149,153}$(AXC, AXC) constructs, respectively. With dCNMOdTPT3/NaMTP,TAT1TP, 81%, 89%, and 93% of the protein had two ncAAs with sfGFP$^{149,151}$(AXC,AXC), sfGFP$^{151,153}$(AXC, AXC), and sfGFP$^{149,153}$(AXC,AXC), respectively, while 19%, 11%, and 6% had a single ncAA. Cells transformed with the sfGFP$^{149,151,153}$(AXC,AXC,AXC) construct expressed protein that produced an even further shifted band, clearly indicating the incorporation of three AzK residues. Quantification of each band relative to total sfGFP revealed that the use of dNaM-dTPT3/NaMTP,TPT3TP resulted in 39%, 24%, and 33% of the protein having three, two and one ncAAs, respectively, and with fluorescence and protein shifts that were highly variable (FIGS. 7A and 7B). In contrast, use of the dCNMO-dTPT3/NaMTP,TAT1TP system resulted in 90% of the produced protein having all three ncAAs, with the remainder having two.

Figure 7C:
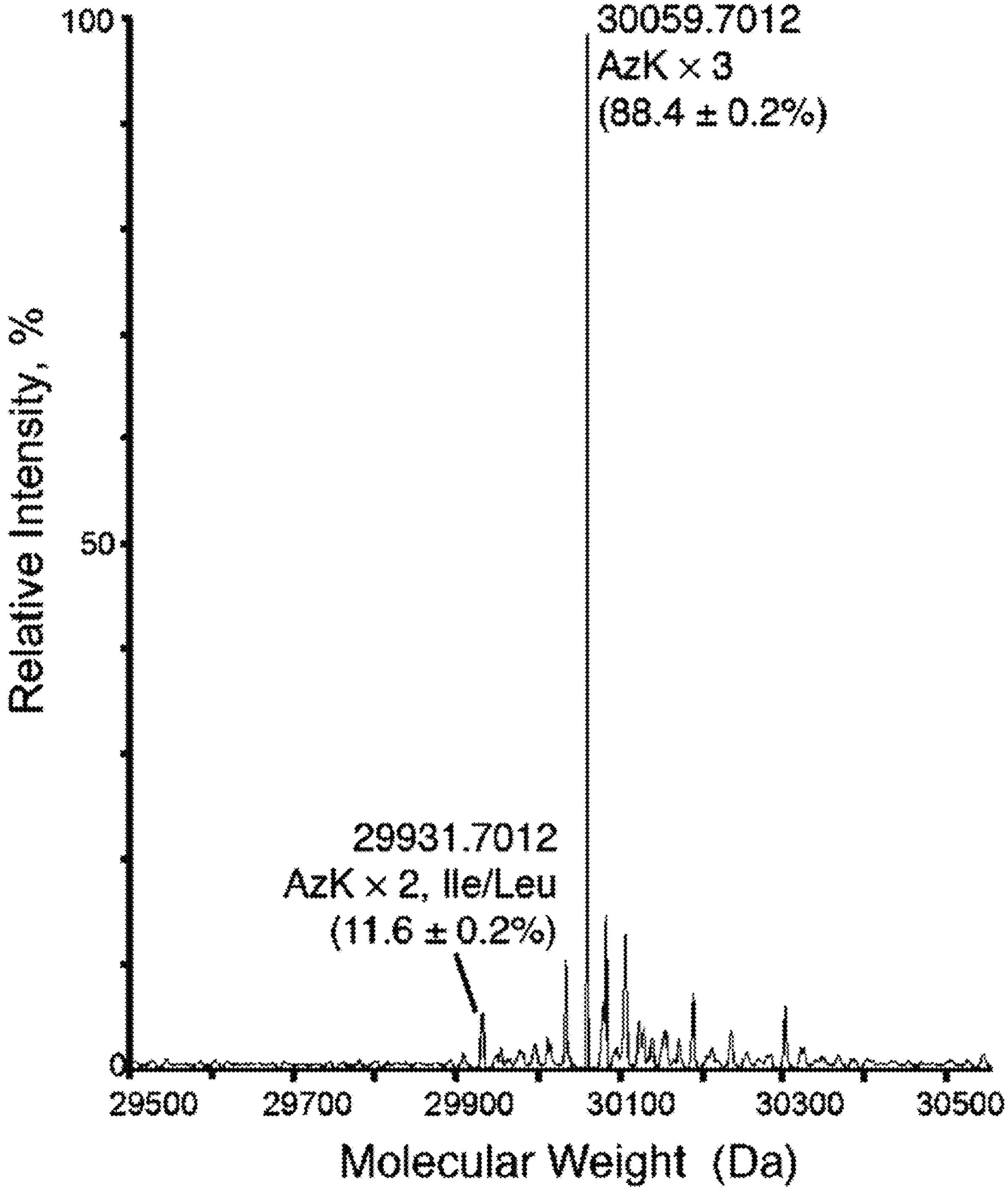
FIG. 7C depicts a representative spectrum of quantitative HRMS analysis of triple labeled protein produced using dCNMOdTPT3/NaMTP, TAT1TP. Peak labels show deconvoluted molecular weight of intact protein, with amino acid residues at positions 149, 151, and 153 shown and quantification of each peak (%, n=3) shown below.

To further verify the successful incorporation of all three ncAAs with the dCNMO-dTPT3/NaMTP,TAT1TP system, isolated sfGFP was analyzed by quantitative intact protein mass spectrometry. Briefly, purified proteins were desalted using centrifugal filter devices (AmiconR Ultra-0.5-Millipore), and analyzed by HRMS (ESI-TOF). The mass spectra acquired were subsequently deconvoluted using the Waters MaxEnt 1 software, which proved to be quantitative upon peak integration (data not shown). In agreement with the gel shift assay, this analysis revealed that that 88% of the isolated protein contained the expected three AzK residues, while the remaining 12% contained two AzK residues and a single Ile or Leu residue (FIG. 7C).

Results. Overall, the SARs identified the dCNMOdTPT3/NaMTP,TAT1TP system as producing high amounts of protein with high fidelity incorporation of the ncAA. The use of dCNMOdTPT3/5FMTP,TAT1TP produces protein with the same high fidelity, and while it produces slightly less protein, it requires the use of significantly less of the unnatural ribonucleotides. The utility of the dCNMO-dTPT3/NaMTP, TAT1TP system is in some instances useful for encoding and retrieval of higher density unnatural information. Both systems produced protein with two ncAAs with high fidelity, but the dCNMOdTPT3/NaMTP, TAT1TP system generally produced the desired protein in greater quantities. Moreover, when encoding three ncAAs, the dNaM-dTPT3/NaMTP, TPT3TP system produced triply labeled protein with significantly reduced and more variable fidelities and yields, while the fidelity and yield with the dCNMO-dTPT3/NaMTP,TAT1TP system remained reproducibly high. Without being bound by theory, the contaminant, where an Ile or Leu replaced a single ncAA, is unlikely to result from unnatural tRNA production, as UBP retention in the tRNA gene was high and similar for the both systems, and even with small differences, the single ncAA-incorporation data suggest that they should not cause significant reductions in the fidelity of unnatural protein production. It is also unlikely to result from mRNA transcription, which should be identical for the two systems (in both cases the dTPT3 directs the incorporation of NaM into the mRNA). Without being bound by theory, the origin of the Leu/Ile contaminant is likely to be loss of the UBP in the mRNA gene during replication; this is also consistent with the most common mutation expected, (dX to dT), which would produce an Ile codon.

The disclosures of all publications, patents, patent applications and published patent applications referred to herein by an identifying citation are hereby incorporated herein by reference in their entirety.

Sequences

Sequence of pGEX-MbPylRS TetR PylRS expression plasmid (5923 bp)

SEQ ID NO: 1

```
GTAAATCACTGCATAATTCGTGTCGCTCAAGGCGCACTCCCGTTCTGGATAATGTTTTTTGCGCCGACAT

CATAACGGTTCTGGCAAATATTCTGAAATGAGCTGTTGACAATTAATCATCGGCTCGTATAATGTGTGGA

ATTGTGAGCGGATAACAATTTCACACAGGAAACAGTATTCATGGATAAAAAACCGCTGGACGTTCTGATC

TCCGCTACGGGTCTGTGGATGAGCCGCACGGGTACGCTGCATAAAATTAAACACCACGAAGTGTCACGTT

CGAAAATCTATATCGAAATGGCGTGCGGTGATCATCTGGTGGTTAACAATAGCCGTTCTTGTCGCACCGC

GCGTGCCTTTCGCCATCACAAATACCGCAAAACGTGCAAACGTTGTCGCGTGTCAGATGAAGACATTAAC

AATTTCCTGACCCGTAGTACGGAATCCAAAAACTCAGTGAAAGTTCGCGTCGTGAGTGCTCCGAAAGTTA

AAAAAGCGATGCCGAAAAGTGTCTCCCGTGCCCCGAAACCGCTGGAAAACTCAGTGTCGGCAAAAGCTTC

CACCAATACGAGCCGCTCTGTTCCGTCGCCGGCAAAAAGCACCCCGAACAGCTCTGTCCCGGCAAGCGCA

CCGGCACCGTCTCTGACGCGTAGTCAGCTGGATCGCGTGGAAGCCCTGCTGTCCCCGGAAGACAAAATCT

CACTGAATATGGCAAAACCGTTTCGTGAACTGGAACCGGAACTGGTTACCCGTCGCAAAAACGATTTCCA

ACGTCTGTATACGAATGATCGCGAAGACTACCTGGGTAAACTGGAACGTGATATCACCAAATTTTTCGTG
```

-continued

GACCGCGGCTTTCTGGAAATCAAATCTCCGATTCTGATCCCGGCTGAATATGTTGAACGCATGGGTATTA

ACAATGATACCGAACTGAGTAAACAGATTTTTCGTGTGGATAAAAACCTGTGCCTGCGGCCGATGCTGGC

ACCGACGCTGTATAATTACCTGCGTAAACTGGATCGCATTCTGCCGGGTCCGATTAAAATCTTTGAAGTG

GGCCCGTGTTATCGTAAAGAATCGGATGGCAAAGAACACCTGGAAGAATTTACCATGGTTAACTTCTGCC

AAATGGGCAGCGGTTGTACGCGCGAAAATCTGGAAGCGCTGATCAAAGAATTCCTGGATTACCTGGAAAT

CGACTTCGAAATCGTCGGTGATTCTTGCATGGTGTATGGCGATACCCTGGACATCATGCATGGTGACCTG

GAACTGAGTTCCGCTGTTGTCGGTCCGGTCAGCCTGGATCGTGAATGGGGCATTGACAAACCGTGGATCG

GCGCGGGTTTTGGCCTGGAACGCCTGCTGAAAGTTATGCACGGCTTCAAAAACATCAAACGTGCGTCTCG

CTCGGAATCGTATTACAACGGCATCTCAACCAATCTGTAATAATGACTGACGATCTGCCTCGCGCGTTTC

GGTGATGACGGTGAAAACCTCTGACACATGCAGCTCCCGGAGACGGTCACAGCTTGTCTGTAAGCGGATG

CCGGGAGCAGACAAGCCCGTCAGGGCGCGTCAGCGGGTGTTGGCGGGTGTCGGGGCGCAGCCATGACCCA

GTCACGTAGCGATAGCGGAGTGTATAATTCTTGAAGACGAAAGGGCCTCGTGATACGCCTATTTTTATAG

GTTAATGTCATGATAATAATGGTTTCTTAGACGTCAGGTGGCACTTTTCGGGGAAATGTGCGCGGAACCC

CTATTTGTTTATTTTTCTAAATACATTCAAATATGTATCCGCTCATGAGACAATAACCCTGATAAATGCT

TCAATAATATTGAAAAAGGAAGAGTATGAGTATTCAACATTTCCGTGTCGCCCTTATTCCCTTTTTTGCG

GCATTTTGCCTTCCTGTTTTTGCTCACCCAGAAACGCTGGTGAAAGTAAAAGATGCTGAAGATCAGTTGG

GTGCACGAGTGGGTTACATCGAACTGGATCTCAACAGCGGTAAGATCCTTGAGAGTTTTCGCCCCGAAGA

ACGTTTTCCAATGATGAGCACTTTTAAAGTTCTGCTATGTGGCGCGGTATTATCCCGTGTTGACGCCGGG

CAAGAGCAACTCGGTCGCCGCATACACTATTCTCAGAATGACTTGGTTGAGTACTCACCAGTCACAGAAA

AGCATCTTACGGATGGCATGACAGTAAGAGAATTATGCAGTGCTGCCATAACCATGAGTGATAACACTGC

GGCCAACTTACTTCTGACAACGATCGGAGGACCGAAGGAGCTAACCGCTTTTTTGCACAACATGGGGGAT

CATGTAACTCGCCTTGATCGTTGGGAACCGGAGCTGAATGAAGCCATACCAAACGACGAGCGTGACACCA

CGATGCCTGCAGCAATGGCAACAACGTTGCGCAAACTATTAACTGGCGAACTACTTACTCTAGCTTCCCG

GCAACAATTAATAGACTGGATGGAGGCGGATAAAGTTGCAGGACCACTTCTGCGCTCGGCCCTTCCGGCT

GGCTGGTTTATTGCTGATAAATCTGGAGCCGGTGAGCGTGGGTCTCGCGGTATCATTGCAGCACTGGGGC

CAGATGGTAAGCCCTCCCGTATCGTAGTTATCTACACGACGGGGAGTCAGGCAACTATGGATGAACGAAA

TAGACAGATCGCTGAGATAGGTGCCTCACTGATTAAGCATTGGTAACTGTCAGACCAAGTTTACTCATAT

ATACTTTAGATTGATTTAAAACTTCATTTTTAATTTAAAAGGATCTAGGTGAAGATCCTTTTTGATAATC

TCATGACCAAAATCCCTTAACGTGAGTTTTCGTTCCACTGAGCGTCAGACCCCGTAGAAAAGATCAAAGG

ATCTTCTTGAGATCCTTTTTTTCTGCGCGTAATCTGCTGCTTGCAAACAAAAAAACCACCGCTACCAGCG

GTGGTTTGTTTGCCGGATCAAGAGCTACCAACTCTTTTTCCGAAGGTAACTGGCTTCAGCAGAGCGCAGA

TACCAAATACTGTCCTTCTAGTGTAGCCGTAGTTAGGCCACCACTTCAAGAACTCTGTAGCACCGCCTAC

ATACCTCGCTCTGCTAATCCTGTTACCAGTGGCTGCTGCCAGTGGCGATAAGTCGTGTCTTACCGGGTTG

GACTCAAGACGATAGTTACCGGATAAGGCGCAGCGGTCGGGCTGAACGGGGGGTTCGTGCACACAGCCCA

GCTTGGAGCGAACGACCTACACCGAACTGAGATACCTACAGCGTGAGCTATGAGAAAGCGCCACGCTTCC

CGAAGGGAGAAAGGCGGACAGGTATCCGGTAAGCGGCAGGGTCGGAACAGGAGAGCGCACGAGGGAGCTT

CCAGGGGGAAACGCCTGGTATCTTTATAGTCCTGTCGGGTTTCGCCACCTCTGACTTGAGCGTCGATTTT

TGTGATGCTCGTCAGGGGGGCGGAGCCTATGGAAAAACGCCAGCAACGCGGCCTTTTTACGGTTCCTGGC

CTTTTGCTGGCCTTTTGCTCACATGTTCTTTCCTGCGTTATCCCCGAGCTCTTAGCGCGAATTGTCGAGG

GAAATTTTTTCTAAATACATTCAAATATGTATCCGCTGATCACACAATAACCCTCATAPATCCTTCAPTA

-continued

ATATTAAATATGGCTGGTTCTCGCAGAAAGAAACATATCCATGAAATCCCGCCCCGAATTGATATGTCCA

GATTAGATAAAAGTAAAGTGATTAACAGCGCATTAGAGCTGCTTAATGAGGTCGGAATCGAAGGTTTAAC

AACCCGTAAACTCGCCCAGAAGCTAGGTGTAGAGCAGCCTACATTGTATTGGCATGTAAAAAATAAGCGG

GCTTTGCTCGACGCCTTAGCCATTGAGATGTTAGATAGGCACCATACTCACTTTTGCCCTTTAGAAGGGG

AAAGCTGGCAAGATTTTTTACGTAATAACGCTAAAAGTTTTAGATGTGCTTTACTAAGTCATCGCGATGG

AGCAAAAGTACATTTAGGTACACGGCCTACAGAAAAACAGTATGAAACTCTCGAAAATCAATTAGCCTTT

TTATGCCAACAAGGTTTTTCACTAGAGAATGCATTATATGCACTCAGCGCTGTGGGGCATTTTACTTTAG

GTTGCGTATTGGAAGATCAAGAGCATCAAGTCGCTAAAGAAGAAAGGGAAACACCTACTACTGATAGTAT

GCCGCCATTATTACGACAAGCTATCGAATTATTTGATCACCAAGGTGCAGAGCCAGCCTTCTTATTCGGC

CTTGAATTGATCATTTGCGGATTAGAAAAACAACTTAAATGTGAAAGTGGGTCTTAAGCACTAGGTCTAG

GGCGGCGGATTTGTCCTACTCAGGAGAGCGTTCACCGACAAACAACAGATAAAACGAAAGGCCCAGTCTT

TCGACTGAGCCTTTCGTTTTATTTGATGCCTCTAGCACGCGTAGAGCTAGAGCCTTCAACCCAGTCAGCT

CCTTCCGGTGGGCGCGGGGCATGACTAACATGAGAATTACAACTTATATCGTATGGGGCTGACTTCAGGT

GCTACATTTGAAGAGATAAATTGCACTGAAATCTAGATGATTCTGTGGATAACCGTATTACCGCCTTTGA

GTGAGCTGATACCGCTCGCCGCAGCCGAACGACCGAGCGCAGCGAGTCAGTGAGCGAGGAAGCGGAAGAG

CGCCTGATGCGGTATTTTCTCCTTACGCATCTGTGCGGTATTTCACACCGCATAAATTCCGACACCATCG

AATGGTGCAAAACCTTTCGCGGTATGGCATGATAGCGCCCGGAAGAGAGTCAATTCAGGGTGGTGAATGT

GAAACCAGTAACGTTATACGATGTCGCAGAGTATGCCGGTGTCTCTTATCAGACCGTTTCCCGCGTGGTG

AACCAGGCCAGCCACGTTTCTGCGAAAACGCGGGAAAAAGTGGAAGCGGCGATGGCGGAGCTGAATTACA

TTCCCAACCGCGTGGCACAACAACTGGCGGGCAAACAGTCGTTGCTGATTGGCGTTGCCACCTCCAGTCT

GGCCCTGCACGCGCCGTCGCAAATTGTCGCGGCGATTAAATCTCGCGCCGATCAACTGGGTGCCAGCGTG

GTGGTGTCGATGGTAGAACGAAGCGGCGTCGAAGCCTGTAAAGCGGCGGTGCACAATCTTCTCGCGCAAC

GCGTCAGTGGGCTGATCATTAACTATCCGCTGGATGACCAGGATGCCATTGCTGTGGAAGCTGCCTGCAC

TAATGTTCCGGCGTTATTTCTTGATGTCTCTGACCAGACACCCATCAACAGTATTATTTTCTCCCATGAA

GACGGTACGCGACTGGGCGTGGAGCATCTGGTCGCATTGGGTCACCAGCAAATCGCGCTGTTAGCGGGCC

CATTAAGTTCTGTCTCGGCGCGTCTGCGTCTGGCTGGCTGGCATAAATATCTCACTCGCAATCAAATTCA

GCCGATAGCGGAACGGGAAGGCGACTGGAGTGCCATGTCCGGTTTTCAACAAACCATGCAAATGCTGAAT

GAGGGCATCGTTCCCACTGCGATGCTGGTTGCCAACGATCAGATGGCGCTGGGCGCAATGCGCGCCATTA

CCGAGTCCGGGCTGCGCGTTGGTGCGGATATCTCGGTAGTGGGATACGACGATACCGAAGACAGCTCATG

TTATATCCCGCCGTTAACCACCATCAAACAGGATTTTCGCCTGCTGGGGCAAACCAGCGTGGACCGCTTG

CTGCAACTCTCTCAGGGCCAGGCGGTGAAGGGCAATCAGCTGTTGCCCGTCTCACTGGTGAAAAGAAAAA

CCACCCTGGCGCCCAATACGCAAACCGCCTCTCCCCGCGCGTTGGCCGATTCATTAATGCAGCTGGCACG

ACAGGTTTCCCGACTGGAAAGCGGGCAGTGAGCGCAACGCAAT.

Sequence of p[sfGFP(gg)151; tRNAPyl(gg)] GG destination plasmid
for sfGFP and tRNA$^{Pyl}$ expression (3101 bp)

SEQ ID NO: 2

TAACTAGCATAACCCCTTGGGGCCTCTAAACGGGTCTTGAGGGGTTTTTTGCTGAAAGGAGGAACTATAT

CCGGATTGGTTAATACGACTCACTATAGGGGAATTGTGAGCGGATAACAATTCCCCTCTAGAAAAGCATT

GGAAACCGAGACCGGTACCGGTCTCTTAGATTCCCGGGGTTTCCGCCAAATTCGAAAAGCCTGCTCAACG

AGCAGGCTTTTTTGCATCTAGCATAACCCCTTGGGGCCTCTAAACGGGTCTTGAGGGGTTTTTTGCCTGA

ACGAGCAGGCTTTTTTGCATAAGCTTCCTAGTGGCAGCGGCTAACTAAGCGGCCTGCTGACTTTCTCGCC

GATCAAAAGGCATTTTGCTATTAAGGGATTGACGAGGGCGTATCTGCGCAGTAAGATGCGCCCCGCATTG

-continued

GAGACGCCATGGCGTCTCGGTTTTAGAGCTAGAAATAGCAAGTTAAAATAAGGCTAGTCCGTTATCAACT
TGAAAAAGTGGCACCGAGTCGGTGCTTTTTTTAATTCGAAAAGCCTGCTCAACGAGCAGGCTTTTTTGGT
CGACAGTAGTGGCAGCGGCTAACTAAGCGGCCTGCTGACTTTCTCGCCGATCAAAAGGCATTTTGCTATT
AAGGGATTGACGAGGGCGTATCTGCGCAGTAAGATGCGCCCCGCATGAGACGGCATGCCGTCTCTAGAGC
TAGAAATAGCAAGTTAAAATAAGGCTAGTCCGTTATCAACTTGAAAAAGTGGCACCGAGTCGGTGCTTTT
TTTAATTCGAAAAGCCTGCTCAACGAGCAGGCTTTTTTGGTCGACAGTTCATAGGTGATTGCGGATCCCG
TCGTTGACAATTAATCATCGGCATAGTATATCGGCATAGTATAATACGACAAGGTGAGGAACTAAACCAT
GGCCAAGTTGACCAGTGCCGTTCCGGTGCTCACCGCGCGCGACGTCGCCGGAGCGGTCGAGTTCTGGACC
GACCGGCTCGGGTTCTCCCGCGACTTCGTGGAGGACGACTTCGCCGGTGTGGTCCGGGACGACGTGACCC
TGTTCATCAGCGCGGTCCAGGACCAGGTGGTGCCGGACAACACCCTGGCCTGGGTGTGGGTGCGCGGCCT
GGACGAGCTGTACGCCGAGTGGTCGGAGGTCGTGTCCACGAACTTCCGGGACGCCTCCGGGCCGGCCATG
ACCGAGATCGGCGAGCAGCCGTGGGGGCGGGAGTTCGCCCTGCGCGACCCGGCCGGCAACTGCGTGCACT
TCGTGGCCGAGGAGCAGGACTGAGAGCTCGCTTGGACTCCTGTTGATAGATCCAGTAATGACCTCAGAAC
TCCATCTGGATTTGTTCAGAACGCTCGGTTGCCGCCGGGCGTTTTTTATTGGTGAGAATCCAAGCACTAG
CTAGTAACAACTTATATCGTATGGGGCTGACTTCAGGTGCTACATTTGAAGAGATAAATTGCACTGAAAT
CTAGTAATATTTTATCTGATTAATAAGATGATCTTCTTGAGATCGTTTTGGTCTGCGCGTAATCTCTTGC
TCTGAAAACGAAAAAACCGCCTTGCAGGGCGGTTTTTCGAAGGTTCTCTGAGCTACCAACTCTTTGAACC
GAGGTAACTGGCTTGGAGGAGCGCAGTCACCAAAACTTGTCCTTTCAGTTTAGCCTTAACCGGCGCATGA
CTTCAAGACTAACTCCTCTAAATCAATTACCAGTGGCTGCTGCCAGTGGTGCTTTTGCATGTCTTTCCGG
GTTGGACTCAAGACGATAGTTACCGGATAAGGCGCAGCGGTCGGACTGAACGGGGGGTTCGTGCATACAG
TCCAGCTTGGAGCGAACTGCCTACCCGGAACTGAGTGTCAGGCGTGGAATGAGACAAACGCGGCCATAAC
AGCGGAATGACACCGGTAAACCGAAAGGCAGGAACAGGAGAGCGCACGAGGGAGCCGCCAGGGGGAAACG
CCTGGTATCTTTATAGTCCTGTCGGGTTTCGCCACCACTGATTTGAGCGTCAGATTTCGTGATGCTTGTC
AGGGGGGCGGAGCCTATGGAAAAACGGCTTTGCCGCGGCCCTCTCACTTCCCTGTTAAGTATCTTCCTGG
CATCTTCCAGGAAATCTCCGCCCCGTTCGTAAGCCATTTCCGCTCGCCGCAGTCGAACGACCGAGCGTAG
CGAGTCAGTGAGCGAGGAAGCGGAATATATCCCTTAATACGACTCACTATAGGGTCCCTATCAGTGATAG
AGAGGTCTAGAAATAATTTTGTTTAACTTTAAGAAGGAGATATACATATGTCGAAAGGCGAAGAACTGTT
TACGGGAGTGGTGCCTATCCTGGTAGAGCTCGACGGAGATGTAAACGGTCACAAATTTTCAGTCCGCGGG
GAAGGCGAAGGCGATGCGACCAACGGTAAATTAACTTTGAAGTTTATTTGCACCACCGGCAAATTACCGG
TGCCTTGGCCGACGCTTGTGACGACCCTGACTTACGGGGTGCAGTGTTTCAGTCGCTACCCAGATCACAT
GAAACGCCATGACTTCTTCAAATCTGCGATGCCGGAAGGCTATGTGCAGGAACGTACAATTAGCTTTAAA
GACGACGGCACGTATAAAACGCGGGCAGAGGTTAAATTTGAGGGAGATACCCTGGTAAACCGTATTGAAC
TGAAAGGCATCGATTTTAAAGAAGATGGGAACATCTTGGGCCACAAGAGACCGGTACCGGTCTCGGAATC
AAAGCAAATTTCAAGATCCGTCATAACGTGGAGGACGGTTCCGTGCAGCTTGCAGATCACTATCAGCAGA
ATACGCCGATTGGCGATGGCCCGGTGCTGCTGCCCGATAATCACTACCTCTCTACTCAGAGTGTTTTATC
GAAAGACCCGAACGAGAAGCGTGATCACATGGTGCTGCTTGAATTTGTTACCGCGGCAGGTATTACACAC
GGCATGGATGAGTTGTATAAGGGATCCGCTTGGAGCCACCCGCAGTTCGAGAAAGGTGGAGGTTCCGGAG
GTGGATCGGGAGGTTCGGCGTGGAGCCACCCGCAGTTCGAAAAATAAAAGCTTAATTAGCTGAGCTTGGA
CTCCCTGCCACCGCTGAGCAA.

What is claimed is:

1. A nucleobase of the structure:

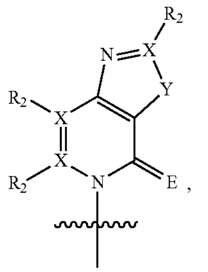

wherein:

each X is independently carbon or nitrogen;

$R_2$ is present when X is carbon and is independently hydrogen, alkyl, alkenyl, alkynyl, methoxy, methanethiol, methaneseleno, halogen, cyano, or azide group;

Y is sulfur, oxygen, or selenium; and

E is sulfur;

wherein the wavy line indicates a point of bonding to a ribosyl, deoxyribosyl, or dideoxyribosyl moiety, wherein the ribosyl, deoxyribosyl, or dideoxyribosyl moiety is optionally modified at the 2' position, at the 3' position, or at the 5' position, wherein the ribosyl, deoxyribosyl, or dideoxyribosyl moiety is in free form, is connected to a mono-phosphate, diphosphate, triphosphate, α-thiotriphosphate, β-thiotriphosphate, or γ-thiotriphosphate group, or is included in a polynucleotide, optionally wherein the polynucleotide is an RNA, DNA, bicyclic nucleic acid, linked nucleic acid, peptide nucleic acid (PNA), locked nucleic acid (LNA), or a phosphorothioate-containing nucleic acid.

2. The nucleobase of claim 1, wherein X is carbon and/or Y is sulfur.

3. The nucleobase of claim 1, which has the structure

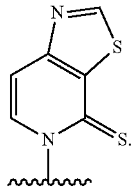 [SMILES: *n1ccc2ncsc2c1=S]

4. The nucleobase of claim 1, which is bound to a complementary base-pairing nucleobase to form an unnatural base pair (UBP), wherein the complementary base-pairing nucleobase is selected from:

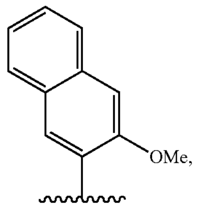,
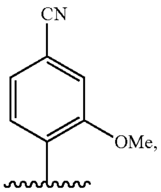,

-continued

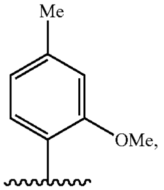,
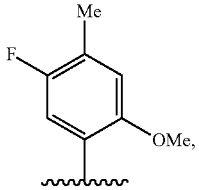,
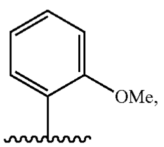,
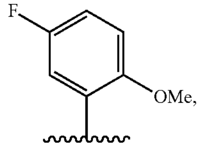,
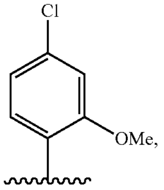,
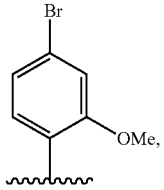,
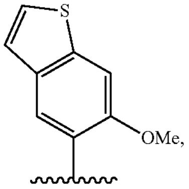,
and
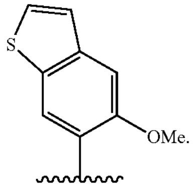.

5. A double stranded oligonucleotide duplex wherein a first oligonucleotide strand comprises the nucleobase of claim 1, and a second complementary oligonucleotide strand comprises a complementary base-pairing nucleobase in a complementary base-pairing site thereof.

6. The double stranded oligonucleotide duplex of claim 5, wherein the first oligonucleotide strand comprises

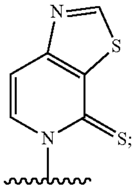 [SMILES: *n1ccc2ncsc2c1=S]

and the second strand comprises a complementary base pairing nucleobase selected from:

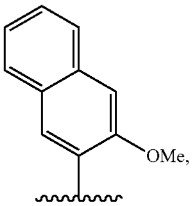,
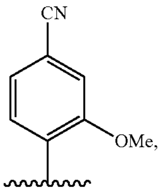,
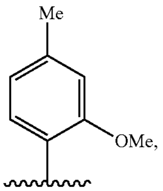,
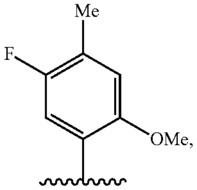,
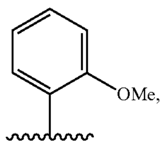,

-continued
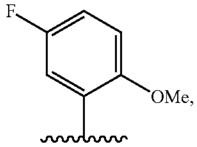
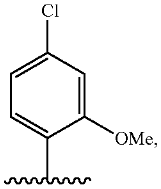
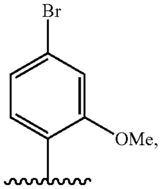
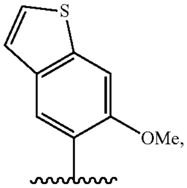
and
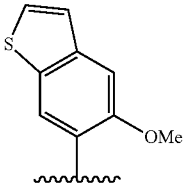
in a complementary base-pairing site thereof.
7. A DNA comprising a nucleobase having the structure
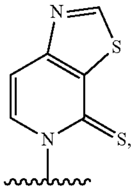 [SMILES: *n1ccc2ncsc2c1=S]
and a complementary base-pairing nucleobase having the structure
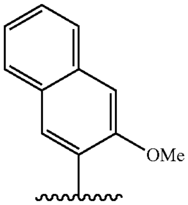 [SMILES: *c1cc2ccccc2cc1OC]
or a nucleobase having the structure
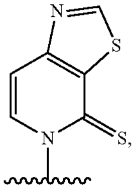
and a complementary base-pairing nucleobase having the structure
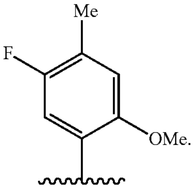 [SMILES: *c1cc(F)c(C)cc1OC]
* * * * *

UNITED STATES PATENT AND TRADEMARK OFFICE

CERTIFICATE OF CORRECTION

PATENT NO. : 11,879,145 B2
APPLICATION NO. : 16/900154
DATED : January 23, 2024
INVENTOR(S) : Romesberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 522 days.

Signed and Sealed this
First Day of July, 2025

Coke Morgan Stewart
*Acting Director of the United States Patent and Trademark Office*